US008642742B2

(12) United States Patent
Hofer et al.

(10) Patent No.: US 8,642,742 B2
(45) Date of Patent: Feb. 4, 2014

(54) ANTI-CEA ANTIBODIES

(75) Inventors: Thomas U. Hofer, Zurich (CH); Ralf Hosse, Cham (CH); Ekkehard Moessner, Kreuzlingen (CH); Pablo Umana, Wollerau (CH)

(73) Assignee: Roche Glycart AG, Schileren (CH)

( * ) Notice: Subject to any disclaimer, the term of this patent is extended or adjusted under 35 U.S.C. 154(b) by 0 days.

(21) Appl. No.: 13/408,171

(22) Filed: Feb. 29, 2012

(65) Prior Publication Data

US 2012/0251529 A1    Oct. 4, 2012

(30) Foreign Application Priority Data

Mar. 2, 2011    (EP) .................................... 11156665

(51) Int. Cl.
   *C07K 16/30*    (2006.01)
   *A61K 39/395*    (2006.01)

(52) U.S. Cl.
   USPC .................. 530/388.8; 530/387.3; 424/133.1; 424/174.1

(58) Field of Classification Search
   None
   See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |
| 5,591,828 | A | 1/1997 | Bosslet et al. |
| 5,872,215 | A | 2/1999 | Osbourne et al. |
| 5,876,691 | A | 3/1999 | Chester et al. |
| 5,965,710 | A | 10/1999 | Bodmer et al. |
| 6,180,370 | B1 | 1/2001 | Queen et al. |
| 6,602,684 | B1 | 8/2003 | Umana et al. |
| 6,632,927 | B2 | 10/2003 | Adair et al. |
| 6,737,056 | B1 | 5/2004 | Presta |
| 6,815,184 | B2 | 11/2004 | Stomp et al. |
| 6,946,292 | B2 | 9/2005 | Kanda et al. |
| 7,074,406 | B2 | 7/2006 | Black et al. |
| 7,232,888 | B2 | 6/2007 | Begent et al. |
| 7,321,026 | B2 | 1/2008 | Leung |
| 7,432,063 | B2 | 10/2008 | Balint et al. |
| 2003/0040606 | A1 | 2/2003 | Leung |
| 2003/0115614 | A1 | 6/2003 | Kanda et al. |
| 2003/0157108 | A1 | 8/2003 | Presta |
| 2003/0175884 | A1 | 9/2003 | Umana et al. |
| 2004/0093621 | A1 | 5/2004 | Shitara et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2004/0241817 | A1 | 12/2004 | Umana et al. |
| 2005/0031613 | A1 | 2/2005 | Nakamura et al. |
| 2010/0092997 | A1 | 4/2010 | Nakamura et al. |
| 2011/0104148 | A1* | 5/2011 | Mossner et al. ............ 424/133.1 |
| 2012/0244112 | A1* | 9/2012 | Ast et al. ....................... 424/85.2 |

FOREIGN PATENT DOCUMENTS

| | | |
|---|---|---|
| CA | 2 019 559 C | 1/2002 |
| EP | 1176195 A1 | 1/2002 |
| WO | 93/01161 A1 | 1/1993 |
| WO | 95/06067 A1 | 3/1995 |
| WO | 99/54342 A1 | 10/1999 |
| WO | 03/056914 A1 | 7/2003 |
| WO | 03/078614 A2 | 9/2003 |
| WO | 03/084570 A1 | 10/2003 |
| WO | 03/085119 A1 | 10/2003 |
| WO | 2004/024927 A1 | 3/2004 |
| WO | 2004/057002 A2 | 7/2004 |
| WO | 2004/063351 A2 | 7/2004 |
| WO | 2004/065540 A2 | 8/2004 |
| WO | 2004/099249 A2 | 11/2004 |
| WO | 2004/101790 A1 | 11/2004 |
| WO | 2011/023787 A1 | 3/2011 |
| WO | 2011/039126 A1 | 4/2011 |
| WO | WO 2012107417 A1 * | 8/2012 |
| WO | 2012/117002 A1 | 9/2012 |

OTHER PUBLICATIONS

Rudikoff et al., Proc. Nat'l Acad. Sci. USA 1982.*
Brown et al., J. Immunol. May 1996; 156(9):3285-91.*
Strome et al., The Oncologist, 2007; 12:1084-95.*
Brand et al., Anticancer Res. 2006; 26:463-70.*
Andersen et al., "Recombinant protein expression for therapeutic applications" Curr Opin Biotechnol. 13(2):117-23 (Apr. 2002).
Ashraf et al., "Humanised IgG1 antibody variants targeting membrane-bound carcinoembryonic antigen by antibody-dependent cellular cytotoxicity and phagocytosis" Br J Cancer 101(10):1758-68 (Nov. 2009).
Berinstein, "Carcinoembryonic antigen as a target for therapeutic anticancer vaccines: a review" J Clin Oncol. 20(8):2197-207 ( 2002).
Borth et al., "Efficient selection of high-producing subclones during gene amplification of recombinant Chinese hamster ovary cells by flow cytometry and cell sorting" Biotechnol Bioeng. 71(4):266-73 ( 2001).
Bowie et al., "Deciphering the message in protein sequences: tolerance to amino acid substitutions" Science 247(4948):1306-10 ( 1990).
Boxer et al., "Factors influencing variability of localisation of antibodies to carcinoembryonic antigen (CEA) in patients with colorectal carcinoma—implications for radioimmunotherapy" Br J Cancer 65(6):825-31 ( 1992) .
Brutlag et al., "Improved sensitivity of biological sequence database searches" Comput Appl Biosci. 6(3):237-245 ( 1990).
Carter et al., "Humanization of an anti-p185\\\superscript:HER2\\\ antibody for human cancer therapy" Proc. Natl. Acad. Sci. USA 89:4285-4289 (May 1992).

(Continued)

*Primary Examiner* — Misook Yu
*Assistant Examiner* — Jessica H Roark
(74) *Attorney, Agent, or Firm* — Roche Glycart AG

(57) ABSTRACT

The present invention provides antigen binding molecules (ABMs) which bind membrane-bound CEA, including ABMs with improved therapeutic properties, and methods of using the same.

18 Claims, 41 Drawing Sheets

(56) References Cited

OTHER PUBLICATIONS

Chadd et al., "Therapeutic antibody expression technology" Curr Opin Biotechnol. 12(2):188-94 ( 2001).
Champe et al., "Monoclonal antibodies that block the activity of leukocyte function-associated antigen 1 recognize three discrete epitopes in the inserted domain of CD11a" J Biol Chem 270:1388-1394 ( 1995).
Chau et al., "The value of routine serum carcino-embryonic antigen measurement and computed tomography in the surveillance of patients after adjuvant chemotherapy for colorectal cancer" J Clin Oncol. 22(8):1420-9 ( 2004).
Chiang and McConlogue, "Amplification and Expression of Heterologous Ornitine Decarboxylase in Chinese Hamster Cells" Molecular and Cellular Biology 8(2):764-69 ( 1988).
Chothia and Lesk, "Canonical structures for the hypervariable regions of immunoglobulins" J. Mol. Biol. 196:901-917 ( 1987).
Colbère-Garapin et al., "A new dominant hybrid selective marker for higher eukaryotic cells" J Mol Biol. 150(1):1-14 ( 1981).
Conaghan et al., "Targeted killing of colorectal cancer cell lines by a humanised IgG1 monoclonal antibody that binds to membrane-bound carcinoembryonic antigen" Br J Cancer 98(7):1217-25 ( 2008).
Cumming et al., "Glycosylation of recombinant protein therapeutics: control and functional implications" Glycobiology 1(2):115-30 (Mar. 1991).
Davies et al., "Affinity improvement of single antibody VH domains: residues in all three hypervariable regions affect antigen binding" Immunotechnology 2:169-179 ( 1996).
Deo et al., "Clinical significance of IgG Fc receptors and Fc gamma R-directed immunotherapies" Immunol Today 18(3):127-35 ( 1997).
Dillman, "Magic bullets at last! Finally—approval of a monoclonal antibody for the treament of cancer!!!" Cancer Biother Radiopharm. 12(4):223-5 ( 1997).
Durbin et al., "An epitope on carcinoembryonic antigen defined by the clinically relevant antibody PR1A3" Proc Natl Acad Sci U S A. 91(10):4313-7 ( 1994).
Flamini et al., "Free DNA and carcinoembryonic antigen serum levels: an important combination for diagnosis of colorectal cancer" Clin Cancer Res. 12(23):6985-8 ( 2006).
Frost et al., "A phase I/IB trial of murine monoclonal anti-GD2 antibody 14.G2a plus interleukin-2 in children with refractory neuroblastoma: a report of the Children's Cancer Group" Cancer 80(2):317-33 ( 1997).
Garambois et al., "Fully human IgG and IgM antibodies directed against the carcinoembryonic antigen (CEA) Gold 4 epitope and designed for radioimmunotherapy (RIT) of colorectal cancers" BMC Cancer 4:75 (Oct. 15, 2004).
Giddings, "Transgenic plants as protein factories" Curr Opin Biotechnol. 12(5):450-4 ( 2001).
Gold et al., "Demonstration of Tumor-Specific Antigens in Human Colonic Carcinomata by Immunological Tolerance and Absorption" J Exp Med. 121:439-62 ( 1965).
Goldenberg, "Cancer imaging with CEA antibodies: historical and current perspective" Int J Biol Markers 7(3):183-8 ( 1992).
Granowska et al., "Radioimmunoscintigraphy with technetium-99m labelled monoclonal antibody, 1A3, in colorectal cancer" Eur J Nucl Med. 20(8):690-8 ( 1993).
Hammarström, "The carcinoembryonic antigen (CEA) family: structures, suggested functions and expression in normal and malignant tissues" Semin Cancer Biol 9(2):67-81 ( 1999).
Hartman et al., "Two dominant-acting selectable markers for gene transfer studies in mammalian cells" Proc Natl Acad Sci U S A. 85(21):8047-51 ( 1988).
Hefta et al., "Expression of carcinoembryonic antigen and its predicted immunoglobulin-like domains in HeLa cells for epitope analysis" Cancer Res. 52(20):5647-55 ( 1992).
Holliger et al., "Diabodies': Small bivalent and bispecific antibody fragments" P Natl Acad Sci USA 90:6444-6448 (Jul. 1993).
Holt et al., "Domain antibodies: proteins for therapy" Trends Biotechnol 21(11):484-490 (Nov. 2003).
Hu et al., "Minibody: A novel engineered anti-carcinoembryonic antigen antibody fragment (single-chain Fv-CH3) which exhibits rapid, high-level targeting of xenografts" Cancer Res 56(13):3055-3061 (Jul. 1, 1996).
Hudson et al., "Engineered antibodies" Nature Medicine 9(1):129-134 (Jan. 2003).
Huse et al., "Generation of a large combinatorial library of the immunoglobulin repertoire in phage lambda" Science 246:1275-1281 ( 1989).
Jefferis et al., "IgG-Fc-mediated effector functions: molecular definition of interaction sites for effector ligands and the role of glycosylation" Immunol Rev 163:59-76 ( 1998).
Jenkins et al., "Getting the glycosylation right: Implications for the biotechnology industry" Nature Biotechnol 14:975-981 (Aug. 1996).
Jones et al., "Replacing the complementarity-determining regions in a human antibody with those from a mouse" Nature 321:522-525 (May 1986).
Kang et al., "Linkage of recognition and replication functions by assembling combinatorial antibody Fab libraries along phage surfaces" P Natl Acad Sci USA 88(10):4363-4366 (May 15, 1991).
Kim et al., "Enhancement of colorectal tumor targeting using a novel biparatopic monoclonal antibody against carcinoembryonic antigen in experimental radioimmunoguided surgery" Int J Cancer 97(4):542-7 ( 2002).
Ledermann et al., "Repeated antitumour antibody therapy in man with suppression of the host response by cyclosporin A" Br J Cancer 58(5):654-7 ( 1988).
Liersch et al., "Update of carcinoembryonic antigen radioimmunotherapy with (131)I-labetuzumab after salvage resection of colorectal liver metastases: comparison of outcome to a contemporaneous control group" Ann Surg Oncol. 14(9):2577-90 ( 2007).
Lifely et al., "Glycosylation and Biological Activity of CAMPATH-1H Expressed in Different Cell Lines and Grown Under Different Culture Conditions." Glycobiology 5(8):813-822 (Dec. 1995).
Lowy et al., "Isolation of transforming DNA: cloning the hamster aprt gene" Cell 22(3):817-23 ( 1980).
Lund et al., "Multiple Interactions of the IgG with Its Core Oligosaccharide Can Modulate Recognition by Complement and Human Fcγ Receptor I and Influence the Synthesis of Its Oligosaccharide Chains" J Immunol 157:4963-4969 ( 1996).
Mansi et al., "Diagnosis of Ovarian Cancer with Radiolabelled Monoclonal Antibodies: Our Experience Using 131I-B72.3" Int J Rad Appl Instrum B. 16(2):127-35 ( 1989).
Marshall et al., "Carcinoembryonic antigen-based vaccines" Semin Oncol. 30( Suppl 8):30-6(2003).
Morrison et al., "Chimeric human antibody molecules: Mouse antigen-binding domains with human constant region domains" P Natl Acad Sci USA 81:6851-6855 (Nov. 1984).
Morrison et al., "Genetically Engineered Antibody Molecules" Adv Immunol 44:65-92 (1989).
Mulligan et al., "Selection for animal cells that express the *Escherichia coli* gene coding for xanthine-guanine phosphoribosyltransferase" Proc Natl Acad Sci U S A. 78(4):2072-6 ( 1981).
Nap et al., "Immunohistochemistry of carcino-embryonic antigen in the embryo, fetus and adult" Tumour Biol. 9:145-53 ( 1988).
Nap et al., "Specificity and affinity of monoclonal antibodies against carcinoembryonic antigen" Cancer Res. 52(8):2329-39 ( 1992).
NCBI, '*H. sapiens* gene for Ig kappa light chain variable region '012',' accessed at //www.ncbi.nlm nih.gov/nuccore/33247,,pp. 2, GenBank X59315, Nov. 14, 2006.
NCBI, '*H. sapiens* gene for immunoglobulin joining region (kappa light chain),'accessed at //www.ncbi.nlm.nih.gov/nuccore/34013, pp. 2, GenBank X61584 Nov. 14, 2006.
NCBI, '*H. sapiens* VI-4.1B gene for immunoglobulin heavy chain,' accessed at //www.ncbi.nlm.nih.gov/nuccore/37837, pp. 2, GenBank X62110.1 Nov. 14, 2006.
NCBI, 'Human Ig germline H-chain J6-region, partial cds,' accessed at //www.ncbi.nlm.nih.gov/nuccore/185637,, pp. 1, GenBank M63030.1 Jan. 3, 1995.
O'hare et al., "Transformation of mouse fibroblasts to methotrexate resistance by a recombinant plasmid expressing a prokaryotic dihydrofolate" Proc Natl Acad Sci U S A. 78(3):1527-31 ( 1981).

(56) References Cited

OTHER PUBLICATIONS

Padlan et al., "Identification of specificity-determining residues in antibodies" FASEB J. 9(1):133-9 (1995).
Padlan, "A possible procedure for reducing the immunogenicity of antibody variable domains while preserving their ligand-binding properties" Mol Immunol 28(4/4):489-498 (1991).
Padlan, E., "Anatomy of the Antibody Molecule" Mol Immunol 31(3):169-217 (1994).
PCT IPRP for PCT/EP2010/062527, Aug. 30, 2011.
PCT ISR for PCT/EP2010/062527, Nov. 26, 2010.
PCT ISR for PCT/EP2012/053390, May 7, 2012.
Pedley et al., "Comparative radioimmunotherapy using intact or F(ab')2 fragments of 131I anti-CEA antibody in a colonic xenograft model" Br J Cancer 68(1):69-73 (1993).
Pluckthun, A. The Pharmacology of Monoclonal Antibodies: Handbook of Pharmacology "Antibodies from *Escherichia coli*" (Chapter 11), Rosenberg and Moore, eds., Berlin:Springer-Verlag, vol. 113:269-315 (1994).
Presta et al., "Humanization of an antibody directed against IgE" J Immunol 151(5):2623-2632 (Sep. 1993).
Presta, "Antibody Engineering" Curr Opin Struc Biol 2:593-596 (1992).
Reichmann et al., "Reshaping human antibodies for therapy" Nature 332:323-327 (Mar. 24, 1988).
Richman et al., "Monoclonal antibodies to human colorectal epithelium: markers for differentiation and tumour characterization" Int J Cancer 39(3):317-28 (1987).
Sakurai et al., "Conformational epitopes specific to carcinoembryonic antigen defined by monoclonal antibodies raised against colon cancer xenografts" J Surg Oncol. 42(1):39-46 (1989).
Santerre et al., "Expression of prokaryotic genes for hygromycin B and G418 resistance as dominant-selection markers in mouse L cells" Gene 30:147-56 (1984).
Schachter, "Biosynthetic controls that determine the branching and microheterogeneity of protein-bound oligosaccharides" Biochem Cell Biol. 64(3):163-81 (1986).
Sheahan et al., "Differential reactivities of carcinoembryonic antigen (CEA) and CEA-related monoclonal and polyclonal antibodies in common epithelial malignancies" Am J Clin Pathol. 94(2):157-64 (1990).
Silacci et al., "Design, construction, and characterization of a large synthetic human antibody phage display library" Proteomics 5(9):2340-50 (2005).
Sims et al., "A Humanized CD18 Antibody Can Block Function Without Cell Destruction" J Immunol 151(4):2296-2308 (Aug. 15, 1993).
Steidl et al., "In vitro affinity maturation of human GM-CSF antibodies by targeted CDR-diversification" Mol Immunol. 46(1):135-44 (2008).
Stewart et al., "Humanisation and characterisation of PR1A3, a monoclonal antibody specific for cell-bound carcinoembryonic antigen" Cancer Immunol Immunother. 47(6):299-306. (1999).
Surfus et al., "Anti-renal-cell carcinoma chimeric antibody G250 facilitates antibody-dependent cellular cytotoxicity with in vitro and in vivo interleukin-2-activated effectors" J Immunother Emphasis Tumor Immunol. 19(3):184-91 (1996).
Szybalska, "Genetics of human cess line. IV. DNA-mediated heritable transformation of a biochemical trait" Proc Natl Acad Sci U S A. 48:2026-34 (1962).
Tang et al., "Regulation of antibody-dependent cellular cytotoxicity by IgG intrinsic and apparent affinity for target antigen" J Immunol. 179(5):2815-23 (2007).
Thompson, "Carcinoembryonic antigen gene family: molecular biology and clinical perspectives" J Clin Lab Anal. 5(5):344-66 (1991).
Umana et al., "Engineered glycoforms of an antineuroblastoma IgG1 with optimized antibody-dependent cellular cytotoxic activity" Nat Biotechnol 17:176-180 (Feb. 1999).
Verhoeyen et al., "Reshaping Human Antibodies: Grafting an Antilysozyme Activity" Science 239:1534-1536 (Mar. 1988).
Werner et al., "Appropriate mammalian expression systems for biopharmaceuticals" Arznei-Forschung/Drug Res 48(8):870-880 (1998).
Wigler et al., "Transfer of purified herpes virus thymidine kinase gene to cultured mouse cells" Cell 11(1):223-232 (May 1977).
Wigler et al., "Transformation of Mammalian Cells with an Amplifiable Dominant-acting Gene" P Natl Acad Sci USA 77(6):3567-3570 (Jun. 1980).
Wilkinson et al., "Evaluation of a transgenic mouse model for anti-human CEA radioimmunotherapeutics" J Nucl Med. 43(10):1368-76 (Oct. 2002).
Wong et al., "Pilot trial evaluating an 123I-labeled 80-kilodalton engineered anticarcinoembryonic antigen antibody fragment (cT84.66 minibody) in patients with colorectal cancer" Clin Cancer Res. 10(15):5014-21 (2004).
Wormald et al., "Variations in Oligosaccharide-Protein Interactions in Immunoglobulin G Determine the Site-Specific Glycosylation Profiles and Modulate the Fc Oligosaccharides" Biochemistry—US 36:1370-1380 (1997).
Wright and Morrison, "Effect of glycosylation on antibody function: Implications for genetic engineering" Trends Biotechnol 15:26-32 (1997).
Yang et al., "CDR walking mutagenesis for the affinity maturation of a potent human anti-HIV-1 antibody into the picomolar range" J Mol Biol 254(3):392-403 (Dec. 1, 1995).
Zbar et al., "Immune responses in advanced colorectal cancer following repeated intradermal vaccination with the anti-CEA murine monoclonal antibody, PR1A3: results of a phase I study" Int J Colorectal Dis. 20(5):403-14 (2005).
Office Action for U.S. Appl. No. 12/872,908 mailed Mar. 11, 2013.
PCT Written Opinion for PCT/EP2012/053390, May 7, 2012.
PCT Written Opinion of the ISA for PCT/EP2010/062527, Nov. 26, 2010.

* cited by examiner

VL's

| | CDR L1 | CDR L2 |
|---|---|---|
| Kabat V | | |
| PR1A3-VL | DIVMTQSQRFMSTSVGDRVSVTCKASQNVGTNVAWYQQKPGQSPKALIYSASYRYSGVPDR | |
| Randomized Positions: | X X X X X X | X X A S X X X X |

| | CDR L3 |
|---|---|
| | FTGSGSGTDFTLTLSNVQSEDLAEYFCHQYYTYPLFTFGSGTKLEMKR |
| | X X X X X X T Y P L |
| | X Y T Y P L |
| | X Y T X P L |
| | Y Y X Y P L |
| | Y Y T X P L |
| | Y Y T Y X L |
| | Y Y T Y P X |

Fig. 4

| CDR | | Amino Acid Sequence | SEQ ID NO |
|---|---|---|---|
| Heavy Chain CDR1 | Kabat | EFGMN | 1 |
| | | EYGMN | 2 |
| | | EYSMN | 3 |
| | | EFGMS | 5 |
| | Chothia | GYTFTEF | 6 |
| | | GYTFTEY | 7 |
| | AbM | GYTFTEFGMN | 8 |
| | | GYTFTEYGMN | 9 |
| | | GYTFTEYSMN | 10 |
| | | GYTFTEFGMS | 12 |
| Heavy Chain CDR2 | Kabat | WINTKTGEATYVEEFKG | 13 |
| | | WINTKTGEATYIEEFKG | 14 |
| | | WINTKSGEATYVEEFKG | 15 |
| | | YINTKNGEANYVEEFKG | 16 |
| | | WINTKNGEATYIEEFKG | 17 |
| | Chothia | NTKTGEAT | 18 |
| | | NTKSGEAT | 19 |
| | | NTKNGEAN | 20 |
| | AbM | WINTKTGEAT | 21 |
| | | WINTKSGEAT | 22 |
| | | YINTKNGEAT | 23 |
| | | WINTKNGEAT | 24 |
| Heavy Chain CDR3 | Kabat Chothia and AbM | WDFYDYVEAMDY | 25 |
| | | WDFYHYVEAMDY | 26 |
| | | WDFVDYVEAMDY | 27 |
| | | WDFYWYVEAMDY | 28 |
| | | WDAFEYVKALDY | 29 |
| | | WDFFEYFKTMDY | 30 |
| | | WDFFYYVQTMDY | 31 |
| | | WDFSYYVEAMDY | 32 |
| | | WDFAHYFQTMDY | 33 |
| | | WDFAYYFQTMDY | 34 |
| | | WDFAYYLEAMDY | 35 |

| CDR | Amino Acid Sequence | SEQ ID NO |
|---|---|---|
| Light Chain CDR1 | KASQNVGTNVA | 36 |
| | KASANVGNNVA | 37 |
| | KASKNVGTNVA | 38 |
| | KASAAVGTYVA | 39 |
| | KASQYASTNVA | 40 |
| | KASHNVGTNVA | 41 |
| | KASQIMGPNVA | 42 |
| | KASQIVGTNVA | 43 |
| | KASQKVLTNVA | 44 |
| | KASQTVSANVA | 45 |
| Light Chain CDR2 | SASYRYS | 46 |
| | YLASNLSG | 47 |
| | YLASYPQI | 48 |
| | YSASYRKR | 49 |
| | YWASYRYS | 50 |
| | YSASHRYS | 51 |
| | YLASYHES | 52 |
| | YSASHRPS | 53 |
| | YLASYRYS | 54 |
| | YLASYRYR | 55 |
| Light Chain CDR3 | HQYYTYPLFT | 56 |

Fig. 32

| SEQ ID NO: | LIGHT CHAIN CONSTRUCT | AMINO ACID SEQUENCE |
|---|---|---|
| 207 | pAC21 (3A1) | DIQMTQSPSSLSASVGDRVTITCKASANVGNNVAWYQQKPGKAPKLLIYLASNRSGGVPSRFSG SGSGTDFTLTISSLQPEDFATYYCHQYYTYPLFTFGQGTKLEIKRT |
| 208 | pAC19 (2C6) | DIQMTQSPSSLSASVGDRVTITCKASKNVGTNVAWYQQKPGKAPKPLIYLASYPQIGVPSRFSGS GSGTDFTLTISSLQPEDFATYYCHQYYTYPLFTFGQGTKLEIKRT |
| 209 | pAC18 (2F1) | DIQMTQSPSSLSASVGDRVTITCKASAAVGTYVAWYQQKPGKAPKLLIYSASYRKRGVPSRFSGS GSGTDFTLTISSLQPEDFATYYCHQYYTYPLFTFGQGTKLEIKRT |
| 210 | pAC23 (2F11) | DIQMTQSPSSLSASVGDRVTITCKASQIASTNVAWYQQKPGKAPKLLIYWASYRYSGVPSRFSGS GSGTDFTLTISSLQPEDFATYYCHQYYTYPLFTFGQGTKLEIKRT |
| 211 | H4E9 light chain | DIQMTQSPSSLSASVGDRVTITCKASQNVGTNVAWYQQKPGKAPKPLIYSASYRYSGVPSRFSG SGSGTDFTLTISSLQPEDFATYYCHQYYTYPLFTFGQGTKLEIKRT |
| 212 | L2D2 | DIQMTQSPSSLSASVGDRVTITCKASHNVGTNVAWYQQKPGKAPKLLIYSASHRYSGVPSRFSG SGSGTDFTLTISSLQPEDFATYYCHQYYTYPLFTFGQGTKLEIKRT |
| 213 | pAC6 (C1) | DIQMTQSPSSLSASVGDRVTITCKASQIMGPNVAWYQQKPGKAPKLLIYLASYHESGVPSRFSGS GSGTDFTLTISSLQPEDFATYYCHQYYTYPLFTFGQGTKLEIKRT |
| 214 | pAC7 (E10) | DIQMTQSPSSLSASVGDRVTITCKASQIVGTNVAWYQQKPGKAPKLLIYSASHRPSGVPSRFSGS GSGTDFTLTISSLQPEDFATYYCHQYYTYPLFTFGQGTKLEIKRT |
| 215 | pAC12 (H7) | DIQMTQSPSSLSASVGDRVTITCKASQKVLTNVAWYQQKPGKAPKLLIYLASYRYSGVPSRFSGS GSGTDFTLTISSLQPEDFATYYCHQYYTYPLFTFGQGTKLEIKRT |
| 216 | pAC13 (H11) | DIQMTQSPSSLSASVGDRVTITCKASQTVSANVAWYQQKPGKAPKLLIYLASYRYRGVPSRFSGS GSGTDFTLTISSLQPEDFATYYCHQYYTYPLFTFGQGTKLEIKRT |

Fig. 33

| SEQ ID NO: | CDR-H3 (randomized residues are underlined selected residues in bold) | Affinity (determined by Biacore) | Construct |
|---|---|---|---|
| 25 | WDFYDYVEAMDY | 3681 nM | PMS22 |
| 26 | WDFYHYVEAMDY | 586 nM | 1C8 |
| 27 | WDFVDYVEAMDY | 1893 nM | 3E1 |
| 28 | WDFYWYVEAMDY | 746 nM | 2D7 |
| 33 | WDFAHYFQTMDY | 59 nM | Affinity Matured CDRH-3 |
| 34 | WDFAYYFQTMD | 44 nM | Affinity Matured CDRH-3 |
| 35 | WDFAYYLEAMD | 69 nM | Affinity Matured CDRH-3 |
| 29 | WDAFEYVKALDY | 26 nM | H3 Full (5) 19 |
| 30 | WDFFEYFKTMDY | 51 nM | H3 Full (5) 8 |
| 31 | WDFFYYVQTMDY | 81 nM | H3 Full (5) 28 |
| 33 | WDFSYYVEAMDY | 132 nM | H3 Full (5) 27 |
| | CDR-H1 and CDR-H2 | | |
| 1 and 13 | EFGMN and WINTKTGEATYVEEFKG | 3681 nM | pMS22 |
| 1 and 14 | EFGMN and WINTKTGEATYIEEFKG | 402 nM | H4E9 |
| 1 and 15 | EFGMN and WINTKSGEATYVEEFKG | | pAC14 (B9) |
| 2 and 15 | EYGMN and WINTKSGEATYVEEFKG | | pAC15 (F9) |
| 3 and 16 | EYSMN and YINTKNGEANYVEEFKG | | H1/H2 (5) 2 |

Fig. 34A

| SEQ ID NO: | CDR-H3 (randomized residues are underlined selected residues in bold) | Affinity (determined by Biacore) | Construct |
|---|---|---|---|
| 2 and 17 | EYGMN and WINTKNGEATYIEEFKG | | H1/H2 (5) 11 |
| 1 and 16 | EFGMN and YINTKNGEANYVEEFKG | | H1/H2 (5) 13 |
| 2 and 16 | EYGMN and YINTKNGEANYVEEFKG | | H1/H2 (5) 14 |
| 5 and 13 | EFGMS and WINTKTGEATYVEEFKG | 26 nM | H3 Full (5) 19 |
| | CDR-L1 and CDR-L2 | | |
| 36 and 46 | QNVGTN and YSASYRYS | 3681 nM | pMS22 |
| 37 and 47 | ANVGNN and YLASNLSG | 250 nM | pAC21 (3A1) |
| 38 and 48 | KNVGTN and YLASYPQI | 700 nM | pAC19 (2C6) |
| 39 and 49 | AAVGTY and YSASYRKR | 220 nM | pAC18 (2F1) |
| 40 and 50 | QYASTN and YWASYRYS | 290 nM | pAC23 (2F11) |
| 36 and | QNVGTN and PLI-YSASYRYS | 402 nM | H4E9 |
| 41 and 51 | HNVGTN and YSASHRYS | 2255 nM | L2D2 |
| 42 and 52 | QIMGPN and YLASYHES | | pAC6 (C1) |
| 43 and 53 | QIVGTN and YSASHRPS | | pAC7 (E10) |
| 44 and 54 | QKVLTN and YLASYRYS | | pAC12 (H7) |
| 45 and 55 | QTVSAN and YLASYRYR | | pAC13 (H11) |
| | CDR-L3 | | |
| 56 | HQYYTYPLFT | | pMS22 |

Fig. 34B

| Clone Name | Chain | Monovalent Affinity | Bivalent Affinity |
|---|---|---|---|
| PR1A3 | wt/wt | $k_{on}$: 6.74x10$^3$ 1/Ms; $k_{off}$: 2.48x10$^{-2}$ 1/s; KD 3681x10$^{-9}$M | $k_{on}$: 2.82x10$^5$ 1/Ms; $k_{off}$: 5.52x10$^{-4}$ 1/s; KD: 2x10$^{-9}$M |
| 1C8 | hc/wt | $k_{on}$: 12.9x10$^3$ 1/Ms; $k_{off}$: 0.76x10$^{-2}$ 1/s; KD 586x10$^{-9}$M | $k_{on}$: 4.67x10$^5$ 1/Ms; $k_{off}$: 3.24x10$^{-4}$ 1/s; KD: 0.693x10$^{-9}$M |
| H4E9 | hc/wt | $k_{on}$: 5.22x10$^3$ 1/Ms; $k_{off}$: 0.21x10$^{-2}$ 1/s; KD 402x10$^{-9}$M | $k_{on}$: 2.92x10$^5$ 1/Ms; $k_{off}$: 2.04x10$^{-3}$ 1/s; KD: 0.7x10$^{-9}$M |
| H3 Full (5) 19 | hc/wt | $k_{on}$: 54.2x10$^3$ 1/Ms; $k_{off}$: 0.13x10$^{-2}$ 1/s; KD 24x10$^{-9}$M | $k_{on}$: 9.02x10$^5$ 1/Ms; $k_{off}$: 1.75x10$^{-4}$ 1/s; KD: 0.19x10$^{-9}$M |
| H3 Full (5) 8 | hc/wt | $k_{on}$: 27.3x10$^3$ 1/Ms; $k_{off}$: 0.14x10$^{-2}$ 1/s; KD 51x10$^{-9}$M | N/D |
| 3A1 | wt/lc | $k_{on}$: 46.8x10$^3$ 1/Ms; $k_{off}$: 1.17x10$^{-2}$ 1/s; KD 250x10$^{-9}$M | $k_{on}$: 2.42x10$^5$ 1/Ms; $k_{off}$: 3.64x10$^{-4}$ 1/s; KD: 1.5x10$^{-9}$M |
| 2F1 | wt/lc | $k_{on}$: 95.7x10$^3$ 1/Ms; $k_{off}$: 2.07x10$^{-2}$ 1/s; KD 220x10$^{-9}$M | $k_{on}$: 4.23x10$^5$ 1/Ms; $k_{off}$: 4.10x10$^{-4}$ 1/s; KD: 0.952x10$^{-9}$M |
| 5L1A10 | hc/wt | $k_{on}$: 15.6x10$^3$ 1/Ms; $k_{off}$: 0.09x10$^{-2}$ 1/s; KD 59x10$^{-9}$M | N/D |
| 5HFF12 | hc/wt | $k_{on}$: 20.8x10$^3$ 1/Ms; $k_{off}$: 0.09x10$^{-2}$ 1/s; KD 44x10$^{-9}$M | N/D |
| M4F1 | hc/wt | $k_{on}$: 25.7x10$^3$ 1/Ms; $k_{off}$: 0.17x10$^{-2}$ 1/s; KD 69x10$^{-9}$M | N/D |
| H4E9 x 2F1 | hc/lc | $k_{on}$: 36.4x10$^3$ 1/Ms; $k_{off}$: 0.35x10$^{-2}$ 1/s; KD 96x10$^{-9}$M | $k_{on}$: 4.23x10$^5$ 1/Ms; $k_{off}$: 1.91x10$^{-4}$ 1/s; KD: 0.452x10$^{-9}$M |
| H4E9 x 3A1 | hc/lc | N/D | $k_{on}$: 2.46x10$^5$ 1/Ms; $k_{off}$: 1.36x10$^{-4}$ 1/s; KD: 0.55x10$^{-9}$M |
| 1C8 x 2F1 | hc/lc | $k_{on}$: 68.1x10$^3$ 1/Ms; $k_{off}$: 0.87x10$^{-2}$ 1/s; KD 128x10$^{-9}$M | $k_{on}$: 9.68x10$^5$ 1/Ms; $k_{off}$: 6.36x10$^{-4}$ 1/s; KD: 0.66x10$^{-9}$M |
| 1C8 x 3A1 | hc/lc | N/D | $k_{on}$: 2.89x10$^5$ 1/Ms; $k_{off}$: 2.57x10$^{-4}$ 1/s; KD: 0.888x10$^{-9}$M |
| H3 Full (5) 19 x 2F1 | hc/lc | $k_{on}$: 206x10$^3$ 1/Ms; $k_{off}$: 0.25x10$^{-2}$ 1/s; KD: 12.2x10$^{-9}$M | $k_{on}$: 1.76x10$^6$ 1/Ms; $k_{off}$: 2.84x10$^{-4}$ 1/s; KD: 0.16x10$^{-9}$M |
| H3 Full (5) 8 x 2F1 | hc/lc | N/D | $k_{on}$: 9.93x10$^5$ 1/Ms; $k_{off}$: 2.71x10$^{-4}$ 1/s; KD: 0.28x10$^{-9}$M |

Fig. 35

| SEQ ID NO: | CDR-H3 CONSTRUCTS | AMINO ACID SEQUENCE |
|---|---|---|
| 25 | PR1A3 CDR-H3 | WDFYDYVEAMDY |
| 33 | 5HFF12 CDR-H3 | WDFAHYFQTMDY |
| 34 | 5L1A10 CDR-H3 | WDFAYYFQTMDY |
| 217 | PR1A3 (Y98A) | WDFADYVEAMDY |
| 218 | PR1A3 (D99Y) | WDFYYYVEAMDY |
| 219 | PR1A3 (D99H) | WDFYHYVEAMDY |
| 220 | PR1A3 (V101F) | WDFYDYFEAMDY |
| 221 | PR1A3 (E101aQ) | WDFYDYVQAMDY |
| 222 | PR1A3 (A103T) | WDFYDYVETMDY |
| 223 | PR1A3 (Y98A / D99Y) | WDFAYYVEAMDY |
| 224 | PR1A3 (W95Y) | YDFYDYVEAMDY |

Fig. 36

| SEQ. ID NO: | HEAVY CHAIN CONSTRUCT | AMINO ACID SEQUENCE |
|---|---|---|
| 225 | CH7A (Y98A) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARWDFADYVEAMDYWGQGTTVTVSS |
| 226 | CH7A (D99Y) | QVQLVQSGSELKKPGASVKVSCKASGYTFTEFGMNWVRQAPGQGLEWMGWINTKTGEATYVEE FKGRFVFSLDTSVSTAYLQISLKAEDTAVYYCARWDFYYVEAMDYWGQGTTVTVSS |
| 227 | CH7A (D99H) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARWDFYHYVEAMDYWGQGTTVTVSS |
| 228 | CH7A (V101F) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARWDFYDYFEAMDYWGQGTTVTVSS |
| 229 | CH7A (E102Q) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARWDFYDYVQAMDYWGQGTTVTVSS |
| 230 | CH7A (A103T) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARWDFYDYVETMDYWGQGTTVTVSS |
| 231 | CH7A (Y98A / D99Y) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARWDFAYYVEAMDYWGQGTTVTVSS |
| 232 | CH7A (W95Y) | QVQLVQSGSELKKPGASVKVSCKASGYTFTEFGMNWVRQAPGQGLEWMGWINTKTGEATYVEE FKGRFVFSLDTSVSTAYLQISSLKAEDTAVYYCARYDFYDYVEAMDYWGQGTTVTVSS |
| 233 | CH1A1A (Y98A) | QVQLVQSGAEVKKPGASVKVSCKASGYTFTEFGMNWVRQAPGQGLEWMGWINTKTGEATYVEE FKGRVTFTTDTSTSTAYMELRSLRSDDTAVYYCARWDFADYVEAMDYWGQGTTVTVSS |
| 234 | CH1A1A (D99Y) | QVQLVQSGAEVKKPGASVKVSCKASGYTFTEFGMNWVRQAPGQGLEWMGWINTKTGEATYVEE FKGRVTFTTDTSTSTAYMELRSLRSDDTAVYYCARWDFYYVEAMDYWGQGTTVTVSS |

Fig. 37A

| SEQ. ID NO: | HEAVY CHAIN CONSTRUCT | AMINO ACID SEQUENCE |
|---|---|---|
| 235 | CH1A1A (D99H) | QVQLVQSGAEVKKPGASVKVSCKASGYTFTEFGMNWVRQAPGQGLEWMGWINTKTGEATY VEEFKGRVTFTTDTSTSTAYMELRSLRSDDTAVYYCARWDFYHYVEAMDYWGQGTTVTVSS |
| 236 | CH1A1A (V101F) | QVQLVQSGAEVKKPGASVKVSCKASGYTFTEFGMNWVRQAPGQGLEWMGWINTKTGEATY VEEFKGRVTFTTDTSTSTAYMELRSLRSDDTAVYYCARWDFYDYFEAMDYWGQGTTVTVSS |
| 237 | CH1A1A (E102Q) | QVQLVQSGAEVKKPGASVKVSCKASGYTFTEFGMNWVRQAPGQGLEWMGWINTKTGEATY VEEFKGRVTFTTDTSTSTAYMELRSLRSDDTAVYYCARWDFYDYVQAMDYWGQGTTVTVSS |
| 238 | CH1A1A (A103T) | QVQLVQSGAEVKKPGASVKVSCKASGYTFTEFGMNWVRQAPGQGLEWMGWINTKTGEATY VEEFKGRVTFTTDTSTSTAYMELRSLRSDDTAVYYCARWDFYDYVETMDYWGQGTTVTVSS |
| 239 | CH1A1A (Y98A / D99Y) | QVQLVQSGAEVKKPGASVKVSCKASGYTFTEFGMNWVRQAPGQGLEWMGWINTKTGEATY VEEFKGRVTFTTDTSTSTAYMELRSLRSDDTAVYYCARWDFAYYVEAMDYWGQGTTVTVSS |
| 240 | CH1A1B (W95Y) | QVKLQQSGAEVKKPGASVKVSCKASGYTFTEFGMNWVRQAPGQGLEWMGWINTKTGEATY VEEFKGRVTMTTDTSTSTAYMELRSLRSDDTAVYYCARYDFYDYVEAMDYWGQGTTVTVSS |
| 241 | CH1A1B (Y98A) | QVKLQQSGAEVKKPGASVKVSCKASGYTFTEFGMNWVRQAPGQGLEWMGWINTKTGEATY VEEFKGRVTMTTDTSTSTAYMELRSLRSDDTAVYYCARWDFADYVEAMDYWGQGTTVTVSS |
| 242 | CH1A1B (D99Y) | QVKLQQSGAEVKKPGASVKVSCKASGYTFTEFGMNWVRQAPGQGLEWMGWINTKTGEATY VEEFKGRVTMTTDTSTSTAYMELRSLRSDDTAVYYCARWDFYYYVEAMDYWGQGTTVTVSS |
| 243 | CH1A1B (D99H) | QVKLQQSGAEVKKPGASVKVSCKASGYTFTEFGMNWVRQAPGQGLEWMGWINTKTGEATY VEEFKGRVTMTTDTSTSTAYMELRSLRSDDTAVYYCARWDFYHYVEAMDYWGQGTTVTVSS |
| 244 | CH1A1B (V101F) | QVKLQQSGAEVKKPGASVKVSCKASGYTFTEFGMNWVRQAPGQGLEWMGWINTKTGEATY VEEFKGRVTMTTDTSTSTAYMELRSLRSDDTAVYYCARWDFYDYFEAMDYWGQGTTVTVSS |

Fig. 37B

| SEQ. ID NO: | HEAVY CHAIN CONSTRUCT | AMINO ACID SEQUENCE |
|---|---|---|
| 245 | CH1A1B (E102Q) | QVKLQQSGAEVKKPGASVKVSCKASGYTFTEFGMNWVRQAPGQGLEWMGWINTKTGEATYVEEFKGRVTMTTDTSTSTAYMELRSLRSDDTAVYYCARWDFYDYQAMDYWGQGTTVTVSS |
| 246 | CH1A1B (A103T) | QVKLQQSGAEVKKPGASVKVSCKASGYTFTEFGMNWVRQAPGQGLEWMGWINTKTGEATYVEEFKGRVTMTTDTSTSTAYMELRSLRSDDTAVYYCARWDFYDYVETMDYWGQGTTVTVSS |
| 247 | CH1A1B (Y98A / D99Y) | QVKLQQSGAEVKKPGASVKVSCKASGYTFTEFGMNWVRQAPGQGLEWMGWINTKTGEATYVEEFKGRVTMTTDTSTSTAYMELRSLRSDDTAVYYCARWDFAYYVEAMDYWGQGTTVTVSS |
| 248 | CH1A1B (W95Y) | QVKLQQSGAEVKKPGASVKVSCKASGYTFTEFGMNWVRQAPGQGLEWMGWINTKTGEATYVEEFKGRVTMTTDTSTSTAYMELRSLRSDDTAVYYCARYDFYDYVEAMDYWGQGTTVTVSS |
| 261 | CH1A1A | QVQLVQSGAEVKKPGASVKVSCKASGYTFTEFGMNWVRQAPGQGLEWMGWINTKTGEATYVEEFKGRVTFTDTSTSTAYMELRSLRSDDTAVYYCARWDFYDYVEAMDYWGQGTTVTVSS |
| 262 | CH1A1B | QVKLQQSGAEVKKPGASVKVSCKASGYTFTEFGMNWVRQAPGQGLEWMGWINTKTGEATYVEEFKGRVTMTTDTSTSTAYMELRSLRSDDTAVYYCARWDFYDYVEAMDYWGQGTTVTVSS |
| 263 | CH1A1C | QVQLVQSGPELKKPGASVKVSCKASGYTFTEFGMNWVRQAPGQGLEWMGWINTKTGEATYVEEFKGRVTMTTDTSTSTAYMELRSLRSDDTAVYYCARWDFYDYVEAMDYWGQGTTVTVSS |

SEQUENCE LISTING

```
<160> NUMBER OF SEQ ID NOS: 281

<210> SEQ ID NO 1
<211> LENGTH: 5
<212> TYPE: PRT
<213> ORGANISM: Artificial Sequence
<220> FEATURE:
<223> OTHER INFORMATION: Heavy Chain CDR1 Kabat

<400> SEQUENCE: 1

Glu Phe Gly Met Asn
```

```
1               5

<210> SEQ ID NO 2
<211> LENGTH: 5
<212> TYPE: PRT
<213> ORGANISM: Artificial Sequence
<220> FEATURE:
<223> OTHER INFORMATION: Heavy Chain CDR1 Kabat

<400> SEQUENCE: 2

Glu Tyr Gly Met Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Heavy Chain CDR1 Kabat

<400> SEQUENCE: 3

Glu Tyr Ser Met Asn
1               5

<210> SEQ ID NO 4
<211> LENGTH: 121
<212> TYPE: PRT
<213> ORGANISM: Artificial Sequence
<220> FEATURE:
<223> OTHER INFORMATION: Heavy Chain Variable Region
<220> FEATURE:
<221> NAME/KEY: MISC_FEATURE
<222> LOCATION: (32)..(32)
<223> OTHER INFORMATION: Xaa = Tyr or Phe
<220> FEATURE:
<221> NAME/KEY: MISC_FEATURE
<222> LOCATION: (33)..(33)
<223> OTHER INFORMATION: Xaa = Ser or Gly
<220> FEATURE:
<221> NAME/KEY: MISC_FEATURE
<222> LOCATION: (35)..(35)
<223> OTHER INFORMATION: Xaa = Asn or ser
<220> FEATURE:
<221> NAME/KEY: MISC_FEATURE
<222> LOCATION: (50)..(50)
<223> OTHER INFORMATION: Xaa = Trp or Tyr
<220> FEATURE:
<221> NAME/KEY: MISC_FEATURE
<222> LOCATION: (55)..(55)
<223> OTHER INFORMATION: Xaa = Thr, Ser, or Asn
<220> FEATURE:
<221> NAME/KEY: MISC_FEATURE
<222> LOCATION: (59)..(59)
<223> OTHER INFORMATION: Xaa = Thr or Asn
<220> FEATURE:
<221> NAME/KEY: MISC_FEATURE
<222> LOCATION: (61)..(61)
<223> OTHER INFORMATION: Xaa = Val or Met
<220> FEATURE:
<221> NAME/KEY: MISC_FEATURE
<222> LOCATION: (101)..(101)
<223> OTHER INFORMATION: Xaa = Phe or Ala
<220> FEATURE:
<221> NAME/KEY: MISC_FEATURE
<222> LOCATION: (102)..(102)
<223> OTHER INFORMATION: Xaa = Val, Phe, Ser, Tyr, or Ala
<220> FEATURE:
<221> NAME/KEY: MISC_FEATURE
<222> LOCATION: (103)..(103)
<223> OTHER INFORMATION: Xaa = Asp, His, Trp, Glu or Tyr
<220> FEATURE:
<221> NAME/KEY: MISC_FEATURE
<222> LOCATION: (105)..(105)
<223> OTHER INFORMATION: Xaa = Val, Phe, or Leu
<220> FEATURE:
```

```
<221> NAME/KEY: MISC_FEATURE
<222> LOCATION: (106)..(106)
<223> OTHER INFORMATION: Xaa = Glu, Lys or Gln
<220> FEATURE:
<221> NAME/KEY: MISC_FEATURE
<222> LOCATION: (107)..(107)
<223> OTHER INFORMATION: Xaa = Ala or Thr
<220> FEATURE:
<221> NAME/KEY: MISC_FEATURE
<222> LOCATION: (108)..(108)
<223> OTHER INFORMATION: Xaa = Met or Leu

<400> SEQUENCE: 4

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Xaa
            20                  25                  30

Xaa Met Xaa Trp Val Arg Gln Ala Pro Gly Gln Gly Leu Glu Trp Met
        35                  40                  45

Gly Xaa Ile Asn Thr Lys Xaa Gly Glu Ala Xaa Tyr Xaa Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Xaa Xaa Xaa Tyr Xaa Xaa Xaa Xaa Asp Tyr Trp Gly
            100                 105                 110

Gln Gly Thr Thr Val Thr Val Ser Ser
        115                 120

<210> SEQ ID NO 5
<211> LENGTH: 5
<212> TYPE: PRT
<213> ORGANISM: Artificial Sequence
<220> FEATURE:
<223> OTHER INFORMATION: Heavy Chain CDR1 Kabat

<400> SEQUENCE: 5

Glu Phe Gly Met Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Heavy Chain CDR1 Chothia

<400> SEQUENCE: 6

Gly Tyr Thr Phe Thr Glu Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Heavy Chain CDR1 Chothia

<400> SEQUENCE: 7

Gly Tyr Thr Phe Thr Glu Tyr
1               5

<210> SEQ ID NO 8
<211> LENGTH: 10
```

-continued

```
<212> TYPE: PRT
<213> ORGANISM: Artificial Sequence
<220> FEATURE:
<223> OTHER INFORMATION: Heavy Chain CDR1 AbM

<400> SEQUENCE: 8

Gly Tyr Thr Phe Thr Glu Phe Gly Met Asn
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 9

Gly Tyr Thr Phe Thr Glu Tyr Gly Met Asn
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 10

Gly Tyr Thr Phe Thr Glu Tyr Ser Met Asn
1               5                   10

<210> SEQ ID NO 11
<211> LENGTH: 108
<212> TYPE: PRT
<213> ORGANISM: Artificial Sequence
<220> FEATURE:
<223> OTHER INFORMATION: Light Chain Variable Region
<220> FEATURE:
<221> NAME/KEY: MISC_FEATURE
<222> LOCATION: (27)..(27)
<223> OTHER INFORMATION: Xaa = Gln, Ala, Lys, or His
<220> FEATURE:
<221> NAME/KEY: MISC_FEATURE
<222> LOCATION: (28)..(28)
<223> OTHER INFORMATION: Xaa = Asn, Ala, Tyr, Ile, Lys, or Thr
<220> FEATURE:
<221> NAME/KEY: MISC_FEATURE
<222> LOCATION: (29)..(29)
<223> OTHER INFORMATION: Xaa = Val, Ala, Gly, or Met
<220> FEATURE:
<221> NAME/KEY: MISC_FEATURE
<222> LOCATION: (30)..(30)
<223> OTHER INFORMATION: Xaa = Gly, Ser, Thr, or Leu
<220> FEATURE:
<221> NAME/KEY: MISC_FEATURE
<222> LOCATION: (31)..(31)
<223> OTHER INFORMATION: Xaa = Thr, Asn, Pro, or Ala
<220> FEATURE:
<221> NAME/KEY: MISC_FEATURE
<222> LOCATION: (32)..(32)
<223> OTHER INFORMATION: Xaa = Asn or Tyr
<220> FEATURE:
<221> NAME/KEY: MISC_FEATURE
<222> LOCATION: (46)..(46)
<223> OTHER INFORMATION: Xaa = Pro or Leu
<220> FEATURE:
<221> NAME/KEY: MISC_FEATURE
<222> LOCATION: (50)..(50)
<223> OTHER INFORMATION: Xaa = Ser, Leu, or Trp
<220> FEATURE:
<221> NAME/KEY: MISC_FEATURE
<222> LOCATION: (53)..(53)
<223> OTHER INFORMATION: Xaa = Tyr, Asn, or His
<220> FEATURE:
```

```
<221> NAME/KEY: MISC_FEATURE
<222> LOCATION: (54)..(54)
<223> OTHER INFORMATION: Xaa = Arg, Leu, Pro, or His
<220> FEATURE:
<221> NAME/KEY: MISC_FEATURE
<222> LOCATION: (55)..(55)
<223> OTHER INFORMATION: Xaa = Tyr, Ser, Gln, Lys, Phe, Pro, or Glu
<220> FEATURE:
<221> NAME/KEY: MISC_FEATURE
<222> LOCATION: (56)..(56)
<223> OTHER INFORMATION: Xaa = Ser, Gly, Ile, or Arg

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Xaa Xaa Xaa Xaa Xaa
            20                  25                  30

Val Ala Trp Tyr Gln Gln Lys Pro Gly Lys Ala Pro Lys Xaa Leu Ile
            35                  40                  45

Tyr Xaa Ala Ser Xaa Xaa Xaa Xaa Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 12
<211> LENGTH: 10
<212> TYPE: PRT
<213> ORGANISM: Artificial Sequence
<220> FEATURE:
<223> OTHER INFORMATION: Heavy Chain CDR1 AbM

<400> SEQUENCE: 12

Gly Tyr Thr Phe Thr Glu Phe Gly Met Ser
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 13

Trp Ile Asn Thr Lys Thr Gly Glu Ala Thr Tyr Val Glu Glu Phe Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 14

Trp Ile Asn Thr Lys Thr Gly Glu Ala Thr Tyr Ile Glu Glu Phe Lys
1               5                   10                  15

Gly

<210> SEQ ID NO 15
```

```
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 15

Trp Ile Asn Thr Lys Ser Gly Glu Ala Thr Tyr Val Glu Glu Phe Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 16

Tyr Ile Asn Thr Lys Asn Gly Glu Ala Asn Tyr Val Glu Glu Phe Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Heavy Chain CDR2 Kabat

<400> SEQUENCE: 17

Trp Ile Asn Thr Lys Asn Gly Glu Ala Thr Tyr Ile Glu Glu Phe Lys
1               5                   10                  15

Gly

<210> SEQ ID NO 18
<211> LENGTH: 8
<212> TYPE: PRT
<213> ORGANISM: Artificial Sequence
<220> FEATURE:
<223> OTHER INFORMATION: Heavy Chain CDR2 Chothia

<400> SEQUENCE: 18

Asn Thr Lys Thr Gly Glu Ala Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Heavy Chain CDR2 Chothia

<400> SEQUENCE: 19

Asn Thr Lys Ser Gly Glu Ala Thr
1               5

<210> SEQ ID NO 20
<211> LENGTH: 8
<212> TYPE: PRT
<213> ORGANISM: Artificial Sequence
<220> FEATURE:
<223> OTHER INFORMATION: Heavy Chain CDR2 Chothia

<400> SEQUENCE: 20

Asn Thr Lys Asn Gly Glu Ala Asn
```

```
<210> SEQ ID NO 21
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 21

Trp Ile Asn Thr Lys Thr Gly Glu Ala Thr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 22

Trp Ile Asn Thr Lys Ser Gly Glu Ala Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 23

Tyr Ile Asn Thr Lys Asn Gly Glu Ala Asn
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Heavy Chain CDR2 AbM

<400> SEQUENCE: 24

Trp Ile Asn Thr Lys Asn Gly Glu Ala Thr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 25

Trp Asp Phe Tyr Asp Tyr Val Glu Ala Met Asp Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 26

Trp Asp Phe Tyr His Tyr Val Glu Ala Met Asp Tyr
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 27

Trp Asp Phe Val Asp Tyr Val Glu Ala Met Asp Tyr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 28

Trp Asp Phe Tyr Trp Tyr Val Glu Ala Met Asp Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 29

Trp Asp Ala Phe Glu Tyr Val Lys Ala Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 30

Trp Asp Phe Phe Glu Tyr Phe Lys Thr Met Asp Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 31

Trp Asp Phe Phe Tyr Tyr Val Gln Thr Met Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 32

Trp Asp Phe Ser Tyr Tyr Val Glu Ala Met Asp Tyr
1               5                   10

<210> SEQ ID NO 33

```
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 33

Trp Asp Phe Ala His Tyr Phe Gln Thr Met Asp Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 34

Trp Asp Phe Ala Tyr Tyr Phe Gln Thr Met Asp Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 35

Trp Asp Phe Ala Tyr Tyr Leu Glu Ala Met Asp Tyr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 36

Lys Ala Ser Gln Asn Val Gly Thr Asn Val Ala
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 37

Lys Ala Ser Ala Asn Val Gly Asn Asn Val Ala
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 38

Lys Ala Ser Lys Asn Val Gly Thr Asn Val Ala
1               5                   10

<210> SEQ ID NO 39
<211> LENGTH: 11
<212> TYPE: PRT
```

```
<213> ORGANISM: Artificial Sequence
<220> FEATURE:
<223> OTHER INFORMATION: Light Chain CDR1

<400> SEQUENCE: 39

Lys Ala Ser Ala Ala Val Gly Thr Tyr Val Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 40

Lys Ala Ser Gln Tyr Ala Ser Thr Asn Val Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 41

Lys Ala Ser His Asn Val Gly Thr Asn Val Ala
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 42

Lys Ala Ser Gln Ile Met Gly Pro Asn Val Ala
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 43

Lys Ala Ser Gln Ile Val Gly Thr Asn Val Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 44

Lys Ala Ser Gln Lys Val Leu Thr Asn Val Ala
1               5                   10

<210> SEQ ID NO 45
<211> LENGTH: 11
<212> TYPE: PRT
<213> ORGANISM: Artificial Sequence
<220> FEATURE:
```

<223> OTHER INFORMATION: Light Chain CDR1

<400> SEQUENCE: 45

Lys Ala Ser Gln Thr Val Ser Ala Asn Val Ala
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 46

Ser Ala Ser Tyr Arg Tyr Ser
1               5

<210> SEQ ID NO 47
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 47

Tyr Leu Ala Ser Asn Leu Ser Gly
1               5

<210> SEQ ID NO 48
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 48

Tyr Leu Ala Ser Tyr Pro Gln Ile
1               5

<210> SEQ ID NO 49
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 49

Tyr Ser Ala Ser Tyr Arg Lys Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 50

Tyr Trp Ala Ser Tyr Arg Tyr Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Light Chain CDR2

```
<400> SEQUENCE: 51

Tyr Ser Ala Ser His Arg Tyr Ser
1               5

<210> SEQ ID NO 52
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 52

Tyr Leu Ala Ser Tyr His Glu Ser
1               5

<210> SEQ ID NO 53
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 53

Tyr Ser Ala Ser His Arg Pro Ser
1               5

<210> SEQ ID NO 54
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 54

Tyr Leu Ala Ser Tyr Arg Tyr Ser
1               5

<210> SEQ ID NO 55
<211> LENGTH: 8
<212> TYPE: PRT
<213> ORGANISM: Artificial Sequence
<220> FEATURE:
<223> OTHER INFORMATION: Light Chain CDR2

<400> SEQUENCE: 55

Tyr Leu Ala Ser Tyr Arg Tyr Arg
1               5

<210> SEQ ID NO 56
<211> LENGTH: 10
<212> TYPE: PRT
<213> ORGANISM: Artificial Sequence
<220> FEATURE:
<223> OTHER INFORMATION: Light Chain CDR3

<400> SEQUENCE: 56

His Gln Tyr Tyr Thr Tyr Pro Leu Phe Thr
1               5                   10

<210> SEQ ID NO 57
<211> LENGTH: 30
<212> TYPE: DNA
<213> ORGANISM: Artificial Sequence
<220> FEATURE:
<223> OTHER INFORMATION: Heavy Chain CDR1

<400> SEQUENCE: 57
```
ggatacacct tcactgagtt tggaatgaac                                        30

<210> SEQ ID NO 58
<211> LENGTH: 30
<212> TYPE: DNA
<213> ORGANISM: Artificial Sequence
<220> FEATURE:
<223> OTHER INFORMATION: Heavy Chain CDR1

<400> SEQUENCE: 58
ggatacacct tcactgagta tggtatgaac                                        30

<210> SEQ ID NO 59
<211> LENGTH: 30
<212> TYPE: DNA
<213> ORGANISM: Artificial Sequence
<220> FEATURE:
<223> OTHER INFORMATION: Heavy Chain CDR1

<400> SEQUENCE: 59
ggatacacct tcactgagta ttctatgaac                                        30

<210> SEQ ID NO 60

<400> SEQUENCE: 60

000

<210> SEQ ID NO 61
<211> LENGTH: 30
<212> TYPE: DNA
<213> ORGANISM: Artificial Sequence
<220> FEATURE:
<223> OTHER INFORMATION: Heavy Chain CDR1

<400> SEQUENCE: 61
ggatacacct tcactgagtt tggaatgagc                                        30

<210> SEQ ID NO 62
<211> LENGTH: 51
<212> TYPE: DNA
<213> ORGANISM: Artificial Sequence
<220> FEATURE:
<223> OTHER INFORMATION: Heavy Chain CDR2

<400> SEQUENCE: 62
tggataaaca ccaaaactgg agaggcaaca tatgttgaag agtttaaggg a                51

<210> SEQ ID NO 63
<211> LENGTH: 51
<212> TYPE: DNA
<213> ORGANISM: Artificial Sequence
<220> FEATURE:
<223> OTHER INFORMATION: Heavy Chain CDR2

<400> SEQUENCE: 63
tggataaaca ccaaaactgg agaggcaaca tatattgaag agtttaaggg a                51

<210> SEQ ID NO 64
<211> LENGTH: 51
<212> TYPE: DNA
<213> ORGANISM: Artificial Sequence
<220> FEATURE:
<223> OTHER INFORMATION: Heavy Chain CDR2

<400> SEQUENCE: 64
tggataaaca ccaaaagtgg agaggcaaca tatgttgaag agtttaaggg a                51

<210> SEQ ID NO 65
<211> LENGTH: 51
<212> TYPE: DNA
<213> ORGANISM: Artificial Sequence
<220> FEATURE:
<223> OTHER INFORMATION: Heavy Chain CDR2

<400> SEQUENCE: 65
tatataaaca ccaaaaatgg agaggcaaac tatgttgaag agtttaaggg a        51

<210> SEQ ID NO 66
<211> LENGTH: 51
<212> TYPE: DNA
<213> ORGANISM: Artificial Sequence
<220> FEATURE:
<223> OTHER INFORMATION: Heavy Chain CDR2

<400> SEQUENCE: 66
tggataaaca ccaaaaatgg agaggcaaca tatattgaag agtttaaggg a        51

<210> SEQ ID NO 67
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 67
tgggacttct atgattacgt ggaggctatg gactac                         36

<210> SEQ ID NO 68
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 68
tgggacttct atcattacgt ggaggctatg gactac                         36

<210> SEQ ID NO 69
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 69
tgggacttcg tggattacgt ggaggctatg gactac                         36

<210> SEQ ID NO 70
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 70
tgggacttct attggtacgt ggaggctatg gactac                         36

<210> SEQ ID NO 71
<211> LENGTH: 36
<212> TYPE: DNA
<213> ORGANISM: Artificial Sequence
<220> FEATURE:
<223> OTHER INFORMATION: Heavy Chain CDR3

```
<400> SEQUENCE: 71
tgggacgcct ttgagtacgt gaaggcgctg gactac                                    36

<210> SEQ ID NO 72
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 72
tgggatttct ttgagtattt taagactatg gactac                                    36

<210> SEQ ID NO 73
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 73
tgggactttt tttattacgt gcagactatg gactac                                    36

<210> SEQ ID NO 74
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 74
tgggattttt cttattacgt tgaggcgatg gactac                                    36

<210> SEQ ID NO 75
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 75
tgggactttg ctcattactt tcagactatg gactac                                    36

<210> SEQ ID NO 76
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 76
tgggacttcg cttattactt tcagactatg gactac                                    36

<210> SEQ ID NO 77
<211> LENGTH: 36
<212> TYPE: DNA
<213> ORGANISM: Artificial Sequence
<220> FEATURE:
<223> OTHER INFORMATION: Heavy Chain CDR3

<400> SEQUENCE: 77
tgggatttcg cgtattacct tgaggctatg gactac                                    36

<210> SEQ ID NO 78
<211> LENGTH: 33
```

```
<212> TYPE: DNA
<213> ORGANISM: Artificial Sequence
<220> FEATURE:
<223> OTHER INFORMATION: Light Chain CDR1

<400> SEQUENCE: 78
aaggccagtc agaatgtggg tactaatgtt gcc                                    33

<210> SEQ ID NO 79
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 79
aaggccagtg ccaatgtggg taataatgtt gcc                                    33

<210> SEQ ID NO 80
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 80
aaggccagta agaatgtggg gactaatgtt gcg                                    33

<210> SEQ ID NO 81
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 81
aaggccagtg cggctgtggg tacgtatgtt gcg                                    33

<210> SEQ ID NO 82
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 82
aaggccagtc agatagcgag tactaatgtt gcc                                    33

<210> SEQ ID NO 83
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 83
aaggccagtc acaatgtggg taccaacgtt gcg                                    33

<210> SEQ ID NO 84
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 84
aaggccagtc agattatggg tcctaatgtt gcg                                    33
```

<210> SEQ ID NO 85
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 85
aaggccagtc aaattgtggg tactaatgtt gcg          33

<210> SEQ ID NO 86
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 86
aaggccagtc agaaggtgct tactaatgtt gcg          33

<210> SEQ ID NO 87
<211> LENGTH: 33
<212> TYPE: DNA
<213> ORGANISM: Artificial Sequence
<220> FEATURE:
<223> OTHER INFORMATION: Light Chain CDR1

<400> SEQUENCE: 87
aaggccagtc agactgtgag tgctaatgtt gcg          33

<210> SEQ ID NO 88
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 88
tattcggcat cctaccgcta cagt          24

<210> SEQ ID NO 89
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 89
tatttggcct ccaacctctc cggt          24

<210> SEQ ID NO 90
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 90
tacctggcat cctaccccca gatt          24

<210> SEQ ID NO 91
<211> LENGTH: 24
<212> TYPE: DNA
<213> ORGANISM: Artificial Sequence
<220> FEATURE:
<223> OTHER INFORMATION: Light Chain CDR2

```
<400> SEQUENCE: 91
tattcggcat cctaccgcaa aagg                                              24

<210> SEQ ID NO 92
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 92
tattgggcat cctaccgcta tagt                                              24

<210> SEQ ID NO 93
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 93
tattcggcat cccaccggta cagt                                              24

<210> SEQ ID NO 94
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 94
tatttggcat cctaccacga aagt                                              24

<210> SEQ ID NO 95
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 95
tattcggcat cccaccgtcc cagt                                              24

<210> SEQ ID NO 96
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 96
tatttggcat cctaccgcta cagt                                              24

<210> SEQ ID NO 97
<211> LENGTH: 24
<212> TYPE: DNA
<213> ORGANISM: Artificial Sequence
<220> FEATURE:
<223> OTHER INFORMATION: Light Chain CDR2

<400> SEQUENCE: 97
tatttggcat cctaccgcta caga                                              24

<210> SEQ ID NO 98
<211> LENGTH: 30
```

-continued

```
<212> TYPE: DNA
<213> ORGANISM: Artificial Sequence
<220> FEATURE:
<223> OTHER INFORMATION: Light Chain CDR3

<400> SEQUENCE: 98
caccaatatt acacctatcc tctattcacg                                    30

<210> SEQ ID NO 99
<211> LENGTH: 121
<212> TYPE: PRT
<213> ORGANISM: Artificial Sequence
<220> FEATURE:
<223> OTHER INFORMATION: PR1A3 VH

<400> SEQUENCE: 99
```

Gln Val Lys Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Glu Phe
            20                  25                  30

Gly Met Asn Trp Val Lys Gln Ala Pro Gly Lys Gly Leu Lys Trp Met
        35                  40                  45

Gly Trp Ile Asn Thr Lys Thr Gly Glu Ala Thr Tyr Val Glu Glu Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Lys Tyr Phe Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 100
<211> LENGTH: 121
<212> TYPE: PRT
<213> ORGANISM: Artificial Sequence
<220> FEATURE:
<223> OTHER INFORMATION: pEM1496 huPR1A3 VH

<400> SEQUENCE: 100
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 101
<211> LENGTH: 121
```

```
<212> TYPE: PRT
<213> ORGANISM: Artificial Sequence
<220> FEATURE:
<223> OTHER INFORMATION: CH7A

<400> SEQUENCE: 101

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 102
<211> LENGTH: 98
<212> TYPE: PRT
<213> ORGANISM: Artificial Sequence
<220> FEATURE:
<223> OTHER INFORMATION: IGHV7-4-1*02

<400> SEQUENCE: 102

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg

<210> SEQ ID NO 103
<211> LENGTH: 110
<212> TYPE: PRT
<213> ORGANISM: Artificial Sequence
<220> FEATURE:
<223> OTHER INFORMATION: PR1A3 VL

<400> SEQUENCE: 103

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45
```

Tyr Ser Ala Ser Tyr Arg Tyr Ser Gly Val Pro Asp Arg Phe Thr Gly
            50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys His Gln Tyr Tyr Thr Tyr Pro Leu
                85                  90                  95

Phe Thr Phe Gly Ser Gly Thr Lys Leu Glu Met Lys Arg Thr
            100                 105                 110

<210> SEQ ID NO 104
<211> LENGTH: 109
<212> TYPE: PRT
<213> ORGANISM: Artificial Sequence
<220> FEATURE:
<223> OTHER INFORMATION: pEM1495 huPR1A3 VL

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Tyr Tyr Thr Tyr Pro Leu
                85                  90                  95

Phe Ser Phe Gly Gln Gly Thr Lys Val Glu Ile Lys Arg
            100                 105

<210> SEQ ID NO 105
<211> LENGTH: 108
<212> TYPE: PRT
<213> ORGANISM: Artificial Sequence
<220> FEATURE:
<223> OTHER INFORMATION: CL1A

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 106
<211> LENGTH: 95
<212> TYPE: PRT
<213> ORGANISM: Artificial Sequence
<220> FEATURE:

<223> OTHER INFORMATION: IMGT_hVK_1_39

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 107
<211> LENGTH: 121
<212> TYPE: PRT
<213> ORGANISM: Artificial Sequence
<220> FEATURE:
<223> OTHER INFORMATION: CH7 rF9

<400> SEQUENCE: 107

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Tyr
            20                  25                  30

Gly Met Asn Trp Val Arg Gln Ala Pro Gly Gln Gly Leu Glu Trp Met
        35                  40                  45

Gly Trp Ile Asn Thr Lys Ser Gly Glu Ala Thr Tyr Val Glu Glu Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 108
<211> LENGTH: 110
<212> TYPE: PRT
<213> ORGANISM: Artificial Sequence
<220> FEATURE:
<223> OTHER INFORMATION: CLA1 rH11

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Thr Val Ser Ala Asn
            20                  25                  30

Val Ala Trp Tyr Gln Gln Lys Pro Gly Lys Ala Pro Lys Leu Leu Ile
        35                  40                  45

Tyr Leu Ala Ser Tyr Arg Tyr Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 109

<400> SEQUENCE: 109

000

<210> SEQ ID NO 110

<400> SEQUENCE: 110

000

<210> SEQ ID NO 111
<211> LENGTH: 363
<212> TYPE: DNA
<213> ORGANISM: Artificial Sequence
<220> FEATURE:
<223> OTHER INFORMATION: PR1A3 VH

<400> SEQUENCE: 111
caggtgaagc tgcagcagtc aggacctgag ttgaagaagc tggagagac agtcaagatc      60 tcctgcaagg cttctggata taccttcaca gaattcggaa tgaactgggt gaagcaggct    120
cctggaaagg gtttaaagtg gatgggctgg ataaacacca aaactggaga ggcaacatat    180
gttgaagagt ttaagggacg gtttgccttc tctttggaga cctctgccac cactgcctat    240
ttgcagatca acaacctcaa aaatgaggac acggctaaat atttctgtgc tcgatgggat    300
ttctatgact atgttgaagc tatggactac tggggccaag ggaccaccgt gaccgtctcc    360
tca                                                                  363

<210> SEQ ID NO 112
<211> LENGTH: 362
<212> TYPE: DNA
<213> ORGANISM: Artificial Sequence
<220> FEATURE:
<223> OTHER INFORMATION: pEM1496

<400> SEQUENCE: 112
caggtgcagc tggtgcaatc tgggtctgag ttgaagaagc ctggggcctc agtgaaggtt      60
tcctgcaagg cttctggata caccttcact gagttggaat gaactgggtg cgacaggccc    120
ctggacaagg gcttgagtgg atgggatgga taaacaccaa aactggagag caacatatg     180 ttgaagagtt taagggacgg tttgtcttct ccttggacac ctctgtcagc acggcatatc    240
tgcagatcag cagcctaaag gctgacgaca ctgccgtgta ttactgtgcg agatgggact    300
tctatgatta cgtggaggct atggactact ggggccaagg gaccacggtc accgtctcct    360
ca                                                                   362

<210> SEQ ID NO 113
<211> LENGTH: 363
<212> TYPE: DNA
<213> ORGANISM: Artificial Sequence
<220> FEATURE:
<223> OTHER INFORMATION: CH7A

<400> SEQUENCE: 113
caggtgcaat ggtgcaatc tgggtctgag ttgaagaagc ctggggcctc agtgaaggtt       60
```

```
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggac    300
ttctatgatt acgtggaggc tatggactac tggggccaag ggaccacggt caccgtctcc    360
tca                                                                  363

<210> SEQ ID NO 114
<211> LENGTH: 294
<212> TYPE: DNA
<213> ORGANISM: Artificial Sequence
<220> FEATURE:
<223> OTHER INFORMATION: IGHV7-4-1*02

<400> SEQUENCE: 114
caggtgcagc tggtgcaatc tgggtctgag ttgaagaagc ctggggcctc agtgaaggtt     60
tcctgcaagg cttctggata caccttcact agctatgcta tgaattgggt gcgacaggcc    120
cctggacaag ggcttgagtg gatgggatgg atcaacacca cactgggaa cccaacgtat    180 gcccagggct tcacaggacg gtttgtcttc tccttggaca cctctgtcag cacggcatat    240
ctgcagatca gcagcctaaa ggctgaggac actgccgtgt attactgtgc gaga          294

<210> SEQ ID NO 115
<211> LENGTH: 330
<212> TYPE: DNA
<213> ORGANISM: Artificial Sequence
<220> FEATURE:
<223> OTHER INFORMATION: PR1A3 VL

<400> SEQUENCE: 115
gatatcgtga tgacccagtc tcaaagattc atgtccacat cagtaggaga cagggtcagc     60
gtcacctgca aggccagtca gaatgtgggt actaatgttg cctggtatca acagaaacca    120
ggacaatccc ctaaagcact gatttactcg gcatcctacc ggtacagtgg agtccctgat    180
cgcttcacag gcagtggatc tgggacagat ttcactctca ccatcagcaa tgtacagtct    240
gaagacttgg cggagtattt ctgtcaccaa tattacacct atcctctatt cacgttcggc    300
tcggggacaa agttggaaat gaaacgtacg                                     330

<210> SEQ ID NO 116
<211> LENGTH: 327
<212> TYPE: DNA
<213> ORGANISM: Artificial Sequence
<220> FEATURE:
<223> OTHER INFORMATION: pEM1495

<400> SEQUENCE: 116
gacatccaga tgactcagag cccaagcagc ctgagcgcca gcgtgggtga cagagtgacc     60
atcacctgta aggccagtca gaatgtgggt actaatgttg cctggtacca gcagaagcca    120
ggtaaggctc caaagctgct gatctactcg gcatcctacc ggtacagtgg tgtgccaagc    180
agattcagcg gtagcggtag cggtaccgac ttcaccttca ccatcagcag cctccagcca    240
gaggacatcg ccacctacta ctgccaccaa tattacacct atcctctatt cagcttcggc    300
caagggacca aggtggaaat caaacgt                                        327

<210> SEQ ID NO 117
<211> LENGTH: 324
```

```
<212> TYPE: DNA
<213> ORGANISM: Artificial Sequence
<220> FEATURE:
<223> OTHER INFORMATION: CL1A

<400> SEQUENCE: 117
gatatccaga tgacccagtc tccatcctcc ctgtctgcat ctgtgggaga cagagtcacc      60
atcacttgca aggccagtca gaatgtgggt actaatgttg cctggtatca gcagaaacca     120
gggaaagcac ctaagctcct gatctattcg gcatcctacc gctacagtgg agtcccatca    180
aggttcagtg gcagtggatc tgggacagat ttcactctca ccatcagcag tctgcaacct    240
gaagatttcg caacttacta ctgtcaccaa tattacacct atcctctatt cacgtttggc    300
cagggcacca agctcgagat caag                                            324

<210> SEQ ID NO 118
<211> LENGTH: 285
<212> TYPE: DNA
<213> ORGANISM: Artificial Sequence
<220> FEATURE:
<223> OTHER INFORMATION: IMGT_hVK_1_39

<400> SEQUENCE: 118
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccct                    285

<210> SEQ ID NO 119
<211> LENGTH: 369
<212> TYPE: DNA
<213> ORGANISM: Artificial Sequence
<220> FEATURE:
<223> OTHER INFORMATION: CH7 rF9

<400> SEQUENCE: 119
caggtgcaat ggtgcaatc tgggtctgag ttgaagaagc ctggggcctc agtgaaggtt      60
tcctgcaagg cttctggata caccttcact gagtatggta tgaactgggt gcgacaggcc    120
cctggacaag gcttgagtg gatgggatgg ataaacacga atctggaga ggcaacctat     180 gttgaagagt ttaagggacg gtttgtcttc tccttggaca cctctgtcag cacggcatat    240
ctgcagatca gcagcctaaa ggctgaagac actgccgtgt attactgtgc gagatgggac    300
ttctatgatt acgtggaggc tatggactac tggggccaag gaccacggt caccgtctcc    360 tcagctagc                                                            369

<210> SEQ ID NO 120
<211> LENGTH: 330
<212> TYPE: DNA
<213> ORGANISM: Artificial Sequence
<220> FEATURE:
<223> OTHER INFORMATION: CLA1 rH11

<400> SEQUENCE: 120
gatatccaga tgacccagtc tccatcctcc ctgtctgcat ctgtgggaga cagagtcacc      60
atcacttgca aggccagtca gactgtgagt gctaatgttg cgtggtatca gcagaaacca    120
gggaaagcac ctaagctcct gatctacttg gcatcctacc gctacagagg agtcccatca    180
aggttcagtg gcagtggatc tgggacagat ttcactctca ccatcagcag tctgcaacct    240
```

```
gaagatttcg caacttacta ctgtcaccaa tattcacct atcctctatt cacgtttggc      300
cagggcacca agctcgagat caagcgtacg                                      330
```

<210> SEQ ID NO 121
<211> LENGTH: 987
<212> TYPE: DNA
<213> ORGANISM: Artificial Sequence
<220> FEATURE:
<223> OTHER INFORMATION: IgG1

<400> SEQUENCE: 121

```
accaagggcc catcggtctt ccccctggca ccctcctcca gagcacctc tgggggcaca       60 gcggccctgg gctgcctggt caaggactac ttccccgaac cggtgacggt gtcgtggaac     120
tcaggcgccc tgaccagcgg cgtgcacacc ttcccggctg tcctacagtc ctcaggactc     180
tactccctca gcagcgtggt gaccgtgccc tccagcagct tgggcaccca gacctacatc     240
tgcaacgtga atcacaagcc cagcaacacc aaggtggaca gaaagcaga gcccaaatct     300 tgtgacaaaa ctcacacatg cccaccgtgc ccagcacctg aactcctggg gggaccgtca     360
gtcttcctct tccccccaaa acccaaggac accctcatga tctcccggac ccctgaggtc     420
acatgcgtgg tggtggacgt gagccacgaa gaccctgagg tcaagttcaa ctggtacgtg     480
gacggcgtgg aggtgcataa tgccaagaca aagccgcggg aggagcagta caacagcacg     540
taccgtgtgg tcagcgtcct caccgtcctg caccaggact ggctgaatgg caaggagtac     600
aagtgcaagg tctccaacaa agccctccca gcccccatcg agaaaaccat ctccaaagcc     660
aaagggcagc cccgagaacc acaggtgtac accctgcccc catcccggga tgagctgacc     720
aagaaccagg tcagcctgac ctgcctggtc aaaggcttct atcccagcga catcgccgtg     780
gagtgggaga gcaatgggca gccggagaac aactacaaga ccacgcctcc cgtgctggac     840
tccgacggct ccttcttcct ctacagcaag ctcaccgtgg acaagagcag gtggcagcag     900
gggaacgtct tctcatgctc cgtgatgcat gaggctctgc acaaccacta cacgcagaag     960
agcctctccc tgtctccggg taaatga                                         987
```

<210> SEQ ID NO 122
<211> LENGTH: 328
<212> TYPE: PRT
<213> ORGANISM: Artificial Sequence
<220> FEATURE:
<223> OTHER INFORMATION: IgG1

<400> SEQUENCE: 122

```
Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Ala
                85                  90                  95

Glu Pro Lys Ser Cys Asp Lys Thr His Thr Cys Pro Pro Cys Pro Ala
            100                 105                 110
```

```
Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 123
<211> LENGTH: 42
<212> TYPE: DNA
<213> ORGANISM: Artificial Sequence
<220> FEATURE:
<223> OTHER INFORMATION: Primer MS-43

<400> SEQUENCE: 123
ccagccggcc atggccgata tccagatgac ccagtctcca tc                          42

<210> SEQ ID NO 124
<211> LENGTH: 26
<212> TYPE: DNA
<213> ORGANISM: Artificial Sequence
<220> FEATURE:
<223> OTHER INFORMATION: Primer MS-52

<400> SEQUENCE: 124
gaagaccgat gggcctttgg tgctag                                            26

<210> SEQ ID NO 125
<211> LENGTH: 30
<212> TYPE: DNA
<213> ORGANISM: Artificial Sequence
<220> FEATURE:
<223> OTHER INFORMATION: Primer MS-55

<400> SEQUENCE: 125
gcaacatatg ttgaagagtt taagggacgg                                        30

<210> SEQ ID NO 126
```

```
<211> LENGTH: 25
<212> TYPE: DNA
<213> ORGANISM: Artificial Sequence
<220> FEATURE:
<223> OTHER INFORMATION: MS-56

<400> SEQUENCE: 126
atgaactggg tgcgacaggc ccctg                                              25

<210> SEQ ID NO 127
<211> LENGTH: 56
<212> TYPE: DNA
<213> ORGANISM: Artificial Sequence
<220> FEATURE:
<223> OTHER INFORMATION: Primer EAB-679
<220> FEATURE:
<221> NAME/KEY: misc_feature
<222> LOCATION: (26)..(26)
<223> OTHER INFORMATION: m is a or c
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(30)
<223> OTHER INFORMATION: w is a or t

<400> SEQUENCE: 127
caggggcctg tcgcacccag ttcatmnnaw actcagtgaa ggtgtatcca gaagcc          56

<210> SEQ ID NO 128
<211> LENGTH: 81
<212> TYPE: DNA
<213> ORGANISM: Artificial Sequence
<220> FEATURE:
<223> OTHER INFORMATION: Primer EAB-680

<400> SEQUENCE: 128 ccgtcccttaa aactcttcaa cataggttgc ctctccagtt ttggtgttta tccatcccat      60
ccactcaagc ccttgtccag g                                                  81

<210> SEQ ID NO 129
<211> LENGTH: 50
<212> TYPE: DNA
<213> ORGANISM: Artificial Sequence
<220> FEATURE:
<223> OTHER INFORMATION: Primer EAB-685

<400> SEQUENCE: 129
cagctatgac catgattacg ccaagcttgc atgcaaattc tatttcaagg                50

<210> SEQ ID NO 130
<211> LENGTH: 27
<212> TYPE: DNA
<213> ORGANISM: Artificial Sequence
<220> FEATURE:
<223> OTHER INFORMATION: Primer EAB-686

<400> SEQUENCE: 130
gttgcgtggt atcagcagaa accaggg                                            27

<210> SEQ ID NO 131
<211> LENGTH: 34
<212> TYPE: DNA
<213> ORGANISM: Artificial Sequence
<220> FEATURE:
<223> OTHER INFORMATION: Primer EAB-687
```

```
<400> SEQUENCE: 131
gctctttgtg acgggcgagc tcaggccctg atgg                              34

<210> SEQ ID NO 132
<211> LENGTH: 35
<212> TYPE: DNA
<213> ORGANISM: Artificial sequence
<220> FEATURE:
<223> OTHER INFORMATION: Primer EAB-688

<400> SEQUENCE: 132
ggagtcccat caaggttcag tggcagtgga tctgg                             35

<210> SEQ ID NO 133
<211> LENGTH: 70
<212> TYPE: DNA
<213> ORGANISM: Artificial Sequence
<220> FEATURE:
<223> OTHER INFORMATION: Primer EAB-681

<400> SEQUENCE: 133
cctggtttct gctgatacca cgcaacatta gtacccacat tctgactggc cttgcaagtg  60
atggtgactc                                                         70

<210> SEQ ID NO 134
<211> LENGTH: 77
<212> TYPE: DNA
<213> ORGANISM: Artificial Sequence
<220> FEATURE:
<223> OTHER INFORMATION: Primer EAB-682

<400> SEQUENCE: 134
ctgccactga accttgatgg gactccactg tagcggtagg atgccgaata gatcaggagc  60
ttaggtgctt tccctgg                                                 77

<210> SEQ ID NO 135
<211> LENGTH: 64
<212> TYPE: DNA
<213> ORGANISM: Artificial Sequence
<220> FEATURE:
<223> OTHER INFORMATION: Primer AC7
<220> FEATURE:
<221> NAME/KEY: misc_feature
<222> LOCATION: (37)..(37)
<223> OTHER INFORMATION: m is a or c
<220> FEATURE:
<221> NAME/KEY: misc_feature
<222> LOCATION: (38)..(39)
<223> OTHER INFORMATION: n is a, c, g, or t

<400> SEQUENCE: 135
ccagtagtcc atagcctcca cgtaatcata gaagtcmnnt ctcgcacagt aatacacggc  60
agtg                                                               64

<210> SEQ ID NO 136
<211> LENGTH: 64
<212> TYPE: DNA
<213> ORGANISM: Artificial Sequence
<220> FEATURE:
<223> OTHER INFORMATION: Primer AC8
<220> FEATURE:
<221> NAME/KEY: misc_feature
<222> LOCATION: (34)..(34)
<223> OTHER INFORMATION: m is a or c
<220> FEATURE:
<221> NAME/KEY: misc_feature
<222> LOCATION: (35)..(36)
```

<223> OTHER INFORMATION: n is a, c, g, or t

<400> SEQUENCE: 136
ccagtagtcc atagcctcca cgtaatcata gaamnnccat ctcgcacagt aatacacggc    60
agtg    64

<210> SEQ ID NO 137
<211> LENGTH: 64
<212> TYPE: DNA
<213> ORGANISM: Artificial Sequence
<220> FEATURE:
<223> OTHER INFORMATION: Primer AC9
<220> FEATURE:
<221> NAME/KEY: misc_feature
<222> LOCATION: (31)..(31)
<223> OTHER INFORMATION: m is a or c
<220> FEATURE:
<221> NAME/KEY: misc_feature
<222> LOCATION: (32)..(33)
<223> OTHER INFORMATION: n is a, c, g, or t

<400> SEQUENCE: 137
ccagtagtcc atagcctcca cgtaatcata mnngtcccat ctcgcacagt aatacacggc    60
agtg    64

<210> SEQ ID NO 138
<211> LENGTH: 64
<212> TYPE: DNA
<213> ORGANISM: Artificial Sequence
<220> FEATURE:
<223> OTHER INFORMATION: Primer AC10
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)
<223> OTHER INFORMATION: n is a, c, g, or t

<400> SEQUENCE: 138
ccagtagtcc atagcctcca cgtaatcmnn gaagtcccat ctcgcacagt aatacacggc    60
agtg    64

<210> SEQ ID NO 139
<211> LENGTH: 64
<212> TYPE: DNA
<213> ORGANISM: Artificial Sequence
<220> FEATURE:
<223> OTHER INFORMATION: Primer AC11
<220> FEATURE:
<221> NAME/KEY: misc_feature
<222> LOCATION: (25)..(25)
<223> OTHER INFORMATION: m is a or c
<220> FEATURE:
<221> NAME/KEY: misc_feature
<222> LOCATION: (26)..(27)
<223> OTHER INFORMATION: n is a, c, g, or t

<400> SEQUENCE: 139
ccagtagtcc atagcctcca cgtamnnata gaagtcccat ctcgcacagt aatacacggc    60
agtg    64

<210> SEQ ID NO 140
<211> LENGTH: 64
<212> TYPE: DNA
<213> ORGANISM: Artificial Sequence
<220> FEATURE:

```
<223> OTHER INFORMATION: Primer AC12
<220> FEATURE:
<221> NAME/KEY: misc_feature
<222> LOCATION: (37)..(37)
<223> OTHER INFORMATION: m is a or c
<220> FEATURE:
<221> NAME/KEY: misc_feature
<222> LOCATION: (38)..(39)
<223> OTHER INFORMATION: n is a, c, g, or t

<400> SEQUENCE: 140
cgtggtccct tggccccagt agtccatagc ctccacmnna tcatagaagt cccatctcgc      60
acag                                                                  64

<210> SEQ ID NO 141
<211> LENGTH: 64
<212> TYPE: DNA
<213> ORGANISM: Artificial Sequence
<220> FEATURE:
<223> OTHER INFORMATION: Primer AC13
<220> FEATURE:
<221> NAME/KEY: misc_feature
<222> LOCATION: (34)..(34)
<223> OTHER INFORMATION: m is a or c
<220> FEATURE:
<221> NAME/KEY: misc_feature
<222> LOCATION: (35)..(36)
<223> OTHER INFORMATION: n is a, c, g, or t

<400> SEQUENCE: 141
cgtggtccct tggccccagt agtccatagc ctcmnngtaa tcatagaagt cccatctcgc      60
acag                                                                  64

<210> SEQ ID NO 142
<211> LENGTH: 64
<212> TYPE: DNA
<213> ORGANISM: Artificial Sequence
<220> FEATURE:
<223> OTHER INFORMATION: Primer AC14
<220> FEATURE:
<221> NAME/KEY: misc_feature
<222> LOCATION: (31)..(31)
<223> OTHER INFORMATION: m is a or c
<220> FEATURE:
<221> NAME/KEY: misc_feature
<222> LOCATION: (32)..(33)
<223> OTHER INFORMATION: n is a, c, g, or t

<400> SEQUENCE: 142
cgtggtccct tggccccagt agtccatagc mnncacgtaa tcatagaagt cccatctcgc      60
acag                                                                  64

<210> SEQ ID NO 143
<211> LENGTH: 64
<212> TYPE: DNA
<213> ORGANISM: Artificial Sequence
<220> FEATURE:
<223> OTHER INFORMATION: Primer AC15
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)
<223> OTHER INFORMATION: n is a, c, g, or t

<400> SEQUENCE: 143
cgtggtccct tggccccagt agtccatmnn ctccacgtaa tcatagaagt cccatctcgc      60
``` acag                                                                64

<210> SEQ ID NO 144
<211> LENGTH: 64
<212> TYPE: DNA
<213> ORGANISM: Artificial Sequence
<220> FEATURE:
<223> OTHER INFORMATION: Primer AC16
<220> FEATURE:
<221> NAME/KEY: misc_feature
<222> LOCATION: (25)..(25)
<223> OTHER INFORMATION: m is a or c
<220> FEATURE:
<221> NAME/KEY: misc_feature
<222> LOCATION: (26)..(27)
<223> OTHER INFORMATION: n is a, c, g, or t

<400> SEQUENCE: 144
cgtggtccct tggccccagt agtcmnnagc ctccacgtaa tcatagaagt cccatctcgc      60
acag                                                                64

<210> SEQ ID NO 145
<211> LENGTH: 77
<212> TYPE: DNA
<213> ORGANISM: Artificial Sequence
<220> FEATURE:
<223> OTHER INFORMATION: Primer AC17

<400> SEQUENCE: 145
cgtggtccct tggccccagt agtccatagc ctccacgtaa tcatagaagt cccatctcgc      60
acagtaatac acggcag                                                  77

<210> SEQ ID NO 146
<211> LENGTH: 25
<212> TYPE: DNA
<213> ORGANISM: Artificial Sequence
<220> FEATURE:
<223> OTHER INFORMATION: Primer EAB-749

<400> SEQUENCE: 146
ccatcagggc ctgagctcgc ccgtc                                         25

<210> SEQ ID NO 147
<211> LENGTH: 30
<212> TYPE: DNA
<213> ORGANISM: Artificial Sequence
<220> FEATURE:
<223> OTHER INFORMATION: Primer EAB-750

<400> SEQUENCE: 147
cgtggaggct atggactact ggggccaagg                                    30

<210> SEQ ID NO 148
<211> LENGTH: 29
<212> TYPE: DNA
<213> ORGANISM: Artificial Sequence
<220> FEATURE:
<223> OTHER INFORMATION: Primer EAB-751

<400> SEQUENCE: 148
gactactggg gccaagggac cacggtcac                                     29

<210> SEQ ID NO 149
<211> LENGTH: 23
<212> TYPE: DNA
<213> ORGANISM: Artificial Sequence
<220> FEATURE:

<223> OTHER INFORMATION: Primer EAB-752

<400> SEQUENCE: 149
ggtcagggcg cctgagttcc acg                                                    23

<210> SEQ ID NO 150
<211> LENGTH: 60
<212> TYPE: DNA
<213> ORGANISM: Artificial Sequence
<220> FEATURE:
<223> OTHER INFORMATION: Primer AC1
<220> FEATURE:
<221> NAME/KEY: misc_feature
<222> LOCATION: (37)..(37)
<223> OTHER INFORMATION: m is a or c
<220> FEATURE:
<221> NAME/KEY: misc_feature
<222> LOCATION: (38)..(39)
<223> OTHER INFORMATION: n is a, c, g, or t

<400> SEQUENCE: 150
ggtgccctgg ccaaacgtga atagaggata ggtgtamnnt tggtgacagt agtaagttgc            60

<210> SEQ ID NO 151
<211> LENGTH: 60
<212> TYPE: DNA
<213> ORGANISM: Artificial Sequence
<220> FEATURE:
<223> OTHER INFORMATION: Primer AC2
<220> FEATURE:
<221> NAME/KEY: misc_feature
<222> LOCATION: (34)..(34)
<223> OTHER INFORMATION: m is a or c
<220> FEATURE:
<221> NAME/KEY: misc_feature
<222> LOCATION: (35)..(36)
<223> OTHER INFORMATION: n is a, c, g, or t

<400> SEQUENCE: 151
ggtgccctgg ccaaacgtga atagaggata ggtmnnatat tggtgacagt agtaagttgc            60

<210> SEQ ID NO 152
<211> LENGTH: 60
<212> TYPE: DNA
<213> ORGANISM: Artificial Sequence
<220> FEATURE:
<223> OTHER INFORMATION: Primer AC3
<220> FEATURE:
<221> NAME/KEY: misc_feature
<222> LOCATION: (31)..(31)
<223> OTHER INFORMATION: m is a or c
<220> FEATURE:
<221> NAME/KEY: misc_feature
<222> LOCATION: (32)..(33)
<223> OTHER INFORMATION: n is a, c, g, or t

<400> SEQUENCE: 152
ggtgccctgg ccaaacgtga atagaggata mnngtaatat tggtgacagt agtaagttgc            60

<210> SEQ ID NO 153
<211> LENGTH: 60
<212> TYPE: DNA
<213> ORGANISM: Artificial Sequence
<220> FEATURE:
<223> OTHER INFORMATION: Primer AC4
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)

<223> OTHER INFORMATION: n is a, c, g, or t

<400> SEQUENCE: 153
ggtgccctgg ccaaacgtga atagaggmnn ggtgtaatat tggtgacagt agtaagttgc    60

<210> SEQ ID NO 154
<211> LENGTH: 60
<212> TYPE: DNA
<213> ORGANISM: Artificial Sequence
<220> FEATURE:
<223> OTHER INFORMATION: Primer AC5
<220> FEATURE:
<221> NAME/KEY: misc_feature
<222> LOCATION: (22)..(22)
<223> OTHER INFORMATION: m is a or c
<220> FEATURE:
<221> NAME/KEY: misc_feature
<222> LOCATION: (23)..(24)
<223> OTHER INFORMATION: n is a, c, g, or t

<400> SEQUENCE: 154
ggtgccctgg ccaaacgtga amnnaggata ggtgtaatat tggtgacagt agtaagttgc    60

<210> SEQ ID NO 155
<211> LENGTH: 60
<212> TYPE: DNA
<213> ORGANISM: Artificial Sequence
<220> FEATURE:
<223> OTHER INFORMATION: Primer AC6

<400> SEQUENCE: 155
ggtgccctgg ccaaacgtga atagaggata ggtgtaatat tggtgacagt agtaagttgc    60

<210> SEQ ID NO 156
<211> LENGTH: 36
<212> TYPE: DNA
<213> ORGANISM: Artificial Sequence
<220> FEATURE:
<223> OTHER INFORMATION: Primer EAB-746

<400> SEQUENCE: 156
cgcttgatct cgagcttggt gccctggcca aacgtg    36

<210> SEQ ID NO 157

<400> SEQUENCE: 157

000

<210> SEQ ID NO 158
<211> LENGTH: 428
<212> TYPE: PRT
<213> ORGANISM: Artificial Sequence
<220> FEATURE:
<223> OTHER INFORMATION: pETR6592

<400> SEQUENCE: 158

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln

```
                65                  70                  75                  80
Asn Asp Thr Gly Phe Tyr Thr Leu Gln Val Ile Lys Ser Asp Leu Val
                    85                  90                  95
Asn Glu Glu Ala Thr Gly Gln Phe His Val Tyr Pro Glu Leu Pro Lys
                100                 105                 110
Pro Ser Ile Ser Ser Asn Ser Asn Pro Val Glu Asp Lys Asp Ala
            115                 120                 125
Met Ala Phe Thr Cys Glu Pro Glu Thr Gln Asp Thr Thr Tyr Leu Trp
        130                 135                 140
Trp Ile Asn Asn Gln Ser Leu Pro Val Ser Pro Arg Leu Gln Leu Ser
145                 150                 155                 160
Asn Gly Asn Arg Thr Leu Thr Leu Leu Ser Val Thr Arg Asn Asp Thr
                165                 170                 175
Gly Pro Tyr Glu Cys Glu Ile Gln Asn Pro Val Ser Ala Asn Arg Ser
                180                 185                 190
Asp Pro Val Thr Leu Asn Val Thr Tyr Gly Pro Asp Thr Pro Thr Ile
                195                 200                 205
Ser Pro Pro Asp Ser Ser Tyr Leu Ser Gly Ala Asn Leu Asn Leu Ser
        210                 215                 220
Cys His Ser Ala Ser Asn Pro Ser Pro Gln Tyr Ser Trp Arg Ile Asn
225                 230                 235                 240
Gly Ile Pro Gln Gln His Thr Gln Val Leu Phe Ile Ala Lys Ile Thr
                245                 250                 255
Pro Asn Asn Asn Gly Thr Tyr Ala Cys Phe Val Ser Asn Leu Ala Thr
                260                 265                 270
Gly Arg Asn Asn Ser Ile Val Lys Ser Ile Thr Val Ser Ala Leu Ser
            275                 280                 285
Pro Val Val Ala Lys Pro Gln Ile Lys Ala Ser Lys Thr Thr Val Thr
        290                 295                 300
Gly Asp Lys Asp Ser Val Asn Leu Thr Cys Ser Thr Asn Asp Thr Gly
305                 310                 315                 320
Ile Ser Ile Arg Trp Phe Phe Lys Asn Gln Ser Leu Pro Ser Ser Glu
                325                 330                 335
Arg Met Lys Leu Ser Gln Gly Asn Ile Thr Leu Ser Ile Asn Pro Val
                340                 345                 350
Lys Arg Glu Asp Ala Gly Thr Tyr Trp Cys Glu Val Phe Asn Pro Ile
            355                 360                 365
Ser Lys Asn Gln Ser Asp Pro Ile Met Leu Asn Val Asn Tyr Asn Ala
        370                 375                 380
Leu Pro Gln Glu Asn Leu Ile Asn Val Asp Leu Glu Val Leu Phe Gln
385                 390                 395                 400
Gly Pro Gly Ser Gly Leu Asn Asp Ile Phe Glu Ala Gln Lys Ile Glu
                405                 410                 415
Trp His Glu Ala Arg Ala His His His His His
                420                 425

<210> SEQ ID NO 159
<211> LENGTH: 363
<212> TYPE: DNA
<213> ORGANISM: Artificial Sequence
<220> FEATURE:
<223> OTHER INFORMATION: PMS22

<400> SEQUENCE: 159
caggtgcaat tggtgcaatc tgggtctgag ttgaagaagc ctggggcctc agtgaaggtt      60
```

```
tcctgcaagg cttctggata caccttcact gagtttggaa tgaactgggt gcgacaggcc      120
cctggacaag ggcttgagtg gatgggatgg ataaacacca aaactggaga ggcaacatat      180
gttgaagagt ttaagggacg gtttgtcttc tccttggaca cctctgtcag cacggcatat      240
ctgcagatca gcagcctaaa ggctgaagac actgccgtgt attactgtgc gagatgggac      300
ttctatgatt acgtggaggc tatggactac tggggccaag gaccacggt caccgtctcc      360 tca                                                                    363
```

<210> SEQ ID NO 160
<211> LENGTH: 363
<212> TYPE: DNA
<213> ORGANISM: Artificial Sequence
<220> FEATURE:
<223> OTHER INFORMATION: Primer 1C8

<400> SEQUENCE: 160

```
caggtgcaat tggtgcaatc tgggtctgag ttgaagaagc ctggggcctc agtgaaggtt       60
tcctgcaagg cttctggata caccttcact gagtttggaa tgaactgggt gcgacaggcc      120
cctggacaag ggcttgagtg gatgggatgg ataaacacca aaactggaga ggcaacatat      180
gttgaagagt ttaagggacg gtttgtcttc tccttggaca cctctgtcag cacggcatat      240
ctgcagatca gcagcctaaa ggctgaagac actgccgtgt attactgtgc gagatgggac      300
ttctatcatt acgtggaggc tatggactac tggggccaag gaccacggt caccgtctcc      360 tca                                                                    363
```

<210> SEQ ID NO 161
<211> LENGTH: 363
<212> TYPE: DNA
<213> ORGANISM: Artificial Sequence
<220> FEATURE:
<223> OTHER INFORMATION: 3E1

<400> SEQUENCE: 161

```
caggtgcaat tggtgcaatc tgggtctgag ttgaagaagc ctggggcctc agtgaaggtt       60
tcctgcaagg cttctggata caccttcact gagtttggaa tgaactgggt gcgacaggcc      120
cctggacaag ggcttgagtg gatgggatgg ataaacacca aaactggaga ggcaacatat      180
gttgaagagt ttaagggacg gtttgtcttc tccttggaca cctctgtcag cacggcatat      240
ctgcagatca gcagcctaaa ggctgaagac actgccgtgt attactgtgc gagatgggac      300
ttcgtggatt acgtggaggc tatggactac tggggccaag gaccacggt caccgtctcc      360 tca                                                                    363
```

<210> SEQ ID NO 162
<211> LENGTH: 363
<212> TYPE: DNA
<213> ORGANISM: Artificial Sequence
<220> FEATURE:
<223> OTHER INFORMATION: 2D7

<400> SEQUENCE: 162

```
caggtgcaat tggtgcaatc tgggtctgag ttgaagaagc ctggggcctc agtgaaggtt       60
tcctgcaagg cttctggata caccttcact gagtttggaa tgaactgggt gcgacaggcc      120
cctggacaag ggcttgagtg gatgggatgg ataaacacca aaactggaga ggcaacatat      180
gttgaagagt ttaagggacg gtttgtcttc tccttggaca cctctgtcag cacggcatat      240
ctgcagatca gcagcctaaa ggctgaagac actgccgtgt attactgtgc gagatgggac      300
```

```
ttctattggt acgtggaggc tatggactac tggggccaag ggaccacggt caccgtctcc    360
tca                                                                  363
```

<210> SEQ ID NO 163
<211> LENGTH: 363
<212> TYPE: DNA
<213> ORGANISM: Artificial Sequence
<220> FEATURE:
<223> OTHER INFORMATION: Affinity Matured Heavy Chain

<400> SEQUENCE: 163

```
caggtgcaat tggtgcaatc tgggtctgag ttgaagaagc ctggggcctc agtgaaggtt    60
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggac    300
tttgctcatt actttcagac tatggactac tggggccaag ggaccacggt caccgtctcc    360
tca                                                                  363
```

<210> SEQ ID NO 164
<211> LENGTH: 363
<212> TYPE: DNA
<213> ORGANISM: Artificial Sequence
<220> FEATURE:
<223> OTHER INFORMATION: Affinity Matured Heavy Chain

<400> SEQUENCE: 164

```
caggtgcaat tggtgcaatc tgggtctgag ttgaagaagc ctggggcctc agtgaaggtt    60
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggac    300
ttcgcttatt actttcagac tatggactac tggggccaag ggaccacggt caccgtctcc    360
tca                                                                  363
```

<210> SEQ ID NO 165
<211> LENGTH: 363
<212> TYPE: DNA
<213> ORGANISM: Artificial Sequence
<220> FEATURE:
<223> OTHER INFORMATION: Affinity Matured Heavy Chain

<400> SEQUENCE: 165

```
caggtgcaat tggtgcaatc tgggtctgag ttgaagaagc ctggggcctc agtgaaggtt    60
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggat    300
ttcgcgtatt accttgaggc tatggactac tggggccaag ggaccacgat caccgtctcc    360
tca                                                                  363
```

<210> SEQ ID NO 166
<211> LENGTH: 363
<212> TYPE: DNA

```
<213> ORGANISM: Artificial Sequence
<220> FEATURE:
<223> OTHER INFORMATION: H3 Full (5) 19

<400> SEQUENCE: 166
caggtgcaat tggtgcaatc tgggtctgag ttgaagaagc ctggggcctc agtgaaggtt      60
tcctgcaagg cttctggata caccttcact gagtttggaa tgagctgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgctgtgt attactgtgc gagatgggac    300
gcctttgagt acgtgaaggc gctggactac tggggccaag gaccacggt caccgtctcc    360 tca                                                                  363

<210> SEQ ID NO 167
<211> LENGTH: 363
<212> TYPE: DNA
<213> ORGANISM: Artificial Sequence
<220> FEATURE:
<223> OTHER INFORMATION: H3 Full (5) 8

<400> SEQUENCE: 167
caggtgcaat tggtgcaatc tgggtctgag ttgaagaagc ctggggcctc agtgaaggtt      60
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggat    300
ttctttgagt attttaagac tatggactac tggggccaag gaccacggt caccgtctcc    360 tca                                                                  363

<210> SEQ ID NO 168
<211> LENGTH: 363
<212> TYPE: DNA
<213> ORGANISM: Artificial Sequence
<220> FEATURE:
<223> OTHER INFORMATION: H3 Full (5) 28

<400> SEQUENCE: 168
caggtgcaat tggtgcaatc tgggtctgag ttgaagaagc ctggggcctc agtgaaggtt      60
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggac    300 ttttttttatt acgtgcagac tatggactac tggggccaag gaccacggt caccgtctcc    360 tca                                                                  363

<210> SEQ ID NO 169
<211> LENGTH: 363
<212> TYPE: DNA
<213> ORGANISM: Artificial Sequence
<220> FEATURE:
<223> OTHER INFORMATION: H3 Full (5) 27

<400> SEQUENCE: 169
caggtgcaat tggtgcaatc tgggtctgag ttgaagaagc ctggggcctc agtgaaggtt      60
```

```
tcctgcaagg cttctggata caccttcact gagtttggaa tgaactgggt gcgacaggcc    120
cctggacaag gcttgagtg gatgggatgg ataaacacca aaactggaga ggcaacatat     180
gttgaagagt ttaagggacg gtttgtcttc tccttggaca cctctgtcag cacggcatat    240
ctgcagatca gcagcctaaa ggctgaagac actgccgtgt attactgtgc gagatgggat    300
ttttcttatt acgttgaggc gatggactac tggggccaag gaccacagt caccgtctcc     360 tca                                                                  363
```

<210> SEQ ID NO 170
<211> LENGTH: 363
<212> TYPE: DNA
<213> ORGANISM: Artificial Sequence
<220> FEATURE:
<223> OTHER INFORMATION: H4E9 Heavy Chain

<400> SEQUENCE: 170

```
caggtgcaat tggtgcaatc tgggtctgag ttgaagaagc ctggggcctc agtgaaggtt    60
tcctgcaagg cttctggata caccttcact gagtttggta tgaactgggt gcgacaggcc    120
cctggacaag gcttgagtg gatgggatgg ataaatacca aaactggaga ggcaacttat     180
attgaagagt ttaagggacg gtttgtcttc tccttggaca cctctgtcag cacggcatat    240
ctgcagatca gcagcctaaa ggctgaagac actgccgtgt attactgtgc gagatgggac    300
ttctatgatt acgtggaggc tatggactac tggggccaag gaccacggt caccgtctcc     360 tca                                                                  363
```

<210> SEQ ID NO 171
<211> LENGTH: 363
<212> TYPE: DNA
<213> ORGANISM: Artificial Sequence
<220> FEATURE:
<223> OTHER INFORMATION: pAC14 (B9)

<400> SEQUENCE: 171

```
caggtgcaat tggtgcaatc tgggtctgag ttgaagaagc ctggggcctc agtgaaggtt    60
tcctgcaagg cttctggata caccttcact gagtttggta tgaactgggt gcgacaggcc    120
cctggacaag gcttgagtg gatgggatgg ataaacacca aagtggaga ggcaacctat      180 gttgaagagt ttaagggacg gtttgtcttc tccttggaca cctctgtcag cacggcatat    240
ctgcagatca gcagcctaaa ggctgaagac actgccgtgt attactgtgc gagatgggac    300
ttctatgatt acgtggaggc tatggactac tggggccaag gaccacggt caccgtctcc     360 tca                                                                  363
```

<210> SEQ ID NO 172
<211> LENGTH: 363
<212> TYPE: DNA
<213> ORGANISM: Artificial Sequence
<220> FEATURE:
<223> OTHER INFORMATION: pAC15 (F9)

<400> SEQUENCE: 172

```
caggtgcaat tggtgcaatc tgggtctgag ttgaagaagc ctggggcctc agtgaaggtt    60
tcctgcaagg cttctggata caccttcact gagtatggta tgaactgggt gcgacaggcc    120
cctggacaag gcttgagtg gatgggatgg ataaacacga aatctggaga ggcaacctat     180
gttgaagagt ttaagggacg gtttgtcttc tccttggaca cctctgtcag cacggcatat    240
ctgcagatca gcagcctaaa ggctgaagac actgccgtgt attactgtgc gagatgggac    300
```

```
ttctatgatt acgtggaggc tatggactac tggggccaag ggaccacggt caccgtctcc    360
tca                                                                  363
```

<210> SEQ ID NO 173
<211> LENGTH: 363
<212> TYPE: DNA
<213> ORGANISM: Artificial Sequence
<220> FEATURE:
<223> OTHER INFORMATION: H1/H2 (5) 2

<400> SEQUENCE: 173

```
caggtgcaat tggtgcaatc tgggtctgag ttgaagaagc ctggggcctc agtgaaggtt    60
tcctgcaagg cttctggata caccttcact gagtattcta tgaactgggt gcgacaggcc   120
cctggacaag ggcttgagtg gatgggatac ataaacacca aaaatggaga ggcaaactat   180
gttgaagagt ttaagggacg gtttgtcttc tccttggaca cctctgtcag cacggcatat   240
ctgcagatca gcagcctaaa ggctgaagac actgccgtgt attactgtgc gagatgggac   300
ttctatgatt acgtggaggc tatggactac tggggccaag ggaccacggt caccgtctcc   360
tca                                                                 363
```

<210> SEQ ID NO 174
<211> LENGTH: 363
<212> TYPE: DNA
<213> ORGANISM: Artificial Sequence
<220> FEATURE:
<223> OTHER INFORMATION: H1/H2 (5) 11

<400> SEQUENCE: 174

```
caggtgcaat tggtgcaatc tgggtctgag ttgaagaagc ctggggcctc agtgaaggtt    60
tcctgcaagg cttctggata caccttcact gagtatggta tgaactgggt gcgacaggcc   120
cctggacaag ggcttgagtg gatgggatgg ataaacacca aaaatggaga ggcaacctat   180
attgaagagt ttaagggacg gtttgtcttc tccttggaca cctctgtcag cacggcatat   240
ctgcagatca gcagcctaaa ggctgaagac actgccgtgt attactgtgc gagatgggac   300
ttctatgatt acgtggaggc tatggactac tggggccaag ggaccacggt caccgtctcc   360
tca                                                                 363
```

<210> SEQ ID NO 175
<211> LENGTH: 363
<212> TYPE: DNA
<213> ORGANISM: Artificial Sequence
<220> FEATURE:
<223> OTHER INFORMATION: H1/H2 (5) 13

<400> SEQUENCE: 175

```
caggtgcaat tggtgcaatc tgggtctgag ttgaagaagc ctggggcctc agtgaaggtt    60
tcctgcaagg cttctggata caccttcact gagtttggta tgaactgggt gcgacaggcc   120
cctggacaag ggcttgagtg gatgggatat ataaacacca aaaatggaga ggcaaactat   180
gttgaagagt ttaagggacg gtttgtcttc tccttggacg cctctgtcag cacggcatat   240
ctgcagatca gcagcctaaa ggctgaagac actgccgtgt attactgtgc gagatgggac   300
ttctatgatt acgtggaggc tatggactac tggggccaag ggaccacggt caccgtctcc   360
tca                                                                 363
```

<210> SEQ ID NO 176
<211> LENGTH: 363
<212> TYPE: DNA

```
<213> ORGANISM: Artificial Sequence
<220> FEATURE:
<223> OTHER INFORMATION: H1/H2 (5) 14

<400> SEQUENCE: 176
caggtgcaat tggtgcaatc tgggtctgag ttgaagaagc ctggggcctc agtgaaggtt      60
tcctgcaagg cttctggata caccttcact gagtatggta tgaactgggt gcgacaggcc     120
cctggacaag gcttgagtg gatgggatat ataaacacca aaaatggaga ggcaaactat      180
gttgaagagt ttaagggacg gtttgtcttc tccttggaca cctctgtcag cacggcatat     240
ctgcagatca gcagcctaaa ggctgaagac actgccgtgt attactgtgc gagatgggac     300
ttctatgatt acgtggaggc tatggactac tggggccaag gaccacggt caccgtctcc      360 tca                                                                   363

<210> SEQ ID NO 177
<211> LENGTH: 363
<212> TYPE: DNA
<213> ORGANISM: Artificial Sequence
<220> FEATURE:
<223> OTHER INFORMATION: H3 Full (5) 19

<400> SEQUENCE: 177
caggtgcaat tggtgcaatc tgggtctgag ttgaagaagc ctggggcctc agtgaaggtt      60
tcctgcaagg cttctggata caccttcact gagtttggaa tgagctgggt gcgacaggcc     120
cctggacaag gcttgagtg gatgggatgg ataaacacca aaactggaga ggcaacatat      180
gttgaagagt ttaagggacg gtttgtcttc tccttggaca cctctgtcag cacggcatat     240
ctgcagatca gcagcctaaa ggctgaagac actgctgtgt attactgtgc gagatgggac     300
gcctttgagt acgtgaaggc gctggactac tggggccaag gaccacggt caccgtctcc      360 tca                                                                   363

<210> SEQ ID NO 178
<211> LENGTH: 330
<212> TYPE: DNA
<213> ORGANISM: Artificial Sequence
<220> FEATURE:
<223> OTHER INFORMATION: pAC21 (3A1)

<400> SEQUENCE: 178
gatatccaga tgacccagtc tccatcctcc ctgtctgcat ctgtgggaga cagagtcacc      60
atcacttgca aggccagtgc caatgtgggt aataatgttg cctggtatca gcagaaacca     120
gggaaagcac ctaagctcct gatctatttg gcctccaacc gctccggtgg agtcccatca     180
aggttcagtg gcagtggatc tgggacagat ttcactctca ccatcagcag tctgcaacct     240
gaagatttcg caacttacta ctgtcaccaa tattacacct atcctctatt cacgtttggc     300
cagggcacca agctcgagat caagcgtacg                                      330

<210> SEQ ID NO 179
<211> LENGTH: 330
<212> TYPE: DNA
<213> ORGANISM: Artificial Sequence
<220> FEATURE:
<223> OTHER INFORMATION: pAC19 (2C6)

<400> SEQUENCE: 179
gatatccaga tgacccagtc tccatcctcc ctgtctgcat ctgtgggaga cagagtcacc      60
atcacttgca aggccagtaa gaatgtgggg actaatgttg cgtggtatca gcagaaacca     120
```

```
gggaaagcac ctaagcccct gatctacctg gcatcctacc cccagattgg agtcccatca    180
aggttcagtg gcagtggatc tgggacagat ttcactctca ccatcagcag tctgcaacct    240
gaagatttcg caacttacta ctgtcaccaa tattacacct atcccctatt cacgtttggc    300
cagggcacca agctcgagat caagcgtacg                                     330
```

```
<210> SEQ ID NO 180
<211> LENGTH: 330
<212> TYPE: DNA
<213> ORGANISM: Artificial Sequence
<220> FEATURE:
<223> OTHER INFORMATION: pAC18 (2F1)

<400> SEQUENCE: 180
gatatccaga tgacccagtc tccatcctcc ctgtctgcat ctgtgggaga cagagtcacc     60
atcacttgca aggccagtgc ggctgtgggt acgtatgttg cgtggtatca gcagaaacca    120
gggaaagcac ctaagctcct gatctattcg gcatcctacc gcaaaagggg agtcccatca    180
aggttcagtg gcagtggatc tgggacagat ttcactctca ccatcagcag tctgcaacct    240
gaagatttcg caacttacta ctgtcaccaa tattacacct atcctctatt cacgtttggc    300
cagggcacca agctcgagat caagcgtacg                                     330
```

```
<210> SEQ ID NO 181
<211> LENGTH: 330
<212> TYPE: DNA
<213> ORGANISM: Artificial Sequence
<220> FEATURE:
<223> OTHER INFORMATION: pAC23 (2F11)

<400> SEQUENCE: 181
gatatccaga tgacccagtc tccatcctcc ctgtctgcat ctgtgggaga cagagtcacc     60
atcacttgca aggccagtca gatagcgagt actaatgttg cctggtatca gcagaaacca    120
gggaaagcac ctaagctcct gatctattgg gcatcctacc gctatagtgg agtcccatca    180
aggttcagtg gcagtggatc tgggacagat ttcactctca ccatcagcag tctgcaacct    240
gaagatttcg caacttacta ctgtcaccaa tattacacct atcctctatt cacgtttggc    300
cagggcacca agctcgagat caagcgtacg                                     330
```

```
<210> SEQ ID NO 182
<211> LENGTH: 330
<212> TYPE: DNA
<213> ORGANISM: Artificial Sequence
<220> FEATURE:
<223> OTHER INFORMATION: H4E9 light chain

<400> SEQUENCE: 182
gatatccaga tgacccagtc tccatcctcc ctgtctgcat ctgtgggaga cagagtcacc     60
atcacttgca aggccagtca gaatgtgggt actaatgttg cctggtatca gcagaaacca    120
gggaaagcac ctaagcccct gatctattcg gcatcctacc gctacagtgg agtcccatca    180
aggttcagtg gcagtggatc tgggacagat ttcactctca ccatcagcag tctgcaacct    240
gaagatttcg caacttacta ctgtcaccaa tattacacct atcctctatt cacgtttggc    300
cagggcacca agctcgagat caagcgtacg                                     330
```

```
<210> SEQ ID NO 183
<211> LENGTH: 330
<212> TYPE: DNA
<213> ORGANISM: Artificial Sequence
<220> FEATURE:
```

<223> OTHER INFORMATION: L2D2

<400> SEQUENCE: 183

| | | |
|---|---|---|
| gatatccaga tgacccagtc tccatcctcc ctgtctgcat ctgtgggaga cagagtcacc | 60 |
| atcacttgca aggccagtca caatgtgggt accaacgttg cgtggtatca gcagaaacca | 120 |
| gggaaagcac ctaagctcct gatctattcg gcatcccacc ggtacagtgg agtcccatca | 180 |
| aggttcagtg gcagtggatc tgggacagat ttcactctca ccatcagcag tctgcaacct | 240 |
| gaagatttcg caacttacta ctgtcaccaa tattcacct atcctctatt cacgtttggc | 300 |
| cagggcacca agctcgagat caagcgtacg | 330 |

<210> SEQ ID NO 184
<211> LENGTH: 330
<212> TYPE: DNA
<213> ORGANISM: Artificial Sequence
<220> FEATURE:
<223> OTHER INFORMATION: pAC6 (C1)

<400> SEQUENCE: 184

| | | |
|---|---|---|
| gatatccaga tgacccagtc tccatcctcc ctgtctgcat ctgtgggaga cagagtcacc | 60 |
| atcacttgca aggccagtca gattatgggt cctaatgttg cgtggtatca gcagaaacca | 120 |
| gggaaagcac ctaagctcct gatctatttg gcatcctacc acgaaagtgg agtcccatca | 180 |
| aggttcagtg gcagtggatc tgggacagat ttcactctca ccatcagcag tctgcaacct | 240 |
| gaagatttcg caacttacta ctgtcaccaa tattcacct atcctctatt cacgtttggc | 300 |
| cagggcacca agctcgagat caagcgtacg | 330 |

<210> SEQ ID NO 185
<211> LENGTH: 330
<212> TYPE: DNA
<213> ORGANISM: Artificial Sequence
<220> FEATURE:
<223> OTHER INFORMATION: pAC7 (E10)

<400> SEQUENCE: 185

| | | |
|---|---|---|
| gatatccaga tgacccagtc tccatcctcc ctgtctgcat ctgtgggaga cagagtcacc | 60 |
| atcacttgca aggccagtca aattgtgggt actaatgttg cgtggtatca gcagaaacca | 120 |
| gggaaagcac ctaagctcct gatctattcg gcatcccacc gtcccagtgg agtcccatca | 180 |
| aggttcagtg gcagtggatc tgggacagat ttcactctca ccatcagcag tctgcaacct | 240 |
| gaagatttcg caacttacta ctgtcaccaa tattcacct atcctctatt cacgtttggc | 300 |
| cagggcacca agctcgagat caagcgtacg | 330 |

<210> SEQ ID NO 186
<211> LENGTH: 330
<212> TYPE: DNA
<213> ORGANISM: Artificial Sequence
<220> FEATURE:
<223> OTHER INFORMATION: pAC12 (H7)

<400> SEQUENCE: 186

| | | |
|---|---|---|
| gatatccaga tgacccagtc tccatcctcc ctgtctgcat ctgtgggaga cagagtcacc | 60 |
| atcacttgca aggccagtca gaaggtgctt actaatgttg cgtggtatca gcagaaacca | 120 |
| gggaaagcac ctaagctcct gatctatttg gcatcctacc gctacagtgg agtcccatca | 180 |
| aggttcagtg gcagtggatc tgggacagat ttcactctca ccatcagcag tctgcaacct | 240 |
| gaagatttcg caacttacta ctgtcaccaa tattcacct atcctctatt cacgtttggc | 300 |

```
cagggcacca agctcgagat caagcgtacg                                          330
```

<210> SEQ ID NO 187
<211> LENGTH: 330
<212> TYPE: DNA
<213> ORGANISM: Artificial Sequence
<220> FEATURE:
<223> OTHER INFORMATION: pAC13 (H11)

<400> SEQUENCE: 187

```
gatatccaga tgacccagtc tccatcctcc ctgtctgcat ctgtgggaga cagagtcacc    60
atcacttgca aggccagtca gactgtgagt gctaatgttg cgtggtatca gcagaaacca   120
gggaaagcac ctaagctcct gatctacttg catcctacc gctacagagg agtcccatca   180
aggttcagtg gcagtggatc tgggacagat ttcactctca ccatcagcag tctgcaacct   240
gaagatttcg caacttacta ctgtcaccaa tattcaccct atcctctatt cacgtttggc   300
cagggcacca agctcgagat caagcgtacg                                     330
```

<210> SEQ ID NO 188
<211> LENGTH: 121
<212> TYPE: PRT
<213> ORGANISM: Artificial Sequence
<220> FEATURE:
<223> OTHER INFORMATION: PMS22

<400> SEQUENCE: 188

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

<210> SEQ ID NO 189
<211> LENGTH: 121
<212> TYPE: PRT
<213> ORGANISM: Artificial Sequence
<220> FEATURE:
<223> OTHER INFORMATION: 1C8

<400> SEQUENCE: 189

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60
```

```
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Trp Asp Phe Tyr His Tyr Val Glu Ala Met Asp Tyr Trp Gly
            100                 105                 110

Gln Gly Thr Thr Val Thr Val Ser Ser
            115                 120

<210> SEQ ID NO 190
<211> LENGTH: 121
<212> TYPE: PRT
<213> ORGANISM: Artificial Sequence
<220> FEATURE:
<223> OTHER INFORMATION: 3E1

<400> SEQUENCE: 190

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
             35                  40                  45

Gly Trp Ile Asn Thr Lys Thr Gly Glu Ala Thr Tyr Val Glu Glu Phe
     50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Trp Asp Phe Val Asp Tyr Val Glu Ala Met Asp Tyr Trp Gly
            100                 105                 110

Gln Gly Thr Thr Val Thr Val Ser Ser
            115                 120

<210> SEQ ID NO 191
<211> LENGTH: 121
<212> TYPE: PRT
<213> ORGANISM: Artificial Sequence
<220> FEATURE:
<223> OTHER INFORMATION: 2D7

<400> SEQUENCE: 191

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
             35                  40                  45

Gly Trp Ile Asn Thr Lys Thr Gly Glu Ala Thr Tyr Val Glu Glu Phe
     50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Trp Asp Phe Tyr Trp Tyr Val Glu Ala Met Asp Tyr Trp Gly
            100                 105                 110

Gln Gly Thr Thr Val Thr Val Ser Ser
            115                 120
```

```
<210> SEQ ID NO 192
<211> LENGTH: 121
<212> TYPE: PRT
<213> ORGANISM: Artificial Sequence
<220> FEATURE:
<223> OTHER INFORMATION: Affinity Matured Heavy Chain

<400> SEQUENCE: 192

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Ala His Tyr Phe Gln Thr Met Asp Tyr Trp Gly
                100                 105                 110

Gln Gly Thr Thr Val Thr Val Ser Ser
            115                 120

<210> SEQ ID NO 193
<211> LENGTH: 121
<212> TYPE: PRT
<213> ORGANISM: Artificial Sequence
<220> FEATURE:
<223> OTHER INFORMATION: Affinity Matured Heavy Chain

<400> SEQUENCE: 193

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Ala Tyr Tyr Phe Gln Thr Met Asp Tyr Trp Gly
                100                 105                 110

Gln Gly Thr Thr Val Thr Val Ser Ser
            115                 120

<210> SEQ ID NO 194
<211> LENGTH: 121
<212> TYPE: PRT
<213> ORGANISM: Artificial Sequence
<220> FEATURE:
<223> OTHER INFORMATION: Affinity Matured Heavy Chain

<400> SEQUENCE: 194

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Trp Asp Phe Ala Tyr Tyr Leu Glu Ala Met Asp Tyr Trp Gly
             100                 105                 110

Gln Gly Thr Thr Ile Thr Val Ser Ser
            115                 120
```

<210> SEQ ID NO 195
<211> LENGTH: 121
<212> TYPE: PRT
<213> ORGANISM: Artificial Sequence
<220> FEATURE:
<223> OTHER INFORMATION: H3 Full (5) 19

<400> SEQUENCE: 195

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Glu Phe
            20                  25                  30

Gly Met Ser Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Trp Asp Ala Phe Glu Tyr Val Lys Ala Leu Asp Tyr Trp Gly
             100                 105                 110

Gln Gly Thr Thr Val Thr Val Ser Ser
            115                 120
```

<210> SEQ ID NO 196
<211> LENGTH: 121
<212> TYPE: PRT
<213> ORGANISM: Artificial Sequence
<220> FEATURE:
<223> OTHER INFORMATION: H3 Full (5) 8

<400> SEQUENCE: 196

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
 50                  55                  60

Lys Gly Arg Phe Val Phe Ser Leu Asp Thr Ser Val Ser Thr Ala Tyr
 65                  70                  75                  80
```

```
Leu Gln Ile Ser Ser Leu Lys Ala Glu Asp Thr Ala Val Tyr Tyr Cys
                85                  90                  95

Ala Arg Trp Asp Phe Phe Glu Tyr Phe Lys Thr Met Asp Tyr Trp Gly
            100                 105                 110

Gln Gly Thr Thr Val Thr Val Ser Ser
        115                 120

<210> SEQ ID NO 197
<211> LENGTH: 121
<212> TYPE: PRT
<213> ORGANISM: Artificial Sequence
<220> FEATURE:
<223> OTHER INFORMATION: H3 Full (5) 28

<400> SEQUENCE: 197

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Phe Tyr Tyr Val Gln Thr Met Asp Tyr Trp Gly
            100                 105                 110

Gln Gly Thr Thr Val Thr Val Ser Ser
        115                 120

<210> SEQ ID NO 198
<211> LENGTH: 121
<212> TYPE: PRT
<213> ORGANISM: Artificial Sequence
<220> FEATURE:
<223> OTHER INFORMATION: H3 Full (5) 27

<400> SEQUENCE: 198

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Ser Tyr Tyr Val Glu Ala Met Asp Tyr Trp Gly
            100                 105                 110

Gln Gly Thr Thr Val Thr Val Ser Ser
        115                 120

<210> SEQ ID NO 199
```

```
<211> LENGTH: 121
<212> TYPE: PRT
<213> ORGANISM: Artificial Sequence
<220> FEATURE:
<223> OTHER INFORMATION: H4E9 Heavy Chain

<400> SEQUENCE: 199
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Ile Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 200
<211> LENGTH: 121
<212> TYPE: PRT
<213> ORGANISM: Artificial Sequence
<220> FEATURE:
<223> OTHER INFORMATION: pAC14 (B9)

<400> SEQUENCE: 200
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Ser Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 201
<211> LENGTH: 121
<212> TYPE: PRT
<213> ORGANISM: Artificial Sequence
<220> FEATURE:
<223> OTHER INFORMATION: pAC15 (F9)

<400> SEQUENCE: 201
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Tyr

-continued

```
                    20                  25                  30
Gly Met Asn Trp Val Arg Gln Ala Pro Gly Gln Gly Leu Glu Trp Met
            35                  40                  45
Gly Trp Ile Asn Thr Lys Ser Gly Glu Ala Thr Tyr Val Glu Glu Phe
        50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                85                  90                  95
Ala Arg Trp Asp Phe Tyr Asp Tyr Val Glu Ala Met Asp Tyr Trp Gly
            100                 105                 110
Gln Gly Thr Thr Val Thr Val Ser Ser
        115                 120

<210> SEQ ID NO 202
<211> LENGTH: 121
<212> TYPE: PRT
<213> ORGANISM: Artificial Sequence
<220> FEATURE:
<223> OTHER INFORMATION: H1/H2 (5) 2

<400> SEQUENCE: 202

Gln Val Gln Leu Val Gln Ser Gly Ser Glu Leu Lys Lys Pro Gly Ala
 1               5                  10                  15
Ser Val Lys Val Ser Cys Lys Ala Ser Gly Tyr Thr Phe Thr Glu Tyr
            20                  25                  30
Ser Met Asn Trp Val Arg Gln Ala Pro Gly Gln Gly Leu Glu Trp Met
            35                  40                  45
Gly Tyr Ile Asn Thr Lys Asn Gly Glu Ala Asn Tyr Val Glu Glu Phe
        50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                85                  90                  95
Ala Arg Trp Asp Phe Tyr Asp Tyr Val Glu Ala Met Asp Tyr Trp Gly
            100                 105                 110
Gln Gly Thr Thr Val Thr Val Ser Ser
        115                 120

<210> SEQ ID NO 203
<211> LENGTH: 121
<212> TYPE: PRT
<213> ORGANISM: Artificial Sequence
<220> FEATURE:
<223> OTHER INFORMATION: H1/H2 (5) 11

<400> SEQUENCE: 203

Gln Val Gln Leu Val Gln Ser Gly Ser Glu Leu Lys Lys Pro Gly Ala
 1               5                  10                  15
Ser Val Lys Val Ser Cys Lys Ala Ser Gly Tyr Thr Phe Thr Glu Tyr
            20                  25                  30
Gly Met Asn Trp Val Arg Gln Ala Pro Gly Gln Gly Leu Glu Trp Met
            35                  40                  45
Gly Trp Ile Asn Thr Lys Asn Gly Glu Ala Thr Tyr Ile Glu Glu Phe
        50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
```

```
                    85                  90                  95
Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 204
<211> LENGTH: 121
<212> TYPE: PRT
<213> ORGANISM: Artificial Sequence
<220> FEATURE:
<223> OTHER INFORMATION: H1/H2 (5) 13

<400> SEQUENCE: 204

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Tyr Ile Asn Thr Lys Asn Gly Glu Ala Asn Tyr Val Glu Glu Phe
    50                  55                  60

Lys Gly Arg Phe Val Phe Ser Leu Asp Ala Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 205
<211> LENGTH: 121
<212> TYPE: PRT
<213> ORGANISM: Artificial Sequence
<220> FEATURE:
<223> OTHER INFORMATION: H1/H2 (5) 14

<400> SEQUENCE: 205

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Tyr
            20                  25                  30

Gly Met Asn Trp Val Arg Gln Ala Pro Gly Gln Gly Leu Glu Trp Met
        35                  40                  45

Gly Tyr Ile Asn Thr Lys Asn Gly Glu Ala Asn Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 206
<211> LENGTH: 121
<212> TYPE: PRT
```

```
<213> ORGANISM: Artificial Sequence
<220> FEATURE:
<223> OTHER INFORMATION: H3 Full (5) 19

<400> SEQUENCE: 206

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Ser Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Ala Phe Glu Tyr Val Lys Ala Leu Asp Tyr Trp Gly
            100                 105                 110

Gln Gly Thr Thr Val Thr Val Ser Ser
        115                 120

<210> SEQ ID NO 207
<211> LENGTH: 110
<212> TYPE: PRT
<213> ORGANISM: Artificial Sequence
<220> FEATURE:
<223> OTHER INFORMATION: pAC21 (3A1)

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Asn Val Gly Asn Asn
            20                  25                  30

Val Ala Trp Tyr Gln Gln Lys Pro Gly Lys Ala Pro Lys Leu Leu Ile
        35                  40                  45

Tyr Leu Ala Ser Asn Arg Ser Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 208
<211> LENGTH: 110
<212> TYPE: PRT
<213> ORGANISM: Artificial Sequence
<220> FEATURE:
<223> OTHER INFORMATION: pAC19 (2C6)

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Lys Ala Ser Lys Asn Val Gly Thr Asn
            20                  25                  30

Val Ala Trp Tyr Gln Gln Lys Pro Gly Lys Ala Pro Lys Pro Leu Ile
        35                  40                  45
```

```
Tyr Leu Ala Ser Tyr Pro Gln Ile Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Thr Tyr Pro Leu
                 85                  90                  95

Phe Thr Phe Gly Gln Gly Thr Lys Leu Glu Ile Lys Arg Thr
                100                 105                 110

<210> SEQ ID NO 209
<211> LENGTH: 110
<212> TYPE: PRT
<213> ORGANISM: Artificial Sequence
<220> FEATURE:
<223> OTHER INFORMATION: pAC18 (2F1)

<400> SEQUENCE: 209

Asp Ile Gln Met Thr Gln Ser Pro Ser Ser Leu Ser Ala Ser Val Gly
  1               5                  10                  15

Asp Arg Val Thr Ile Thr Cys Lys Ala Ser Ala Ala Val Gly Thr Tyr
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Lys Arg Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Thr Tyr Pro Leu
                 85                  90                  95

Phe Thr Phe Gly Gln Gly Thr Lys Leu Glu Ile Lys Arg Thr
                100                 105                 110

<210> SEQ ID NO 210
<211> LENGTH: 110
<212> TYPE: PRT
<213> ORGANISM: Artificial Sequence
<220> FEATURE:
<223> OTHER INFORMATION: pAC23 (2F11)

<400> SEQUENCE: 210

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ile Ala Ser Thr Asn
                 20                  25                  30

Val Ala Trp Tyr Gln Gln Lys Pro Gly Lys Ala Pro Lys Leu Leu Ile
             35                  40                  45

Tyr Trp Ala Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Thr Tyr Pro Leu
                 85                  90                  95

Phe Thr Phe Gly Gln Gly Thr Lys Leu Glu Ile Lys Arg Thr
                100                 105                 110

<210> SEQ ID NO 211
<211> LENGTH: 110
<212> TYPE: PRT
<213> ORGANISM: Artificial Sequence
<220> FEATURE:
```

<223> OTHER INFORMATION: H4E9 light chain

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 212
<211> LENGTH: 110
<212> TYPE: PRT
<213> ORGANISM: Artificial Sequence
<220> FEATURE:
<223> OTHER INFORMATION: L2D2

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser His Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 213
<211> LENGTH: 110
<212> TYPE: PRT
<213> ORGANISM: Artificial Sequence
<220> FEATURE:
<223> OTHER INFORMATION: pAC6 (C1)

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ile Met Gly Pro Asn
            20                  25                  30

Val Ala Trp Tyr Gln Gln Lys Pro Gly Lys Ala Pro Lys Leu Leu Ile
        35                  40                  45

Tyr Leu Ala Ser Tyr His Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 214
<211> LENGTH: 110
<212> TYPE: PRT
<213> ORGANISM: Artificial Sequence
<220> FEATURE:
<223> OTHER INFORMATION: pAC7 (E10)

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ile Val Gly Thr Asn
            20                  25                  30

Val Ala Trp Tyr Gln Gln Lys Pro Gly Lys Ala Pro Lys Leu Leu Ile
            35                  40                  45

Tyr Ser Ala Ser His Arg Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 215
<211> LENGTH: 110
<212> TYPE: PRT
<213> ORGANISM: Artificial Sequence
<220> FEATURE:
<223> OTHER INFORMATION: pAC12 (H7)

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Lys Val Leu Thr Asn
            20                  25                  30

Val Ala Trp Tyr Gln Gln Lys Pro Gly Lys Ala Pro Lys Leu Leu Ile
            35                  40                  45

Tyr Leu Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
            100                 105                 110

<210> SEQ ID NO 216
<211> LENGTH: 110
<212> TYPE: PRT
<213> ORGANISM: Artificial Sequence
<220> FEATURE:
<223> OTHER INFORMATION: pAC13 (H11)

<400> SEQUENCE: 216

Asp Ile Gln Met Thr Gln Ser Pro Ser Ser Leu Ser Ala Ser Val Gly
```

```
                1               5                  10                  15
Asp Arg Val Thr Ile Thr Cys Lys Ala Ser Gln Thr Val Ser Ala Asn
                20                  25                  30

Val Ala Trp Tyr Gln Gln Lys Pro Gly Lys Ala Pro Lys Leu Leu Ile
            35                  40                  45

Tyr Leu Ala Ser Tyr Arg Tyr Arg Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr
                100                 105                 110

<210> SEQ ID NO 217
<211> LENGTH: 12
<212> TYPE: PRT
<213> ORGANISM: Artificial Sequence
<220> FEATURE:
<223> OTHER INFORMATION: PR1A3 (Y98A) Heavy Chain CDR3

<400> SEQUENCE: 217

Trp Asp Phe Ala Asp Tyr Val Glu Ala Met Asp Tyr
1               5                   10

<210> SEQ ID NO 218
<211> LENGTH: 12
<212> TYPE: PRT
<213> ORGANISM: Artificial Sequence
<220> FEATURE:
<223> OTHER INFORMATION: PR1A3 (D99Y) Heavy Chain CDR3

<400> SEQUENCE: 218

Trp Asp Phe Tyr Tyr Tyr Val Glu Ala Met Asp Tyr
1               5                   10

<210> SEQ ID NO 219
<211> LENGTH: 12
<212> TYPE: PRT
<213> ORGANISM: Artificial Sequence
<220> FEATURE:
<223> OTHER INFORMATION: PR1A3 (D99H) Heavy Chain CDR3

<400> SEQUENCE: 219

Trp Asp Phe Tyr His Tyr Val Glu Ala Met Asp Tyr
1               5                   10

<210> SEQ ID NO 220
<211> LENGTH: 12
<212> TYPE: PRT
<213> ORGANISM: Artificial Sequence
<220> FEATURE:
<223> OTHER INFORMATION: PR1A3 (V101F) Heavy Chain CDR3

<400> SEQUENCE: 220

Trp Asp Phe Tyr Asp Tyr Phe Glu Ala Met Asp Tyr
1               5                   10

<210> SEQ ID NO 221
<211> LENGTH: 12
<212> TYPE: PRT
<213> ORGANISM: Artificial Sequence
<220> FEATURE:
<223> OTHER INFORMATION: PR1A3 (E101aQ) Heavy Chain CDR3
```

-continued

```
<400> SEQUENCE: 221

Trp Asp Phe Tyr Asp Tyr Val Gln Ala Met Asp Tyr
1               5                   10

<210> SEQ ID NO 222
<211> LENGTH: 12
<212> TYPE: PRT
<213> ORGANISM: Artificial Sequence
<220> FEATURE:
<223> OTHER INFORMATION: PR1A3 (A103T) Heavy Chain CDR3

<400> SEQUENCE: 222

Trp Asp Phe Tyr Asp Tyr Val Glu Thr Met Asp Tyr
1               5                   10

<210> SEQ ID NO 223
<211> LENGTH: 12
<212> TYPE: PRT
<213> ORGANISM: Artificial Sequence
<220> FEATURE:
<223> OTHER INFORMATION: PR1A3 (Y98A / D99Y) Heavy Chain CDR3

<400> SEQUENCE: 223

Trp Asp Phe Ala Tyr Tyr Val Glu Ala Met Asp Tyr
1               5                   10

<210> SEQ ID NO 224
<211> LENGTH: 12
<212> TYPE: PRT
<213> ORGANISM: Artificial Sequence
<220> FEATURE:
<223> OTHER INFORMATION: PR1A3 (W95Y) Heavy Chain CDR3

<400> SEQUENCE: 224

Tyr Asp Phe Tyr Asp Tyr Val Glu Ala Met Asp Tyr
1               5                   10

<210> SEQ ID NO 225
<211> LENGTH: 121
<212> TYPE: PRT
<213> ORGANISM: Artificial Sequence
<220> FEATURE:
<223> OTHER INFORMATION: CH7A (Y98A) Heavy Chain Construct

<400> SEQUENCE: 225

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Ala Asp Tyr Val Glu Ala Met Asp Tyr Trp Gly
            100                 105                 110

Gln Gly Thr Thr Val Thr Val Ser Ser
        115                 120

<210> SEQ ID NO 226
```

```
<211> LENGTH: 121
<212> TYPE: PRT
<213> ORGANISM: Artificial Sequence
<220> FEATURE:
<223> OTHER INFORMATION: CH7A (D99Y) Heavy Chain Construct

<400> SEQUENCE: 226

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr Tyr Tyr Val Glu Ala Met Asp Tyr Trp Gly
            100                 105                 110

Gln Gly Thr Thr Val Thr Val Ser Ser
        115                 120

<210> SEQ ID NO 227
<211> LENGTH: 121
<212> TYPE: PRT
<213> ORGANISM: Artificial Sequence
<220> FEATURE:
<223> OTHER INFORMATION: CH7A (D99H) Heavy Chain Construct

<400> SEQUENCE: 227

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Tyr His Tyr Val Glu Ala Met Asp Tyr Trp Gly
            100                 105                 110

Gln Gly Thr Thr Val Thr Val Ser Ser
        115                 120

<210> SEQ ID NO 228
<211> LENGTH: 121
<212> TYPE: PRT
<213> ORGANISM: Artificial Sequence
<220> FEATURE:
<223> OTHER INFORMATION: CH7A (V101F) Heavy Chain Construct

<400> SEQUENCE: 228

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
```

```
                    20                  25                  30
Gly Met Asn Trp Val Arg Gln Ala Pro Gly Gln Gly Leu Glu Trp Met
            35                  40                  45
Gly Trp Ile Asn Thr Lys Thr Gly Glu Ala Thr Tyr Val Glu Glu Phe
        50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                85                  90                  95
Ala Arg Trp Asp Phe Tyr Asp Tyr Phe Glu Ala Met Asp Tyr Trp Gly
            100                 105                 110
Gln Gly Thr Thr Val Thr Val Ser Ser
        115                 120

<210> SEQ ID NO 229
<211> LENGTH: 121
<212> TYPE: PRT
<213> ORGANISM: Artificial Sequence
<220> FEATURE:
<223> OTHER INFORMATION: CH7A (E102Q) Heavy Chain Construct

<400> SEQUENCE: 229

Gln Val Gln Leu Val Gln Ser Gly Ser Glu Leu Lys Lys Pro Gly Ala
 1               5                  10                  15
Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
            35                  40                  45
Gly Trp Ile Asn Thr Lys Thr Gly Glu Ala Thr Tyr Val Glu Glu Phe
        50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                85                  90                  95
Ala Arg Trp Asp Phe Tyr Asp Tyr Val Gln Ala Met Asp Tyr Trp Gly
            100                 105                 110
Gln Gly Thr Thr Val Thr Val Ser Ser
        115                 120

<210> SEQ ID NO 230
<211> LENGTH: 121
<212> TYPE: PRT
<213> ORGANISM: Artificial Sequence
<220> FEATURE:
<223> OTHER INFORMATION: CH7A (A103T) Heavy Chain Construct

<400> SEQUENCE: 230

Gln Val Gln Leu Val Gln Ser Gly Ser Glu Leu Lys Lys Pro Gly Ala
 1               5                  10                  15
Ser Val Lys Val Ser Cys Lys Ala Ser Gly Tyr Thr Phe Thr Glu Phe
            20                  25                  30
Gly Met Asn Trp Val Arg Gln Ala Pro Gly Gln Gly Leu Glu Trp Met
            35                  40                  45
Gly Trp Ile Asn Thr Lys Thr Gly Glu Ala Thr Tyr Val Glu Glu Phe
        50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
```

```
                85                  90                  95
Ala Arg Trp Asp Phe Tyr Asp Tyr Val Glu Thr Met Asp Tyr Trp Gly
            100                 105                 110

Gln Gly Thr Thr Val Thr Val Ser Ser
        115                 120

<210> SEQ ID NO 231
<211> LENGTH: 121
<212> TYPE: PRT
<213> ORGANISM: Artificial Sequence
<220> FEATURE:
<223> OTHER INFORMATION: CH7A (Y98A / D99Y) Heavy Chain Construct

<400> SEQUENCE: 231

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 232
<211> LENGTH: 121
<212> TYPE: PRT
<213> ORGANISM: Artificial Sequence
<220> FEATURE:
<223> OTHER INFORMATION: CH7A (W95Y) Heavy Chain Construct

<400> SEQUENCE: 232

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 233
<211> LENGTH: 121
<212> TYPE: PRT
```

-continued

<213> ORGANISM: Artificial Sequence
<220> FEATURE:
<223> OTHER INFORMATION: CH1A1A (Y98A)

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Asp Tyr Val Glu Ala Met Asp Tyr Trp Gly
            100                 105                 110

Gln Gly Thr Thr Val Thr Val Ser Ser
        115                 120

<210> SEQ ID NO 234
<211> LENGTH: 121
<212> TYPE: PRT
<213> ORGANISM: Artificial Sequence
<220> FEATURE:
<223> OTHER INFORMATION: CH1A1A (D99Y)

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Tyr Tyr Val Glu Ala Met Asp Tyr Trp Gly
            100                 105                 110

Gln Gly Thr Thr Val Thr Val Ser Ser
        115                 120

<210> SEQ ID NO 235
<211> LENGTH: 121
<212> TYPE: PRT
<213> ORGANISM: Artificial Sequence
<220> FEATURE:
<223> OTHER INFORMATION: CH1A1A (D99H)

<400> SEQUENCE: 235

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr His Tyr Val Glu Ala Met Asp Tyr Trp Gly
            100                 105                 110

Gln Gly Thr Thr Val Thr Val Ser Ser
            115                 120

<210> SEQ ID NO 236
<211> LENGTH: 121
<212> TYPE: PRT
<213> ORGANISM: Artificial Sequence
<220> FEATURE:
<223> OTHER INFORMATION: CH1A1A (V101F)

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Phe Glu Ala Met Asp Tyr Trp Gly
            100                 105                 110

Gln Gly Thr Thr Val Thr Val Ser Ser
            115                 120

<210> SEQ ID NO 237
<211> LENGTH: 121
<212> TYPE: PRT
<213> ORGANISM: Artificial Sequence
<220> FEATURE:
<223> OTHER INFORMATION: CH1A1A (E102Q)

<400> SEQUENCE: 237

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

```
Ala Arg Trp Asp Phe Tyr Asp Tyr Val Gln Ala Met Asp Tyr Trp Gly
            100                 105                 110

Gln Gly Thr Thr Val Thr Val Ser Ser
        115                 120
```

<210> SEQ ID NO 238
<211> LENGTH: 121
<212> TYPE: PRT
<213> ORGANISM: Artificial Sequence
<220> FEATURE:
<223> OTHER INFORMATION: CH1A1A  (A103T)

<400> SEQUENCE: 238

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Thr Met Asp Tyr Trp Gly
            100                 105                 110

Gln Gly Thr Thr Val Thr Val Ser Ser
        115                 120
```

<210> SEQ ID NO 239
<211> LENGTH: 121
<212> TYPE: PRT
<213> ORGANISM: Artificial Sequence
<220> FEATURE:
<223> OTHER INFORMATION: CH1A1A  (Y98A / D99Y)

<400> SEQUENCE: 239

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120
```

<210> SEQ ID NO 240
<211> LENGTH: 121
<212> TYPE: PRT
<213> ORGANISM: Artificial Sequence
<220> FEATURE:

<223> OTHER INFORMATION: CH1A1A (W95Y)

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 241
<211> LENGTH: 121
<212> TYPE: PRT
<213> ORGANISM: Artificial Sequence
<220> FEATURE:
<223> OTHER INFORMATION: CH1A1B (Y98A)

<400> SEQUENCE: 241

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Asp Tyr Val Glu Ala Met Asp Tyr Trp Gly
            100                 105                 110

Gln Gly Thr Thr Val Thr Val Ser Ser
        115                 120

<210> SEQ ID NO 242
<211> LENGTH: 121
<212> TYPE: PRT
<213> ORGANISM: Artificial Sequence
<220> FEATURE:
<223> OTHER INFORMATION: CH1A1B (D99Y)

<400> SEQUENCE: 242

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
            50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Tyr Tyr Tyr Val Glu Ala Met Asp Tyr Trp Gly
                100                 105                 110

Gln Gly Thr Thr Val Thr Val Ser Ser
            115                 120

<210> SEQ ID NO 243
<211> LENGTH: 121
<212> TYPE: PRT
<213> ORGANISM: Artificial Sequence
<220> FEATURE:
<223> OTHER INFORMATION: CH1A1B (D99H)

<400> SEQUENCE: 243

Gln Val Lys Leu Gln Gln Ser Gly Ala Glu Val Lys Lys Pro Gly Ala
 1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
             35                  40                  45

Gly Trp Ile Asn Thr Lys Thr Gly Glu Ala Thr Tyr Val Glu Glu Phe
            50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Tyr His Tyr Val Glu Ala Met Asp Tyr Trp Gly
                100                 105                 110

Gln Gly Thr Thr Val Thr Val Ser Ser
            115                 120

<210> SEQ ID NO 244
<211> LENGTH: 121
<212> TYPE: PRT
<213> ORGANISM: Artificial Sequence
<220> FEATURE:
<223> OTHER INFORMATION: CH1A1B (V101F)

<400> SEQUENCE: 244

Gln Val Lys Leu Gln Gln Ser Gly Ala Glu Val Lys Lys Pro Gly Ala
 1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
             35                  40                  45

Gly Trp Ile Asn Thr Lys Thr Gly Glu Ala Thr Tyr Val Glu Glu Phe
            50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Tyr Asp Tyr Phe Glu Ala Met Asp Tyr Trp Gly
                100                 105                 110

Gln Gly Thr Thr Val Thr Val Ser Ser
        115                 120

<210> SEQ ID NO 245
<211> LENGTH: 121
<212> TYPE: PRT
<213> ORGANISM: Artificial Sequence
<220> FEATURE:
<223> OTHER INFORMATION: CH1A1B (E102Q)

<400> SEQUENCE: 245

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Gln Ala Met Asp Tyr Trp Gly
            100                 105                 110

Gln Gly Thr Thr Val Thr Val Ser Ser
        115                 120

<210> SEQ ID NO 246
<211> LENGTH: 121
<212> TYPE: PRT
<213> ORGANISM: Artificial Sequence
<220> FEATURE:
<223> OTHER INFORMATION: CH1A1B (A103T)

<400> SEQUENCE: 246

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Thr Met Asp Tyr Trp Gly
            100                 105                 110

Gln Gly Thr Thr Val Thr Val Ser Ser
        115                 120

<210> SEQ ID NO 247
<211> LENGTH: 121
<212> TYPE: PRT
<213> ORGANISM: Artificial Sequence
<220> FEATURE:
<223> OTHER INFORMATION: CH1A1B (Y98A / D99Y)

-continued

<400> SEQUENCE: 247

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 248
<211> LENGTH: 121
<212> TYPE: PRT
<213> ORGANISM: Artificial Sequence
<220> FEATURE:
<223> OTHER INFORMATION: CH1A1B (W95Y)

<400> SEQUENCE: 248

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 249
<211> LENGTH: 363
<212> TYPE: DNA
<213> ORGANISM: Artificial Sequence
<220> FEATURE:
<223> OTHER INFORMATION: CH7A (Y98A) Heavy Chain Construct

<400> SEQUENCE: 249
caggtgcagc tggtgcaatc tgggtctgag ttgaagaagc ctggggcctc agtgaaggtt      60
tcctgcaagg cttctggata caccttcact gagtttggaa tgaactgggt gcgacaggcc    120
cctggacaag ggcttgagtg gatgggatgg ataaacacca aaactggaga ggcaacatat    180
gttgaagagt ttaagggacg gtttgtcttc tccttggaca cctctgtcag cacggcatat    240
ctgcagatca gcagcctaaa ggctgaagac actgccgtgt attactgtgc gagatgggac    300

```
ttcgctgatt acgtggaggc tatggactac tggggccaag ggaccacggt caccgtctcc    360
tca                                                                  363

<210> SEQ ID NO 250
<211> LENGTH: 363
<212> TYPE: DNA
<213> ORGANISM: Artificial Sequence
<220> FEATURE:
<223> OTHER INFORMATION: CH7A (D99Y) Heavy Chain Construct

<400> SEQUENCE: 250
caggtgcagc tggtgcaatc tgggtctgag ttgaagaagc tggggcctc  agtgaaggtt    60 tcctgcaagg cttctggata caccttcact gagtttggaa tgaactgggt gcgacaggcc   120
cctggacaag gcttgagtg  gatgggatgg ataaacacca aaactggaga ggcaacatat   180
gttgaagagt ttaagggacg gtttgtcttc tccttggaca cctctgtcag cacggcatat   240
ctgcagatca gcagcctaaa ggctgaagac actgccgtgt attactgtgc gagatgggac   300
ttctattatt acgtggaggc tatggactac tggggccaag ggaccacggt caccgtctcc   360
tca                                                                  363

<210> SEQ ID NO 251
<211> LENGTH: 363
<212> TYPE: DNA
<213> ORGANISM: Artificial Sequence
<220> FEATURE:
<223> OTHER INFORMATION: CH7A (D99H) Heavy Chain Construct

<400> SEQUENCE: 251
caggtgcagc tggtgcaatc tgggtctgag ttgaagaagc tggggcctc  agtgaaggtt    60 tcctgcaagg cttctggata caccttcact gagtttggaa tgaactgggt gcgacaggcc   120
cctggacaag gcttgagtg  gatgggatgg ataaacacca aaactggaga ggcaacatat   180
gttgaagagt ttaagggacg gtttgtcttc tccttggaca cctctgtcag cacggcatat   240
ctgcagatca gcagcctaaa ggctgaagac actgccgtgt attactgtgc gagatgggac   300
ttctatcatt acgtggaggc tatggactac tggggccaag ggaccacggt caccgtctcc   360
tca                                                                  363

<210> SEQ ID NO 252
<211> LENGTH: 364
<212> TYPE: DNA
<213> ORGANISM: Artificial Sequence
<220> FEATURE:
<223> OTHER INFORMATION: CH7A (V101F) Heavy Chain Construct

<400> SEQUENCE: 252
ccaggtgcag ctggtgcaat ctgggtctga gttgaagaag cctggggcct cagtgaaggt    60 tcctgcaag  gcttctggat acaccttcac tgagtttgga atgaactggg tgcgacaggc   120
ccctggacaa gggcttgagt ggatgggatg gataaacacc aaaactggag aggcaacata   180
tgttgaagag tttaagggac ggtttgtctt ctccttggac acctctgtca gcacggcata   240
tctgcagatc agcagcctaa aggctgaaga cactgccgtg tattactgtg cgagatggga   300
cttctatgat tacttcgagg ctatggacta ctggggccaa gggaccacgg tcaccgtctc   360
ctca                                                                 364

<210> SEQ ID NO 253
<211> LENGTH: 364
<212> TYPE: DNA
```

<213> ORGANISM: Artificial Sequence
<220> FEATURE:
<223> OTHER INFORMATION: CH7A (E102Q) Heavy Chain Construct

<400> SEQUENCE: 253

| | |
|---|---|
| ccaggtgcag ctggtgcaat ctgggtctga gttgaagaag cctggggcct cagtgaaggt | 60 |
| ttcctgcaag gcttctggat acaccttcac tgagtttgga atgaactggg tgcgacaggc | 120 |
| ccctggacaa gggcttgagt ggatgggatg ataaacacc aaaactggag aggcaacata | 180 |
| tgttgaagag tttaagggac ggtttgtctt ctccttggac acctctgtca gcacggcata | 240 |
| tctgcagatc agcagcctaa aggctgaaga cactgccgtg tattactgtg cgagatggga | 300 |
| cttctatgat tacgtgcagg ctatggacta ctggggccaa gggaccacgg tcaccgtctc | 360 |
| ctca | 364 |

<210> SEQ ID NO 254
<211> LENGTH: 363
<212> TYPE: DNA
<213> ORGANISM: Artificial Sequence
<220> FEATURE:
<223> OTHER INFORMATION: CH7A (A103T) Heavy Chain Construct

<400> SEQUENCE: 254

| | |
|---|---|
| caggtgcagc tggtgcaatc tgggtctgag ttgaagaagc tggggcctc agtgaaggtt | 60 |
| tcctgcaagg cttctggata caccttcact gagtttggaa tgaactgggt gcgacaggcc | 120 |
| cctggacaag gcttgagtg gatgggatgg ataaacacca aaactggaga ggcaacatat | 180 |
| gttgaagagt ttaagggacg gtttgtcttc tccttggaca cctctgtcag cacggcatat | 240 |
| ctgcagatca gcagcctaaa ggctgaagac actgccgtgt attactgtgc gagatgggac | 300 |
| ttctatgatt acgtggagac tatggactac tggggccaag gaccacggt caccgtctcc | 360 |
| tca | 363 |

<210> SEQ ID NO 255
<211> LENGTH: 363
<212> TYPE: DNA
<213> ORGANISM: Artificial Sequence
<220> FEATURE:
<223> OTHER INFORMATION: CH7A (Y98A / D99Y) Heavy Chain Construct

<400> SEQUENCE: 255

| | |
|---|---|
| caggtgcagc tggtgcaatc tgggtctgag ttgaagaagc tggggcctc agtgaaggtt | 60 |
| tcctgcaagg cttctggata caccttcact gagtttggaa tgaactgggt gcgacaggcc | 120 |
| cctggacaag gcttgagtg gatgggatgg ataaacacca aaactggaga ggcaacatat | 180 |
| gttgaagagt ttaagggacg gtttgtcttc tccttggaca cctctgtcag cacggcatat | 240 |
| ctgcagatca gcagcctaaa ggctgaagac actgccgtgt attactgtgc gagatgggac | 300 |
| ttcgcttatt acgtggaggc tatggactac tggggccaag gaccacggt caccgtctcc | 360 |
| tca | 363 |

<210> SEQ ID NO 256
<211> LENGTH: 363
<212> TYPE: DNA
<213> ORGANISM: Artificial Sequence
<220> FEATURE:
<223> OTHER INFORMATION: CH7A (W95Y) Heavy Chain Construct

<400> SEQUENCE: 256

| | |
|---|---|
| caggtgcagc tggtgcaatc tgggtctgag ttgaagaagc tggggcctc agtgaaggtt | 60 |

```
tcctgcaagg cttctggata caccttcact gagtttggaa tgaactgggt gcgacaggcc      120
cctggacaag ggcttgagtg gatgggatgg ataaacacca aaactggaga ggcaacatat      180
gttgaagagt ttaagggacg gtttgtcttc tccttggaca cctctgtcag cacggcatat      240
ctgcagatca gcagcctaaa ggctgaagac actgccgtgt attactgtgc gagatacgac      300
ttctatgatt acgtggaggc tatggactac tggggccaag gaccacggt caccgtctcc       360 tca                                                                    363
```

```
<210> SEQ ID NO 257
<211> LENGTH: 121
<212> TYPE: PRT
<213> ORGANISM: Artificial Sequence
<220> FEATURE:
<223> OTHER INFORMATION: CH1A1

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Phe
    50                  55                  60

Lys Gly Arg Val Thr Phe Thr Leu Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

```
<210> SEQ ID NO 258
<211> LENGTH: 121
<212> TYPE: PRT
<213> ORGANISM: Artificial Sequence
<220> FEATURE:
<223> OTHER INFORMATION: CH1A2

<400> SEQUENCE: 258

Gln Val Lys Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Phe
    50                  55                  60

Lys Gly Arg Val Thr Met Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

<210> SEQ ID NO 259
<211> LENGTH: 121
<212> TYPE: PRT
<213> ORGANISM: Artificial Sequence
<220> FEATURE:
<223> OTHER INFORMATION: CH1A3

<400> SEQUENCE: 259

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Lys Gln Ala Pro Gly Lys Gly Leu Lys Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

<210> SEQ ID NO 260
<211> LENGTH: 121
<212> TYPE: PRT
<213> ORGANISM: Artificial Sequence
<220> FEATURE:
<223> OTHER INFORMATION: CH1A4

<400> SEQUENCE: 260

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Lys Tyr Phe Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

<210> SEQ ID NO 261
<211> LENGTH: 121
<212> TYPE: PRT
<213> ORGANISM: Artificial Sequence
<220> FEATURE:
<223> OTHER INFORMATION: CH1A1A

<400> SEQUENCE: 261

```
Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
            115                 120

<210> SEQ ID NO 262
<211> LENGTH: 121
<212> TYPE: PRT
<213> ORGANISM: Artificial Sequence
<220> FEATURE:
<223> OTHER INFORMATION: CH1A1B

<400> SEQUENCE: 262

Gln Val Lys Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
            115                 120

<210> SEQ ID NO 263
<211> LENGTH: 121
<212> TYPE: PRT
<213> ORGANISM: Artificial Sequence
<220> FEATURE:
<223> OTHER INFORMATION: CH1A1C

<400> SEQUENCE: 263

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

```
Met Glu Leu Arg Ser Leu Arg Ser Asp Asp Thr Ala Val Tyr Tyr Cys
            85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
            115                 120

<210> SEQ ID NO 264
<211> LENGTH: 121
<212> TYPE: PRT
<213> ORGANISM: Artificial Sequence
<220> FEATURE:
<223> OTHER INFORMATION: CH1A1D

<400> SEQUENCE: 264

Gln Val Gln Leu Val Gln Ser Gly Ala Glu Val Lys Lys Pro Gly Glu
1               5                   10                  15

Thr Val Lys Ile Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
            115                 120

<210> SEQ ID NO 265
<211> LENGTH: 121
<212> TYPE: PRT
<213> ORGANISM: Artificial Sequence
<220> FEATURE:
<223> OTHER INFORMATION: CH1A1E

<400> SEQUENCE: 265

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Phe Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
            115                 120

<210> SEQ ID NO 266
```

```
<211> LENGTH: 121
<212> TYPE: PRT
<213> ORGANISM: Artificial Sequence
<220> FEATURE:
<223> OTHER INFORMATION: CH1A1F

<400> SEQUENCE: 266
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Ser Thr Ala Tyr
65                  70                  75                  80

Leu Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 267
<211> LENGTH: 121
<212> TYPE: PRT
<213> ORGANISM: Artificial Sequence
<220> FEATURE:
<223> OTHER INFORMATION: CH1A1G

<400> SEQUENCE: 267
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Ile Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 268
<211> LENGTH: 363
<212> TYPE: DNA
<213> ORGANISM: Artificial Sequence
<220> FEATURE:
<223> OTHER INFORMATION: CH1A1

<400> SEQUENCE: 268
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
```

```
ccaggccagg gcctcgaatg gatgggctgg atcaacacca agaccggcga ggccacctac    180
gtggaagagt tcaagggcag agtgaccttc accctggaca ccagcaccag caccgcctac    240
atggaactgc ggagcctgag aagcgacgac accgccgtgt actactgcgc cagatgggac    300
ttctacgatt acgtggaagc catggactac tggggccagg gcaccaccgt gaccgtgtct    360
agc                                                                 363

<210> SEQ ID NO 269
<211> LENGTH: 363
<212> TYPE: DNA
<213> ORGANISM: Artificial Sequence
<220> FEATURE:
<223> OTHER INFORMATION: CH1A2

<400> SEQUENCE: 269
caggtcaaac tgcagcagag cggccctgag ctgaagaaac ccggcgagac agtgaagatc    60
agctgcaagg ccagcggcta caccttcacc gagttcggca tgaactgggt ccgacaggca    120
ccaggccagg gcctcgaatg gatgggctgg atcaacacca agaccggcga ggccacctac    180
gtggaagagt tcaagggcag agtgaccatg accaccgaca ccagcaccag caccgcctac    240
atggaactgc ggagcctgag aagcgacgac accgccgtgt actactgcgc cagatgggac    300
ttctacgatt acgtggaagc catggactac tggggccagg gcaccaccgt gaccgtgtct    360
agc                                                                 363

<210> SEQ ID NO 270
<211> LENGTH: 363
<212> TYPE: DNA
<213> ORGANISM: Artificial Sequence
<220> FEATURE:
<223> OTHER INFORMATION: CH1A3

<400> SEQUENCE: 270
caggtgcagc tggtgcagtc tggcgccgaa gtgaagaaac ctggcgccag cgtgaaggtg    60
tcctgcaagg ccagcggcta caccttcacc gagttcggca tgaactgggt caagcaggcc    120
cctggcaagg gcctgaagtg gatgggctgg atcaacacca agaccggcga ggccacctac    180
gtggaagagt tcaagggcag agtgaccatg accaccgaca ccagcaccag caccgcctac    240
atggaactgc ggagcctgag aagcgacgac accgccgtgt actactgcgc cagatgggac    300
ttctacgatt acgtggaagc catggactac tggggccagg gcaccaccgt gaccgtgtct    360
agc                                                                 363

<210> SEQ ID NO 271
<211> LENGTH: 362
<212> TYPE: DNA
<213> ORGANISM: Artificial Sequence
<220> FEATURE:
<223> OTHER INFORMATION: CH1A4

<400> SEQUENCE: 271
aggtgcagct ggtgcagtct ggcgccgaag tgaagaaacc tggcgccagc gtgaaggtgt    60
cctgcaaggc cagcggctac accttcaccg agttcggcat gaactgggtc cgacaggcac    120
caggccaggg cctcgaatgg atgggctgga tcaacaccaa gaccggcgag gccacctacg    180
tggaagagtt caagggcaga ttcgccttca gcctggaaac cagcgccacc accgcctacc    240
tgcagatcaa caacctgaag aacgaggata ccgccaagta cttctgcgcc agatgggact    300
tctacgatta cgtggaagcc atggactact ggggccaggg caccaccgtg accgtgtcta    360
```

-continued

```
gc                                                              362

<210> SEQ ID NO 272
<211> LENGTH: 363
<212> TYPE: DNA
<213> ORGANISM: Artificial Sequence
<220> FEATURE:
<223> OTHER INFORMATION: CH1A1A

<400> SEQUENCE: 272
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca agaccggcga ggccacctac     180
gtggaagagt tcaagggcag agtgaccttc accacggaca ccagcaccag caccgcctac     240
atggaactgc ggagcctgag aagcgacgac accgccgtgt actactgcgc cagatgggac     300
ttctacgatt acgtggaagc catggactac tggggccagg gcaccaccgt gaccgtgtct     360
agc                                                              363

<210> SEQ ID NO 273
<211> LENGTH: 363
<212> TYPE: DNA
<213> ORGANISM: Artificial Sequence
<220> FEATURE:
<223> OTHER INFORMATION: CH1A1B

<400> SEQUENCE: 273
caggtgaagc tgcagcagtc tggcgccgaa gtgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca agaccggcga ggccacctac     180
gtggaagagt tcaagggcag agtgaccatg accacggaca ccagcaccag caccgcctac     240
atggaactgc ggagcctgag aagcgacgac accgccgtgt actactgcgc cagatgggac     300
ttctacgatt acgtggaagc catggactac tggggccagg gcaccaccgt gaccgtgtct     360
agc                                                              363

<210> SEQ ID NO 274
<211> LENGTH: 363
<212> TYPE: DNA
<213> ORGANISM: Artificial Sequence
<220> FEATURE:
<223> OTHER INFORMATION: CH1A1C

<400> SEQUENCE: 274
caggtgcagc tggtgcagtc tggccccgaa ctgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca agaccggcga ggccacctac     180
gtggaagagt tcaagggcag agtgaccatg accacggaca ccagcaccag caccgcctac     240
atggaactgc ggagcctgag aagcgacgac accgccgtgt actactgcgc cagatgggac     300
ttctacgatt acgtggaagc catggactac tggggccagg gcaccaccgt gaccgtgtct     360
agc                                                              363

<210> SEQ ID NO 275
<211> LENGTH: 363
<212> TYPE: DNA
<213> ORGANISM: Artificial Sequence
<220> FEATURE:
```

<223> OTHER INFORMATION: CH1A1D

<400> SEQUENCE: 275

```
caggtgcagc tggtgcagtc tggcgccgaa gtgaagaaac ctggagagac tgtgaagatc      60
tcctgcaagg ccagcggcta caccttcacc gagttcggca tgaactgggt ccgacaggct     120
ccaggccagg gcctcgaatg gatgggctgg atcaacacca gaccggcga ggccacctac      180
gtggaagagt tcaagggcag agtgaccatg accacggaca ccagcaccag caccgcctac     240
atggaactgc ggagcctgag aagcgacgac accgccgtgt actactgcgc cagatgggac     300
ttctacgatt acgtggaagc catggactac tggggccagg gcaccaccgt gaccgtgtct     360
agc                                                                   363
```

<210> SEQ ID NO 276
<211> LENGTH: 363
<212> TYPE: DNA
<213> ORGANISM: Artificial Sequence
<220> FEATURE:
<223> OTHER INFORMATION: CH1A1E

<400> SEQUENCE: 276

```
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca gaccggcga ggccacctac      180
gtggaagagt tcaagggcag attcaccatg accacggaca ccagcaccag caccgcctac     240
atggaactgc ggagcctgag aagcgacgac accgccgtgt actactgcgc cagatgggac     300
ttctacgatt acgtggaagc catggactac tggggccagg gcaccaccgt gaccgtgtct     360
agc                                                                   363
```

<210> SEQ ID NO 277
<211> LENGTH: 363
<212> TYPE: DNA
<213> ORGANISM: Artificial Sequence
<220> FEATURE:
<223> OTHER INFORMATION: CH1A1F

<400> SEQUENCE: 277

```
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
ccaggccagg gcctcgaatg gatgggctgg atcaacacca gaccggcga ggccacctac      180
gtggaagagt tcaagggcag agtgaccatg accacggaca ccagcaccag caccgcctac     240
ctggaactgc ggagcctgag aagcgacgac accgccgtgt actactgcgc cagatgggac     300
ttctacgatt acgtggaagc catggactac tggggccagg gcaccaccgt gaccgtgtct     360
agc                                                                   363
```

<210> SEQ ID NO 278
<211> LENGTH: 363
<212> TYPE: DNA
<213> ORGANISM: Artificial Sequence
<220> FEATURE:
<223> OTHER INFORMATION: CH1A1G

<400> SEQUENCE: 278

```
caggtgcagc tggtgcagtc tggcgccgaa gtgaagaaac ctggagctag tgtgaaggtg      60
tcctgcaagg ccagcggcta caccttcacc gagttcggca tgaactgggt ccgacaggct     120
```

```
ccaggccagg gcctcgaatg gatgggctgg atcaacacca agaccggcga ggccacctac    180
gtggaagagt tcaagggcag agtgaccatg accacggaca ccagcaccag caccgcctac    240
atggaaatcc ggagcctgag aagcgacgac accgccgtgt actactgcgc cagatgggac    300
ttctacgatt acgtggaagc catggactac tggggccagg gcaccaccgt gaccgtgtct    360
agc                                                                  363
```

```
<210> SEQ ID NO 279
<211> LENGTH: 121
<212> TYPE: PRT
<213> ORGANISM: Artificial Sequence
<220> FEATURE:
<223> OTHER INFORMATION: CH1A

<400> SEQUENCE: 279
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

```
<210> SEQ ID NO 280
<211> LENGTH: 363
<212> TYPE: DNA
<213> ORGANISM: Artificial Sequence
<220> FEATURE:
<223> OTHER INFORMATION: CH1A

<400> SEQUENCE: 280
caggtgcagc tggtgcagtc tggcgctgag gtgaagaagc ctggcgcctc ggtgaaggtc    60
tcctgcaagg cctctggtta cacatttacg gaattcggga tgaattgggt cagacaagca    120
cctgggcaag gctcgagtg atgggatgg ataaacacga agacaggcga ggccacctac     180
gtagaagagt tcaaaggaag ggtcacgatg accacagata cttctacctc tactgcgtat    240
atggaactac ggagcttgcg tagcgatgac acagcggtgt actattgtgc tcgatgggat    300
ttctatgact atgttgaagc tatggactac tggggccaag ggaccaccgt gaccgtctcc    360
tca                                                                  363
```

```
<210> SEQ ID NO 281
<211> LENGTH: 121
<212> TYPE: PRT
<213> ORGANISM: Artificial Sequence
<220> FEATURE:
<223> OTHER INFORMATION: PR1A3

<400> SEQUENCE: 281
```

Gln Val Gln Leu Val Gln Ser Gly Ala Glu Val Lys Lys Pro Gly Ala
1               5                   10                  15

-continued

```
Ser Val Lys Val Ser Cys Lys Ala Ser Gly Tyr Thr Phe Thr Glu Phe
            20              25              30

Gly Met Asn Trp Val Arg Gln Ala Pro Gly Gln Gly Leu Glu Trp Met
        35              40              45

Gly Trp Ile Asn Thr Lys Thr Gly Glu Ala Thr Tyr Val Glu Glu Phe
        50              55              60

Lys Gly Arg Phe Val Phe Ser Leu Asp Thr Ser Val Ser Thr Ala Tyr
 65              70              75              80

Leu Gln Ile Ser Ser Leu Lys Ala Glu Asp Thr Ala Val Tyr Tyr Cys
            85              90              95

Ala Arg Trp Asp Phe Tyr Asp Tyr Val Glu Ala Met Asp Tyr Trp Gly
           100             105             110

Gln Gly Thr Thr Val Thr Val Ser Ser
            115             120
```

ANTI-CEA ANTIBODIES

RELATED APPLICATIONS

This application claims the benefit of European Patent Application No. 11156665.9, filed Mar. 2, 2011, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Jun. 11, 2012, is named P4655US_ST25.txt and is 165,776 bytes in size.

FIELD OF THE INVENTION

The present invention relates to antigen binding molecules (ABMs). In particular embodiments, the present invention relates to recombinant monoclonal antibodies, including chimeric, primatized or humanized antibodies which bind to human carcinoembryonic antigen (CEA).

BACKGROUND

Carcinoembryonic Antigen (CEA) and Anti-CEA Antibodies

Carcinoembryonic antigen (CEA, also known as CEACAM-5 or CD66e) is a glycoprotein having a molecular weight of about 180 kDa. CEA is a member of the immunoglobulin superfamily and contains seven domains that are linked to the cell membrane through a glycosylphosphatidylinositol (GPI) anchor (Thompson J. A., J Clin Lab Anal. 5:344-366, 1991) The seven domains include a single N-terminal Ig variable domain and six domains (A1-B1-A2-B2-A3-B3) homologous to the Ig constant domain (Hefta L J, et al., Cancer Res. 52:5647-5655, 1992).

The human CEA family contains 29 genes, of which 18 are expressed: 7 belonging to the CEA subgroup and 11 to the pregnancy-specific glycoprotein subgroup. Several CEA subgroup members are thought to possess cell adhesion properties. CEA is thought to have a role in innate immunity (Hammarström S., Semin Cancer Biol. 9(2):67-81 (1999)). Because of the existence of proteins closely related to CEA, it can be challenging to raise anti-CEA antibodies that are specific for CEA with minimal cross-reactivity to the other closely related proteins.

CEA has long been identified as a tumor-associated antigen (Gold and Freedman, J Exp Med., 121:439-462, 1965; Berinstein N. L., J Clin Oncol., 20:2197-2207, 2002). Originally classified as a protein expressed only in fetal tissue, CEA has now been identified in several normal adult tissues. These tissues are primarily epithelial in origin, including cells of the gastrointestinal, respiratory, and urogential tracts, and cells of colon, cervix, sweat glands, and prostate (Nap et al., Tumour Biol., 9(2-3):145-53, 1988; Nap et al., Cancer Res., 52(8):2329-23339, 1992).

Tumors of epithelial origin, as well as their metastases, contain CEA as a tumor associated antigen. While the presence of CEA itself does not indicate transformation to a cancerous cell, the distribution of CEA is indicative. In normal tissue, CEA is generally expressed on the apical surface of the cell (Hammarström S., Semin Cancer Biol. 9(2):67-81 (1999)), making it inaccessible to antibody in the blood stream. In contrast to normal tissue, CEA tends to be expressed over the entire surface of cancerous cells (Hammarström S., Semin Cancer Biol. 9(2):67-81 (1999)). This change of expression pattern makes CEA accessible to antibody binding in cancerous cells. In addition, CEA expression increases in cancerous cells. Furthermore, increased CEA expression promotes increased intercellular adhesions, which may lead to metastasis (Marshall J., Semin Oncol., 30(a Suppl. 8):30-6, 2003).

CEA is readily cleaved from the cell surface and shed into the blood stream from tumors, either directly or via the lymphatics. Because of this property, the level of serum CEA has been used as a clinical marker for diagnosis of cancers and screening for recurrence of cancers, particularly colorectal cancer (Goldenberg D M., The International Journal of Biological Markers, 7:183-188, 1992; Chau I., et al., J Clin Oncol., 22:1420-1429, 2004; Flamini et al., Clin Cancer Res; 12(23):6985-6988, 2006). This property also presents one of the challenges for using CEA as a target, since serum CEA binds most of the currently available anti-CEA antibodies, hindering them from reaching their target on the cell surface and limiting potential clinical effects.

Multiple monoclonal antibodies have been raised against CEA for research purposes, as diagnostic tools, and for therapeutic purposes (e.g., Nap et al., Cancer Res., 52(8):2329-23339, 1992; Sheahan et al., Am. J. Clin. Path. 94:157-164, 1990; Sakurai et al., J. Surg. Oncol., 42:39-46, 1989; Goldenberg D M., The International Journal of Biological Markers, 7:183-188, 1992; Ledermann J A, Br. J. Cancer, 58:654, 1988; Ledermann J A, Br. J. Cancer, 68:69-73, 1993; Pedley R B, et al., Br. J. Cancer, 68:69-73, 1993; Boxer G M, et al., Br. J. Cancer, 65:825-831, 1992). Chester et al. have isolated a single chain anti-CEA antibody from a phage display library to be used in radioimmunodetection and radioimmunotherapy (U.S. Pat. No. 5,876,691), and the antibody was subsequently humanized (U.S. Pat. No. 7,232,888). Anti-CEA antibodies have also been isolated from human phage display libraries (U.S. Pat. No. 5,872,215).

The mouse monoclonal antibody PR1A3 was raised by fusion of NS1 (P3/NS1/I-Ag-4-1) myeloma cells with spleen cells from mice immunized with normal colorectal epithelium (Richman P. I. and Bodmer W. F., Int. J. Cancer, 39:317-328, 1987). PR1A3 reacts strongly to both well- and poorly-differentiated colorectal carcinomas and has advantages over other colorectal epithelium-reactive antibodies since its antigen appears to be fixed to the tumor and does not appear in the lymphatics or normal lymph nodes draining a tumor (Granowska M. et al., Eur. J. Nucl. Med., 20:690-698, 1989). For example, PR1A3 reacted with 59/60 colorectal tumors (Richman P. I. and Bodmer W. F., Int. J. Cancer, 39:317-328, 1987), whereas the CEA reactive antibody B72.3 reacted with only 75% of colorectal tumors (Mansi L., et al., Int J Rad Appl Instrum B., 16(2):127-35, 1989).

Epitope mapping of PR1A3 shows that the antibody targets the B3 domain and the GPI anchor of the CEA molecule (Durbin H. et al., Proc. Natl. Scad. Sci. USA, 91:4313-4317, 1994). Consequently, the PR1A3 antibody binds only to the membrane-bound CEA, and not the soluble CEA form that can be found in the bloodstreams of cancer patients. Because of this binding property, the PR1A3 antibody is unlikely to be sequestered by the serum CEA; instead, it can target CEA expressed on cancerous cells. The epitope bound by PR1A3 is a conformational epitope, not a linear epitope, which is thought to contribute to the loss of binding of PR1A3 to soluble CEA (Stewart et al., Cancer Immunol Immunother, 47:299-06, 1999).

The PR1A3 antibody was previously humanized by grafting the CDRs of the murine parent antibody to the heavy chain framework regions 1-3 of the human antibody RF-TS3'CL (retaining the murine framework 4 of PR1A3) and the light chain framework regions of the REI antibody. (Stewart et al., Cancer Immunol Immunother, 47:299-06, 1999). This humanized version of PR1A3 retained specificity and for surface-expressed CEA with an affinity similar to that of the murine antibody (Stewart et al., Cancer Immunol Immunother, 47:299-06, 1999; U.S. Pat. No. 5,965,710). A humanized PR1A3 (hPR1A3) antibody was shown to induce targeted killing of colorectal cancer cell lines. (Conaghhan P. J., et al., Br. J. Cancer, 98(7):1217-1225). However, the affinity of hPR1A3 for CEA is relatively low.

Radio-labeled anti-CEA antibodies have been used in clinical trials in patients with colorectal cancer. For example, an $^{123}$I-labeled chimeric minibody T84.66 (cT84.66) was used in a pilot clinical study in patients with colorectal cancer. The radio-labeled minibody was able to target cancer cells. (Wong J. Y. et al., Clin Cancer Res. 10(15):5014-21, (2004)). In another example, $^{(131)}$I-labetuzumab, a radio-labeled humanized anti-CEA antibody, was tested in adjuvant radioimmunotherapy in patients with liver metastases of colorectal cancer, and was found to provide a promising survival advantage. (Liersch T., et al., Ann. Surg. Oncol. 14(9):2577-90, (2007)).

Antibody Glycosylation

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins et al., Nature Biotechnol. 14:975-81, 1996).

Mammalian cells have been the preferred hosts for production of therapeutic glycoproteins due to their capability to glycosylate proteins in the most compatible form for human application. (Cumming et al., Glycobiology 1:115-30, 1991; Jenkins et al., Nature Biotechnol. 14:975-981, 1996). Bacteria very rarely glycosylate proteins and, like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NS0- and SP2/0-mouse myeloma cells. More recently, production from transgenic animals has also been tested (Jenkins et al., Nature Biotechnol. 14:975-81, 1996).

All antibodies contain carbohydrate structures at conserved positions in the heavy chain constant regions, with each isotype possessing a distinct array of N-linked carbohydrate structures, which variably affect protein assembly, secretion or functional activity. (Wright A. and Morrison S. L., Trends Biotech. 15:26-32, 1997). The structure of the attached N-linked carbohydrate varies considerably, depending on the degree of processing, and can include high-mannose, multiply-branched as well as biantennary complex oligosaccharides. (Wright, A., and Morrison, S. L., Trends Biotech. 15:26-32, 1997). Typically, there is heterogeneous processing of the core oligosaccharide structures attached at a particular glycosylation site such that even monoclonal antibodies exist as a population of multiple glycoforms. Likewise, it has been shown that major differences in antibody glycosylation occur between cell lines, and even minor differences are seen for a given cell line grown under different culture conditions. (Lifely, M. R. et al., Glycobiology 5(8): 813-22, 1995).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umaña, P. et al., Nature Biotechnol. 17:176-180 (1999) and U.S. Pat. No. 6,602,684, the entire contents of which are hereby incorporated by reference in their entirety. IgG1-type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5:813-822 (1995); Jefferis, R., et al., Immunol Rev. 163:59-76 (1998); Wright, A. and Morrison, S. L., Trends Biotechnol. 15:26-32 (1997)).

Umaña et al. showed previously that overexpression of β(1,4)-N-acetylglucosaminyltransferase III ("GnTIII"), a glycosyltransferase catalyzing the formation of bisected oligosaccharides, in Chinese hamster ovary (CHO) cells significantly increases the in vitro ADCC activity of an anti-neuroblastoma chimeric monoclonal antibody (chCE7) produced by the engineered CHO cells. (See Umaña, P. et al., Nature Biotechnol. 17:176-180 (1999); and International Publication No. WO 99/54342, the entire contents of which are hereby incorporated by reference). The antibody chCE7 belongs to a large class of unconjugated mAbs which have high tumor affinity and specificity, but have too little potency to be clinically useful when produced in standard industrial cell lines lacking the GnTIII enzyme (Umana, P., et al., Nature Biotechnol. 17:176-180 (1999)). That study was the first to show that large increases of ADCC activity could be obtained by engineering the antibody-producing cells to express GnTIII, which also led to an increase in the proportion of constant region (Fc)-associated, bisected oligosaccharides, including bisected, nonfucosylated oligosaccharides, above the levels found in naturally-occurring antibodies.

There remains a need for enhanced therapeutic approaches targeting CEA, in particular, membrane-bound CEA for the treatment of cancers.

BRIEF SUMMARY OF THE INVENTION

One aspect of the invention provides a variant antigen binding molecule (ABM), such as an antibody, which binds membrane-bound human carcinoembryonic antigen (CEA). In one embodiment, the ABM has an increase in stability as compared to its parent molecule. In one embodiment, the ABM has an increase in stability and maintains, or has an improved, binding affinity for membrane-bound CEA as compared to its parent molecule. In one embodiment, ABM is stable at a temperature that is at least 0.5, 1.0, 1.5, or 2.0 degree Celcius higher than its parent molecule. In one embodiment, the increase in stability is measured using a dynamic light scattering assay. In some embodiments, the parent comparator molecule is PR1A3 antibody or humanized version of PR1A3 antibody. In one embodiment, the parent comparator molecule is a humanized version of PR1A3 antibody which comprises the heavy chain variable region CH7A (SEQ ID NO:101) and the light chain variable region 2F1 (SEQ ID NO: 209). In one embodiment, the variant antigen binding molecule is stable at 67 degrees Celsius or higher, as measured, for example by a dynamic light scattering assay. In one embodiment, the variant antigen binding molecule binds membrane-bound CEA at a Kd of 100 nM or lower. In one embodiment, the variant antigen binding molecule binds membrane-bound CEA at a Kd of 10 nM or lower.

In one embodiment, the ABM comprises a heavy chain variable region comprising a heavy chain CDR1 selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, and SEQ ID NO:12, a heavy chain CDR2 selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24, and a heavy chain CDR3 selected from the group consisting of SEQ ID NO:217, SEQ ID NO:218, SEQ ID NO:219 SEQ ID NO:220, SEQ ID NO:221, SEQ ID NO:222, SEQ ID NO:223, and SEQ ID NO:224. In one embodiment, the ABM comprises a light chain variable region comprising a light chain CDR1 selected from the group consisting of SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45, and a light chain CDR2 selected from the group consisting of SEQ ID NO:46, and SEQ ID NO:47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55, and a light chain CDR3 of SEQ ID NO:56. In another embodiment, the heavy chain variable region of the ABM comprises the heavy chain CDR1 of SEQ ID NO:1, the heavy chain CDR2 of SEQ ID NO:13, a heavy chain CDR3 selected from the group consisting SEQ ID NO:217, SEQ ID NO:218, SEQ ID NO:219 SEQ ID NO:220, SEQ ID NO:221, SEQ ID NO:222, SEQ ID NO:223, and SEQ ID NO:224; and the light chain variable region of the ABM comprises the light chain CDR1 of SEQ ID NO:39, the light chain CDR2 of SEQ ID NO:49, and the light chain CDR3 of SEQ ID NO:56. In a further embodiment, the ABM comprises the framework residues of CH1A1A (SEQ ID NO: 261) or CH1A1B (SEQ ID NO: 262).

In one embodiment, the heavy chain variable region of the ABM comprises an amino acid sequence that is at least 95% identical to a sequence selected from the group consisting of SEQ ID NO: 233, SEQ ID NO: 234, SEQ ID NO: 235, SEQ ID NO: 239, SEQ ID NO: 241, SEQ ID NO: 242, SEQ ID NO: 243, and SEQ ID NO: 247 and the light chain variable region of the ABM comprises an amino acid sequence that is at least 95% identical to the sequence of SEQ ID NO: 209. In one embodiment, the heavy chain variable region of the ABM comprises an amino acid sequence selected from the group consisting of SEQ ID NO: 233, SEQ ID NO: 234, SEQ ID NO: 235, SEQ ID NO: 239, SEQ ID NO: 241, SEQ ID NO: 242, SEQ ID NO: 243, and SEQ ID NO: 247 and the light chain variable region of the ABM comprises the amino acid sequence of SEQ ID NO: 209. In some embodiments, the ABM comprises an Fc region, for example, a human IgG Fc region. In certain embodiments, the ABM or is an antibody or fragment thereof, such as a whole antibody, an scFv fragment, an Fv fragment, an F(ab')2 fragment, a minibody, a diabody, a triabody, or a tetrabody.

Another aspect of the invention provides an isolated antibody which binds membrane-bound CEA, wherein the antibody comprises a heavy chain variable region comprising a heavy chain CDR1 selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, and SEQ ID NO:12, a heavy chain CDR2 selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24, and a heavy chain CDR3 selected from the group consisting of SEQ ID NO:217, SEQ ID NO:218, SEQ ID NO:219 SEQ ID NO:220, SEQ ID NO:221, SEQ ID NO:222, SEQ ID NO:223, and SEQ ID NO:224.

In one embodiment, the antibody has an increase in stability as compared to its parent molecule. In one embodiment, the antibody is stable at a temperature that is at at least 0.5, 1.0, 1.5, or 2.0 degree Celcius higher its parent molecule. In one embodiment, the increase in stability is measured using a dynamic light scattering assay. In some embodiments, the parent comparator molecule is PR1A3 antibody or humanized version of PR1A3 antibody. In one embodiment, the parent comparator moleucule is a humanized version of PR1A3 antibody which comprises the heavy chain variable region CH7A (SEQ ID NO:101) and the light chain variable region 2F1 (SEQ ID NO: 209). In one embodiment, the antibody is stable at 67 degrees Celsius or higher, as measured, for example by a dynamic light scattering assay. In one embodiment, the antibody binds membrane-bound CEA at a Kd of 100 nM or lower. In one embodiment the antibody binds membrane-bound CEA at a Kd of 10 nM or lower.

In one embodiment, the antibody also comprises a light chain variable region comprising a light chain CDR1 selected from the group consisting of SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45, and a light chain CDR2 selected from the group consisting of SEQ ID NO:46, and SEQ ID NO:47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55, and a light chain CDR3 of SEQ ID NO:56. In one embodiment, the heavy chain variable region of the antibody comprises the heavy chain CDR1 of SEQ ID NO:1, the heavy chain CDR2 of SEQ ID NO:13, a heavy chain CDR3 selected from the group consisting SEQ ID NO:217, SEQ ID NO:218, SEQ ID NO:219 SEQ ID NO:220, SEQ ID NO:221, SEQ ID NO:222, SEQ ID NO:223, and SEQ ID NO:224; and the light chain variable region of the antibody comprises the light chain CDR1 of SEQ ID NO:39, the light chain CDR2 of SEQ ID NO:49, and the light chain CDR3 of SEQ ID NO:56. In a further embodiment, the antibody comprises the framework residues of CH1A1A (SEQ ID NO: 261) or CH1A1B (SEQ ID NO: 262). In one embodiment, the heavy chain variable region of the antibody comprises an amino acid sequence that is at least 95% identical to a sequence selected from the group consisting of SEQ ID NO: 233, SEQ ID NO: 234, SEQ ID NO: 235, SEQ ID NO: 239, SEQ ID NO: 241, SEQ ID NO: 242, SEQ ID NO: 243, and SEQ ID NO: 247 and the light chain variable region of the antibody comprises an amino acid sequence that is at least 95% identical to the sequence of SEQ ID NO: 209. In one embodiment, the heavy chain variable region of the antibody comprises an amino acid sequence selected from the group consisting of SEQ ID NO: 233, SEQ ID NO: 234, SEQ ID NO: 235, SEQ ID NO: 239, SEQ ID NO: 241, SEQ ID NO: 242, SEQ ID NO: 243, and SEQ ID NO: 247 and the light chain variable region of the antibody comprises the amino acid sequence of SEQ ID NO: 209.

In certain embodiments, the ABM or antibody of the above embodiments binds the same epitope as, or is capable of competing for binding with, the murine monoclonal antibody PR1A3.

In one embodiment, the ABM or the antibody comprises an Fc region that has been glycoengineered. In one embodiment, at least about 20% to about 100% of the N-linked oligosaccharides in the Fc region of the glycoengineered antibody are nonfucosylated. In one embodiment, at least about 20% to about 100% of the N-linked oligosaccharides in the glycoengineered Fc region are bisected. In one embodiment, wherein at least about 20% to about 50% of the N-linked oligosaccharides in the glycoengineered Fc region are bisected, nonfucosylated. In one embodiment, the glycoengineered ABM or antibody has at least one increased effector function. The increased effector function is, for example, increased Fc receptor binding affinity, increased antibody-mediated cellular cytotoxicity (ADCC), increased binding to NK cells, increased binding to macrophages, increased binding to monocytes, increased binding to polymorphonuclear cells, direct signaling inducing apoptosis, increased dendritic cell maturation, and increased T cell priming. In one embodiment, the glycoengineered ABM or antibody has an increase in ADCC of at least about 40% to about 100% as compared to the non-glycoengineered parent antigen binding molecule.

Another aspect of the invention provides for an isolated polynucleotide encoding the ABM or antibody of any of above described embodiments. Another aspect of the invention provides for a vector comprising the polynucleotide encoding the ABM or antibody of any of above described embodiments. Another aspect of the invention provides for host cell comprising this vector.

Another aspect of the invention provides a composition comprising the ABM or antibody of any of above described embodiments and a pharmaceutically acceptable carrier.

Another aspect of the invention provides a method of inducing cell lysis of a tumor cell comprising contacting the tumor cell with the ABM or antibody of any of above described embodiments. In some embodiments, the tumor cell is a colorectal cancer cell, NSCLC (non-small cell lung cancer), gastric cancer cell, pancreatic cancer cell or breast cancer cell. In one embodiment, the cell lysis is induced by antibody dependent cell cytotoxicity of the ABM or antibody.

Another aspect of the invention provides a method of treating a subject having a cancer that abnormally expresses CEA, the method comprising administering to the subject a therapeutically effective amount of the ABM or antibody of any of above described embodiments Another aspect of the invention provides a method of increasing survival time in a subject having a cancer that abnormally expresses CEA, said method comprising administering to said subject a therapeutically effective amount of the ABM or antibody of any of above described embodiments. In one embodiment, the cancer is colorectal cancer, non-small cell lung cancer (NSCLC), gastric cancer, pancreatic cancer or breast cancer.

In certain embodiments of these methods, the ABM, antibody, or composition is administered in combination with chemotherapy or radiation therapy. In one embodiment, the subject is a human.

Another aspect of the invention provides for use of the ABM or antibody of any of above described embodiments in the manufacture of a medicament for treating a subject having a cancer that abnormally expresses CEA. In one embodiment, the cancer is selected from the group consisting of colorectal cancer, non-small cell lung cancer (NSCLC), gastric cancer, pancreatic cancer and breast cancer.

BRIEF DESCRIPTION OF THE FIGURES

FIG. 4 shows randomization sites for generating an antibody library for affinity maturation of the humanized PR1A3 antibody light chain (SEQ ID NO: 103). Positions marked with an X were randomized.

FIG. 32 shows the amino acid sequences of CDRs for various anti-CEA ABMs.

FIG. 33 shows the amino acid sequences of the light chain constructs for various anti-CEA ABMs.

FIG. 34A-B shows amino acid sequences of affinity matured heavy and light chain CDRs and associated binding affinities FIG. 35 shows affinity constants of the various affinity matured antibody sequences.

FIG. 36 shows the amino acid sequences of CDR-H3 of various anti-CEA ABMs.

FIG. 37A-C shows the amino acid sequences of VH regions of various anti-CEA ABMs.

FIG. 38 shows the amino acid sequence alignments of VH regions of various stability matured anti-CEA antibodies.

DETAILED DESCRIPTION OF THE INVENTION

Definitions

Figure 1:
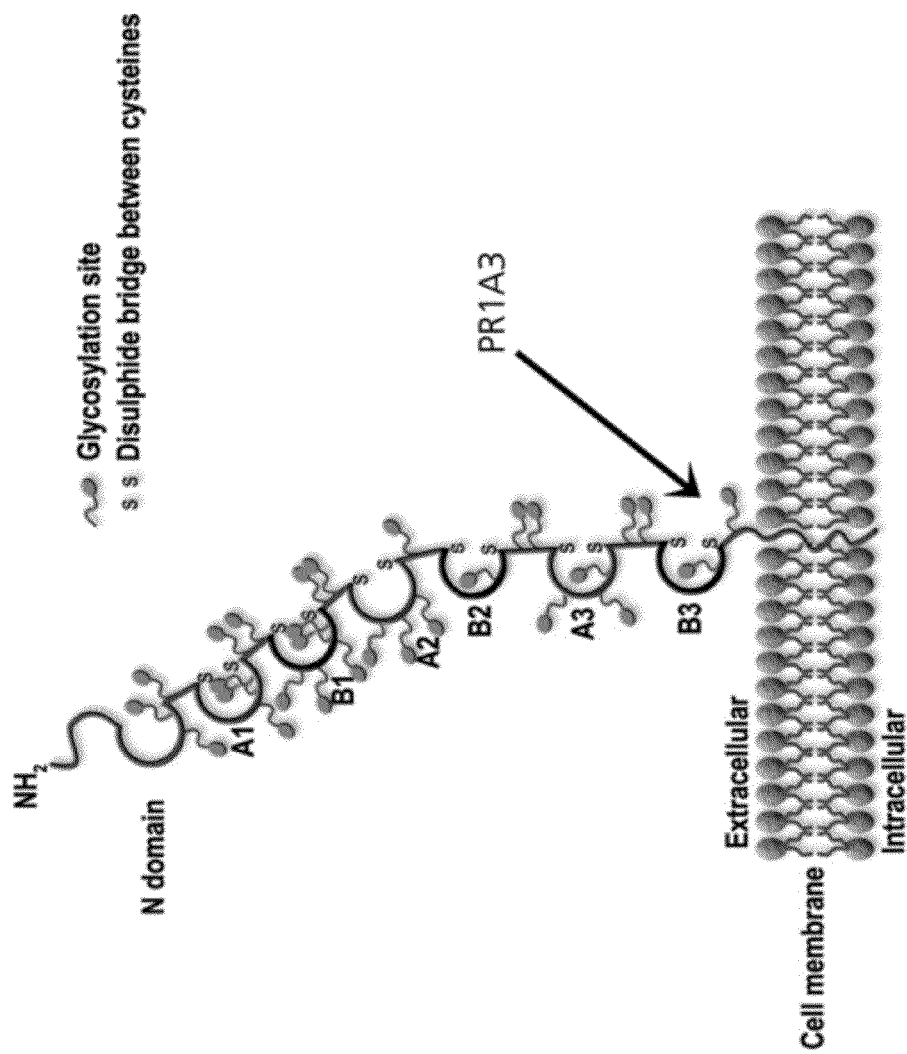
FIG. 1 shows a schematic diagram of the CEA (CEACAM-5, CD66e) antigen. The PR1A3 antibody binds specifically to the B3 domain of the antigen when it is bound to the cell membrane.

Terms are used herein as generally used in the art, unless otherwise defined as follows.

As used herein, the term "antigen binding molecule" refers in its broadest sense to a molecule that specifically binds an antigenic determinant. A non-limiting example of an antigen binding molecule is an antibody or fragment thereof that retains antigen-specific binding. More specifically, as used herein, an antigen binding molecule that binds membrane-bound human carcinoembryonic antigen (CEA) is a ABM that specifically binds to CEA, more particularly to cell surface or membrane-bound CEA. By "specifically binds" is meant that the binding is selective for the antigen and can be discriminated from unwanted or nonspecific interactions.

As used herein, the term "antibody" is intended to include whole antibody molecules, including monoclonal, polyclonal and multispecific (e.g., bispecific) antibodies, as well as antibody fragments having an Fc region and retaining binding specificity, and fusion proteins that include a region equivalent to the Fc region of an immunoglobulin and that retain binding specificity. Also encompassed are antibody fragments that retain binding specificity including, but not limited to, VH fragments, VL fragments, Fab fragments, F(ab')$_2$ fragments, scFv fragments, Fv fragments, minibodies, diabodies, triabodies, and tetrabodies (see, e.g., Hudson and Souriau, Nature Med. 9: 129-134 (2003)).

As used herein, the term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains. Preferably, an antigen binding domain comprises an antibody light chain variable region (VL) and an antibody heavy chain variable region (VH).

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

As used herein "binding affinity" is generally expressed in terms of equilibrium association or dissociation constants ($K_a$ or $K_d$, respectively), which are in turn reciprocal ratios of dissociation and association rate constants ($k_d$ and $k_a$, respectively). Thus, equivalent affinities may comprise different rate constants, so long as the ratio of the rate constants remains the same.

As used herein, the term "Fc region" refers to a C-terminal region of an IgG heavy chain. Although the boundaries of the Fc region of an IgG heavy chain might vary slightly, the human IgG heavy chain Fc region is usually defined to stretch from the amino acid residue at position Cys226 to the carboxyl-terminus.

As used herein, the term "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity. (See, e.g., Bowie, J. U. et al., Science 247:1306-10 (1990).

As used herein, the term "membrane-bound human CEA" refers to human carcinoembryonic antigen (CEA) that is bound to a membrane-portion of a cell or to the surface of a cell, in particular, the surface of a tumor cell. The term "membrane-bound human CEA" may, in certain circumstances, refer to CEA which is not bound to the membrane of a cell, but which has been constructed so as to preserve the epitope to which the PR1A3 antibody binds. The term "soluble CEA" refers to human carcinoembryonic antigen that is not bound to or is cleaved from a cell membrane or cell surface (e.g., a tumor cell surface) and/or which, typically, does not preserve the conformation epitope that is bound by the PR1A3 antibody. Soluble CEA can, for example, be found in the blood stream or lymphatics of a subject with cancer.

As used herein, the term "no substantial cross-reactivity against soluble" CEA means that a molecule (e.g., an antigen binding molecule) does not recognize or specifically bind to soluble CEA, particularly when compared to membrane-bound CEA. For example, an antigen binding molecule may bind less than about 10% to less than about 5% soluble CEA, or may bind soluble CEA at an amount selected from the group consisting of less than about 10%, 9%, 8% 7%, 6%, 5%, 4%, 3%, 2%, 1%, 0.5%, 0.2%, or 0.1%, preferably less than about 2%, 1%, or 0.5% soluble CEA, and most preferably less than about 0.2% or 0.1% soluble CEA.

As used herein, the terms "fusion" and "chimeric," when used in reference to polypeptides such as ABMs, refer to polypeptides comprising amino acid sequences derived from two or more heterologous polypeptides, such as portions of antibodies from different species. For chimeric ABMs, for example, the non-antigen binding components may be derived from a wide variety of species, including primates such as chimpanzees and humans. The constant region of the chimeric ABM is generally substantially identical to the constant region of a natural human antibody; the variable region of the chimeric antibody generally comprises a sequence that is derived from a recombinant anti-CEA antibody having the amino acid sequence of the murine PR1A3 variable region. Humanized antibodies are a particularly preferred form of fusion or chimeric antibody.

As used herein, the term "humanized" is used to refer to an antigen-binding molecule derived in part from a non-human antigen-binding molecule, for example, a murine antibody, that retains or substantially retains the antigen-binding properties of the parent molecule but which is less immunogenic in humans. This may be achieved by various methods (referred to herein as "humanization") including, but not limited to (a) grafting the entire non-human variable domains onto human constant regions to generate chimeric antibodies, (b) grafting only the non-human (e.g., donor antigen binding molecule) CDRs onto human (e.g., recipient antigen binding molecule) framework and constant regions with or without retention of critical framework residues (e.g., those that are important for retaining good antigen binding affinity or antibody functions), or (c) transplanting the entire non-human variable domains, but "cloaking" them with a human-like section by replacement of surface residues. Such methods are disclosed in Jones et al., Morrison et al., Proc. Natl. Acad. Sci., 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994), all of which are incorporated by reference in their entirety herein. There are generally 3 complementarity determining regions, or CDRs, (CDR1, CDR2 and CDR3) in each of the heavy and light chain variable domains of an antibody, which are flanked by four framework subregions (i.e., FR1, FR2, FR3, and FR4) in each of the heavy and light chain variable domains of an antibody: FR1-CDR1-FR2-CDR2-FR3-CDR3-FR4. A discussion of humanized antibodies can be found, inter alia, in U.S. Pat. No. 6,632,927, and in published U.S. Application No. 2003/0175269, both of which are incorporated herein by reference in their entirety. Humanization may also be achieved by transplanting truncated CDRs that contain only the specificity-determining amino acid residues for the given CDR onto a chosen framework. By "specificity-determining residues" is meant those residues that are directly involved in specific interaction with the antigen and/or which are necessary for antigen-specific binding. In general, only about one-fifth to one-third of the residues in a given CDR participate in binding to antigen. The specificity-determining residues in a particular CDR can be identified by, for example, computation of interatomic contacts from three-dimensional modeling and determination of the sequence variability at a given residue position in accordance with the methods described in Padlan et al., FASEB J. 9(1):133-139 (1995), the contents of which are hereby incorporated by reference in their entirety.

In some instances, framework region (FR) residues of the human immunoglobulin are replaced by corresponding non-human residues. Furthermore, humanized antigen binding molecules may comprise residues which are not found in the recipient antibody or in the donor antibody. These modifications are made to further refine antigen binding molecule performance. In general, the humanized antigen binding molecule will comprise substantially all of at least one, and typically two, variable domains, in which at least one, or substantially all, or all of the hypervariable regions correspond to those of a non-human immunoglobulin and all or substantially all of the FRs are those of a human immunoglobulin sequence. The humanized antigen binding molecule optionally also will comprise at least a portion of an immunoglobulin constant region (Fc), typically that of a human immunoglobulin. See, e.g., Jones et al., Nature 321:522-525 (1986); Reichmann et al., Nature 332:323-329 (1988); and Presta, Curr. Op. Struct. Biol. 2:593-596 (1992).

Similarly, as used herein, the term "primatized" is used to refer to an antigen-binding molecule derived from a non-primate antigen-binding molecule, for example, a murine antibody, that retains or substantially retains the antigen-binding properties of the parent molecule but which is less immunogenic in primates.

As used herein, the term "variant" (or analog) polynucleotide or polypeptide refers to a polynucleotide or polypeptide differing from a specifically recited polynucleotide or polypeptide of the invention by insertions, deletions, and substitutions, created using, e.g., recombinant DNA techniques. Specifically, recombinant variants encoding these same or similar polypeptides may be synthesized or selected by making use of the "redundancy" in the genetic code. Various codon substitutions, such as the silent changes that produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

As used herein, the term "variant anti-CEA antigen binding molecule" refers to a molecule that differs in amino acid sequence from a "parent" anti-CEA antigen binding molecule amino acid sequence by virtue of addition, deletion and/or substitution of one or more amino acid residue(s) in the parent antibody sequence. In a specific embodiment, the variant comprises one or more amino acid substitution(s) in one or more hypervariable region(s) or CDRs of the heavy and/or light chain of the parent antigen binding molecule. For example, the variant may comprise at least one, e.g. from about one to about ten (i.e., about 1, 2, 3, 4, 5, 6, 7, 8, 9, or 10), and preferably from about two to about five, substitutions in one or more hypervariable regions or CDRs (i.e., 1, 2, 3, 4, 5, or 6 hypervariable regions or CDRs) of the parent antigen binding molecule. A variant anti-CEA antigen binding molecule may also comprise one or more additions, deletions and/or substitutions in one or more framework regions of either the heavy or the light chain. Ordinarily, the variant will have an amino acid sequence having at least about 75%, 80%, 85%, 90%, 95%, 96%, 97%, 98%, 99%, or 100% amino acid sequence identity with the parent antigen binding molecule heavy or light chain variable domain sequences, typically at least about 80%, 90%, 95% or 99%. Identity with respect to a sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant antigen binding molecule retains the ability to bind membrane-bound human CEA. In one embodiment, the anti-CEA ABM binds the same epitope as that of the parent antigen binding molecule. In one embodiment, the anti-CEA ABM competes for binding to membrane-bound human CEA with the parent antigen binding molecule. In one embodiment, the anti-CEA ABM binds to membrane-bound human CEA and does not bind to soluble human CEA. The anti-CEA ABM has properties which are superior to those of the parent antigen binding molecule. For example, the variant may have a stronger binding affinity, increased stability, and/or enhanced ability to induce antibody-mediated cellular cytotoxicity in vitro and in vivo. In one embodiment, the anti-CEA ABM has increased stability and retains or has improved binding affinity for membrane-bound CEA and retains or has an enhanced ability to induce antibody-mediated cellular cytotoxicity in vitro and in vivo.

To analyze such properties, one should generally compare a variant antigen binding molecule and the parent antigen binding molecule in the same format; for example, an Fab form of the variant antigen binding molecule to an Fab form of the parent antigen binding molecule or a full length form of the variant antigen binding molecule to a full length form of the parent antigen binding molecule. In one embodiment, the variant antigen binding molecule has at least about 2-fold, 3-fold, 4-fold, 5-fold, 6-fold, 7-fold, 8-fold, 9-fold, 10-fold, 11-fold, 12-fold, 13-fold, 14-fold, 15-fold, 15-fold, 16-fold, 17-fold, 18-fold, 19-fold, or 20-fold enhancement in biological activity when compared to the parent antigen binding molecule. In one embodiment, the variant antigen binding molecule is a stability engineered variant that has increased stability as compared to the parent antigen binding molecule. Stability can be assayed by any method known in the art and by methods described herein, specifically in Examples 3-6. In specific embodiments, the variant antigen binding molecule has at least about a 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 15-fold, 16-fold, 17-fold, 18-fold, 19-fold, 20-fold, 40-fold, 50-fold, 100-fold increase in stability as compared to the parent antigen binding molecule.

In some embodiments, the variant antigen binding molecule exhibits an increase in stability that is measured as a change in stability parameter as compared to the parent antigen binding molecule. In some embodiments, the variant antigen binding molecule has at least about a 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 15-fold, 16-fold, 17-fold, 18-fold, 19-fold, 20-fold, 40-fold, 50-fold, 100-fold change in a stability parameter as compared to the parent antigen binding A stability parameter is for example, temperature at which the variant antigen binding molecule unfolds or denatures, the pressure at which the variant antigen binding molecule unfolds or denature, or the time required to denature or unfold the variant antigen binding molecule under conditions designed to render the variant antigen binding molecule unstable. In one embodiment, the increase in stability is determined by a thermal denaturation assay, for example by differential scanning calorimetry (DSC). In one embodiment, the increase in stability is determined by a chemical denaturation assay. In one embodiment, the increase in stability is determined using a high pressure assay. In another embodiment, the stability of the variant antigen binding molecule is determined using a fluorescence polarization assay. In one embodiment, the stability of the variant antigen binding molecule is determined using a dynamic light scattering (DLS) assay. (See the Examples and, for example, Nobbmann, U. et al., Biotech. Genetic Eng. Rev. 24:117-128 (2007). DLS monitors the integrity of a molecule, such as an antibody, where, in general, an increase in light scattering indicates protein unfolding or denaturation. The DLS of molecules can be examined as a function of temperature or chemical denaturants to compare relative stabilities. Those molecules that remain in their native conformation (little or no increase in DLS properties) are considered to be stable under the testing conditions. In one embodiment, the variant antigen binding molecule is stable at a temperature that is at least 0.25, 0.5, 1.0, 1.5, 2.0, 2.5, 3.0, 3.5, 4.0, 4.5, 5.0, 6.0, 7.0, 8.0, 9.0, or 10.0 degrees Celsius higher than the parent ABM, or other appropriate reference molecule, when analyzed using a dynamic light scattering assay. In one embodiment, the variant antigen binding molecule is stable at 60, 61, 62, 63, 64, 65, 66, 67, 68, 69, 70, 71, 72, 73, 74, 75, 76, 77, 78, 79, 80 degrees Celsius or higher. Thermal stability can be measured, for example, using DLS, DSC, or fluorescence polarization. In one embodiment, the thermal stability of the variant antigen binding molecule is measured using DLS. In one embodiment, the DLS assay is performed using 1 mg/ml of the ABM or variant ABM in a buffer of 20 mM Histidine and 140 mM NaCl at pH 6.0. The DLS assay is conducted starting at 25° C. with an incremental temperature increase of 0.05° C./min.

The term "parent" antigen binding molecule refers to an ABM that is used as the starting point or basis for the preparation of the variant. In a specific embodiment, the parent antigen binding molecule has a human framework region and, if present, has human antibody constant region(s). For example, the parent antibody may be a humanized or human antibody.

Amino acid "substitutions" can result in replacing one amino acid with another amino acid having similar structural and/or chemical properties, e.g., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are generally in the range of about 1 to about 20 amino acids, more specifically about 1 to about 10 amino acids, and even more specifically, about 2 to about 5 amino acids. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). The variation allowed may be experimentally determined by systematically making insertions, deletions, or substitutions of amino acids in a polypeptide molecule using recombinant DNA techniques and assaying the resulting recombinant variants for activity.

As used herein, the term "single-chain Fv" or "scFv" refers to an antibody fragment comprising a VH domain and a VL domain as a single polypeptide chain. Typically, the VH and VL domains are joined by a linker sequence. See, e.g., Pluckthun, in: The PHARMACOLOGY OF MONOCLONAL ANTIBODIES, vol. 113, Rosenburg and Moore eds. Springer-Verlag, New York, pp. 269-315 (1994).

As used herein, the term "minibody" refers to a bivalent, homodimeric scFv derivative that contains a constant region, typically the CH3 region of an immunoglobulin, preferably IgG, more preferably IgG1, as the dimerisation region. Generally, the constant region is connected to the scFv via a hinge region and/or a linker region. Examples of minibody proteins can be found in Hu et al. (1996), Cancer Res. 56: 3055-61.

As used herein, the term "diabody" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993). A triabody results from the formation of a trivalent trimer of three scFvs, yielding three binding sites, and a tetrabody is a tetravalent tetramer of four scFvs, resulting in four binding sites.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites (also known as antigen binding regions) found within the variable region of both heavy and light chain polypeptides. CDRs are also referred to as "hypervariable regions" and that term is used interchangeably herein with the term "CDR" in reference to the portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an ABM are according to the Kabat numbering system. The sequences of the sequence listing (i.e., SEQ ID NO:1 to SEQ ID NO:216) are not numbered according to the Kabat numbering system. However, one of ordinary skill in the art is familiar with how to convert the sequences in the Sequence Listing to Kabat numbering.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 80%, 85%, 90%, 95%, 96%, 97%, 98% or 99% identical to a nucleotide sequence or polypeptide sequence of the present invention can be determined conventionally using known computer programs. One method for determining the best overall match between a query sequence (a sequence of the present invention) and a subject sequence, also referred to as a global sequence alignment, can be determined using the FASTDB computer program based on the algorithm of Brutlag et al., Comp. App. Biosci. 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to a reference polypeptide can be determined conventionally using known computer programs. One method for determining the best overall match between a query sequence (a sequence of the present invention) and a subject sequence, also referred to as a global sequence alignment, can be determined using the FASTDB computer program based on the algorithm of Brutlag et al., Comp. App. Biosci. 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

Percent identity of polynucleotides and/or polypeptides can also be determined using the BLAST programs available through the National Center for Biotechnology Information (NCBI), with the default parameters indicated in the programs.

As used herein, a nucleic acid that "hybridizes under stringent conditions" to a nucleic acid sequence of the invention, refers to a polynucleotide that hybridizes under specified conditions, e.g., in an overnight incubation at 42° C. in a solution comprising 50% formamide, 5×SSC (750 M NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

As used herein, the term "polypeptide having GnTIII activity" refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about three-fold less activity relative to the GnTIII.).

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "effector function" refers to those biological activities attributable to the Fc region (a native sequence Fc region or amino acid sequence variant Fc region) of an antibody. Examples of antibody effector functions include, but are not limited to, Fc receptor binding affinity, antibody-dependent cellular cytotoxicity (ADCC), antibody-dependent cellular phagocytosis (ADCP), cytokine secretion, immune-complex-mediated antigen uptake by antigen-presenting cells, down-regulation of cell surface receptors, etc.

As used herein, the terms "engineer, engineered, engineering" particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

As used herein, the term "host cell" covers any kind of cellular system which can be engineered to generate the polypeptides and antigen-binding molecules of the present invention. In one embodiment, the host cell is engineered to allow the production of an antigen binding molecule with modified glycoforms. In a preferred embodiment, the antigen binding molecule, or variant antigen binding molecule, is an antibody, antibody fragment, or fusion protein. In certain embodiments, the host cells have been further manipulated to express increased levels of one or more polypeptides having GnTIII activity. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term "Fc-mediated cellular cytotoxicity" includes antibody-dependent cellular cytotoxicity (ADCC) and cellular cytotoxicity mediated by a soluble Fc-fusion protein containing a human Fc-region. It is an immune mechanism leading to the lysis of "targeted cells" by "human immune effector cells."

As used herein, the term "human immune effector cells" refers to a population of leukocytes that display Fc receptors on their surfaces, through which they bind to the Fc-region of antigen binding molecules or of Fc-fusion proteins and perform effector functions. Such a population may include, but is not limited to, peripheral blood mononuclear cells (PBMC) and/or natural killer (NK) cells.

As used herein, the term "targeted cells" refers to cells to which antigen binding molecules comprising an Fc region (e.g., antibodies or fragments thereof comprising an Fc region) or Fc-fusion proteins specifically bind. The antigen binding molecules or Fc fusion-proteins bind to target cells via the protein part that is N-terminal to the Fc region.

As used herein, the term "increased Fc-mediated cellular cytotoxicity" is defined as either an increase in the number of "targeted cells" that are lysed in a given time, at a given concentration of antigen binding molecule or of Fc-fusion protein in the medium surrounding the target cells, by the mechanism of Fc-mediated cellular cytotoxicity defined above, and/or a reduction in the concentration of antigen binding molecule or of Fc-fusion protein, in the medium surrounding the target cells, required to achieve the lysis of a given number of "targeted cells," in a given time, by the mechanism of Fc-mediated cellular cytotoxicity. The increase in Fc-mediated cellular cytotoxicity is relative to the cellular cytotoxicity mediated by the same antigen binding molecule or Fc-fusion protein produced by the same type of host cells, using the same standard production, purification, formulation and storage methods, (which are known to those skilled in the art) but that has not been produced by host cells engineered to have an altered pattern of glycosylation (e.g., to express the glycosyltransferase, GnTIII, or other glycosyltransferases) by the methods described herein.

By "antigen binding molecule having increased antibody dependent cellular cytotoxicity (ADCC)" is meant an antigen binding molecule, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at 5×106 cells/ml in RPMI cell culture medium;
   ii) the target cells are grown by standard tissue culture methods, harvested from the exponential growth phase with a viability higher than 90%, washed in RPMI cell culture medium, labeled with 100 micro-Curies of 51Cr, washed twice with cell culture medium, and resuspended in cell culture medium at a density of 105 cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microtiter plate is then centrifuged at 50×g for 1 minute and incubated for 1 hour at 4° C.;
   viii) 50 microliters of the PBMC suspension (point i above) are added to each well to yield an effector:target cell ratio of 25:1 and the plates are placed in an incubator under 5% CO2 atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

Anti-CEA Antigen Binding Molecules, Polypeptides, and Polynucleotides

CEA has long been used as a cancer marker for diagnostic purposes. It is abnormally expressed (e.g., overexpressed and/or distributed in a different pattern in the cell) in many tumor tissues compared to non-tumor tissues of the same cell type. However, because CEA is generally cleaved from the tumor cell surface and most of the available anti-CEA antibodies also bind soluble CEA, unconjugated antibodies to CEA are generally not used for therapeutic purposes. For example, the anti-CEA antibodies that are currently in pilot trials are administered as radioconjugates (Wong et al., 2004; Liersch et al., 2007). Several mechanisms are involved in the therapeutic efficacy of anti-CEA antibodies, including antibody dependent cellular cytotoxicity (ADCC) and complement-dependent cytotoxicity (CDC). Increased CEA expression promotes increased intercellular adhesion, which may lead to metastasis of cancerous cells (Marshall J., Semin Oncol. 30(3) Suppl. 8:30-36). Thus, anti-CEA antigen binding molecules may also play a role in inhibiting CEA-mediated cell adhesion and metastasis of cancerous cells.

In one aspect, the invention is directed to a variant antigen binding molecule (e.g., an antibody or fragment thereof) comprising one or more (e.g., one, two, three, four, five, or six) CDRs of the murine PR1A3 antibody, wherein at least one of the CDRs has substitution of at least one amino acid residue compared to the corresponding CDR of PR1A3, and wherein the variant antigen binding molecule has improved affinity for CEA, preferably membrane-bound CEA compared to a parent PR1A3 antigen binding molecule. International Patent Application WO2011023787 describes anti-CEA antigen binding molecules with improved affinity for CEA as compared to a parent PR1A3 antigen binding molecule.

In another aspect, the invention is directed to a variant antigen binding molecule comprising one or more (e.g., one, two, three, four, five, or six) CDRs of the murine PR1A3 antibody, wherein at least one of the CDRs has a substitution of at least one amino acid residue compared to the corresponding CDR of PR1A3, and wherein the variant antigen binding molecule has increased stability compared to a parent PR1A3 antigen binding molecule. In one embodiment, the parent PR1A3 antigen binding molecule is a humanized PR1A3 antigen binding molecule. In one embodiment, the parent PR1A3 antigen binding molecule comprises the heavy chain variable region of CH7A (SEQ ID NO:101). In one embodiment, the parent PR1A3 antigen binding molecule comprises the heavy chain variable regions CH7A (SEQ ID NO:101) and the light chain variable region 2F1 (SEQ ID NO: 209). Such one or more CDRs can be truncated CDRs and will contain, at a minimum, the specificity-determining residues (SDRs), as that term is defined herein, for a given CDR. In one embodiment, the variant antigen binding molecule comprises at least one (e.g., one, two, three, four, five or six) of the CDRs selected from SEQ ID NOs: 1-3, 5-10, 12-56 and 217-224 (FIG. 32 and FIG. 36), comprising the residues of the CDRs that will retain specific binding. In another embodiment, the variant antigen binding molecule comprises at least one (e.g., one, two, three, four, five, or six) CDR selected from SEQ ID NOs: 1-3, 5-10, 12-56 and 217-224, or a variant or truncated form thereof containing at least the specificity-determining residues for said CDR, and comprising a sequence derived from a heterologous polypeptide. In a specific embodiment, where the variant antigen binding molecule comprises a heavy chain CDR1 variant of PR1A3, the HCDR1 has a glutamate substituted for a valine at Kabat position 31. In a specific embodiment, where the variant antigen binding molecule comprises a heavy chain CDR3 variant of PR1A3, the HCDR3 has an alanine substituted for a tyrosine at Kabat position 98 or a tyrosine substituted for an aspartate at Kabat position 99. In a specific embodiment, where the variant antigen binding molecule comprises a heavy chain CDR3 variant of PR1A3, the HCDR3 has an alanine substituted for a tyrosine at Kabat position 98 and a tyrosine substituted for an aspartate at Kabat position 99.

In one embodiment, the variant antigen binding molecule comprises one heavy chain CDR3 selected from SEQ ID NOs: 217-224 (FIG. 36) and two heavy chain CDRs (e.g., HCDR1 and HCDR2) selected from SEQ ID NOs: 1-3, 5-10, and 12-24 and/or three light chain CDRs (e.g. LCDR1, LCDR2, and LCDR3) selected from SEQ ID NOs: 36-56, or variants or truncated forms thereof containing at least the specificity-determining residues for each of the CDRs. In a more specific embodiment, the variant antigen binding molecule comprises one heavy chain CDR3 selected from SEQ ID NOs: 217-224 and two heavy chain CDRs (e.g., HCDR1 and HCDR2) selected from SEQ ID NOs: 1-3, 5-10, and 12-24 and three light chain CDRs (e.g. LCDR1, LCDR2, and LCDR3) selected from SEQ ID NOs: 36-56. In another embodiment, the variant antigen binding molecule comprises the variable region(s) of an antibody light and/or heavy chain, preferably both a heavy and light chain variable region. In a more particular embodiment, the heavy chain and/or light chain variable region is selected from the heavy and/or light chain variable region selected from SEQ ID NOs: 99-108, SEQ ID NOs: 188-216, and SEQ ID NOs: 225-248 (FIG. 33 and FIG. 37A-C) or a combination thereof, wherein, the heavy and light chain variable region is not a combination of SEQ ID NO:99 and SEQ ID NO:103 or SEQ ID NO:100 and SEQ ID NO:104. In some embodiments, the heavy chain comprises the framework residues of CH1A1A (SEQ ID NO: 261) or CH1A1B (SEQ ID NO: 262) (FIG. 37C). In one embodiment, the variant antigen binding molecule comprises a heavy chain variable region selected from SEQ ID NO: 225, SEQ ID NO: 226, SEQ ID NO: 231, SEQ ID NO: 234, SEQ ID NO: 235, SEQ ID NO: 239, SEQ ID NO: 241, SEQ ID NO: 242, SEQ ID NO: 243, or SEQ ID NO: 247.

In one embodiment, the variant antigen binding molecule is a chimeric antibody, more specifically, a humanized antibody. In another embodiment, the variant antigen binding molecule comprises an Fc region. In another embodiment, the variant antigen binding molecule is affinity matured. In another embodiment, the variant antigen binding molecule is engineered to have increased stability (stability matured). In another embodiment, the variant antigen binding molecule has increased ADCC activity compared to PR1A3. In one embodiment, the increased ADCC of the variant antigen binding molecule is due to an increase in affinity of the variant antigen binding molecule for membrane-bound CEA, for example by affinity maturation or other methods of improving affinity (see Tang et al., J. Immunol. 2007, 179:2815-2823, the entire contents of which is herein incorporated by reference). In another embodiment, the variant antigen binding molecule comprises an Fc region that is glycoengineered. In another aspect, the invention is also directed to methods of making such variant antigen binding molecules and their use in the treatment of disease, particularly cell proliferation disorders wherein CEA is expressed, particularly wherein CEA is abnormally expressed (e.g., overexpressed or expressed in a different pattern in the cell) compared to normal tissue of the same cell type. Such disorders include, but are not limited to colorectal cancer, NSCLC (non-small cell lung cancer), gastric cancer, pancreatic cancer and breast cancer. CEA expression levels may be determined by methods known in the art and those described herein (e.g., via immunohistochemistry assay, immunofluorescence assay, immunoenzyme assay, ELISA, flow cytometry, radioimmunoassay, Western blot, ligand binding, kinase activity, etc.).

In another aspect, the invention is also directed to an isolated polynucleotide comprising a sequence that encodes a polypeptide comprising one or more (e.g., one, two, three, four, five, or six) complementarity determining regions of the murine PR1A3 antibody, or variants or truncated forms thereof containing at least the specificity-determining residues for said complementarity determining regions. Typically, such isolated polynucleotides encode one or more fusion polypeptides that form an antigen binding molecule. In one embodiment, the polynucleotide comprises a sequence encoding one or more (e.g., one, two, three, four, five or six) of the CDRs selected from SEQ ID NOs: 1-3, 5-10, 12-56 and 217-224, comprising the residues of the CDRs that will retain specific binding. In one embodiment, the polynucleotide comprises a sequence that encodes at least three heavy chain CDRs (e.g., HCDR1, HCDR2, and HCDR3) and/or three light chain CDRs (e.g. LCDR1, LCDR2, and LCDR3 selected from SEQ ID NOs: 1-3, 5-10, 12-56 and 217-224, or variants or truncated forms thereof containing at least the specificity-determining residues (SDRs) for each of said three complementarity determining regions. In a more specific embodiment, the polynucleotide encodes a polypeptide comprising one heavy CDR3 selected from SEQ ID NOs: 217-224 and two heavy chain CDRs (e.g., HCDR1 and HCDR2) selected from SEQ ID NOs: 1-3, 5-10, and 12-24 and three light chain CDRs (e.g. LCDR1, LCDR2, and LCDR3) selected from SEQ ID NOs: 36-56. In another embodiment, the polynucleotide encodes a polypeptide comprising the variable region(s) of an antibody light and/or heavy chain. The polynucleotides encoding the heavy and light chain variable region polypeptides can be expressed in one or more expression vectors. In a more particular embodiment, the polynucleotide encoding a heavy chain and/or light chain variable region selected from SEQ ID NOs: 99-108, SEQ ID NOs: 188-216, and SEQ ID NOs: 225-248 is selected from the group of polynucleotides of SEQ ID NOs: 159-187 and SEQ ID NOs: 249-256 or a combination thereof, wherein, the heavy and light chain variable regions are not encoded by a combination of SEQ ID NO:11 and SEQ ID NO:115 or SEQ ID NO:112 and SEQ ID NO:116. In one embodiment, the heavy and light chain variable region polypeptides encoded by the polynucleotides combine to form a chimeric antibody, more specifically, a humanized antibody. In a specific embodiment, where the polynucleotide comprises a sequence that encodes heavy chain CDR1 of PR1A3 or a variant thereof, said polynucleotide encodes a glutamate substituted for a valine at Kabat position 31. In a specific embodiment, where the polynucleotide comprises a sequence that encodes heavy chain CDR3 of PR1A3 or a variant thereof, said polynucleotide encodes an alanine substituted for a tyrosine at Kabat position 98 or a tyrosine substituted for an aspartate at Kabat position 99. In a specific embodiment, where the polynucleotide comprises a sequence that encodes heavy chain CDR3 of PR1A3 or a variant thereof, said polynucleotide encodes an alanine substituted for a tyrosine at Kabat position 98 and a tyrosine substituted for an aspartate at Kabat position 99. In one embodiment, the polynucleotide encodes an alanine substituted for a tyrosine at Kabat position 98 or a tyrosine substituted for an aspartate at Kabat position 99 in the framework of CH1A1A (SEQ ID NO: 261) or CH1A1B (SEQ ID NO: 262). In one embodiment, the polynucleotide comprises a sequence encodes the heavy chain of SEQ ID NO: 225, SEQ ID NO: 226, SEQ ID NO:231, SEQ ID NO:234, SEQ ID NO:235, SEQ ID NO:239, SEQ ID NO:241, SEQ ID NO: 242, SEQ ID NO: 243, or SEQ ID NO: 247. In another embodiment, the polynucleotide comprises a sequence that encodes an Fc region. The invention is further directed to the polypeptides encoded by such polynucleotides.

In one aspect, the present invention is related to antigen binding molecules or variant antigen binding molecules (e.g., an antibody or fragment thereof) and polypeptides having the same binding specificity of the murine PR1A3 antibody (e.g., binding to the same epitope of membrane-bound CEA), and having comparable or improved biological activities (e.g., improved affinity for membrane-bound CEA, increased stability, and/or enhanced ADCC). In one embodiment, the variant antigen binding molecule binds the same epitope as that of the parent antigen binding molecule. In one embodiment, the variant antigen binding molecule competes for binding to membrane-bound human CEA with the parent antigen binding molecule. In one embodiment, the variant antigen binding molecule binds to membrane-bound human CEA and does not bind to soluble human CEA. In one aspect, the present invention is related to antigen binding molecules and the variant antigen binding molecule and polypeptides having increased stability as compared to murine PR1A3 antibody, or humanized variant thereof. In one aspect, the present invention is related to antigen binding molecules and variant antigen binding molecules (e.g., an antibody or fragment thereof) and polypeptides which bind membrane bound CEA and have an increased stability as compared to a humanized PR1A3 antibody which comprises the heavy chain variable region of CH7A (SEQ ID NO:101). In one aspect, the present invention is related to antigen binding molecules and variant antigen binding molecules (e.g., an antibody or fragment thereof) and polypeptides which bind membrane bound CEA and have increased stability as compared to a humanized PR1A3 antibody which comprises the heavy chain variable region CH7A (SEQ ID NO:101) and the light chain variable region 2F1 (SEQ ID NO: 209)

In one embodiment, the variant antigen binding molecule or polypeptide comprises at least one (e.g., one, two, three, four, five or six) of the CDRs selected from SEQ ID NOs: 1-3, 5-10, 12-56 and 217-224 (FIG. 32 and FIG. 36). In one embodiment, the variant antigen binding molecule or polypeptide comprises: (a) a heavy chain CDR1 sequence selected from the group consisting of: SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, and SEQ ID NO:12; (b) a heavy chain CDR2 sequence from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24: and (c) a heavy chain CDR3 sequence selected from the group consisting of: SEQ ID NO:217, SEQ ID NO:218, SEQ ID NO:219, SEQ ID NO:220, SEQ ID NO:221, SEQ ID NO:222, SEQ ID NO:223, and SEQ ID NO:224. In another embodiment, the variant antigen binding molecule or polypeptide comprises: (a) a light chain CDR1 sequence selected from the group consisting of: SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45; (b) a light chain CDR sequence selected from the group consisting of: SEQ ID NO:46, and SEQ ID NO:47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55; and (c) a light chain CDR3 of SEQ ID NO:56. In some embodiments, the variant antigen binding molecule or polypeptide comprising the CDRs also comprise the framework residues of CH1A1A (SEQ ID NO: 261) or CH1A1B (SEQ ID NO: 262).

In one aspect, the invention is directed to a variant antigen binding molecule or polypeptide which binds membrane-bound human CEA comprising a heavy chain variable region and/or a light chain variable region. In one embodiment, the heavy chain and/or light chain variable region is selected from the heavy and/or light chain variable region selected from SEQ ID NOs: 99-108, SEQ ID NOs: 188-216, and SEQ ID NOs: 225-248 (FIG. 33 and FIG. 37A-C). In one embodiment, the heavy chain variable region comprises a polypeptide having the sequence of any one of SEQ ID NOs: 225-248. In another specific embodiment, the heavy chain variable region comprises a polypeptide having a sequence that is at least about 80%, 85%, 90%, 95%, 96%, 97%, 98% or 99% identical to the sequence of any one of SEQ ID NOs: 225-248.

In one embodiment, the heavy chain variable region comprises a polypeptide having the sequence of SEQ ID NO: 233; SEQ ID NO: 234, SEQ ID NO: 235, SEQ ID NO: 239, SEQ ID NO: 241, SEQ ID NO: 242, SEQ ID NO: 243, and SEQ ID NO: 247. In another embodiment, the heavy chain variable region comprises a polypeptide having at least about 80%, 85%, 90%, 95%, 96%, 97%, 98%, or 99% identity to the sequence of SEQ ID NO: 233, SEQ ID NO: 234, SEQ ID NO: 235, SEQ ID NO: 239, SEQ ID NO: 241, SEQ ID NO: 242, SEQ ID NO: 243, and SEQ ID NO: 247. In one embodiment, the light chain variable region comprises a polypeptide having the sequence of SEQ ID NO: 209. In another embodiment, the heavy chain variable region comprises a polypeptide having at least about 80%, 85%, 90%, 95%, 96%, 97%, 98%, or 99% identity to the sequence of SEQ ID NO: 209.

In one embodiment, the antigen binding molecule, variant antigen binding molecule, or polypeptide which binds membrane-bound human CEA comprises a heavy chain variable region and a light chain variable region. In a specific embodiment, the heavy chain variable region comprises a polypeptide having the sequence of SEQ ID NO:4 as follows:

```
QVQLVQSGSELKKPGASVKVSCKASGYTFTEX¹X²MX³WVRQAPGQ

GLEWMGX⁴INTKX⁵GEAX⁶YX⁷EEFKGRFVFSLDTSVSTAYLQISSLK

AEDTAVYYCARWDX⁸X⁹X¹⁰YX¹¹X¹²X¹³X¹⁴DYWGQGTTVTVSS
``` wherein $X^1$ is Y or F; $X^2$ is S or G; $X^3$ is N or S; $X^4$ is W or Y; $X^5$ is N, T or S; $X^6$ is T or N; $X^7$ is V or I; $X^8$ is F or A; $X^9$ is Y, A, V, F or S; $X^{10}$ is D, H, W, E, or Y; $X^{11}$ is V, L or F; $X^{12}$ is E, K or Q; $X^{13}$ is A or T; and $X^{14}$ is M or L.

In a specific embodiment, the light chain variable region comprises a polypeptide having the sequence of SEQ ID NO:11 as follows:

DIQMTQSPSSLSASVGDRVTITCKASX15X16X17X18X19X20VAWYQQ

KPGKAPKX21LIYX22ASX23X24X25X26GVPSRFSGSGSGTDFTLTIS

SLQPEDFATYYCHQYYTYPLFTFGQGTKLEIK wherein X15 is Q, A, K, or H; X16 is N, A, Y, I, K, T, or F; X17 is V, A, G, or M; X18 is G, S, T, or L; X19 is T, N, P, or A; X20 is N or Y; X21 is P or L; X22 is S, L, or W; X23 is Y, N, or H; X24 is R, L, P, or H; X25 is Y, S, Q, K, E, F, or P; and X26 is S, G, I, or R.

In another aspect, the invention is further directed to isolated polynucleotides encoding the antigen binding molecules, variant antigen binding molecules, or polypeptides which bind membrane-bound CEA. In one embodiment, the polynucleotide comprises a sequence that encodes at least three heavy chain CDRs (e.g., HCDR1, HCDR2, and HCDR3) and/or three light chain CDRs (e.g. LCDR1, LCDR2, and LCDR3 selected from SEQ ID NOs: 1-3, 5-10, 12-56 and 217-224, or variants or truncated forms thereof containing at least the specificity-determining residues (SDRs) for each of said three complementarity determining regions. In a more specific embodiment, the polynucleotide encodes a polypeptide comprising one heavy CDR3 selected from SEQ ID NOs: 217-224 and two heavy chain CDRs (e.g., HCDR1 and HCDR2) selected from SEQ ID NOs: 1-3, 5-10, and 12-24 and three light chain CDRs (e.g. LCDR1, LCDR2, and LCDR3) selected from SEQ ID NOs: 36-56. In another embodiment, the polynucleotide encodes a polypeptide comprising the variable region(s) of an antibody light and/or heavy chain. The polynucleotides encoding the heavy and light chain variable region polypeptides can be expressed in one or more expression vectors. In a more particular embodiment, the polynucleotide encoding a heavy chain and/or light chain variable region selected from SEQ ID NOs: 99-108, SEQ ID NOs: 188-216, and SEQ ID NOs: 225-248 is selected from the group of polynucleotides selected from SEQ ID NOs: 159-187 and SEQ ID NOs: 249-256 or a combination thereof, wherein, the heavy and light chain variable regions are not encoded by a combination of SEQ ID NO:11 and SEQ ID NO:115 or SEQ ID NO:112 and SEQ ID NO:116. In one embodiment, the heavy and light chain variable region polypeptides encoded by the polynucleotides combine to form a chimeric antibody, more specifically, a humanized antibody.

In one embodiment, the antigen binding molecule, variant antigen binding molecule, or polypeptide binds membrane-bound CEA comprises an Fc region. In a more specific embodiment, the antigen binding molecule, variant antigen binding molecule, or polypeptide is glycoengineered to have an altered pattern of glycosylation in the Fc region. In a particular embodiment, the affinity for membrane-bound CEA of the variant antigen binding molecule or polypeptide is increased compared to the parent PR1A3 antibody. In another embodiment, the stability of the variant antigen binding molecule or polypeptide is increased compared to the parent PR1A3 antibody. In another embodiment, the variant antigen binding molecule or polypeptide has increased ADCC activity. In one embodiment, the increased ADCC of the variant antigen binding molecule or polypeptide is due to an increase in affinity of the polypeptide for membrane-bound CEA, for example by affinity maturation or other methods of improving affinity.

In another aspect, the invention is also directed to use of the antigen binding molecule, variant antigen binding molecule, or polypeptide in the treatment of disease, particularly cell proliferation disorders wherein CEA is expressed, particularly wherein CEA is abnormally expressed (e.g., overexpressed or expressed in a different pattern in the cell) compared to normal tissue of the same cell type. Such disorders include, but are not limited to colorectal cancer, NSCLC (non-small cell lung cancer), gastric cancer, pancreatic cancer and breast cancer. CEA expression levels may be determined by methods known in the art and those described herein (e.g., via immunohistochemistry assay, immunofluorescence assay, immunoenzyme assay, ELISA, flow cytometry, radioimmunoassay, Western blot, ligand binding, kinase activity, etc.).

In a particular embodiment, the invention is directed to a humanized antigen binding molecule or a portion or fragment thereof that binds membrane-bound CEA comprising a heavy chain variable region comprising the sequence of any one of SEQ ID NOs: 225-248. In another embodiment, the invention is directed to a humanized antigen binding molecule or a portion or fragment thereof that binds membrane-bound CEA comprising a light chain variable region comprising the sequence of any one of SEQ ID NOs: 105, 108, or 207-216. In a particular embodiment, the humanized antigen binding molecule or a portion or fragment thereof that binds membrane-bound CEA comprises a heavy chain variable region comprising the sequence of any one of SEQ ID NOs: 225-248 and a light chain variable region comprising the sequence of any one of SEQ ID NOs:105, 108, or 207-216. In one embodiment, the humanized antigen binding molecule further comprises a human heavy chain constant region and/or a human light chain constant region. Such constant regions are described herein and are known in the art. In a more particular embodiment, the humanized antigen binding molecule comprises an Fc region, more particularly, an Fc region that has been glycoengineered.

Methods for humanizing non-human antibodies are known in the art. For example, humanized ABMs of the present invention can be prepared according to the methods of U.S. Pat. No. 5,225,539 to Winter, U.S. Pat. No. 6,180,370 to Queen et al., or U.S. Pat. No. 6,632,927 to Adair et al., the entire contents of each of which is hereby incorporated by reference. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. Typically, humanized antibodies are human antibodies in which some hypervariable region residues and possibly some FR residues are substituted by residues from analogous sites in a non-human (e.g., rodent) antibodies. The subject humanized anti-CEA antibodies will optionally comprise constant regions from a human immunoglobulin.

The choice of light and heavy chain human variable domains for making the humanized antibodies is very important to reduce antigenicity. According to the so-called "best-fit" method, the sequence of the variable domain of a donor (e.g., rodent) antibody is screened against the entire library of known human variable-domain sequences. The human sequence which is closest to that of the donor (e.g., rodent) is then accepted as the human framework region (FR) for the humanized antibody (Sims et al., J. Immunol., 151:2296 (1993); Chothia et al., J. Mol. Biol., 196:901 (1987)). Another method of selecting the human framework sequence is to compare the sequence of each individual subregion of the full donor (e.g., rodent) framework (i.e., FR1, FR2, FR3, and FR4) or some combination of the individual subregions (e.g., FR1 and FR2) against a library of known human variable region sequences that correspond to that framework subregion (e.g., as determined by Kabat numbering), and choose the human sequence for each subregion or combination that is the closest to that of the rodent (Leung U.S. Patent Application Publication No. 2003/0040606A1, published Feb. 27, 2003). Another method uses a particular framework region derived from the consensus sequence of all human antibodies of a particular subgroup of light or heavy chains (Carter et al., Proc. Natl. Acad. Sci. USA, 89:4285 (1992); Presta et al., J. Immunol., 151:2623 (1993)). In one embodiment, the human framework regions are selected from a collection of human germline sequences. Such collections of human germline sequences can be found in databases such as IMGT or VBase. Framework regions can be selected individually (e.g., the FR1-3 selected for the acceptor for the heavy and/or light chain variable regions of the humanized anti-CEA ABMs can be encoded by different germline genes) or as part of the same germline gene. In a more specific embodiment, heavy chain FR1-3 are encoded by the IGHV7_4_1*02 human immunoglobulin germline gene sequence (Accession No. X62110, SEQ ID NO:114). In another specific embodiment, light chain FR1-3 are encoded by the IMGThVK_1_39 human immunoglobulin germline gene sequence (Accession No. X59315, SEQ ID NO:118). In another specific embodiment, heavy chain FR4 is encoded by the JH6 germline gene sequence (See GenBank Accession No. M63030). In another specific embodiment, light chain FR4 is encoded by the JK2 germline gene sequence (See Genbank Accession No. X61584).

It is generally desirable that antigen binding molecules, such as antibodies and fragments thereof, be humanized with retention of high affinity for the antigen and other favorable biological properties. Accordingly, in one embodiment, humanized antibodies are prepared by analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Analysis of these displays helps to elucidate the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In one aspect, the invention is directed to humanized, affinity matured and/or variant anti-CEA antigen binding molecules with desirable properties and characteristics that include, but are not limited to: strong binding affinity for the CEA antigen—in particular, membrane-bound CEA—while having substantially no cross-reactivity against soluble CEA; an ability to induce cell lysis of CEA-expressing cells in vitro and ex vivo, preferably in a dose-dependent manner; an ability to inhibit CEA-mediated cell adhesion in vitro; an ability to inhibit tumor tissue growth and/or induce tumor tissue regression (for example, as demonstrated in tumor models (e.g., xenograft mouse)).

As described herein, in some embodiments, variant antigen binding molecules of the invention have increased binding affinity, for example, due to affinity maturation of a parent antibody comprising one or more CDRs of the PR1A3 antibody. Affinity of the antigen binding molecules and variant antigen binding molecules of the invention can be determined by methods known in the art and as described herein. In a specific embodiment, humanized or variant antigen binding molecules of the invention bind to human CEA, preferably membrane-bound CEA, with a monovalent affinity constant ($K_D$) value of no more than about 1 µM to about 0.001 nM, more specifically no more than about 800 nM to about 1 nM, and even more specifically no more than about 550 nM to about 10 nM. In a specific embodiment, the variant antigen binding molecule is an affinity matured antibody or fragment thereof that binds to membrane-bound CEA with a monovalent affinity constant ($K_D$) value of no more than about 100 nM to about 10 nM. In one embodiment, the variant antigen binding molecule is an affinity matured antibody or fragment thereof that binds to membrane-bound CEA with a monovalent affinity constant ($K_D$) value of no more than about 100 nM to about 0.01 nM. In one embodiment, the variant antigen binding molecule is an affinity matured antibody or fragment thereof that binds to membrane-bound CEA with a monovalent affinity constant ($K_D$) value of no more than about 10 nM to about 0.1 nM. In one embodiment, the variant antigen binding molecule is an affinity matured antibody or fragment thereof that binds to membrane-bound CEA with a monovalent affinity constant ($K_D$) value of 100 nM, 10 nM, 1 nM, 0.1 nM, or lower. In some embodiments, the variant antigen binding molecule is a stability matured (engineered to have increased stability) antibody or fragment thereof that retains the increased binding affinity of its affinity matured parent. In one embodiment, the variant antigen binding molecule binds to the membrane-bound CEA with a higher affinity than it binds to shed CEA. In one embodiment, the variant antigen binding molecule binds to the membrane-bound CEA with 1.5 fold, 2 fold, 3 fold, 4 fold, 5 fold, 10 fold, 20 fold, or higher affinity than it binds to shed CEA.

In one embodiment, the variant antigen binding molecule of the invention typically binds the same epitope as recognized by the mouse antibody PR1A3, or is capable of competing with the PR1A antibody for binding to membrane-bound CEA. To screen for antibodies that bind to the epitope on human CEA bound by an antibody of interest (e.g., those that block binding of the PR1A3 antibody to human CEA), a routine cross-blocking assay such as that described in ANTIBODIES, A LABORATORY MANUAL, Cold Spring Harbor Laboratory, Harlow and Lane eds. (1988), can be performed. Alternatively, epitope mapping, e.g. as described in Champe et al., J. Biol. Chem. 270:1388-1394 (1995), can be performed to determine whether the antibody binds an epitope of interest.

In one embodiment, variant antigen bind molecules specific for human CEA are made from a parent anti-CEA antigen binding molecule comprising at least one CDR of the monoclonal antibody PR1A3, wherein the parent anti-CEA antibody binds the same epitope as the PR1A3 antibody and is capable of competing with PR1A3 for antigen binding. In one embodiment, the parent antigen binding molecule comprises at least one, two, or typically three, heavy chain CDRs of the PR1A3 antibody; in another embodiment, the parent antigen binding molecule comprises at least one, two, or typically three, light chain CDRs of the PR1A3 antibody; in another embodiment, the parent antigen binding molecule comprises the three heavy chain CDRs and the three light chain CDRs of the PR1A3 antibody. Preferably, where the variant antigen binding molecule comprises HCDR1 of PR1A3, said HCDR1 comprises a substitution of glutamate for valine at Kabat position 31. The variant ABMs typically have a greater affinity for CEA than the parent. In one embodiment, the variant ABMS have increased stability as compared to the parent. In one embodiment, the variant ABM comprises an Fc region. In one embodiment, the variant ABM is glycoengineered. In one embodiment the variant ABM has increased ADCC activity compared to the parent ABM. In a particular embodiment, the increased ADCC is result of the increased affinity, achieved, for example, by affinity maturation of the parent ABM to generate the variant ABM. In a more particular embodiment, the increase in ADCC is at least about 40% to about 100% as compared to said parent antigen binding molecule. In another particular embodiment, the variant ABM increases ADCC by at least about 10% to about 100% in an in vitro cytotoxicity assay. In a more particular embodiment, the variant ABM is at least from about 10-fold to about 1000-fold more potent at inducing ADCC at a given concentration compared to the murine PR1A3 antibody. In another particular embodiment, the increased ADCC activity is a result of glycoengineering of the Fc region. In another particular embodiment, the increased ADCC activity is a result of a combination of increased affinity and glycoengineering.

In one embodiment, the variant antigen binding molecules of the invention comprise one or more amino acid substitutions in at least one CDR. The number of amino acid substitution(s) can range from one to ten (e.g., 1, 2, 3, 4, 5, 6, 7, 8, 9, or 10), preferably from two to five (e.g., 2, 3, 4, or 5). In one embodiment, at least one heavy chain CDR comprises one or more amino acid substitution(s). In another embodiment, at least one light chain CDR comprises one or more amino acid substitution(s). In another embodiment, at least one heavy chain CDR comprises one or more substitutions, and at least one light chain CDR comprises one or more substitutions. Preferably, where the variant antigen binding molecule comprises HCDR1 of PR1A3, said HCDR1 comprises a substitution of glutamate for valine at Kabat position 31.

Substantial modifications in the biological properties of the antigen binding molecules are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Variant antigen binding molecules comprising amino acid substitutions may have improved biological activities, for example, improved antigen binding affinity and enhanced ADCC, compared to the parent antigen binding molecule. Amino acid substitutions can be introduced by various techniques known in the art including, but not limited to, site directed mutagenesis and/or affinity maturation of the parent antigen binding molecule e.g., by phage display.

In order to identify candidate sites, e.g., hypervariable region residues, for modification, alanine scanning mutagenesis can be performed to find residues that contribute significantly to antigen binding. Alternatively, or in addition, it may be beneficial to analyze a crystal structure of the antigen-antibody complex to identify contact points between the antibody and human CEA. Such contact residues and neighboring residues are candidates for substitution according by methods known in the art and/or described herein. Once such variants are generated, the panel of variants can be screened by methods known in the art and/or described herein and antibodies with superior properties in one or more relevant assays can be selected for further development.

Phage display can be used to generate a repertoire of hypervariable region sequences from a parent antigen binding molecule that containing random amino acid mutation(s). For example, several hypervariable region sites (e.g. 6-7 sites) are mutated to generate all possible amino substitutions at each site. Alternatively, random mutagenesis can be performed on heavy and/or light chain variable regions. Mutations can be generated by techniques known in the art, including but not limited to using mutagenesis primers, controlling the number of cycles and using mutagenic nucleotide analogues 8-oxo-dGTP and dPTP during PCR amplification. The antibody variants thus generated are displayed in a monovalent fashion from filamentous phage particles as fusions to the gene III product of M13 packaged within each particle. The phage-displayed variants are then screened for their biological activities (e.g. binding affinity) as herein disclosed and candidates that have one or more improved activities will be used for further development. Methods for making phage display libraries can be found in Huse et al., Science, 246:1275-1281 (1989); Proc. Nat'l Acad. Sci., USA, 88:4363-4366 (1991), the entire contents of each of which are hereby incorporated by reference. An alternative method for identifying affinity matured antigen binding molecules can be found in, for example, U.S. Pat. No. 7,432,063 to Balint et al., the entire contents of which are hereby incorporated by reference.

In some embodiments, the antigen binding molecules and variant antigen binding molecules of the present invention comprise a Fc region, preferably a human Fc region. The sequences and structures of Fc regions are known in the art and have been characterized. In a specific embodiment, the human constant region is IgG1, as set forth in SEQ ID NOs 121 and 122.

However, variants and isoforms of the human Fc region are also encompassed by the present invention. For example, variant Fc regions suitable for use in the present invention can be produced according to the methods taught in U.S. Pat. No. 6,737,056 to Presta (Fc region variants with altered effector function due to one or more amino acid modifications); or in U.S. Pat. Appl. Nos. 60/439,498; 60/456,041; 60/514,549; or WO 2004/063351 (variant Fc regions with increased binding affinity due to amino acid modification); or in U.S. patent application Ser. No. 10/672,280 or WO 2004/099249 (Fc variants with altered binding to FcγR due to amino acid modification), the contents of each of which is herein incorporated by reference in its entirety. In a particular embodiment, the anti-CEA ABMs and variant ABMs comprise an Fc region that has been glycoengineered to alter the effector function activity of the ABM (e.g., decrease fucosylation, improve Fc receptor binding affinity, increase ADCC, etc.). Methods of glycoengineering that can be used are described in detail herein below and are known in the art.

In one embodiment, the antigen binding molecule or a variant antigen binding molecule of the present invention is conjugated to an additional moiety, such as a radiolabel or a toxin. Such conjugated antigen binding molecules can be produced by numerous methods that are well known in the art. Anti-CEA ABM conjugates of the invention are described in detail herein below in the section entitled "Anti-CEA Antigen Binding Molecule Conjugates."

Expression Vectors and Host Cells

In one aspect, the present invention is directed to an expression vector and/or a host cell that comprises one or more isolated polynucleotides of the present invention. For example, the host cell or expression vector comprises any one or more of the polynucleotides or polynucleotides encoding the polypeptides, ABMs and/or variant ABMs described herein. In another aspect, the present invention is directed to a method of producing an ABM that binds membrane-bound human CEA, the method comprising: culturing a host cell comprising one or more isolated polynucleotides of the present invention or an expression vector comprising one or more isolated polynucleotides of the present invention in a medium under conditions allowing the expression of said one or more polynucleotide, wherein said one or more polynucleotides encodes one or more polypeptides that form part of the ABM; and recovering said ABM, wherein said ABM or a portion thereof binds membrane-bound CEA.

Generally, any type of cultured cell line can be used to express the ABM of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

In a specific embodiment, the host cell or expression vector comprises one or more polynucleotides encoding an anti-CEA ABM as provided herein. In one embodiment, the antibody is affinity matured. The affinity matured antibody generally has improved binding affinity than that of the reference antibody from which the affinity matured antibody is derived. In another embodiment, the antibody has desirable therapeutic properties including but not limited to: strong binding affinity for the CEA antigen, in particular, membrane-bound CEA, while having substantially no cross-reactivity against soluble CEA; an ability to induce cell lysis of CEA-expression cells in vitro and ex-vivo, preferably in a dose-dependent manner; an ability to inhibit CEA mediated cell adhesion in vitro; an ability to inhibit tumor tissue growth and/or induce tumor tissue regression in tumor models in mice (e.g., xenograft mouse). In another embodiment, the antibody has increased stability as compared to the parent antibody from which the more stable antibody is derived. In another embodiment, the variant antibody or fragment thereof comprises a human Fc.

In one embodiment, one or several polynucleotides encoding an ABM of the present invention may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding an ABM of the present invention are comprised within the host cell system, some of them may be expressed under the control of a constitutive promoter, while others are expressed under the control of a regulated promoter. The maximal expression level is considered to be the highest possible level of stable polypeptide expression that does not have a significant adverse effect on cell growth rate, and will be determined using routine experimentation. Expression levels are determined by methods generally known in the art, including Western blot analysis using an antibody specific for the ABM or an antibody specific for a peptide tag fused to the ABM; and Northern blot analysis. In a further alternative, the polynucleotide may be operatively linked to a reporter gene; the expression levels of an ABM disclosed herein are determined by measuring a signal correlated with the expression level of the reporter gene. The reporter gene may be transcribed together with the nucleic acid(s) encoding said ABM as a single mRNA molecule; their respective coding sequences may be linked either by an internal ribosome entry site (IRES) or by a cap-independent translation enhancer (CITE). The reporter gene may be translated together with at least one nucleic acid encoding an ABM disclosed herein such that a single polypeptide chain is formed. The nucleic acids encoding an ABM of the present invention may be operatively linked to the reporter gene under the control of a single promoter, such that the nucleic acid encoding the ABM and the reporter gene are transcribed into an RNA molecule which is alternatively spliced into two separate messenger RNA (mRNA) molecules; one of the resulting mRNAs is translated into said reporter protein, and the other is translated into the ABM.

Methods which are well known to those skilled in the art can be used to construct expression vectors containing the coding sequence of an anti-CEA ABM provided herein along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y (1989).

A variety of host-expression vector systems may be utilized to express the coding sequence of the ABMs of the present invention. Preferably, mammalian cells are used as host cell systems transfected with recombinant plasmid DNA or cosmid DNA expression vectors containing the coding sequence of the protein of interest and the coding sequence of the fusion polypeptide. Most preferably, CHO cells, BHK cells, NS0 cells, SP2/0 cells, YO myeloma cells, P3X63 mouse myeloma cells, PER cells, PER. C6 cells or hybridoma cells, other mammalian cells, yeast cells, insect cells, or plant cells are used as host cell system. Some examples of expression systems and selection methods are described in the following references and references cited therein: Borth et al., Biotechnol. Bioen. 71(4):266-73 (2000-2001), in Werner et al., Arzneimittelforschung/Drug Res. 48(8):870-80 (1998), in Andersen and Krummen, Cliff. Op. Biotechnol. 13:117-123 (2002), in Chadd and Chamow, Cliff. Op. Biotechnol. 12:188-194 (2001), and in Giddings, Curr. Op. Biotechnol. 12: 450-454 (2001).

In alternate embodiments, other eukaryotic host cell systems may be used, including yeast cells transformed with recombinant yeast expression vectors containing the coding sequence of an ABM of the present invention, such as the expression systems taught in U.S. Pat. Appl. No. 60/344,169 and WO 03/056914 (methods for producing human-like glycoprotein in a non-human eukaryotic host cell) (the contents of each of which are incorporated by reference in their entirety); insect cell systems infected with recombinant virus expression vectors (e.g., baculovirus) containing the coding sequence of an anti-CEA; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the ABM of the invention including, but not limited to, the expression systems taught in U.S. Pat. No. 6,815,184 (methods for expression and secretion of biologically active polypeptides from genetically engineered duckweed); WO 2004/057002 (production of glycosylated proteins in bryophyte plant cells by introduction of a glycosyl transferase gene) and WO 2004/024927 (methods of generating extracellular heterologous non-plant protein in moss protoplast); and U.S. Pat. Appl. Nos. 60/365,769, 60/368,047, and WO 2003/078614 (glycoprotein processing in transgenic plants comprising a functional mammalian GnTIII enzyme) (the contents of each of which is herein incorporated by reference in its entirety); or animal cell systems infected with recombinant virus expression vectors (e.g., adenovirus, vaccinia virus) including cell lines engineered to contain multiple copies of the DNA encoding a chimeric anti-CEA ABM either stably amplified (CHO/dhfr) or unstably amplified in double-minute chromosomes (e.g., murine cell lines). In one embodiment, the vector comprising the polynucleotide(s) encoding the ABM of the invention is polycistronic. Also, in one embodiment the ABM discussed above is an antibody or a fragment thereof. In one embodiment, the ABM is an affinity matured antibody. In one embodiment, the ABM is a stability matured antibody.

Stable expression is generally preferred to transient expression because it typically achieves more reproducible results and also is more amenable to large-scale production; however, it is within the skill of one in the art to determine whether transient expression is better for a particular situation. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:2026 (1962)), and adenine phosphoribosyltransferase (Lowy et al., Cell 22:817 (1980)) genes, which can be employed in tk$^-$, hgprt$^-$ or aprt$^-$ cells, respectively. Also, antimetabolite resistance can be used as the basis of selection for dhfr, which confers resistance to methotrexate (Wigler et al., Natl. Acad. Sci. USA 77:3567 (1989); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Colberre-Garapin et al., J. Mol. Biol. 150:1 (1981)); and hygro, which confers resistance to hygromycin (Santerre et al., Gene 30:147 (1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047 (1988)); the glutamine synthase system; and ODC (ornithine decarboxylase) which confers resistance to the ornithine decarboxylase inhibitor, 2-(difluoromethyl)-DL-ornithine, DFMO (McConlogue, in: Current Communications in Molecular Biology, Cold Spring Harbor Laboratory ed. (1987)).

The present invention is further directed to a method for modifying the glycosylation profile of the ABMs of the present invention that are produced by a host cell, comprising expressing in said host cell a nucleic acid encoding an ABM of the invention and a nucleic acid encoding a polypeptide with a glycosyltransferase activity, or a vector comprising such nucleic acids. Genes with glycosyltransferase activity include β(1,4)-N-acetylglucosaminyltransferase III (GnTIII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). In one embodiment, a combination of genes with glycosyltransferase activity are expressed in the host cell (e.g., GnTIII and Man II). Likewise, the method also encompasses expression of one or more polynucleotide(s) encoding the ABM in a host cell in which a glycosyltransferase gene has been disrupted or otherwise deactivated (e.g., a host cell in which the activity of the gene encoding α1-6 core fucosyltransferase has been knocked out). In another embodiment, the ABMs of the present invention can be produced in a host cell that further expresses a polynucleotide encoding a polypeptide having GnTIII activity to modify the glycosylation pattern. In a specific embodiment, the polypeptide having GnTIII activity is a fusion polypeptide comprising the Golgi localization domain of a Golgi resident polypeptide. In another preferred embodiment, the expression of the ABMs of the present invention in a host cell that expresses a polynucleotide encoding a polypeptide having GnTIII activity results in ABMs with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an ABM of the present invention, such as a chimeric, primatized or humanized antibody that binds human CEA. In a preferred embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in U.S. Provisional Pat. Appl. No. 60/495,142 and U.S. Pat. Appl. Publ. No. 2004/0241817, the entire contents of which are expressly incorporated herein by reference. In a particular embodiment, the modified ABM produced by the host cell has an IgG constant region or a fragment thereof comprising the Fc region. In another particular embodiment the ABM is a humanized antibody or a fragment thereof comprising an Fc region.

The ABMs with altered glycosylation produced by the host cells of the invention typically exhibit increased Fc receptor binding affinity and/or increased effector function as a result of the modification of the host cell (e.g., by expression of a glycosyltransferase gene). Preferably, the increased Fc receptor binding affinity is increased binding to a Fcγ activating receptor, such as the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

Generation and Use of ABMs Having Increased Effector Function Including Antibody-Dependent Cellular Cytotoxicity In one aspect, the present invention provides glycoforms of anti-CEA ABMs (e.g., variant ABMs) having increased effector function, including antibody-dependent cellular cytotoxicity. Glycosylation engineering of antibodies has been previously described. See, e.g., U.S. Pat. No. 6,602,684, incorporated herein by reference in its entirety. Methods of producing ABMs from host cells that have altered activity of genes involved in glyocsylation are also described herein in detail (See, e.g., preceding section entitled "Expression Vectors and Host Cells"). Increases in ADCC of the ABMs of the present invention is also achieved by increasing affinity of the antigen binding molecule for membrane-bound CEA, for example by affinity maturation or other methods of improving affinity (see Tang et al., J. Immunol. 2007, 179:2815-2823). Combinations of these approaches are also encompassed by the present invention.

Clinical trials of unconjugated monoclonal antibodies (mAbs) for the treatment of some types of cancer have recently yielded encouraging results. Dillman, Cancer Biother. & Radiopharm. 12:223-25 (1997); Deo et al., Immunology Today 18:127 (1997). A chimeric, unconjugated IgG1 has been approved for low-grade or follicular B-cell non-Hodgkin's lymphoma. Dillman, Cancer Biother. & Radiopharm. 12:223-25 (1997), while another unconjugated mAb, a humanized IgG1 targeting solid breast tumors, has also showed promising results in phase III clinical trials. Deo et al., Immunology Today 18:127 (1997). The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., Cancer 80:317-33 (1997); Surfus et al., J. Immunother. 19:184-91 (1996). For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., Cancer 80:317-33 (1997); Surfus et al., J. Immunother. 19:184-91 (1996). ADCC, a lytic attack on targeted cells, is triggered upon binding of leukocyte receptors to the constant region (Fc) of antibodies. Deo et al., Immunology Today 18:127 (1997).

A different, but complementary, approach to increase ADCC activity of unconjugated IgG1s is to engineer the Fc region of the antibody. Protein engineering studies have shown that FcγRs interact with the lower hinge region of the IgG CH2 domain. Lund et al., J. Immunol. 157:4963-69 (1996). However, FcγR binding also requires the presence of oligosaccharides covalently attached at the conserved Asn 297 in the CH2 region. Lund et al., J. Immunol. 157:4963-69 (1996); Wright and Morrison, Trends Biotech. 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., Biochemistry 36:130-38 (1997), with a low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., J. Immunol. 157:4963-69 (1996)

The mouse- or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., Glycobiology 318:813-22 (1995). In contrast, it was recently observed that a rat myeloma-produced, humanized IgG1 (CAMPATH-1H) carried a bisecting GlcNAc in some of its glycoforms. Lifely et al., Glycobiology 318:813-22 (1995). The rat cell-derived antibody reached a similar maximal in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc. Lifely et al., Glycobiology 318:813-22 (1995). In the N-linked glycosylation pathway, a bisecting GlcNAc is added by GnTIII. Schachter, Biochem. Cell Biol. 64:163-81 (1986).

Previous studies used a single, antibody-producing CHO cell line that was previously engineered to express, in an externally-regulated fashion, different levels of a cloned GnTIII enzyme gene (Umaña, P., et al., Nature Biotechnol. 17:176-180 (1999)). This approach established for the first time a rigorous correlation between expression of a glycosyltransferase (e.g., GnTIII) and the ADCC activity of the modified antibody. Thus, the invention contemplates a variant ABM (e.g., an affinity matured ABM) that binds membrane-bound CEA, comprising an Fc region or region equivalent to an Fc region having altered glycosylation resulting from changing the expression level of a glycosyltransferase gene in the ABM-producing host cell. In a specific embodiment, the change in gene expression level is an increase in GnTIII activity. Increased GnTIII activity results in an increase in the percentage of bisected oligosaccharides, as well as a decrease in the percentage of fucose residues, in the Fc region of the ABM. This antibody, or fragment thereof, has increased Fc receptor binding affinity and increased effector function The present invention is also directed to a method for producing an anti-CEA ABM of the present invention having modified oligosaccharides, comprising (a) culturing a host cell engineered to express at least one nucleic acid encoding a polypeptide having glycosyltransferase activity under conditions which permit the production of an ABM according to the present invention, wherein said polypeptide having glycosyltransferase activity is expressed in an amount sufficient to modify the oligosaccharides in the Fc region of said ABM produced by said host cell; and (b) isolating said ABM. In one embodiment, the polypeptide having glycosyltransferase activity is GnTIII. In another embodiment, there are two polypeptides having glycosyltransferase activity. In a particular embodiment, the two peptides having glycosyltransferase activity are GnTIII and ManII. In another embodiment, the polypeptide having glycosltransferase activity is a fusion polypeptide comprising the catalytic domain of GnTIII. In a more specific embodiment, the fusion polypeptide further comprises the Golgi localization domain of a Golgi resident polypeptide. Preferably, the Golgi localization domain is the localization domain of mannosidase II or GnTI. Alternatively, the Golgi localization domain is selected from the group consisting of: the localization domain of mannosidase I, the localization domain of GnTII, and the localization domain of α1-6 core fucosyltransferase. The ABMs produced by the methods of the present invention have increased Fc receptor binding affinity and/or increased effector function. Generally, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. The increased Fc receptor binding affinity is preferably increased binding to Fc activating receptors such as FcγRIIIa. In a particularly preferred embodiment the ABM is a humanized antibody or a fragment thereof.

In one embodiment, the percentage of bisected N-linked oligosaccharides in the Fc region of the ABM is at least about 10% to about 100%, specifically at least about 50%, more specifically, at least about 60%, at least about 70%, at least about 80%, or at least about 90-95% of the total oligosaccharides. In yet another embodiment, the antigen binding molecule or variant antigen binding molecule produced by the methods of the invention has an increased proportion of non-fucosylated oligosaccharides in the Fc region as a result of the modification of its oligosaccharides by the methods of the present invention. In one embodiment, the percentage of non-fucosylated oligosaccharides is at least about 20% to about 100%, specifically at least about 50%, at least about 60% to about 70%, and more specifically, at least about 75%. The nonfucosylated oligosaccharides may be of the hybrid or complex type. In yet another embodiment, the antigen binding molecule or variant antigen binding molecule produced by the methods of the invention has an increased proportion of bisected oligosaccharides in the Fc region as a result of the modification of its oligosaccharides by the methods of the present invention. In one embodiment, the percentage of bisected oligosaccharides is at least about 20% to about 100%, specifically at least about 50%, at least about 60% to about 70%, and more specifically, at least about 75%. In a particularly preferred embodiment, the ABM produced by the host cells and methods of the invention has an increased proportion of bisected, nonfucosylated oligosaccharides in the Fc region. The bisected, nonfucosylated oligosaccharides may be either hybrid or complex. Specifically, the methods of the present invention may be used to produce antigen binding molecules in which at least about 10% to about 100%, specifically at least about 15%, more specifically at least about 20% to about 50%, more specifically at least about 20% to about 25%, and more specifically at least about 30% to about 35% of the oligosaccharides in the Fc region of the antigen binding molecule or variant antigen binding molecule are bisected, nonfucosylated. The ABMs of the present invention may also comprise an Fc region in which at least about 10% to about 100%, specifically at least about 15%, more specifically at least about 20% to about 25%, and more specifically at least about 30% to about 35% of the oligosaccharides in the Fc region of the ABM are bisected hybrid nonfucosylated.

In another embodiment, the present invention is directed to an anti-CEA antigen binding molecule (e.g., a variant ABM)) engineered to have increased effector function and/or increased Fc receptor binding affinity, produced by the methods of the invention. The increased effector function can include, but is not limited to one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a preferred embodiment, the increased Fc receptor binding affinity is increased binding to an Fc activating receptor, most preferably FcγRIIIa. In one embodiment, the antigen binding molecule or variant antigen binding molecule is an antibody, an antibody fragment containing the Fc region, or a fusion protein that includes a region equivalent to the Fc region of an immunoglobulin. In a particularly preferred embodiment, the antigen binding molecule or variant antigen binding molecule is a humanized affinity matured antibody.

The present invention further provides methods for the generation and use of host cell systems for the production of glycoforms of the ABMs of the present invention, having increased Fc receptor binding affinity, preferably increased binding to Fc activating receptors, and/or having increased effector functions, including antibody-dependent cellular cytotoxicity. The glycoengineering methodology that can be used with the ABMs of the present invention has been described in greater detail in U.S. Pat. No. 6,602,684, U.S. Pat. Appl. Publ. No. 2004/0241817 A1, U.S. Pat. Appl. Publ. No. 2003/0175884 A1, Provisional U.S. Patent Application No. 60/441,307 and WO 2004/065540, the entire contents of each of which is incorporated herein by reference in its entirety. The ABMs of the present invention can alternatively be glycoengineered to have reduced fucose residues in the Fc region according to the techniques disclosed in U.S. Pat. Appl. Pub. No. 2003/0157108 (Genentech), or in EP 1 176 195 A1, WO 03/084570, WO 03/085119 and U.S. Pat. Appl. Pub. Nos. 2003/0115614, 2004/093621, 2004/110282, 2004/110704, 2004/132140 (Kyowa). The contents of each of these documents are herein incorporated by reference in their entireties. Glycoengineered ABMs of the invention may also be produced in expression systems that produce modified glycoproteins, such as those taught in U.S. Pat. Appl. Pub. No. 60/344,169 and WO 03/056914 (GlycoFi, Inc.) or in WO 2004/057002 and WO 2004/024927 (Greenovation), the contents of each of which are hereby incorporated by reference in their entirety.

Generation of Cell Lines for the Production of Proteins with Altered Glycosylation Pattern In one aspect, the present invention provides host cell expression systems for the generation of the ABMs of the present invention having modified glycosylation patterns. In particular, the present invention provides host cell systems for the generation of glycoforms of the ABMs of the present invention having an improved therapeutic value. Therefore, the invention provides host cell expression systems selected or engineered to express a polypeptide having a glycosyltransferase activity. In a specific embodiment, the glycosyltransferase activity is a GnTIII activity. In one embodiment, the polypeptide having GnTIII activity is a fusion polypeptide comprising the Golgi localization domain of a heterologous Golgi resident polypeptide. Specifically, such host cell expression systems may be engineered to comprise a recombinant nucleic acid molecule encoding a polypeptide having GnTIII, operatively linked to a constitutive or regulated promoter system.

In one specific embodiment, the present invention provides a host cell that has been engineered to express at least one nucleic acid encoding a fusion polypeptide having GnTIII activity and comprising the Golgi localization domain of a heterologous Golgi resident polypeptide. In one aspect, the host cell is engineered with a nucleic acid molecule comprising at least one gene encoding a fusion polypeptide having GnTIII activity and comprising the Golgi localization domain of a heterologous Golgi resident polypeptide.

Generally, any type of cultured cell line, including the cell lines discussed above, can be used as a background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The invention is contemplated to encompass any engineered host cells expressing a polypeptide having glycosyltransferase activity, e.g., GnTIII activity, including a fusion polypeptide that comprises the Golgi localization domain of a heterologous Golgi resident polypeptide as defined herein.

One or several nucleic acids encoding a polypeptide having glycosyltransferase activity, e.g., GnTIII activity, may be expressed under the control of a constitutive promoter or, alternately, a regulated expression system. Such systems are well known in the art, and include the systems discussed above. If several different nucleic acids encoding fusion polypeptides having glycosyltransferase activity, e.g., GnTIII activity, and comprising the Golgi localization domain of a heterologous Golgi resident polypeptide are comprised within the host cell system, some of them may be expressed under the control of a constitutive promoter, while others are expressed under the control of a regulated promoter. Expression levels of the fusion polypeptides having glycosyltransferase activity, e.g., GnTIII activity, are determined by methods generally known in the art, including Western blot analysis, Northern blot analysis, reporter gene expression analysis or measurement of glycosyltransferase activity, e.g., GnTIII activity. Alternatively, a lectin may be employed which binds to biosynthetic products of the GnTIII, for example, $E_4$-PHA lectin. Alternatively, a functional assay which measures the increased Fc receptor binding or increased effector function mediated by antibodies produced by the cells engineered with the nucleic acid encoding a polypeptide with glycosyltransferase activity, e.g., GnTIII activity, may be used.

Identification of Transfectants or Transformants that Express the Protein Having a Modified Glycosylation Pattern The host cells which contain the coding sequence of a variant anti-CEA ABM (e.g., a humanized, affinity matured and/or stability matured ABM) and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of a variant anti-CEA and/or the coding sequence of the polypeptide having glycosyltransferase (e.g., GnTIII) activity can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the ABM of the invention, or a fragment thereof, and/or the coding sequence of the polypeptide having glycosyltransferase (e.g., GnTIII) activity are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the ABM of the invention and/or the coding sequence of the polypeptide having glycosyltransferase (e.g., GnTIII) activity.

In the third approach, transcriptional activity for the coding region of the ABM of the invention, or a fragment thereof, and/or the coding sequence of the polypeptide having glycosyltransferase (e.g., GnTIII) activity can be assessed by hybridization assays. For example, RNA can be isolated and analyzed by Northern blot using a probe homologous to the coding sequences of the ABM of the invention, or a fragment thereof, and/or the coding sequence of the polypeptide having glycosyltransferase (e.g., GnTIII) activity or particular portions thereof. Alternatively, total nucleic acids of the host cell may be extracted and assayed for hybridization to such probes.

In the fourth approach, the expression of the protein products can be assessed immunologically, for example by Western blots, immunoassays such as radioimmuno-precipitation, enzyme-linked immunoassays and the like. The ultimate test of the success of the expression system, however, involves the detection of the biologically active gene products.

Therapeutic Applications and Methods of Using Anti-CEA of Antigen Binding Molecules The invention is also directed to a method for targeting in vivo or in vitro cells expressing CEA. Cells that express CEA may be targeted for therapeutic purposes (e.g., to treat a disorder by targeting CEA-expressing cells for destruction by the immune system). In one embodiment, the present invention is directed to a method for targeting cells expressing CEA in a subject comprising administering to the subject a composition comprising an ABM of the invention. Cells that express CEA may also be targeted for diagnostic purposes (e.g., to determine if they are expressing CEA, either normally or abnormally). Thus, the invention is also directed to methods for detecting the presence of CEA or a cell expressing CEA, either in vivo or in vitro. One method of detecting CEA expression according to the present invention comprises contacting a sample to be tested, optionally with a control sample, with an ABM of the present invention, under conditions that allow for formation of a complex between the ABM and CEA. The complex formation is then detected (e.g., by ELISA or other methods known in the art). When using a control sample with the test sample, any statistically significant difference in the formation of ABM-CEA complexes when comparing the test and control samples is indicative of the presence of CEA in the test sample.

In one aspect, ABMs and/or variant ABMs of the present invention can be used target cells in vivo or in vitro that express CEA. The cells expressing CEA can be targeted for diagnostic or therapeutic purposes. In one aspect, the ABMs of the present invention can be used to detect the presence of CEA in a sample. CEA is abnormally expressed (e.g., over-expressed) in many human tumors compared to non-tumor tissue of the same cell type. Thus, the ABMs and/or variant ABMs of the invention are particularly useful in the prevention of tumor formation, eradication of tumors and inhibition of tumor growth or metastasis. The ABMs and/or variant ABMs of the invention also act to arrest the cell cycle, cause apoptosis of the target cells (e.g., tumor cells), and inhibit angiogenesis and/or differentiation of target cells. The ABMs and/or variant ABMs of the invention can be used to treat any tumor expressing CEA. Particular malignancies that can be treated with the ABMs and/or variant ABMs of the invention include, but are not limited to, colorectal cancer, non-small cell lung cancer, gastric cancer, pancreatic cancer and breast cancer.

The anti-CEA ABMs and/or variant ABMs disclosed herein can be used alone to inhibit tumor growth or kill tumor cells. For example, the anti-CEA ABMs can bind to CEA that is on the membrane or cell surface of cancerous cells and elicit, e.g., ADCC or other effector mediated killing of the cancerous cells. The anti-CEA ABMs and/or variant ABMs can be humanized, specifically, affinity and/or stability matured, more specifically, glycoengineered, stability, and affinity matured.

The ABMs and/or variant ABMs can alternatively be used alone in order to block the activity of the CEA antigen, particularly by physically interfering with its binding of another compound. For example, the antigen binding molecules and variant antigen binding molecules can be used to block CEA mediated cell-adhesion.

The anti-CEA ABMs and/or variant ABMs of the invention are administered to a mammal, preferably a human, in a pharmaceutically acceptable dosage form such as those discussed below, including those that may be administered to a human intravenously as a bolus or by continuous infusion over a period of time, by intramuscular, intraperitoneal, intracerebrospinal, subcutaneous, intra-articular, intrasynovial, intrathecal, oral, topical, or inhalation routes. The ABMs also are suitably administered by intra tumoral, peritumoral, intralesional, or perilesional routes, to exert local as well as systemic therapeutic effects. The intraperitoneal route is expected to be particularly useful, for example, in the treatment of colorectal tumors.

For the treatment of disease, the appropriate dosage of ABM and/or variant ABM will depend on the type of disease to be treated, the severity and course of the disease, previous therapy, the patient's clinical history and response to the antibody, and the discretion of the attending physician. The ABM is suitably administered to the patient at one time or over a series of treatments.

The present invention provides a method for selectively killing tumor cells expressing CEA. This method comprises reacting the antigen binding molecules or the conjugates (e.g., the immunotoxin) of the invention with said tumor cells. These tumor cells may be from a human carcinoma including colorectal carcinoma, non-small cell lung carcinoma (NSCLC), gastric carcinoma, pancreatic carcinoma and breast carcinoma.

In one embodiment, the present invention provides a method inhibiting CEA-mediated cell adhesion of a tumor cell. This method comprises contacting said tumor cell with the antigen binding molecules or variant antigen binding molecules of the invention or the conjugates thereof. These tumor cells may be from human cells, including colorectal cancer cells, non-small cell lung cancer cells (NSCLC), gastric cancer cells, pancreatic cancer cells and breast cancer cells.

Additionally, this invention provides a method of treating carcinomas (for example, human carcinomas) in vivo. This method comprises administering to a subject a pharmaceutically effective amount of a composition containing at least one of the antigen binding molecules or the immunoconjugates (e.g., the immunotoxin) of the invention.

In a further aspect, the invention is directed to a method for treating cancers characterized by CEA over-expression, including but not limited to colorectal cancer cells, NSCLC (non-small cell lung cancer), gastric cancer cells, pancreatic cancer cells and breast cancer cells, by administering a therapeutically effective amount of the anti-CEA antigen binding molecules or variant antigen binding molecules disclosed herein.

In a further embodiment, the invention is directed to a method for inducing tumor tissue regression in a subject using anti-CEA antigen binding molecules or variant antigen binding molecules disclosed herein. Non-limiting examples of the tumor tissue includes colorectal tumor, non-small cell lung tumor, gastric tumor, pancreatic tumor and breast tumor. In a particular embodiment, the tumor tissue is a colorectal tumor.

In accordance with the practice of this invention, the subject may be a human, equine, porcine, bovine, murine, canine, feline, and avian subjects. Other warm blooded animals are also included in this invention.

The invention further provides methods for inhibiting the growth of tumor cells, treating a tumor in a subject, and treating a proliferative type disease in a subject. These methods comprise administering to the subject an effective amount of the composition of the invention.

In another aspect, the invention is directed to the use of the anti-CEA antigen binding molecules or variant antigen binding molecules disclosed herein for the manufacture of a medicament for treating a disease related to abnormal CEA expression. In a particular embodiment, the disease is a cancer that overexpresses CEA, including but not limited to colorectal tumor, non-small cell lung tumor, gastric tumor, pancreatic tumor and breast tumor. In a particular embodiment, the tumor is a colorectal tumor.

Anti-CEA Antigen Binding Molecule Conjugates

The invention also provides immunoconjugates comprising an anti-CEA ABM or variant ABM herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer*

*Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-CEA ABM or variant ABM as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an anti-CEA ABM or variant ABM as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pd^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinyl-sulfone)benzoate) which are commercially available (e.g., from Pierce Biotechnology, Inc., Rockford, Ill., U.S.A).

Compositions, Formulations, Dosages, and Routes of Administration

In one aspect, the present invention is directed to pharmaceutical compositions comprising the anti-CEA ABMs or variant ABMs of the present invention and a pharmaceutically acceptable carrier. The present invention is further directed to the use of such pharmaceutical compositions in the method of treatment of disease, such as cancer, or in the manufacture of a medicament for the treatment of disease, such as cancer. Specifically, the present invention is directed to a method for the treatment of disease, and more particularly, for the treatment of cancer, the method comprising administering a therapeutically effective amount of the pharmaceutical composition of the invention.

In one aspect, the present invention encompasses pharmaceutical compositions, combinations and methods for treating human carcinomas, for example colorectal carcinoma. For example, the invention includes pharmaceutical compositions for use in the treatment of human carcinomas comprising a pharmaceutically effective amount of an antibody of the present invention and a pharmaceutically acceptable carrier.

The ABM compositions of the invention can be administered using conventional modes of administration including, but not limited to, intravenous, intraperitoneal, oral, intralymphatic or administration directly into the tumor. Intravenous administration is preferred.

In one aspect of the invention, therapeutic formulations containing the ABMs of the invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed.

The formulations to be used for in vivo administration must be sterile. This is readily accomplished by filtration through sterile filtration membranes.

The most effective mode of administration and dosage regimen for the pharmaceutical compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention will generally be in the range of from about 0.01 to about 2000 mg/kg.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The composition comprising an ABM of the present invention will be formulated, dosed, and administered in a fashion consistent with good medical practice. Factors for consideration in this context include the particular disease or disorder being treated, the particular mammal being treated, the clinic condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-CEA ABM.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Unless otherwise specified, references to the numbering of specific amino acid residue positions in the following Examples are according to the Kabat numbering system.

Example 1

Generation of Affinity Maturation Libraries

H1/H2 Library

Figure 11:
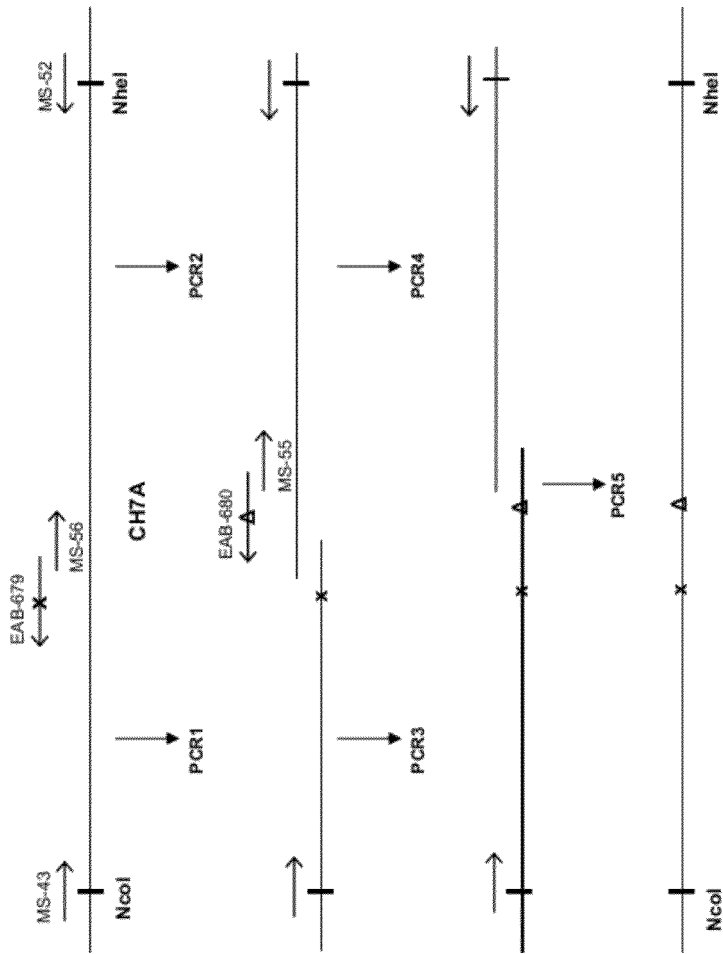
FIG. 11 shows a schematic overview of the PCR strategy for the CDR1 and CDR2 randomization of the humanized CH7A anti-CEA antibody heavy chain.

For generation of an affinity maturation library randomized in the HCDR1 and HCDR2 region, triplets encoding positions F32 G33 in CDR1 and positions W50 N52 T52a K52b T54 E56 T58 in CDR2 were randomized. In a first step, a DNA fragment (fragment 1) was amplified using pMS22 as a template and primers MS-43 (SEQ ID NO: 123) and EAB-679 (SEQ ID NO: 127) which contains the randomized CDR1 positions (FIG. 11). Using the same template, primers MS-56 (SEQ ID NO: 126) and MS-52 (SEQ ID NO: 124) amplified a second fragment (fragment 2) which has an overlapping region with the 3'end of fragment 1. Amplification conditions included an initial 5-min 94° C. incubation step followed by 25 cycles, each consisting of a 1-min 94° C. denaturation, a 1-min 55° C. annealing, and a 20-sec and 50-sec 72° C. elongation step, for fragment 1 and fragment2, respectively. A final 10-min 72° C. incubation step was performed at the end. Both fragments were purified on an agarose gel. An overlapping extension PCR with fragment 1 and 2 using primers MS-43 (SEQ ID NO: 123) and EAB-680 (SEQ ID NO: 128), which harboured randomized positions of CDR2, generated a fragment with both CDRs randomized (fragment 3). For the assembly of fragments 1 and 2, equimolar amounts of fragment 1 and fragment 2 were used. Amplification conditions included an initial 5-min 94° C. incubation step followed by 5 cycles without primers, each cycle consisting of a 1-min 94° C. denaturation, a 1-min 55° C. annealing, and a 40-sec 72° C. elongation step. After the addition of the outer primers, 20 additional cycles were performed using the same parameters. A fourth fragment (fragment 4) which overlaps with the 3' region of fragment 3 was PCR-amplified using again pMS22 as a template and primers MS-55 (SEQ ID NO: 125) and MS-52 (SEQ ID NO: 124). After gel purification, a final overlap extension PCR using fragment 3 and 4 as templates and primers MS-43 and MS-52 generated a fragment containing CL and parts of VH. For this, equimolar amounts of fragment 3 and fragment 4 were used. Amplification conditions included an initial 5-min 94° C. incubation step followed by 5 cycles without primers, each cycle consisting of a 1-min 94° C. denaturation, a 1-min 55° C. annealing, and a 80-sec 72° C. elongation step. After the addition of the outer primers, 20 additional cycles were performed using the same parameters. The resulting fragment was then gel-purified and ligated with pMS22 after NcoI/NheI digestion.

L1/L2 Library

Figure 12:
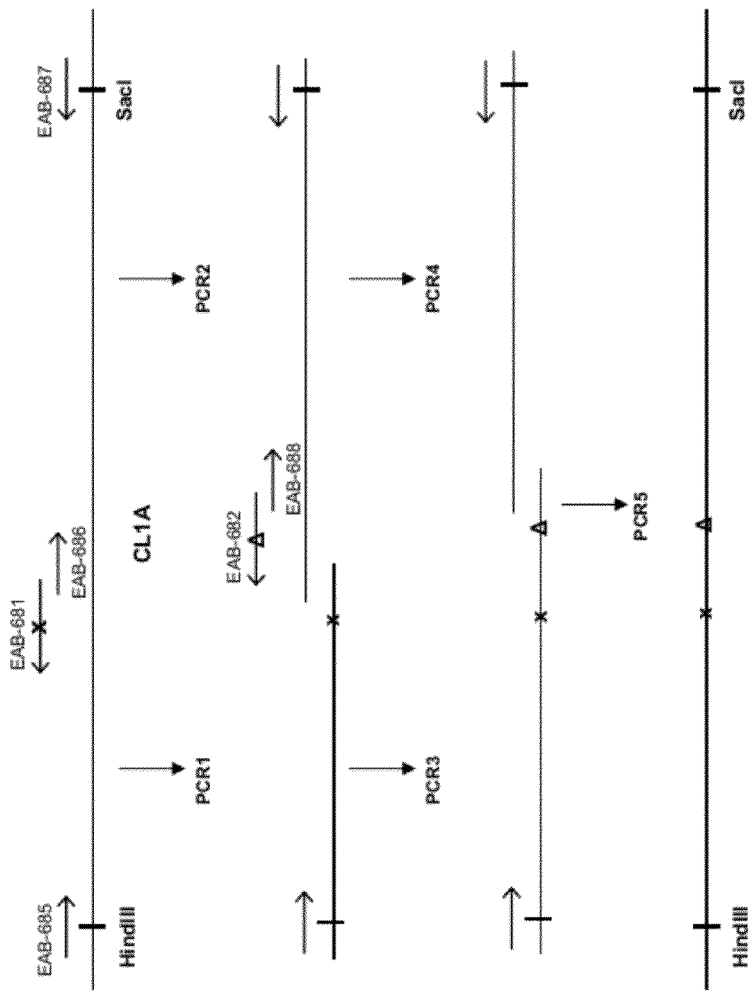
FIG. 12 shows a schematic overview of the PCR strategy for the CDR1 and CDR2 randomization of the humanized CL1A anti-CEA antibody light chain.

For the generation of an affinity maturation library randomized in the LCDR1 and LCDR2 region, triplets encoding positions Q27, N28, V29, G30 T31 N32 in CDR1 and positions Y49 S50 Y53 R54Y55 S56 in CDR2 were randomized. In a first step, a DNA fragment (fragment 1) was amplified using pMS22 as a template and primers EAB-685 (SEQ ID NO: 129) and EAB-681 (SEQ ID NO: 133) which contains the randomized CDR1 positions (FIG. 12). Using the same template, primers EAB-686 (SEQ ID NO: 130) and EAB-687 (SEQ ID NO: 131) amplified a second fragment (fragment 2) which has an overlapping region with the 3'end of fragment 1. Amplification conditions included an initial 5-min 94° C. incubation step followed by 25 cycles, each consisting of a 1-min 94° C. denaturation, a 1-min 55° C. annealing, and a 60-sec 72° C. elongation step, for fragment 1 and fragment2, respectively. A final 10-min 72° C. incubation step was performed at the end. Both fragments were purified on a agarose gel. An overlapping extension PCR with fragment 1 and 2 using primers EAB-685 (SEQ ID NO: 129) and EAB-682 (SEQ ID NO: 134), which harboured randomized positions of CDR2, generated a fragment with both CDRs randomized (fragment 3). For the assembly of fragments 1 and 2, equimolar amounts of fragment 1 and fragment 2 were used. Amplification conditions included an initial 5-min 94° C. incubation step followed by 5 cycles without primers, each cycle consisting of a 1-min 94° C. denaturation, a 1-min 55° C. annealing, and a 60-sec 72° C. elongation step. After the addition of the outer primers, 20 additional cycles were performed using the same parameters. A fourth fragment (fragment 4) which overlaps with the 3' region of fragment 3 was PCR-amplified using again pMS22 as a template and primers EAB-688 (SEQ ID NO: 132) and EAB-687 (SEQ ID NO: 131). After gel purification, a final overlap extension PCR using fragment 3 and 4 as templates and primers EAB-685 (SEQ ID NO: 129) and EAB-687 (SEQ ID NO: 131) generated a fragment containing VL and parts of CL. For this, equimolar amounts of fragment 3 and fragment 4 were used. Amplification conditions included an initial 5-min 94° C. incubation step followed by 5 cycles without primers, each cycle consisting of a 1-min 94° C. denaturation, a 1-min 55° C. annealing, and a 80-sec 72° C. elongation step. After the addition of the outer primers, 20 additional cycles were performed using the same parameters. This fragment was then ligated with pMS22 after HindIII/SacI digestion.

H3 Libraries

Figure 13:
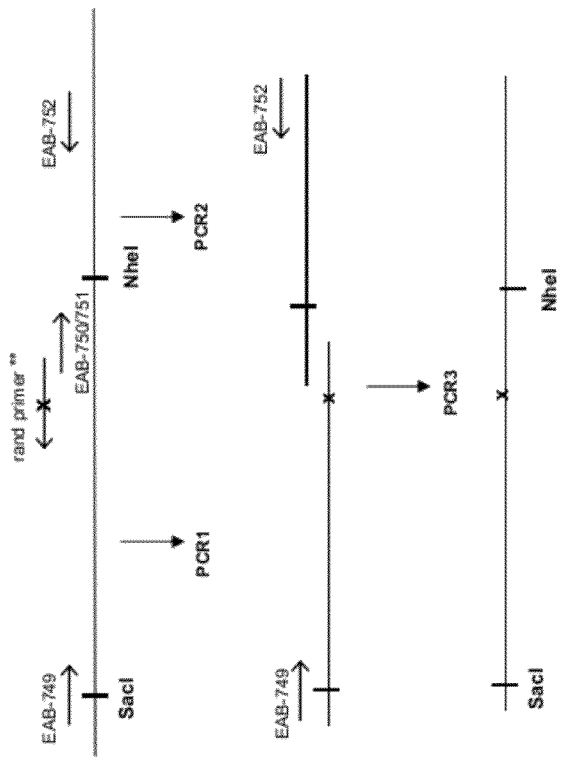
FIG. 13 shows a schematic overview of the PCR strategy for the CDR3 randomization of the humanized CH7A anti-CEA antibody heavy chain.

For the generation of affinity maturation libraries randomized in the HCDR3 region, triplets encoding positions W95, D96, F97, Y98, D99, Y100, V100a, E100b, A100c, and M100d were randomized in two different approaches: (1) randomization of the entire segment (H3 full library) or (2) individual randomization of each position resulting in ten sublibraries. Sublibraries containing clones with individually randomized positions were pooled after transformation into bacteria (H3 pooled library). For the randomization of the HCDR3 region, fragments were PCR-amplified using a primer that annealed in the 3' end of CL and primers that harbour the randomized sequences of HCDR3 (FIG. 13). An overlap extension PCR was then performed with a second fragment that overlaps with the 3' end of fragment 1, and comprises the end of VH and the 5' region of CH1. The assembled fragments were then ligated into pMS22 after SacI/NheI digestion. For the generation of the H3 pooled library, ten DNA fragments were separately PCR-amplified using each of primers AC7-AC16 (SEQ ID NO: 135; SEQ ID NO: 144) in combination with primer EAB-749 (SEQ ID NO: 146). For the generation of the L3 full library, primers AC17 (SEQ ID NO: 145) and EAB-749 (SEQ ID NO: 146) were used. Plasmid pMS22 was used as a template. Amplification conditions included an initial 5-min 94° C. incubation step followed by 25 cycles, each consisting of a 1-min 94° C. denaturation, a 1-min 55° C. annealing, and a 36-sec 72° C. elongation step, followed by a final 10-min 72° C. incubation step. This resulted in about 580 bp long fragments which were purified on an agarose gel. For the overlap extension PCR, a second fragment was amplified using either primer EAB-750 (SEQ ID NO: 147) or EAB-751 (SEQ ID NO: 148) in combination with EAB-752 (SEQ ID NO: 149). While primer EAB-750 SEQ ID NO: 147) had an overlapping sequence with randomization primers AC7-11 (SEQ ID NO: 139), EAB-751 (SEQ ID NO: 148) shared sequence homologies with randomization primers AC 12-17 (SEQ ID NOs: 140-145). Amplification conditions included an initial 5-min 94° C. incubation step followed by 25 cycles, each consisting of a 1-min 94° C. denaturation, a 1-min 55° C. annealing, and a 12-sec 72° C. elongation step, followed by a final 10-min 72° C. incubation step. The resulting fragments were about 180 bp long. For the assembly of both fragments, equimolar amounts of fragment 1 and the corresponding fragment 2 were used. Amplification conditions included an initial 5-min 94° C. incubation step followed by 5 cycles without primers, each cycle consisting of a 1-min 94° C. denaturation, a 1-min 55° C. annealing, and a 60-sec 72° C. elongation step. After the addition of the outer primers EAB-749 (SEQ ID NO: 146) and EAB-752 (SEQ ID NO: 149), 20 additional cycles were performed using the same parameters. At the end, a final 10-min 72° C. incubation step was performed. The gel-purified fragments were then ligated into pMS22 after SacI/NheI-digestion and purified ligations were transformed into TG1 bacteria by electropration.

L3 Libraries

Figure 14:
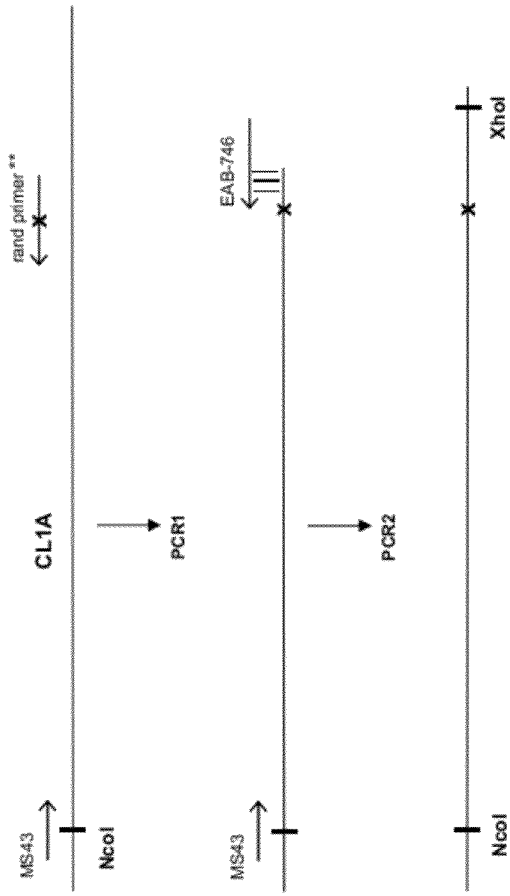
FIG. 14 shows a schematic overview of the PCR strategy for the CDR3 randomization of the humanized CL1A anti-CEA antibody light chain.

For the generation of affinity maturation libraries randomized in the CDR3 region of the light chain, triplets encoding positions Y91, Y92, T93, Y94, and L95a were either randomized throughout the segment (L3 full library) or individually resulting in five sublibraries. Sublibraries containing clones with individually randomized positions were pooled after transformation into bacteria (L3 pooled library). For the generation of the five sublibraries, five DNA fragments were PCR-amplified using each of primers AC1-AC5 (SEQ ID NOs: 150-154) in combination with primer MS43 (SEQ ID NO: 123). For the generation of the L3 full library, primer combination AC6 (SEQ ID NO: 155) and MS43 (SEQ ID NO: 123) were used (FIG. 14). Plasmid pMS22 was used as a template. Amplification conditions included an initial 5-min 94° C. incubation step followed by 25 cycles, each consisting of a 1-min 94° C. denaturation, a 1-min 55° C. annealing, and a 25-sec 72° C. elongation step, followed by a final 10-min 72° C. incubation step. The resulting fragments which encompass positions 1-104 of the VL domain were purified on an agarose gel and used as a template for an additional PCR amplification. All reactions were performed with primer EAB-746 (SEQ ID NO: 156) which has an overlapping sequence with the randomization primers and MS43 (SEQ ID NO: 123) using the same conditions described above. The purified fragments as well as pMS22 were digested with NcoI/XhoI. For all five sublibraries, 0.5 µg insert were ligated with 0.5 µg pAC16. For the L3 full library, ligation was performed with 9.8 µg insert and 9.8 µg pMS22. Purified ligations were transformed into TG1 bacteria by electroporation.

Generation of the Antigens

Because both murine and humanized PR1A3 antibodies recognize only membrane bound but not shed soluble human CEA, a recombinant chimeric protein which contains the epitope of PR1A3 was generated for in vitro affinity maturation of humanized PR1A3 (SEQ ID NO:7 and 8). Generation of this hybrid protein was performed as described in Steward et al., 1999. In brief, DNA sequence of the B domain of human biliary glycoprotein (BGP) was replaced with the sequence of the human CEA-B3 domain, which contains the epitope of PR1A3. As a result, the sequence encodes a hybrid protein which comprises the N and A1 domains of BGP, the B3 domain of CEA and the A2 domain of BGP (N-A1-B3-A2, huNABA). This fusion product was then either linked to the Fc portion of human IgG1 (huNABA-Fc) (Steward et al., Cancer Immunol Immunother, 47:299-306, 1999) or fused to a sequence encoding the precision protease cleavage site, an avi tag and a $(His)_6$ tag (huNABA-avi-his) (SEQ ID NO:158). huNABA-Fc was purified from the supernatant of a stably transfected CHO cell line using a protein A column. huNABA-avi-his (SEQ ID NO: 158) was transiently transfected into HEK 293 cells, stably expressing the EBV-derived protein EBNA. A simultaneously co-transfected plasmid encoding a biotin ligase allowed avi tag-specific biotinlylation in vivo. The protein was then purified by immobilized metal affinity chromatography (IMAC) followed by gel filtration.

Affinity Maturation of Humanized PR1A3

Generation of affinity-matured humanized PR1A3 Fabs was carried out by phage display using standard protocols (Silacci et al, Proteomics, 5(9):2340-2350, 2005). Selections with all affinity maturation libraries were carried out in solution according to the following procedure: 1. binding of ~1012 phagemid particles of each affinity maturation libraries to 100 nM biotinylated huNABA-avi-his for 0.5 h in a total volume of 1 ml, 2. capture of biotinylated huNABA-avi-his and specifically bound phage particles by addition of $5.4 \times 10^7$ streptavidin-coated magnetic beads for 10 min, 3. washing of beads using 5-10×1 ml PBS/Tween20 and 5-10×1 ml PBS, 4. elution of phage particles by addition of 1 ml 100 mM TEA (triethylamine) for 10 min and neutralization by adding 500 ul 1M Tris/HCl pH 7.4 and 5. re-infection of exponentially growing E. coli TG1 bacteria, infection with helper phage VCSM13 and subsequent PEG/NaCl precipitation of phagemid particles to be used in subsequent selection rounds. Selections were carried out over 3-5 rounds using either constant or decreasing (from $10^{-7}$M to $2 \times 10^{-9}$M) antigen concentrations. In round 2, capture of antigen: phage complexes was performed using neutravidin plates instead of streptavidin beads. Specific binders were identified by ELISA as follows: 100 ul of 10 nM biotinylated huNABA-avi-his per well were coated on neutravidin plates. Fab-containing bacterial supernatants were added and binding Fabs were detected via their Flag-tags by using an anti-Flag/HRP secondary antibody. ELISA-positive clones were bacterially expressed as soluble Fab fragments in 96-well format and supernatants were subjected to a kinetic screening experiment by SPR-analysis using BIACORE T100. Clones expressing Fabs with the highest affinity constants were identified and the corresponding phagemids were sequenced.

Purification of Fabs and Measurement of the Kinetic Parameters

For the exact analysis of the kinetic parameters, Fabs were purified from bacterial cultures. A 500 ml culture was inoculated and induced with 1 mM IPTG at an OD600 0.9. Bacteria were incubated at 25° C. overnight and harvested by centrifugation. After the incubation of the resuspended pellet for 20 min in 25 ml PPB buffer (30 mM Tris-HCl pH8, 1 mM EDTA, 20% sucrose), bacteria were centrifuged again and the supernatant was harvested. This incubation step was repeated once with 25 ml of a 5 mM $MgSO_4$ solution. The supernatants of both incubation steps were pooled, filtered and loaded on a IMAC column (His gravitrap, GE Healthcare). Subsequently, the column was washed with 40 volumes. After the elution (500 mM NaCl, 500 mM Imidazole, 20 mM $NaH_2PO_4$ pH 7.4) the eluate was re-buffered using PD10 columns (GE Healthcare). The kinetic parameters of the purified Fabs were then studied by SPR-analysis in a dilution row that ranged from 200 nM to 6.25 nM.

Example 2

Figure 2:
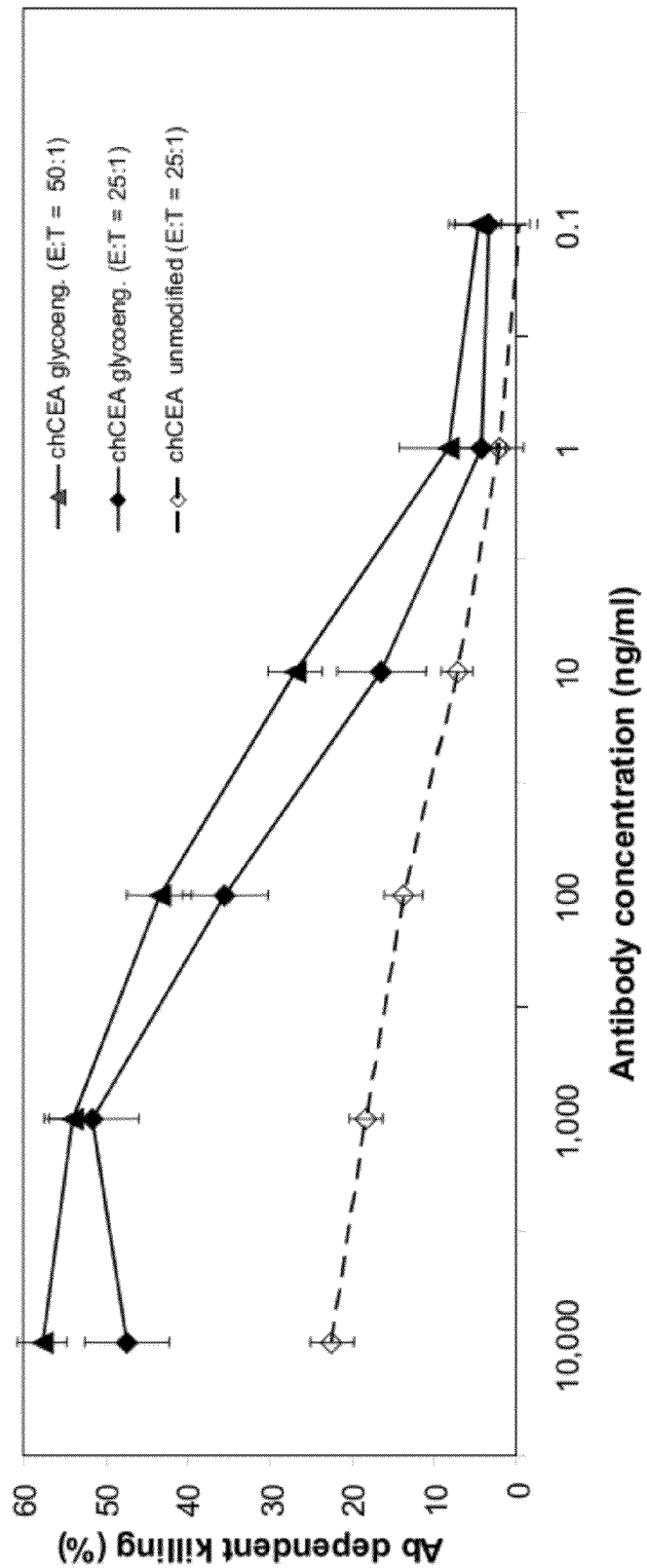
FIG. 2 shows enhanced ADCC activity of a glycoengineered chimeric PR1A3 antibody in comparison to non-glycoengineered chimeric PR1A3 antibody with human PBMCs as effectors.

The PR1A3 antibody was chimerized to have a human IgG1/kappa constant region, and expressed using the Gylco-Mab technology in order to have a high degree of afucosylated sugars in the Fc. The glycoengineered and non-glycoengineered antibodies were compared at a effector to target ratio of 25:1. The maximal amount of antibody dependent target cell killing was doubled by glycoengineering of the Fc region (FIG. 2). A further increase in cell killing was achieved by increasing the effector to target ratio (FIG. 2).

Figure 3:
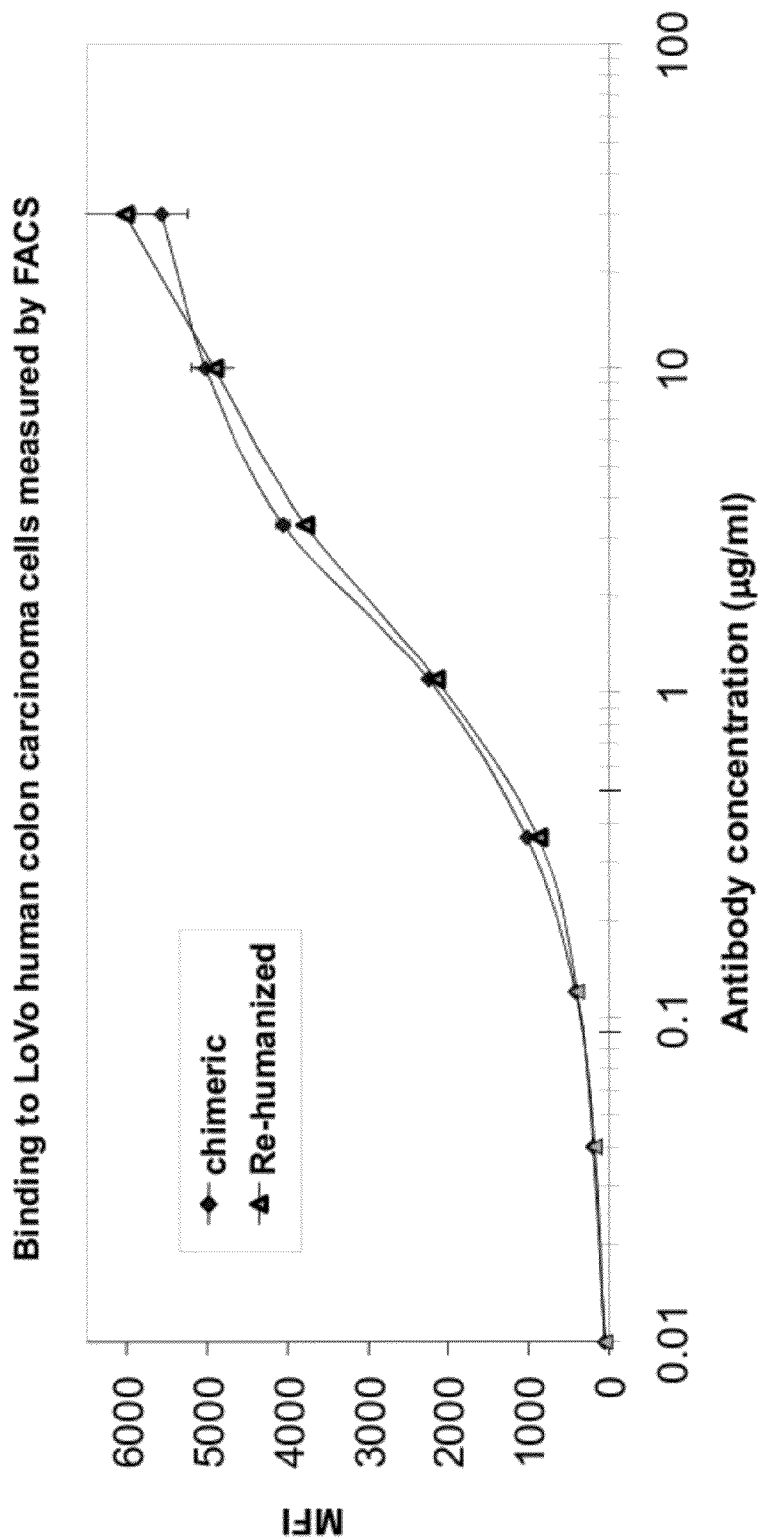
FIG. 3 shows antigen binding activity of a humanized PR1A3 antibody comprising a heavy chain variable region construct, CH7A, and a light chain variable region construct, CL1A, in comparison to chimeric PR1A3 antibody.

PR1A3 was humanized using frameworks identical to human germline sequences. The IMGT sequence IGHV7-4-1*02 (Accession No. X62110) was the acceptor for VH humanized and IMGT_hVK_1_39 (Accession No. X59315) was the acceptor for VL humanization. A humanized PR1A3 antibody comprising a heavy chain variable region construct CH7A and a light chain variable region construct CL1A showed satisfactory binding to human colon carcinoma cells as measured by flow cytometry (FIG. 3).

Figure 5:
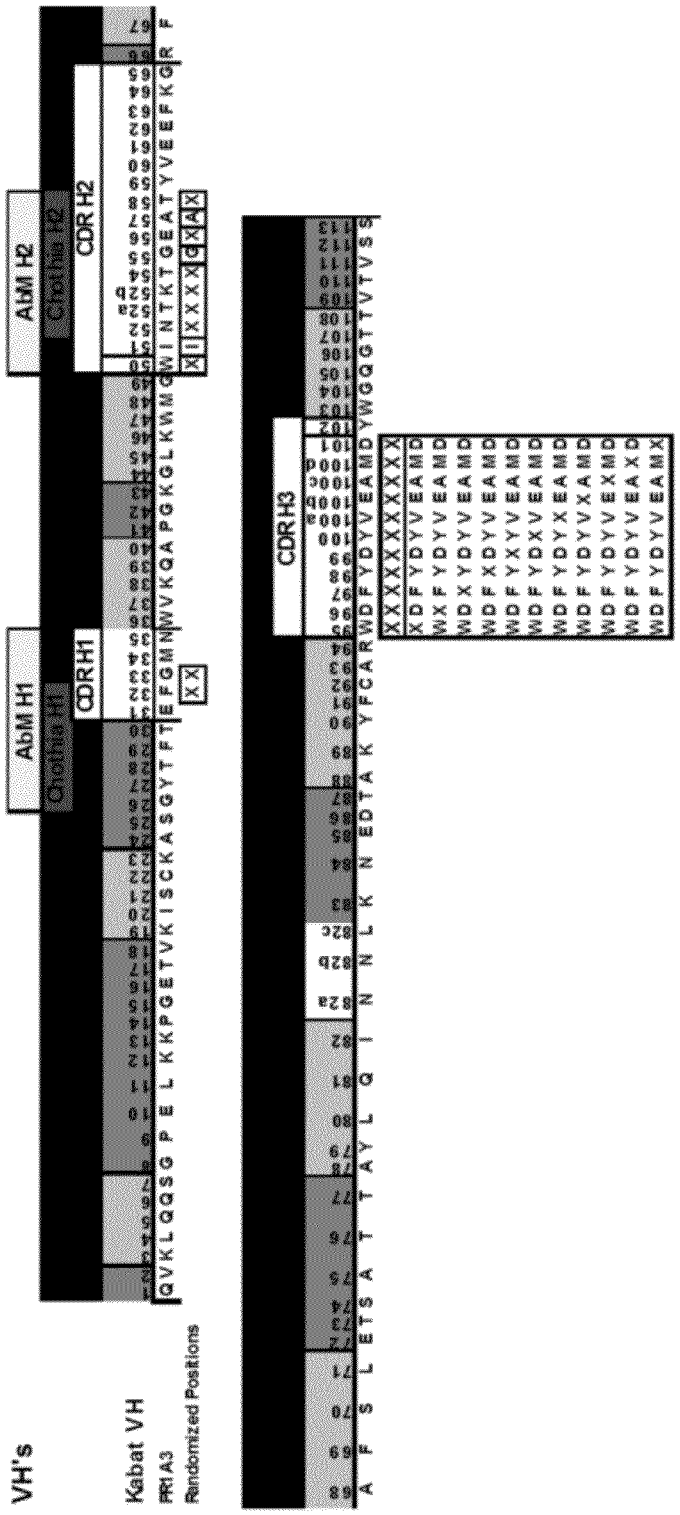
FIG. 5 shows randomization sites for generating an antibody library for affinity maturation of the humanized PR1A3 antibody heavy chain (SEQ ID NO: 99). Positions marked with an X were randomized.

Affinity maturation of PR1A3 by phage display was performed using standard protocols as described in detail in Example 1, herein. The parent humanized PR1A3 antibody that was used for affinity maturation comprises a heavy chain variable region construct CH7A and a light chain variable region construct CL1A. Tables 3-6 below show the libraries used for affinity maturation. For the L1/L2 library, positions Valine 29, Alanine-50, or Serine-51 within the CDRs were kept constant. For the H1/H2 library, positions Isoleucine-51, Glycine-55, or Alanine-57 within the CDRs were kept constant (FIGS. 4 and 5).

Figure 6:
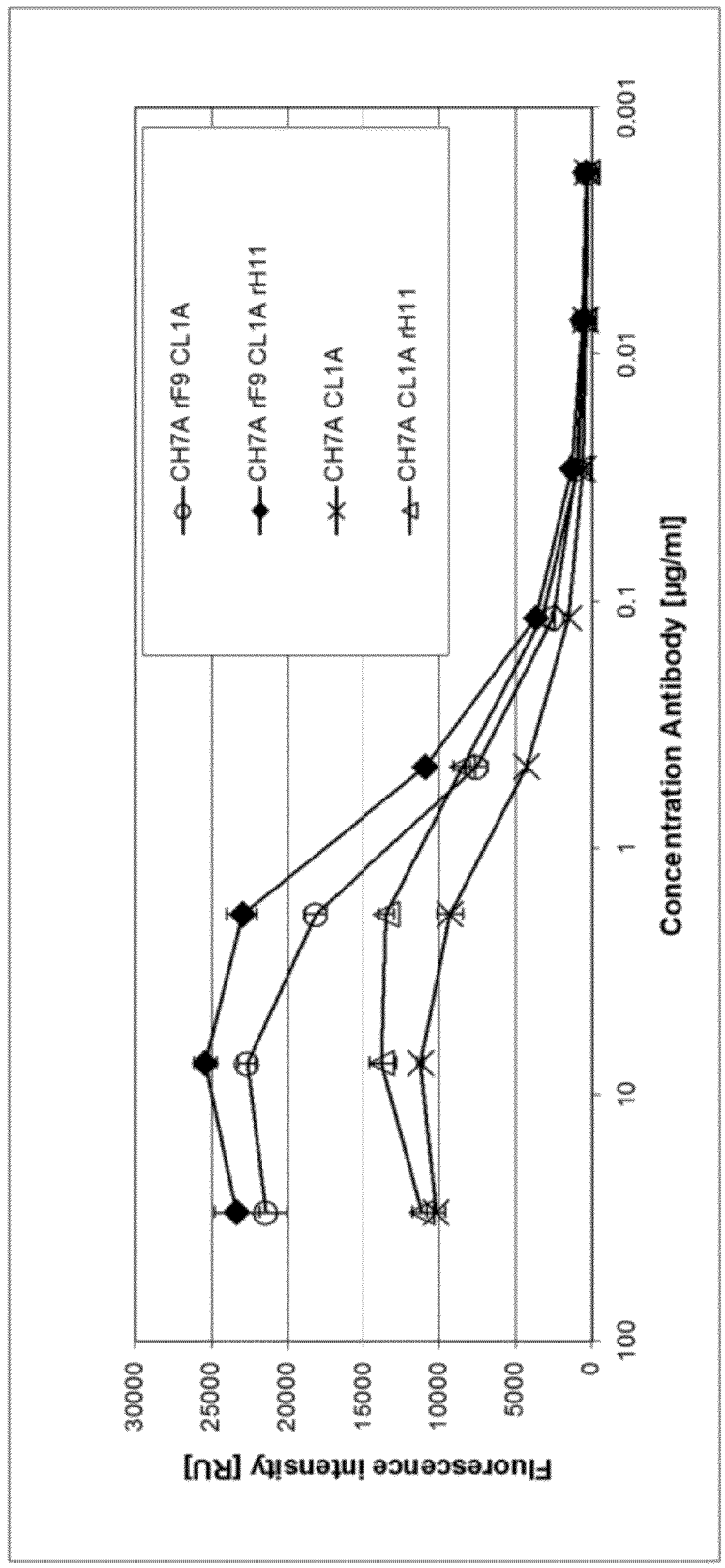
FIG. 6 shows binding activity of affinity matured anti-CEA antibodies derived from a humanized PR1A3 antibody comprising a heavy chain variable region construct CH7ArF9 and a light chain variable region construct CL1ArH11.
Figure 7:
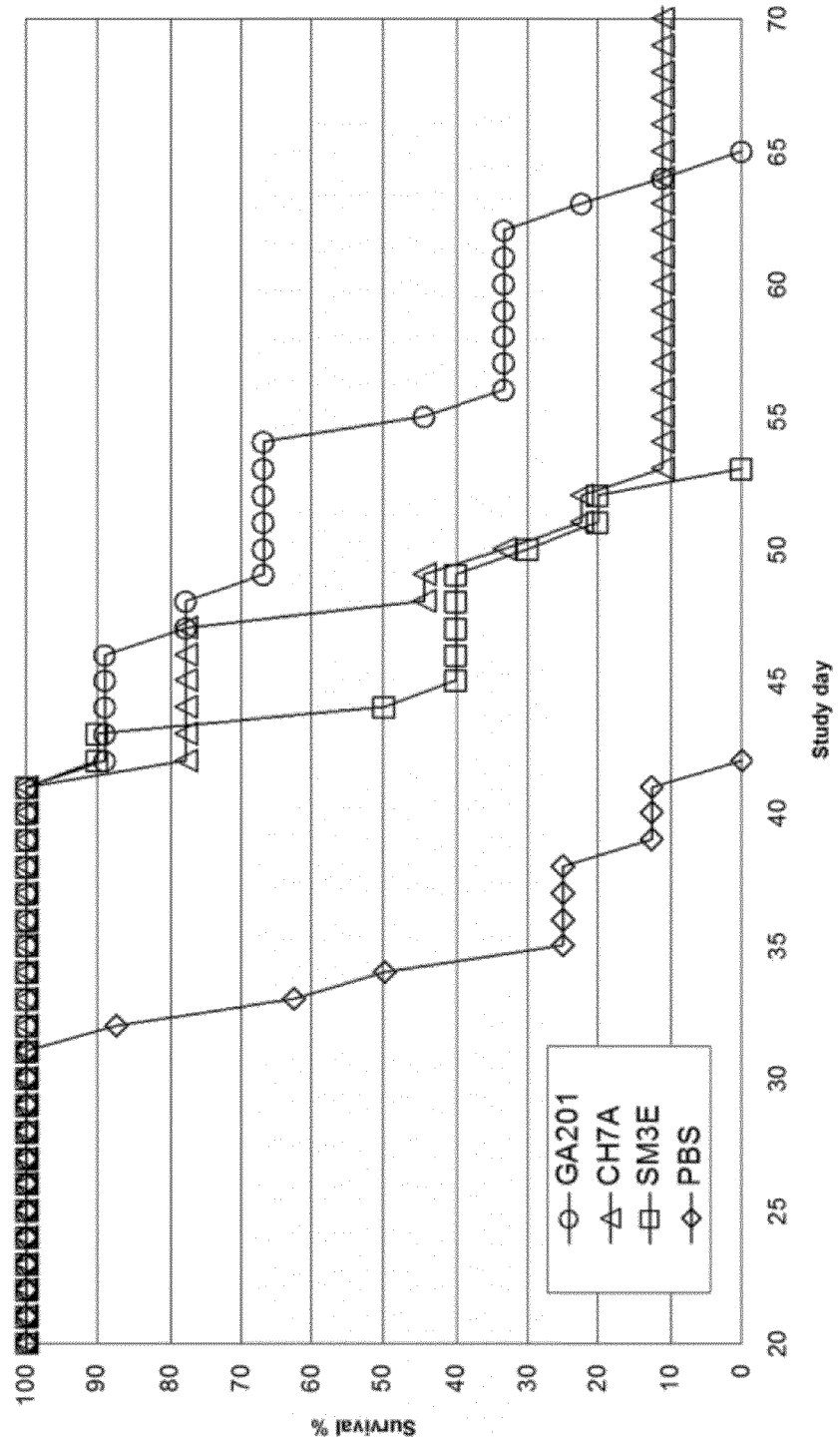
FIG. 7 shows the results of an efficacy study in SCID/bg mice that were intrasplenically administered LS174T human colorectal carcinoma cells in order to have an orthotopic tumor model. Antibody therapy was started at seven days later by injection of the antibodies at a dose of 25 mg/kg body weight, followed by two additional weekly injections. "CH7A" represents a humanized antibody comprising the CDRs of PR1A3 as described herein. "SM3E" refers to a previously generated anti-CEA antibody. "GA201" represents a humanized anti-EGF antibody used as a positive control. "PBS" refers to phosphate buffered saline, which was used as a negative control. Survival was measured according to the termination criteria defined by the Swiss regulatory authority.
Figure 8:
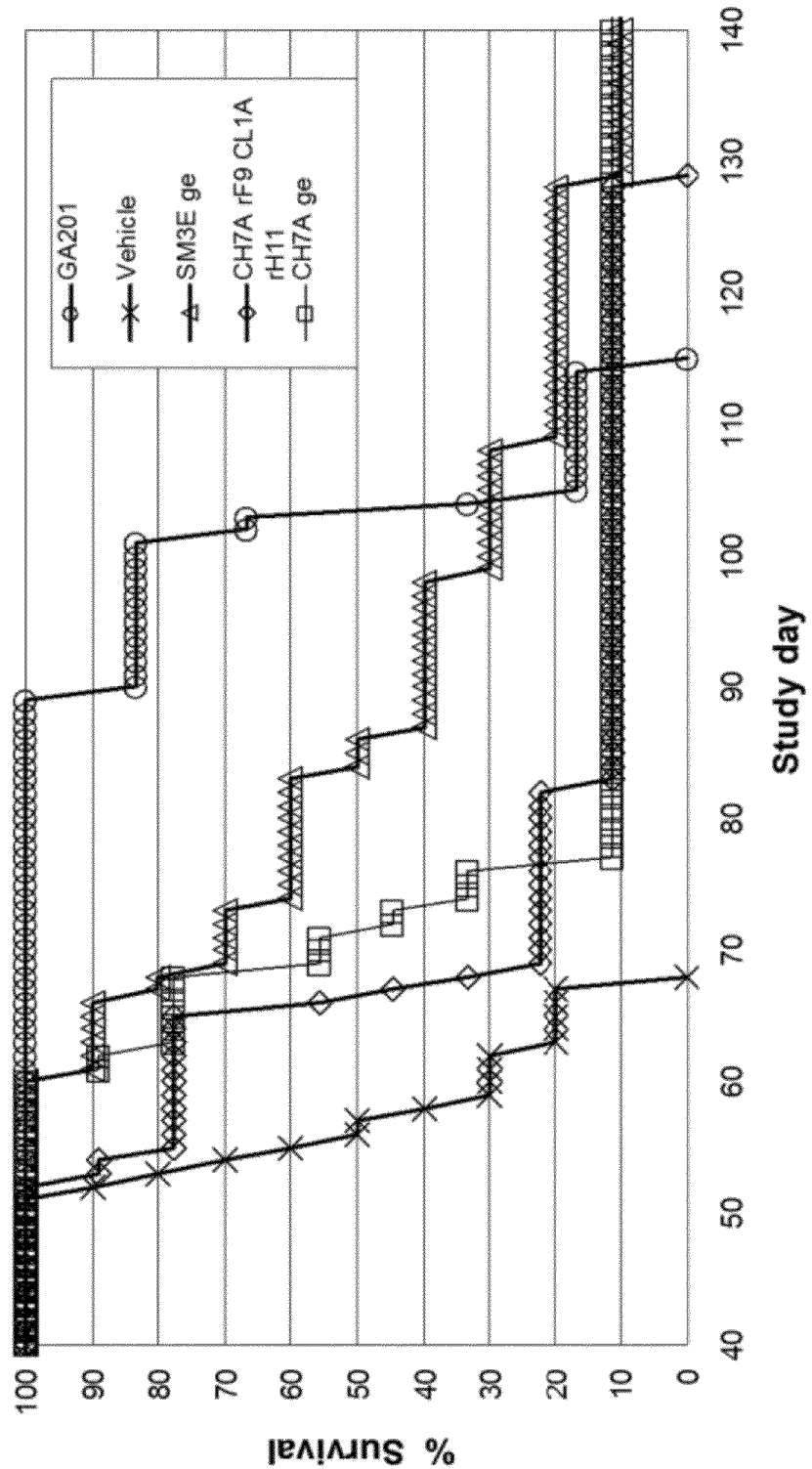
FIG. 8 shows the results of an efficacy study in SCID/bg mice that were injected intravenously with A549 lung carcinoma cells, where the tumor engrafts in the lung of the animals. Antibody therapy was started at seven days later by injection of the antibodies at a dose of 25 mg/kg body weight, followed by two additional weekly injections. "CH7A," "SM3E," and "GA201" are as set forth for FIG. 7, above. The designation "CH7ArF9 CL1A rH11" represents a CH7A antibody variant with affinity matured heavy and light chains. The designation "ge" indicates that the antibody has been glycoengineered to have reduced numbers of fucosylated oligosaccharides in the Fc region. "Vehicle" refers to the negative control. A549 lung carcinoma cells are strongly positive for EGFR expression and weakly positive for CEA expression.
Figure 9:
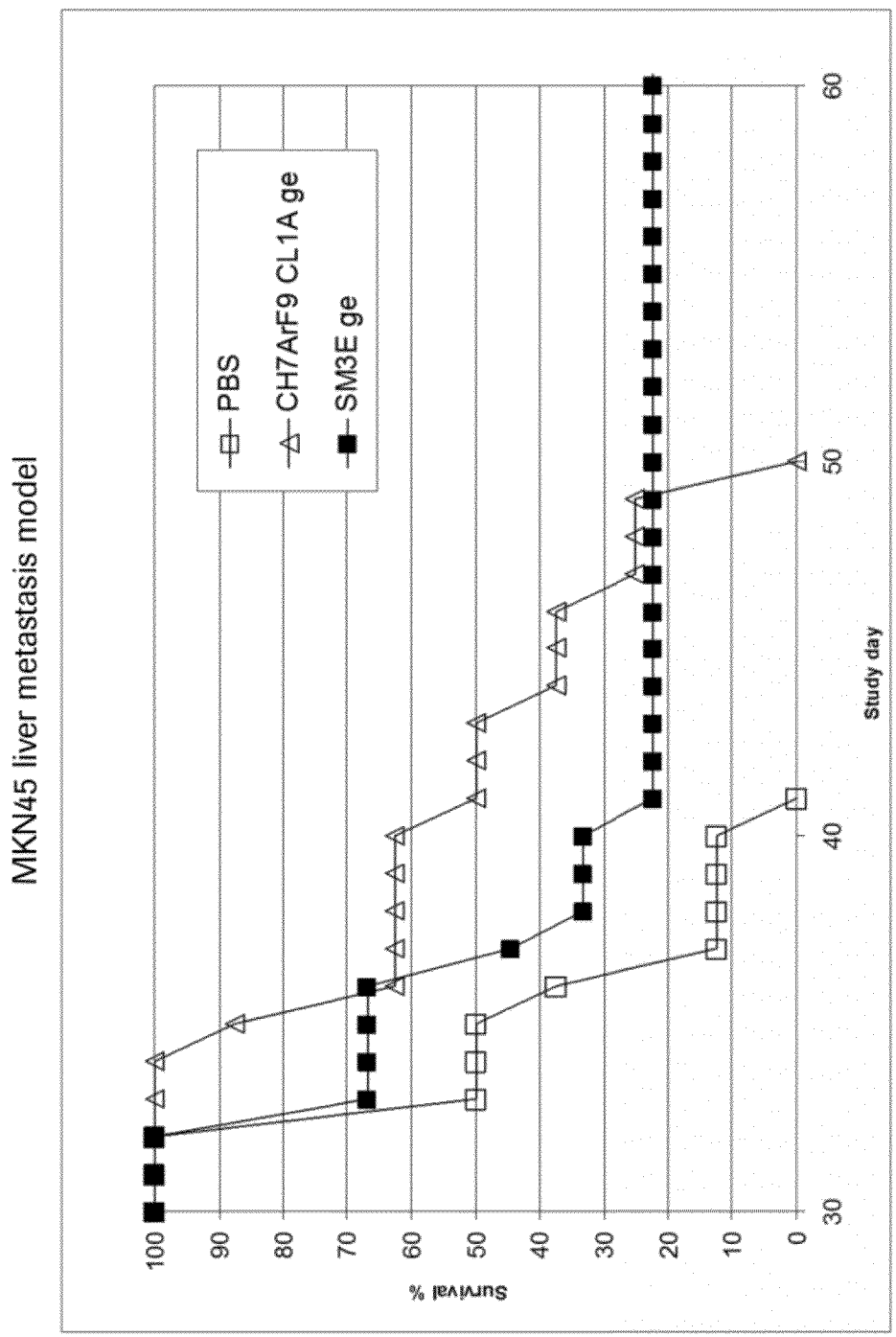
FIG. 9 shows the results of an efficacy study in SCID/bg mice that were intrasplenically administered MKN45 gastric carcinoma cells, which generates tumor metastasis in the liver of the animals. The designations, "CH7ArF9 CL1A rH11," "SM3E," "ge," and "PBS" are as set forth for FIGS. 7 and 8, above.
Figure 10:
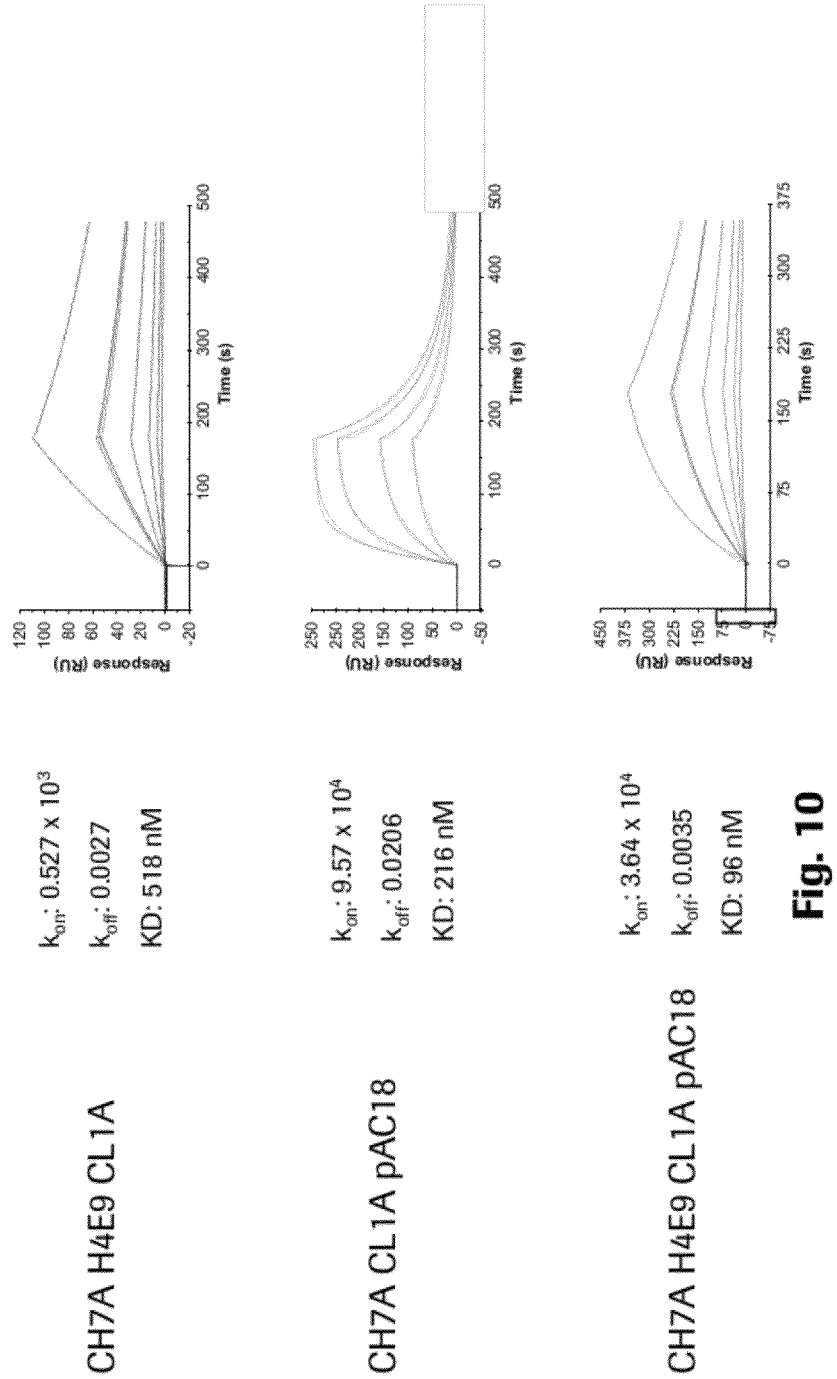
FIG. 10 shows kinetic analysis of affinity matured clones: (a) shows a sensorgram of anti-CEA Fabs with an affinity matured heavy chain CH7A H4E9 (SEQ ID NO: 199) together with unmatured light chain CL1A (SEQ ID NO:105); an affinity matured light chain CL1A pAC18 (SEQ ID NO:209) combined with unmatured heavy chain CH7A; and a combination thereof, CH7A H4E9 and CL1A pAC18 (SEQ ID NOs:199 and 209); (b) summary of kinetic analysis of affinity matured clones.
Figure 15:
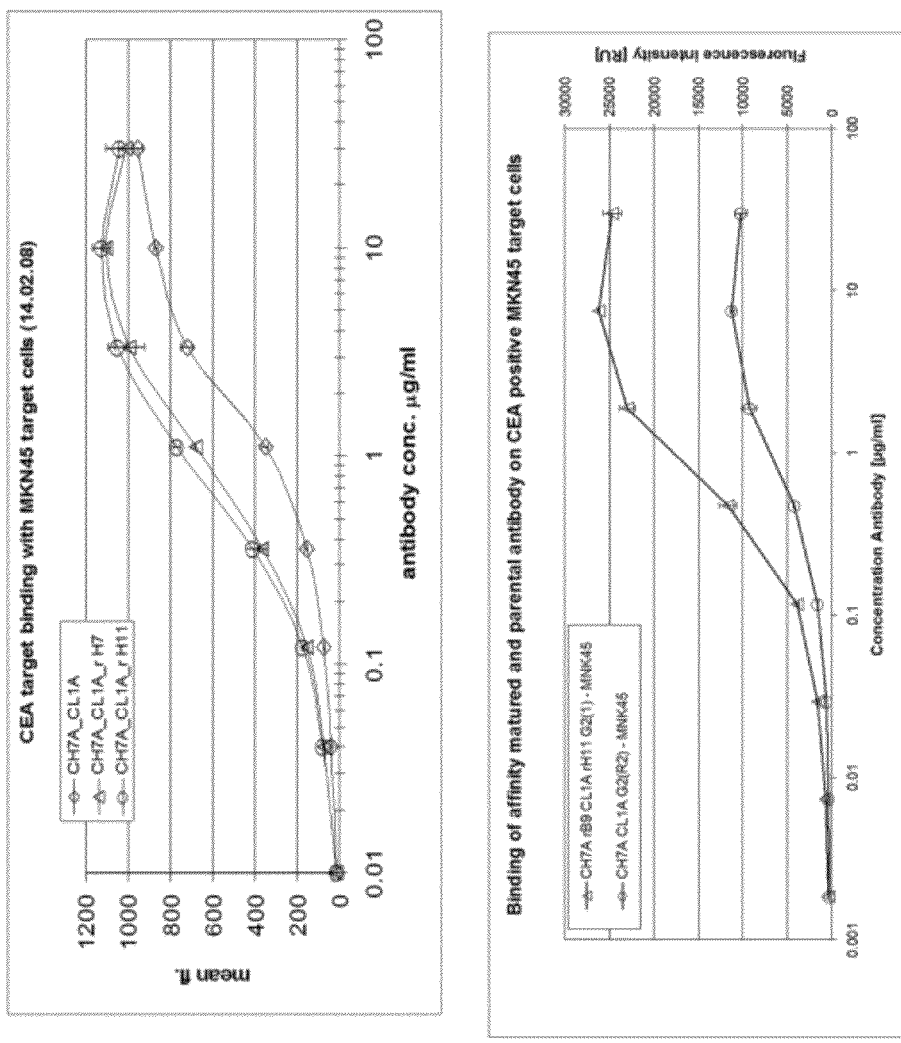
FIG. 15 shows binding affinity of anti-CEA antibodies for membrane-bound CEA on MKN45 target cells. Humanized anti-CEA antibodies with either an affinity matured light chain (Panel A, CH7A,CL1ArH7 or CH7A,CL1ArH11) or affinity matured heavy and light chains (Panel B, CH7A rB9, CL1A rH11 G2(1)) that have been converted to IgG show improved binding as compared to the control antibody (CH7A,CL1A).
Figure 16:
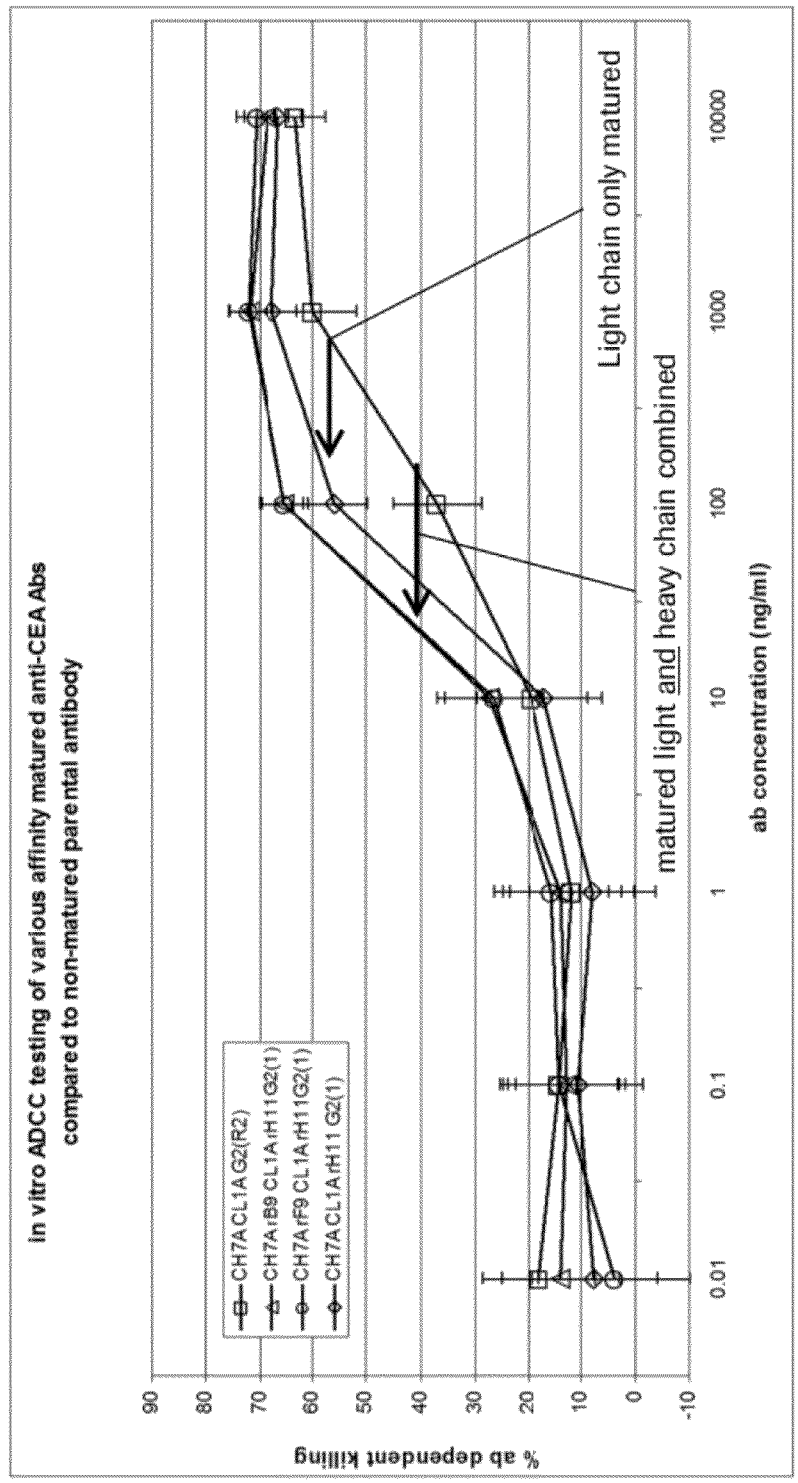
FIG. 16 shows the results of an assay testing antibody-dependent cellular cytotoxicity (ADCC) by affinity matured antibodies (CH7ArB9, CL1A rH11G2(1), CH7Arf9, CL1A rH11G2(1), and CH7A, CL1A rH11 G2(1)) compared to control antibodies (CH7A, CL1A G2(R2).

An affinity matured heavy chain variable region construct, CH7A rF9, and an affinity matured light chain variable region construct, CL1A rH11, were paired with the parent light chain variable region construct and the heavy chain variable region construct, respectively, and with each other. All antibodies were converted into human IgG1/kappa and binding to the CEA-positive cell-line MKN45 was measured by flow cytometry. Antibodies comprising either one affinity matured heavy or light chain variable regions or both affinity matured heavy or light chain variable regions showed improved binding characteristic as compared to the humanized parent antibody (FIG. 6). FIGS. 6, 10 and 15 show several examples where the matured light and heavy chains independently contribute to increased affinity. The parental antibody CH7A CL1A has the lowest signal intensity, as well as the highest EC50 value in FIGS. 6 and 15. The matured light chain shifts the EC50 values to lower numbers, whereas the matured heavy chains (rF9 in FIG. 6, and rB9 in FIG. 15) shift the total fluorescence signal intensity in a flow-cytometry measurement. FIG. 10 shows the individual contributions of heavy and light chain measured by Biacore methodology. The combination of these two chains increases the affinity even further. Additionally, as shown in FIG. 16, improvement of affinity leads to improvement of ADCC characteristics.

The binding affinities of the affinity matured heavy and light chain CDRs were determined by Biacore and listed FIGS. 34A and B.

FIG. 35 summarizes the affinity constants of the various affinity matured antibody sequences. The parental antibody PR1A3 is listed as well as several light chain and heavy chain combinations of matured and non matured sequences. All values were obtained by Biacore technology by measuring the association ($k_{on}$) and dissociation ($k_{off}$) rate constants of the various soluble antibody constructs in Fab format on a Biacore chip with immobilized NABA-avi-his reagent (SEQ ID NO 158) as the antigen. The affinity constant is labeled with KD.

Example 3

Figure 17:
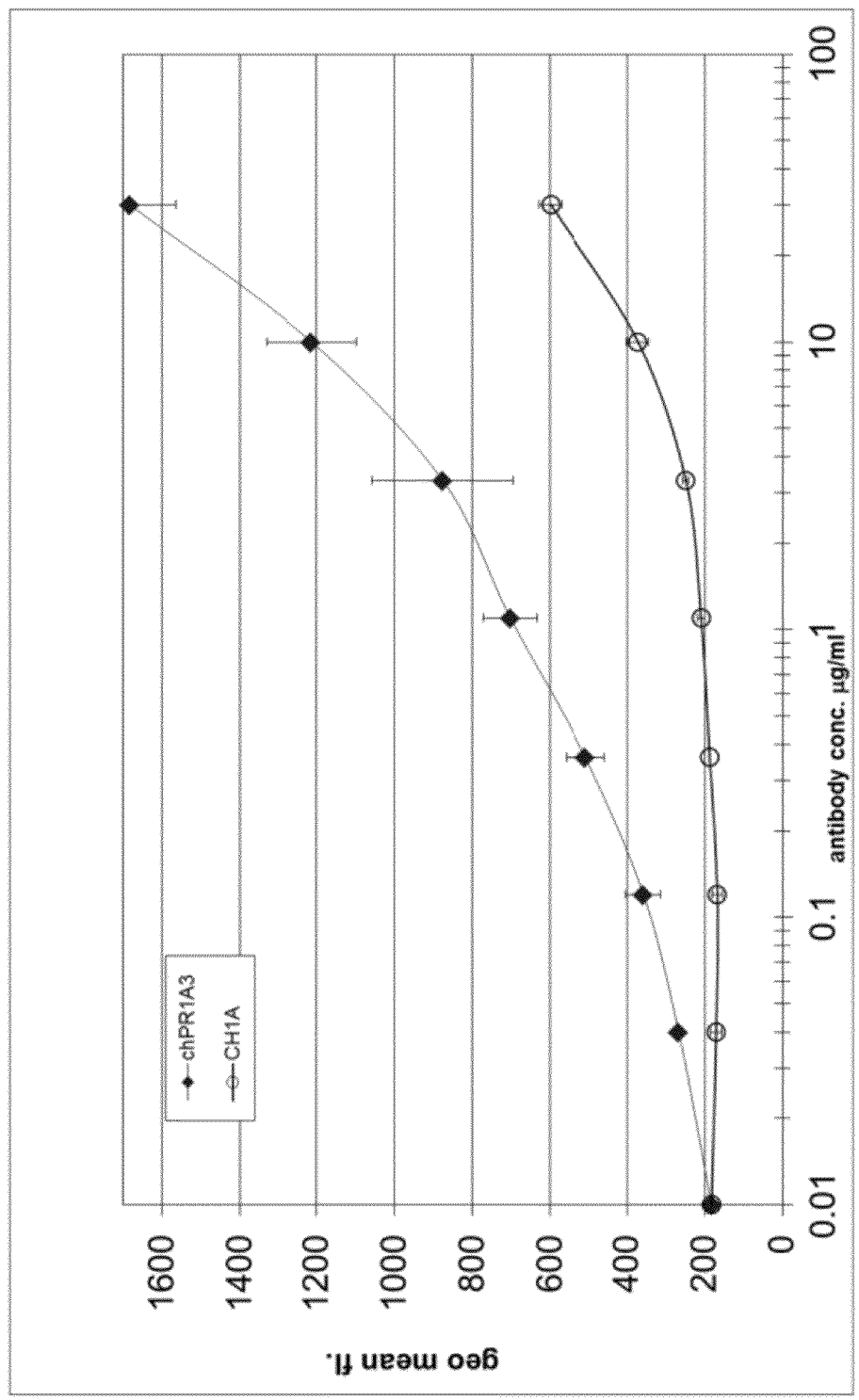
FIG. 17 shows the results of a cell binding assay for anti-CEA antibody with heavy chain CH1A as compared to the mouse-human chimeric antibody chPR1A3.

The acceptor framework used in generating the affinity matured anti-CEA antibodies described in Example 2 was of the human VH7 class. In order to increase stability, a more stable acceptor framework sequence was used as the basis for stability engineering of the antibody. Based on sequence homology of the murine antibody PR1A3, and the assumption that VH1 derived sequences should have a higher intrinsic stability than VH7, or the even numbers of the human VH clans (Ewert, S., Huber, T., Honegger, A. and Plückthun, A. (2003) J. Mol. Biol., 325, 531-553), the sequence IGHV-1-18; Acc No.:M99641 was used as the new acceptor framework. Conventional CDR loop-grafting of the PR1A3 antibody lead to construct CH1A (SEQ ID NO: 279). Unfortunately, this molecule did not show significant binding activity towards the CEA antigen. The binding activity of this construct was compared to the binding activity of the chimeric antibody PR1A3 harbouring mouse-derived variable domains at various concentrations. BxPC3 cells were used for specific binding of the antibodies to CEA and binding intensity was measured by FACS analysis. FIG. 17.

Figure 18:
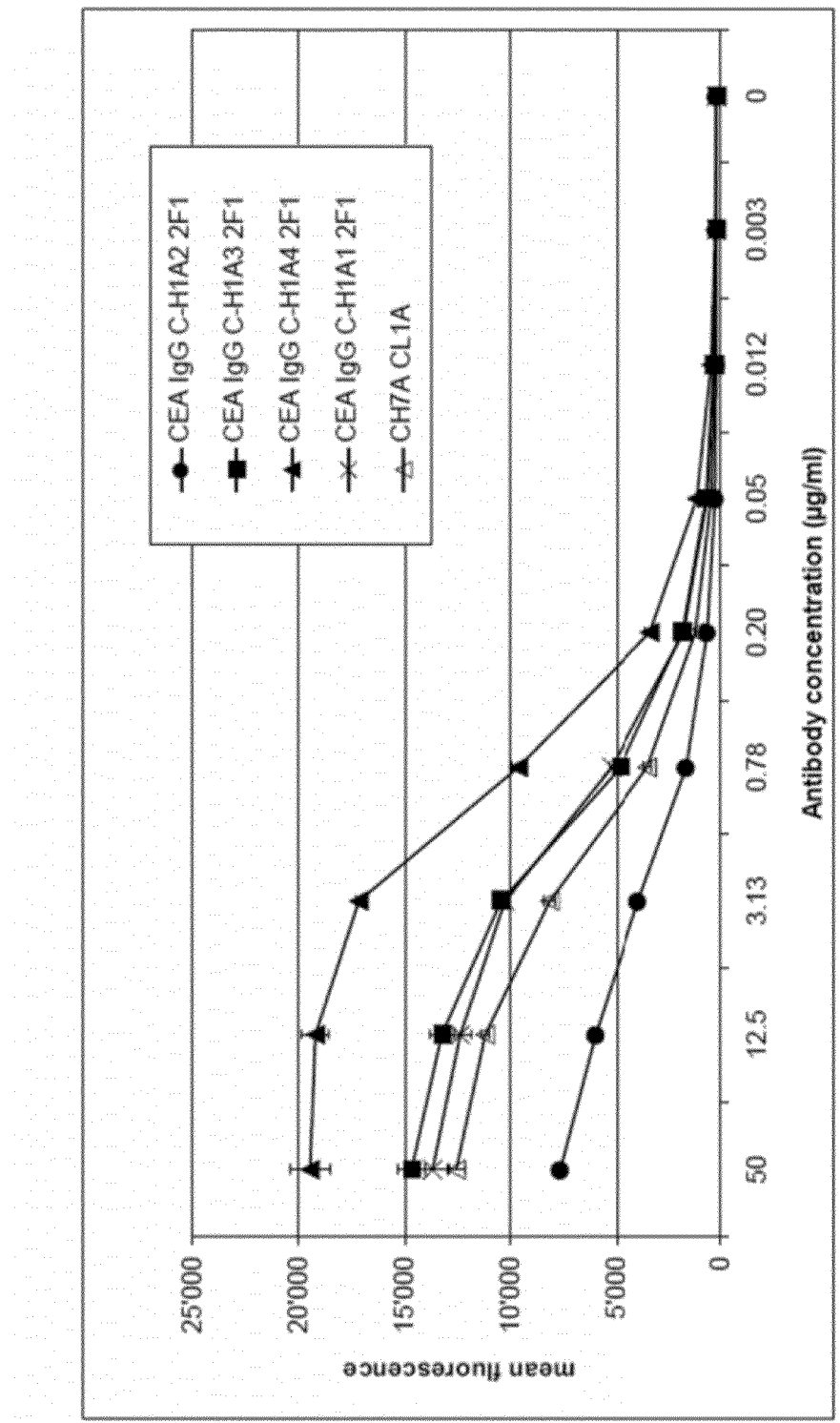
FIG. 18 shows the results of a binding assay for anti-CEA antibodies with heavy chain CH1A1, CH1A2, CH1A3, or CH1A4 and light chain 2F1.
Figure 19:
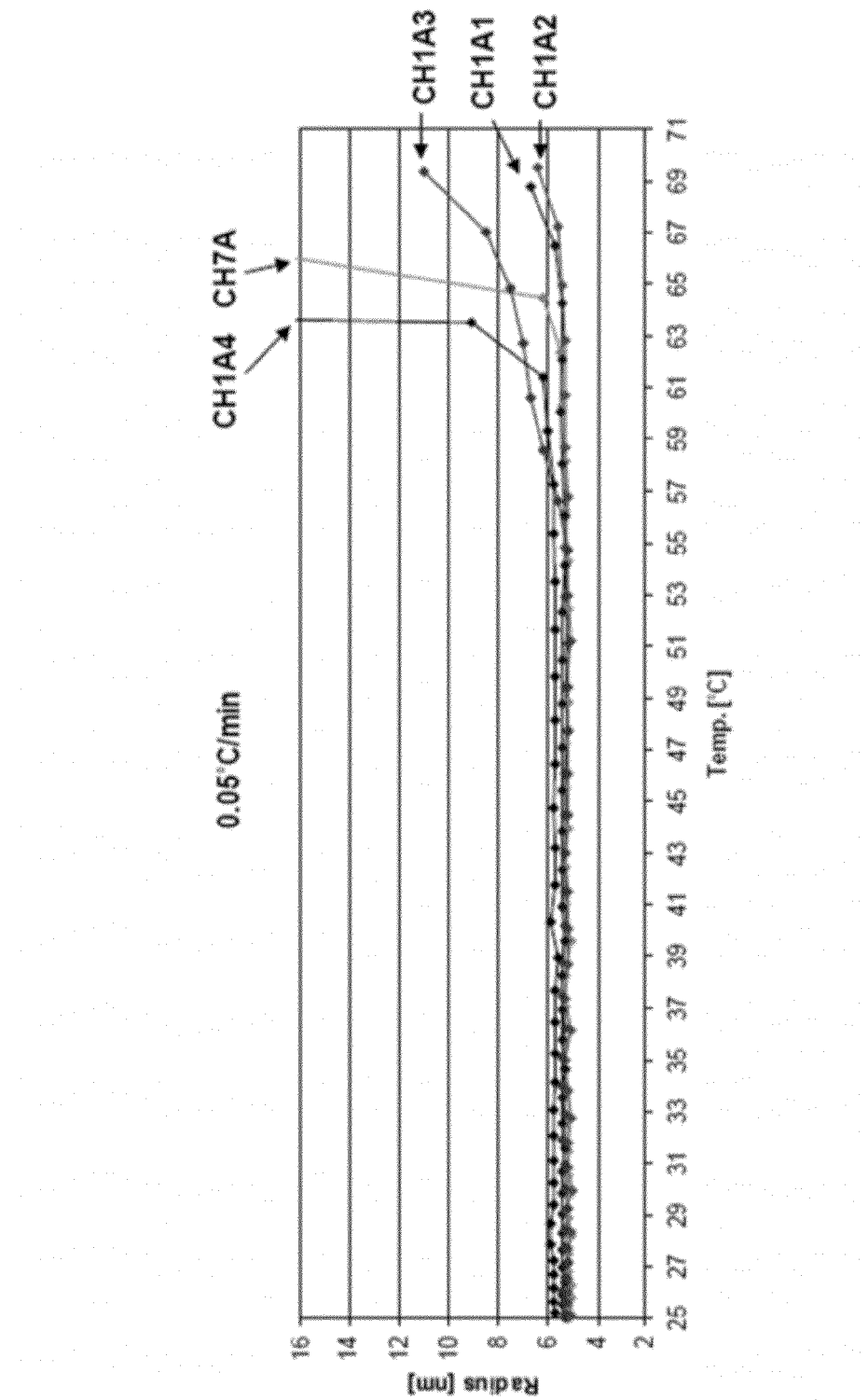
FIG. 19 shows the results of a stability assay for anti-CEA antibodies with heavy chain CH1A1, CH1A2, CH1A3, or CH1A4.

In order to recover binding affinity, several back-mutations were introduced into the CH1A sequence to generated new heavy chains CH1A1 (SEQ ID NO: 257), CH1A2 (SEQ ID NO:258), CH1A3 (SEQ ID NO: 259), and CH1A4 (SEQ ID NO: 260). CH1A1 includes the M69F/T71L double point mutation. The latter three variants have the entire frameworks 1, 2, or 3, respectively, replaced by the murine counterpart. FIG. 18 shows the binding of those constructs when paired with the 2F1 light chain (SEQ ID NO: 209). In this assay, cell binding of the CH1A-based antibody variants to CEA-expressing MKN-45 cells was analyzed at various concentrations. The affinity-matured light chain 2F1 was identical for all antibodies tested except for the parental antibody where the original light chain CL1A was used. Mean fluorescence was determined by FACS analysis. FIG. 19 shows the stabilities of those constructs when paired with the 2F1 light chain, as measured by dynamic light scattering (DLS) of the samples. The DLS assay was performed using 1 mg/ml of the antibodies in a buffer of 20 mM Histidine and 140 mM NaCl at pH 6.0. The assay was conducted starting at 25° C. with an incremental temperature increase of 0.05° C./min up to 70° C. All antibodies tested in this assay had 2F1 as the light chain.

Figure 20:
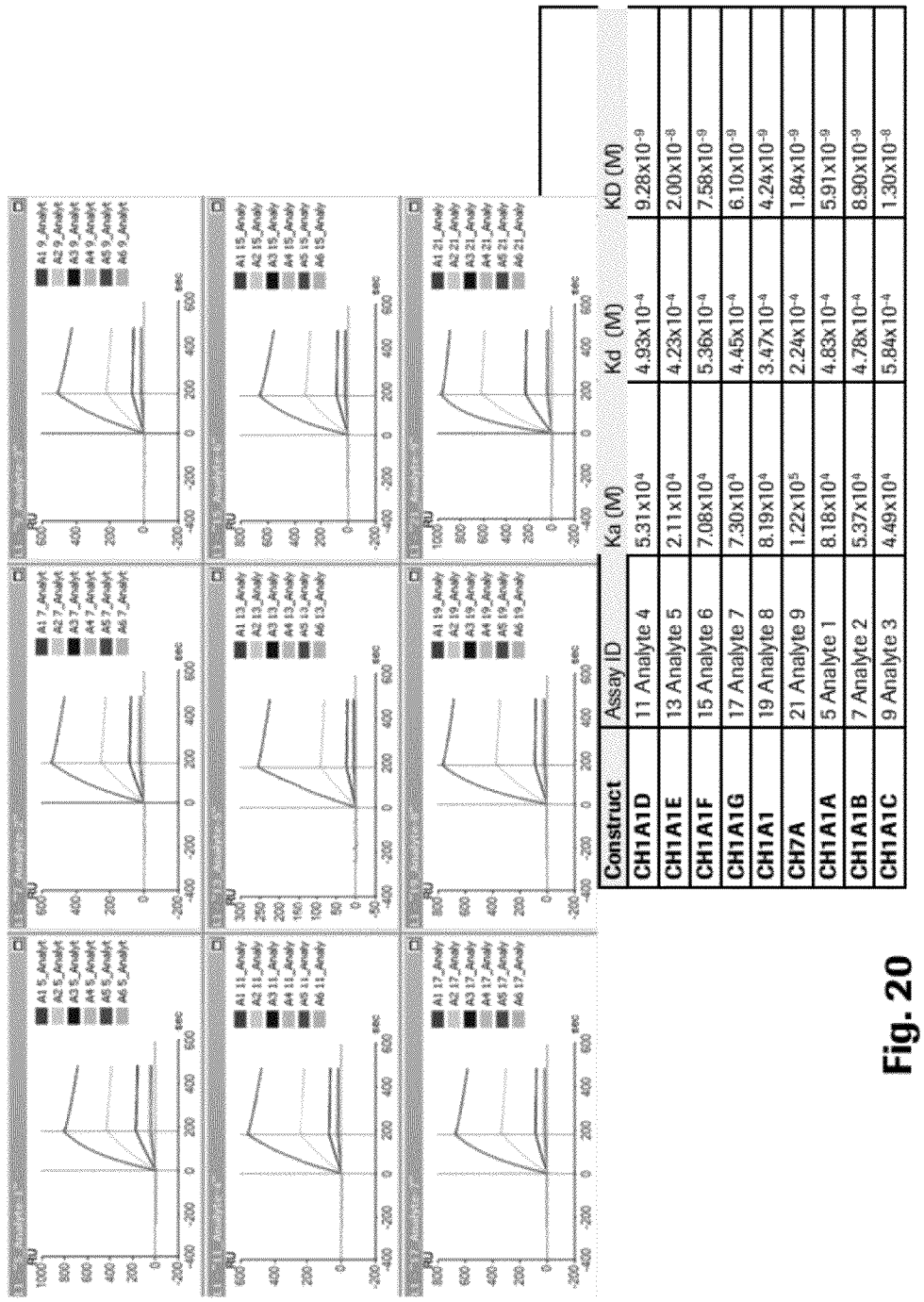
FIG. 20 shows the result of Surface Plasmon Resonance (SPR) analysis for anti-CEA antibodies generated from CH1A1.
Figure 21:
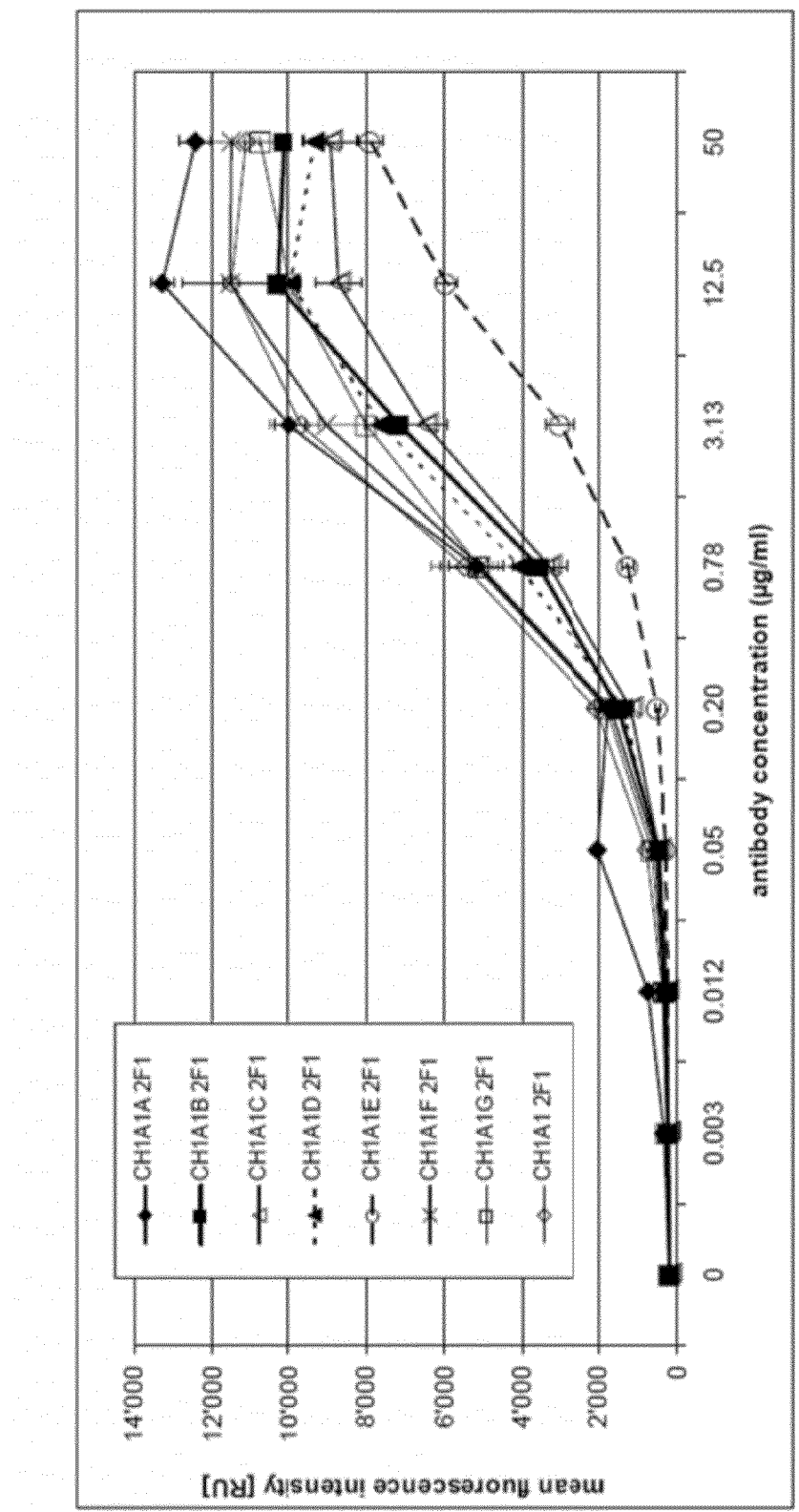
FIG. 21 shows the result of cell binding assays for anti-CEA antibodies generated from CH1A1.

Since CH1A1 still keeps the original stability, and also shows some significant (but somewhat less than CH1A4, that was of highest affinity, but lowest stability) binding, this construct was chosen for further optimization of binding. New heavy chains CH1A1A (SEQ ID NO: 261), CH1A1B (SEQ ID NO: 262), CH1A1C (SEQ ID NO: 263), CH1A1D (SEQ ID NO: 264), CH1A1E (SEQ ID NO: 265), CH1A1F (SEQ ID NO: 266), and CH1A1G (SEQ ID NO: 267) were generated. These are essentially variants of CH1A1 with only a few backmutations in the FR1 and the FR3 region. FIGS. 20 and 21 shows that their affinities are all comparable, albeit still slightly inferior to the VH7 based humanized construct CH7A. FIG. 20 shows Proteon (Biacore) sensorgrams obtained for the binding of the CH1A1-based framework variants to the CEA antigen-harbouring chimeric protein NABA. Biotinylated NABA was immobilized on a Neutravidin-coated chip and antibodies were used as analytes at concentrations of 100, 50, 25, 12.5, 6.25, and 0 nM. The precursor clone CH1A1 and the parental antibody CH7A were included for direct comparison. The light chain 2F1 was identical for all antibodies tested. FIG. 21 shows the binding intensity of the seven CH1A1-based variants carrying additional framework mutations. Antibodies were incubated with the CEA-expressing MKN45 cells in a concentration series and binding intensity was measured by FACS analysis. The precursor clone CH1A1 was included for direct comparison. All antibodies tested in this assay had 2F1 as the light chain. Variants CH1A1A and CH1A1B were chosen as final variants of the VH1 based humanization based on their comparatively better purification yields and monomeric behavior.

Example 4

The residues of CDR-H3 that were selected in the affinity maturation process were individually introduced into the PR1A3 sequence to test for increased antibody stability. FIG. 36.

Figure 22:
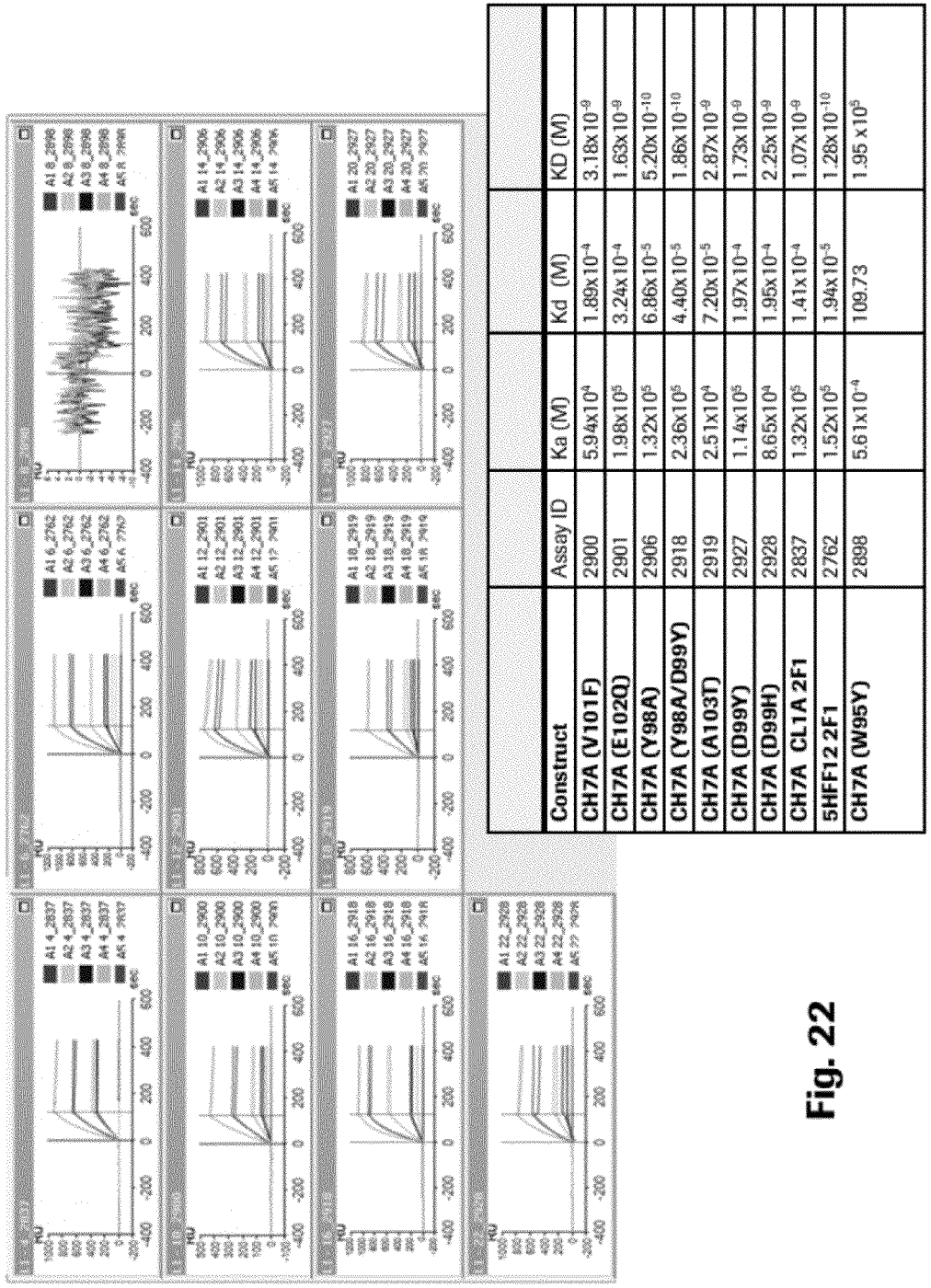
FIG. 22 shows the Surface Plasmon Resonance (SPR) measurements of the affinity (as measured in the bivalent form) of stability engineered anti-CEA antibodies as compared to the parent 5HFF12 heavy chain.

FIG. 22 shows the Surface Plasmon Resonance (SPR) measurements of the affinity (as measured in the bivalent form) of each antibody towards the CEA antigen (NABA reagent as described by Stewart et al. Cancer Immunol Immunother (1999) 47:299-306). Shown in FIG. 22 are Proteon (Biacore) sensorgrams obtained for the binding of the CDR-H3 antibody variants to the CEA antigen-harbouring chimeric protein NABA. Biotinylated NABA was immobilized on a Neutravidin-coated chip and antibodies were used as analytes at concentrations of 100, 50, 25, 12.5, 6.25, and 0 nM. The affinity matured precursor clone 5HFF12 and the parental antibody CH7A were included for direct comparison. All antibodies tested in this assay had 2F1 as the light chain. Variant CH7A (W95Y) shows no measurable activity in this assay, all the other variants exhibit an affinity to target within a factor of ten of each other. The relative affinity of each, measured in the bivalent form, is as follows: 5HFF12>CH7A (Y98A/D99Y)>CH7A (Y98A)>CH7A>CH7A (E102Q)>CH7A (D99Y)>CH7A (D99H)>CH7A (A103T)>CH7A (V101F)>CH7A (W95Y).

Figure 23:
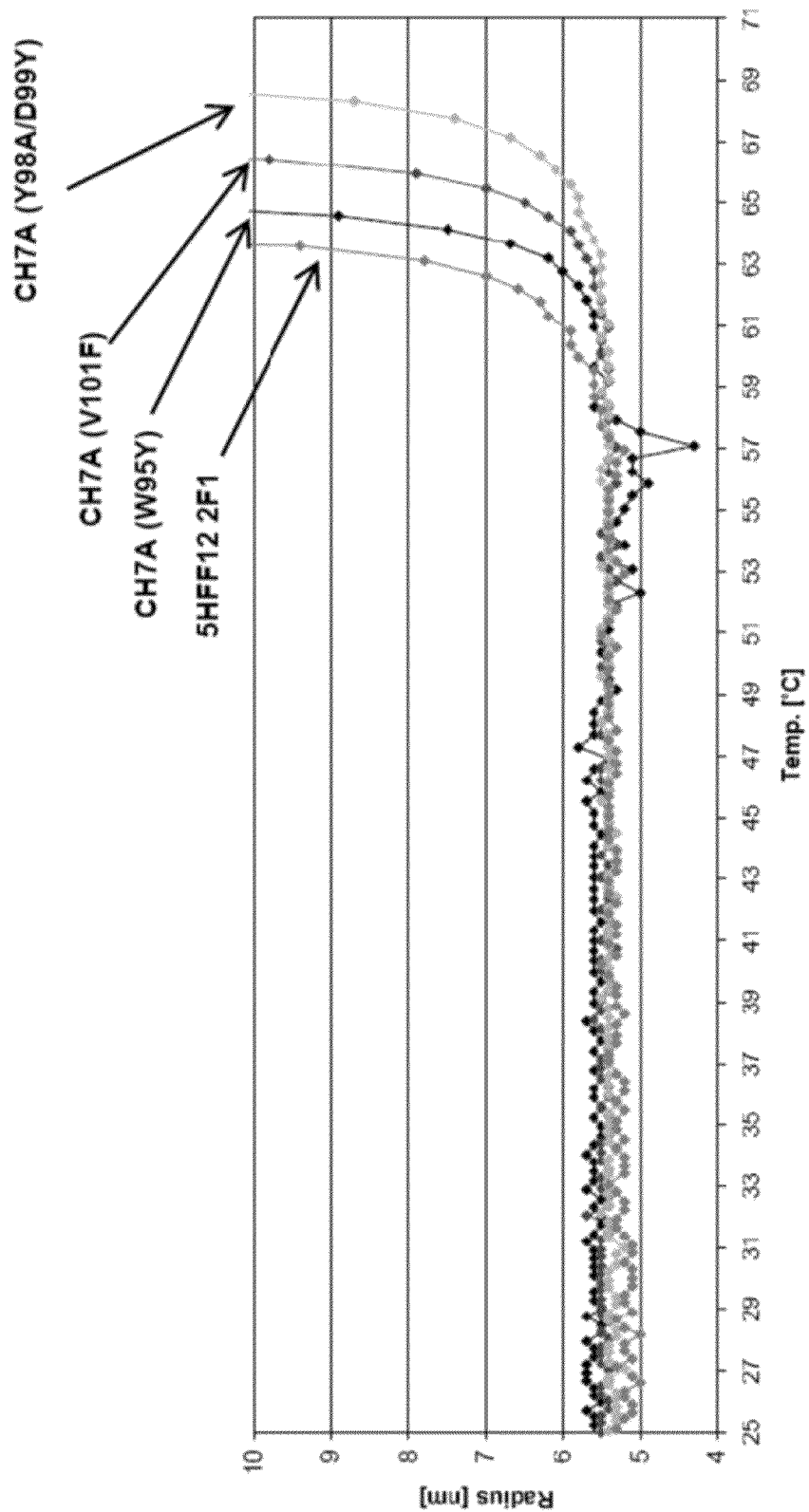
FIGS. 23 and 24 show the results of a stability assay for affinity-matured antibody 5HFF12 as compared to its parental heavy chain CH7A with the individual point mutations introduced that were selected in 5HFF12.
Figure 24:
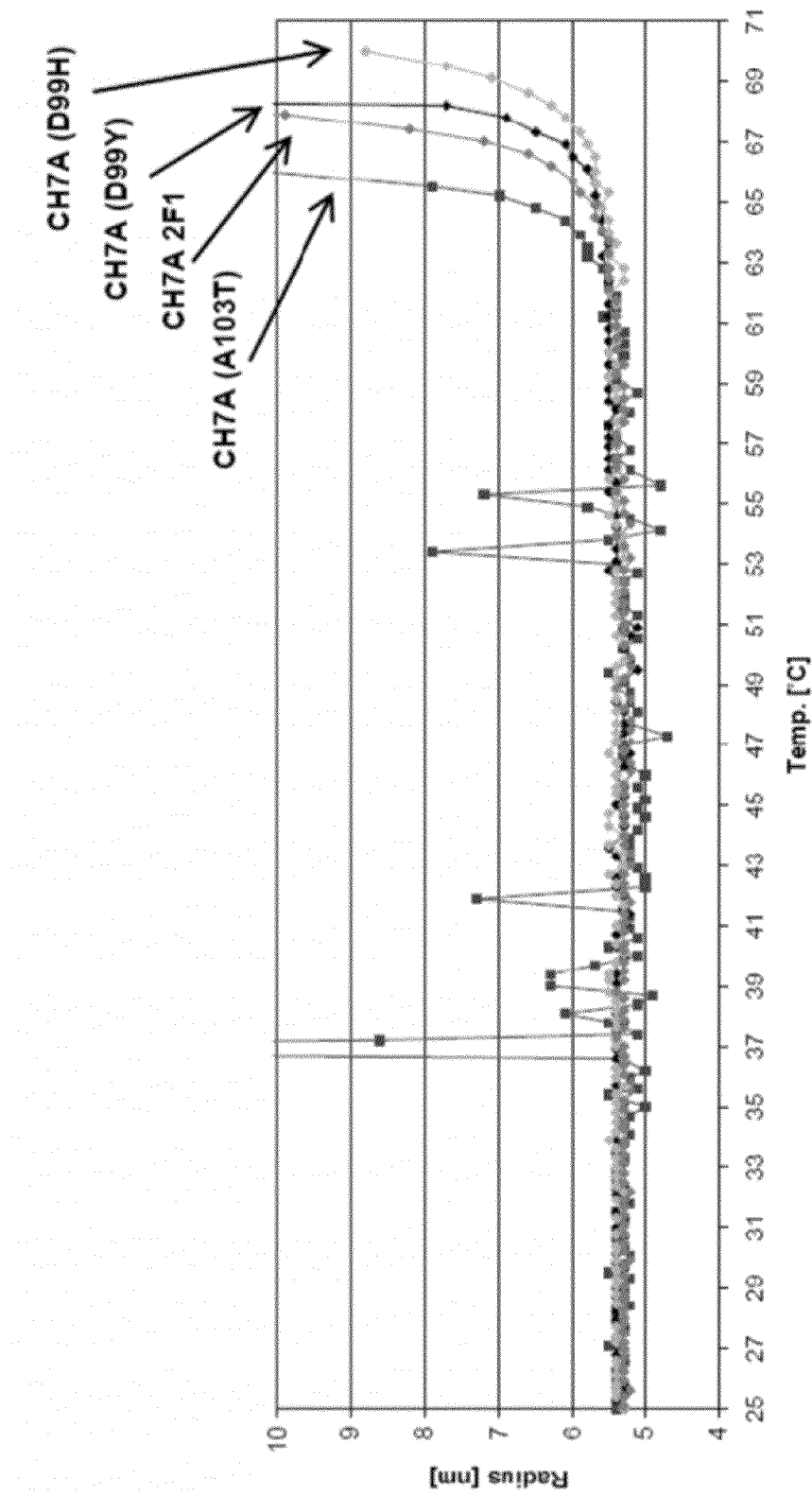

DLS analysis was performed on the antibodies as compared with their precursor 5HFF12 and the parental antibody harbouring heavy chain CH7A. The light chain 2F1 was identical for all antibodies tested in this experiment. FIGS. 23 and 24. The results of this analysis provided the following ranking in stabilities: CH7A (D99Y)>CH7A (Y98A/D99Y)>CH7A (V101F)>CH7A (D99H)>CH7A (A103T)>CH7A (W95Y)>CH7Ax2F1 (=PR1A3)> 5HFF12. The DLS assay was performed using 1 mg/ml of the antibodies in a buffer of 20 mM Histidine and 140 mM NaCl at pH 6.0. The assay was conducted starting at 25° C. with an incremental temperature increase of 0.05° C./min up to 70° C.

The double mutant (Y98A/D99Y) (SEQ ID NO: 223) was chosen for further stability engineering as it exhibited high stability while retaining high affinity for the CEA target.

Example 5

The double mutant (Y98A/D99Y) of the humanized PR1A3 derivative CH7A was introduced into the final variants of the VH1 based humanization-constructs CH1A1A, and CH1A1B.

Figure 25:
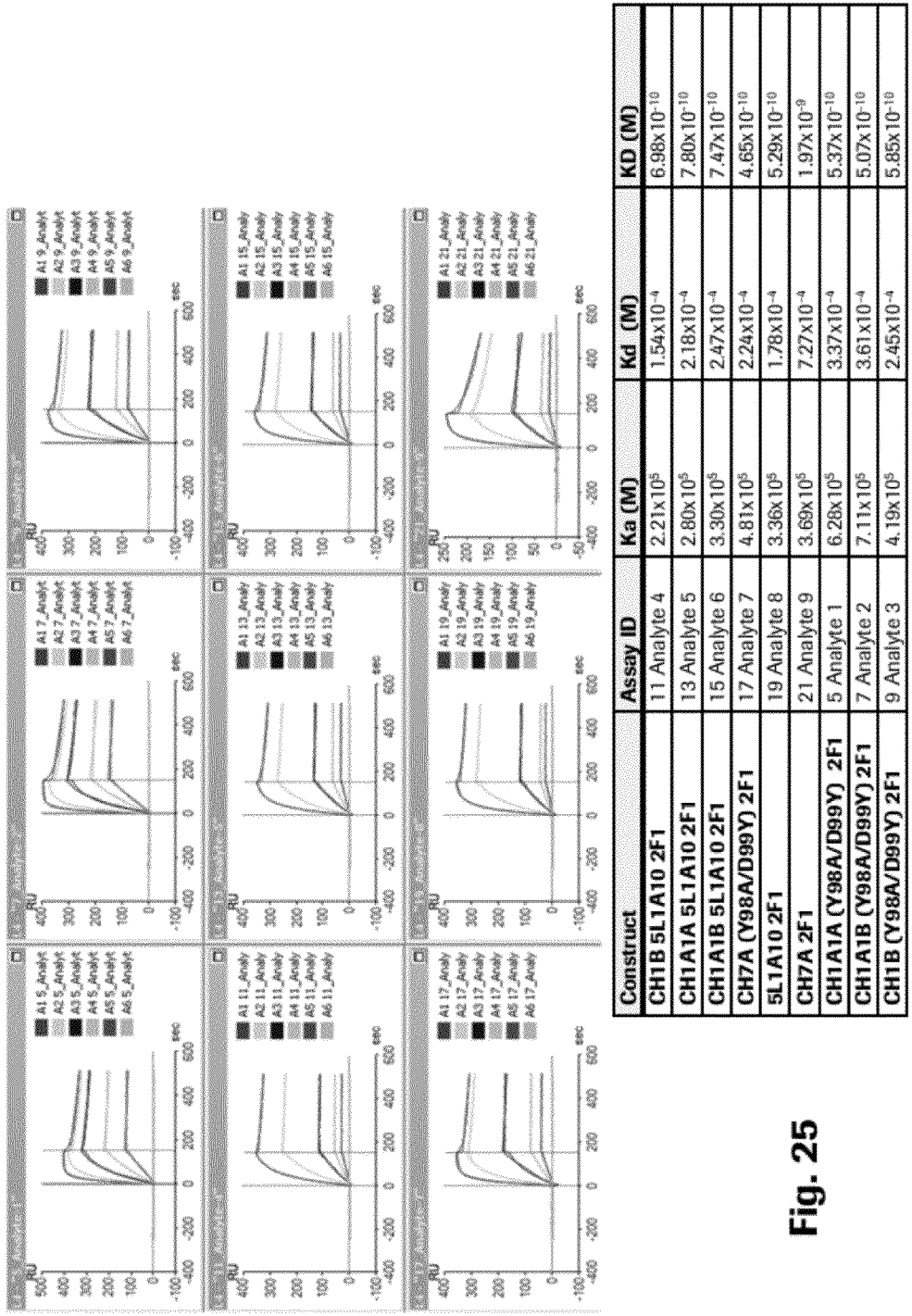
FIG. 25 shows Surface Plasmon Resonance analysis of the combined framework and CDR-H3 variants.

Proteon (Biacore) sensorgrams were obtained for the binding of the combined framework and CDR-H3 variants to the CEA antigen-harbouring chimeric protein NABA. Biotinylated NABA was immobilized on a Neutravidin-coated chip and antibodies were used as analytes at concentrations of 100, 50, 25, 12.5, 6.25, and 0 nM. The precursor clone 5L1A10 and the parental antibody CH7A were included for direct comparison. All antibodies tested in this assay had 2F1 as the light chain. FIG. 25.

Example 6

Figure 26:
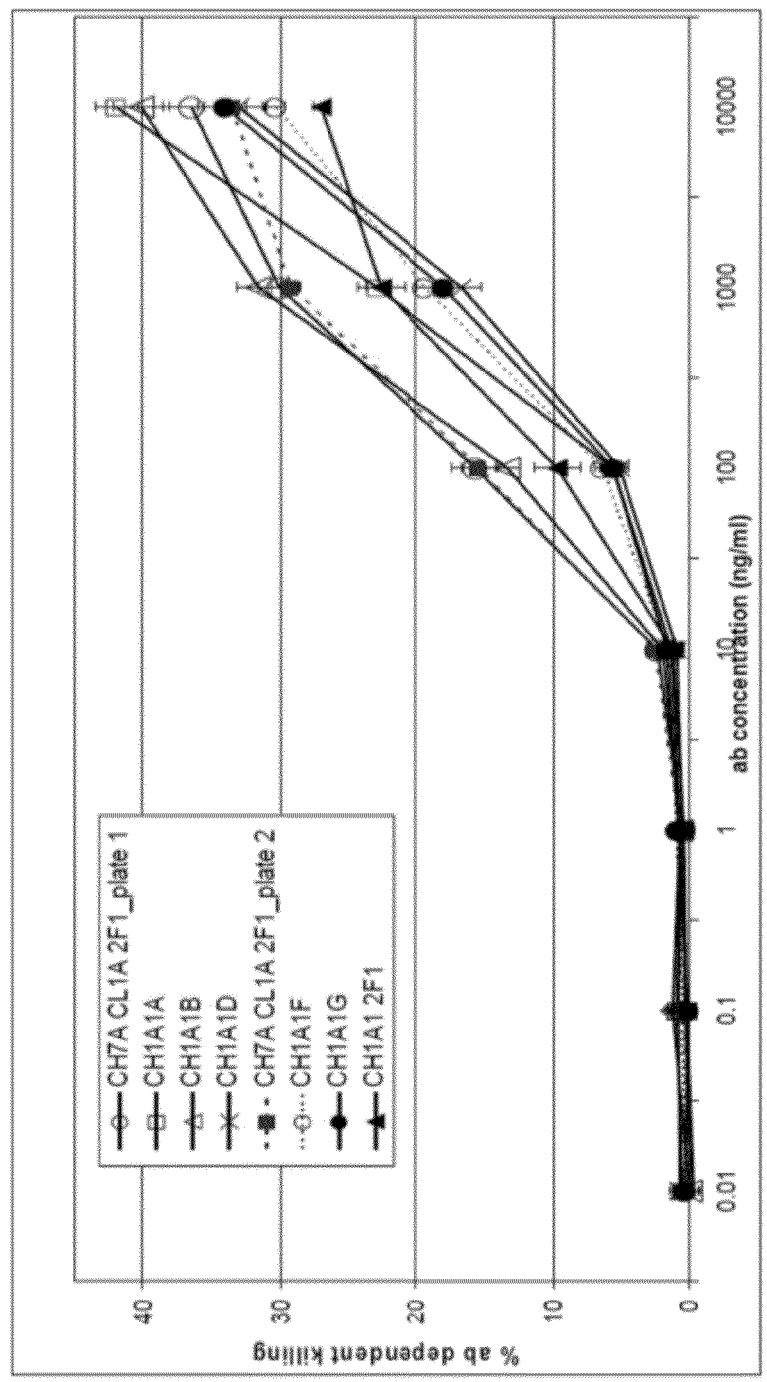
FIG. 26 shows the ADCC activity of the CHA1A-based framework variants.
Figure 27:
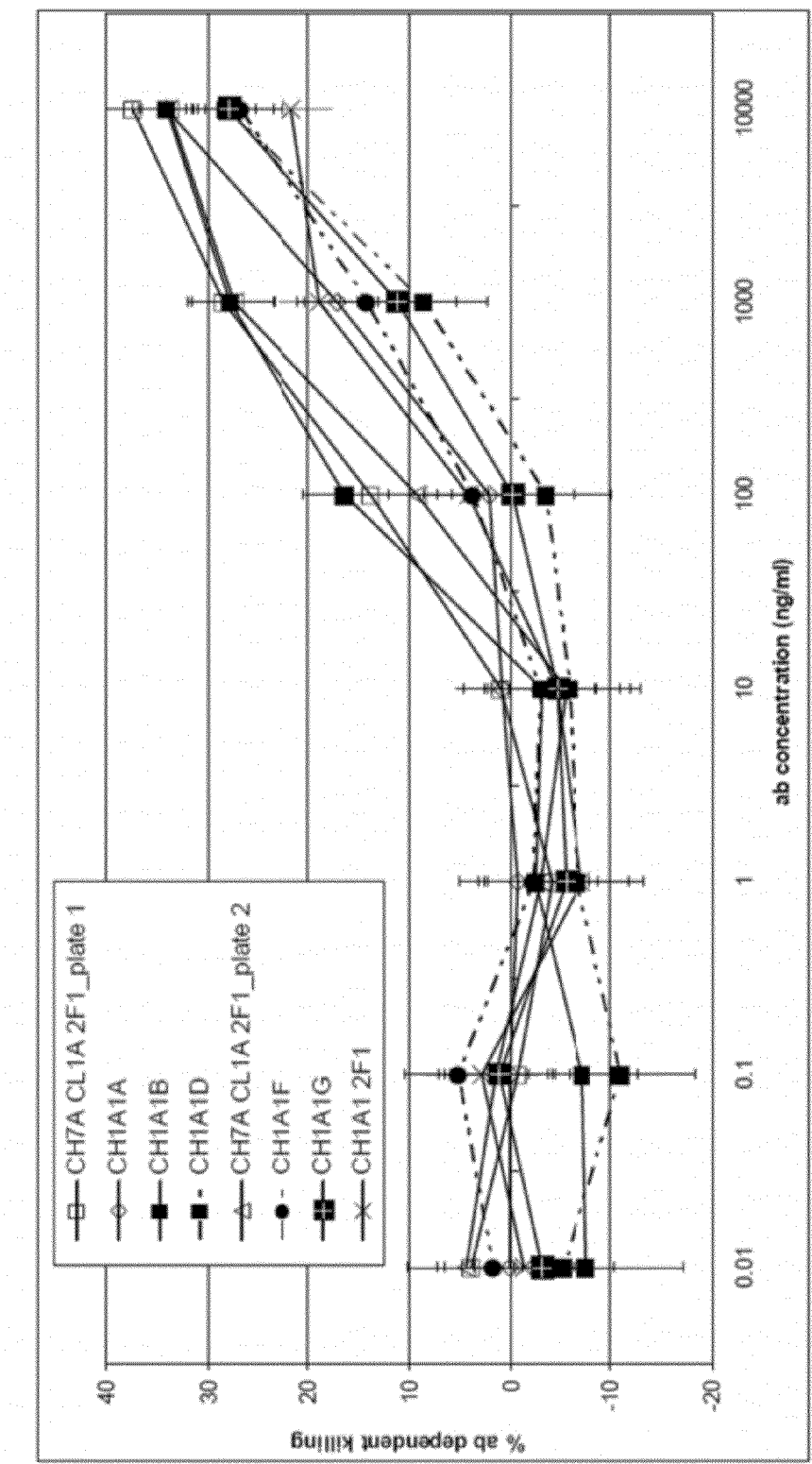
FIG. 27 shows the ADCC activity of the CHA1A-based framework variants.

The CH1A1A and CH1A1B constructs exhibited ADCC activity. ADCC mediated by CH1A1A and CH1A1B variants, their precursor variant CH1A1, and the parental CH7A variant was measured after 4 h by lactate dehydrogenase release using MKN45 cells as target cells (T) and human PBMC as effector cells (E) at E:T ratios of 25:1. Lactate dehydrogenase release is proportionate to target cell lysis and shown as percent cytotoxicity. FIG. 26. ADCC activity for these variants was confirmed as measured by calceine release using MKN45 cells as target cells (T) and human PBMC as effector cells (E) at E:T ratios of 25:1. Calceine release is proportionate to target cell lysis and shown as percent cytotoxicity with mean±standard deviation values. FIG. 27.

Figure 28:
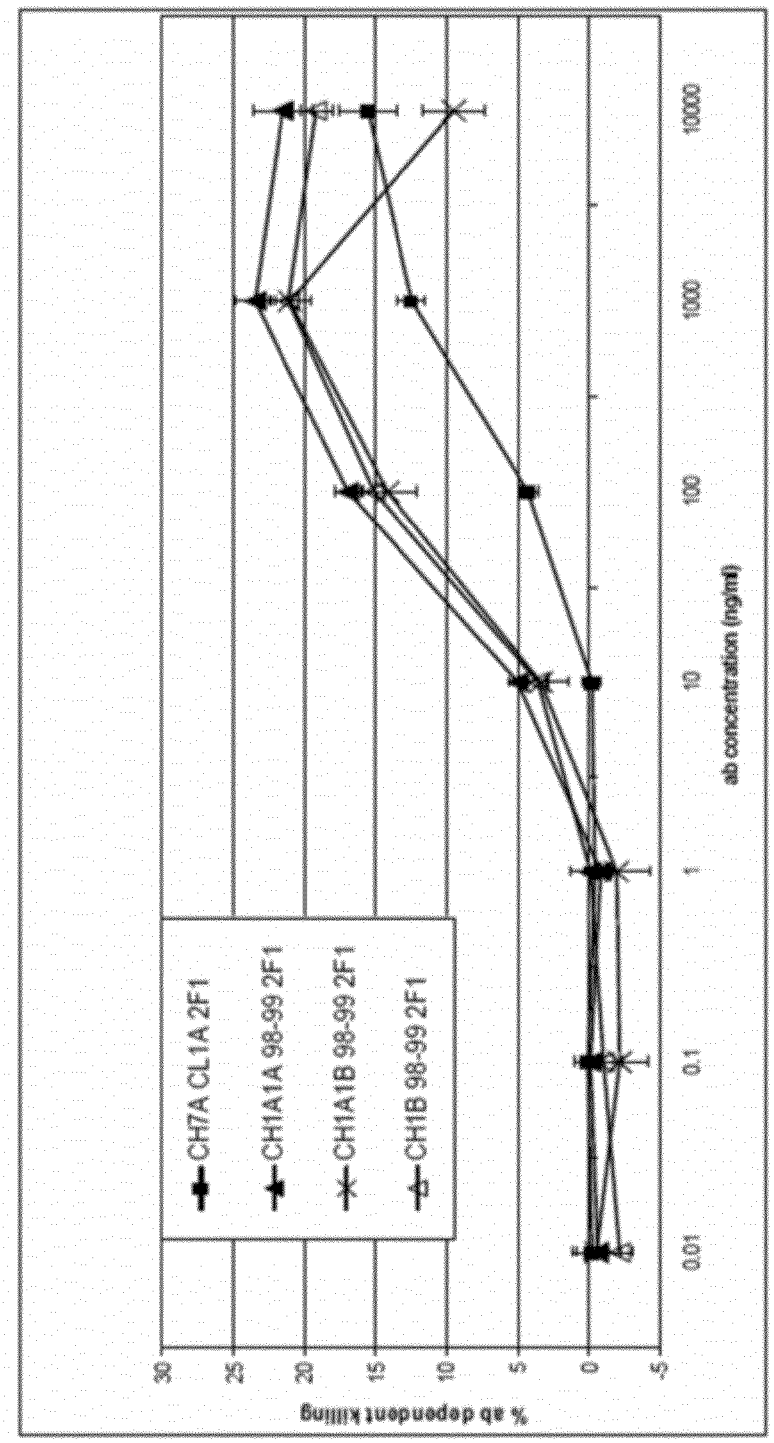
FIG. 28 shows the ADCC activity of the combined framework and CDR-H3 variants.
Figure 29:
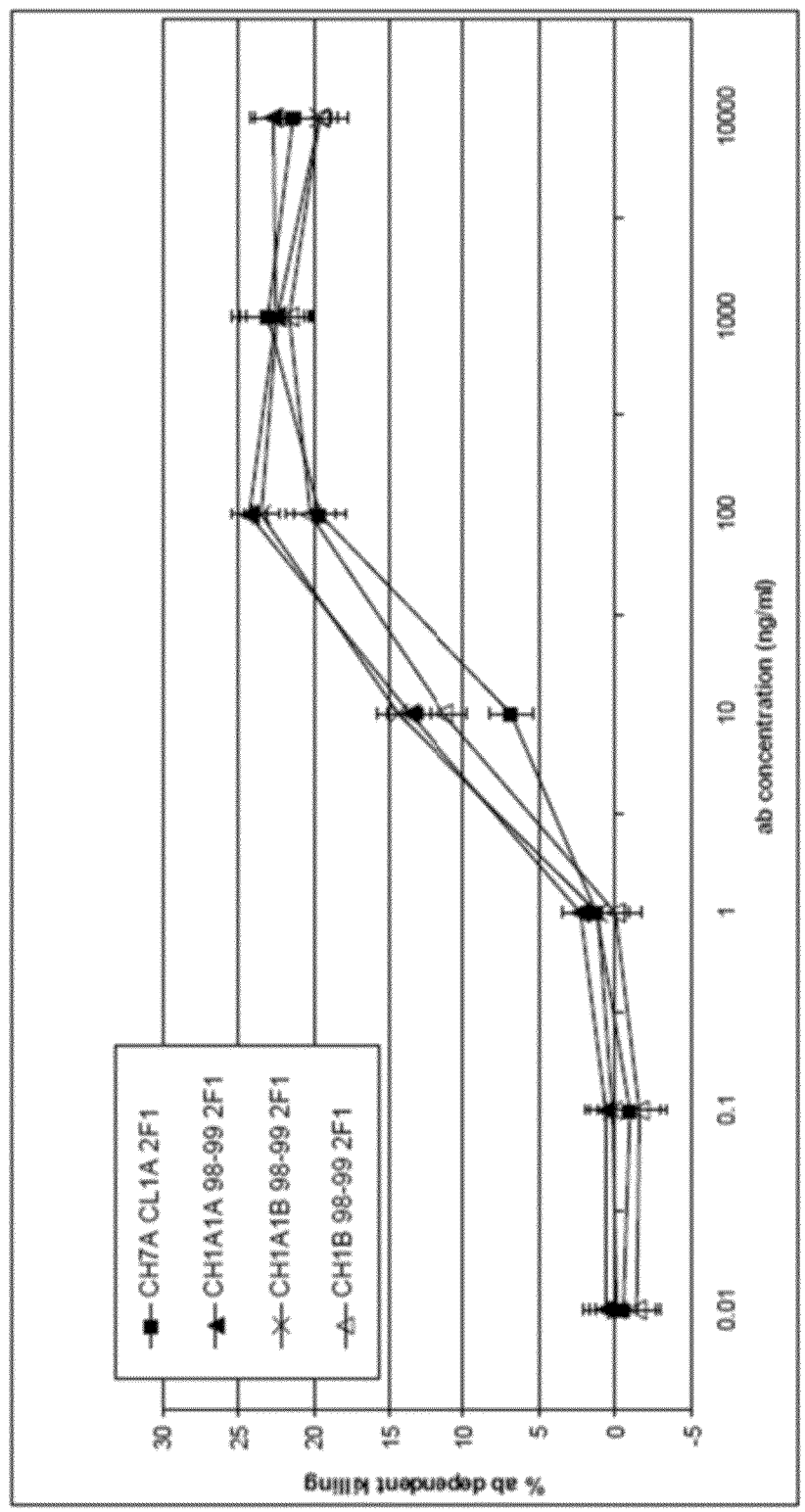
FIG. 29 shows the ADCC activity of the combined framework and CDR-H3 variants.
Figure 38:
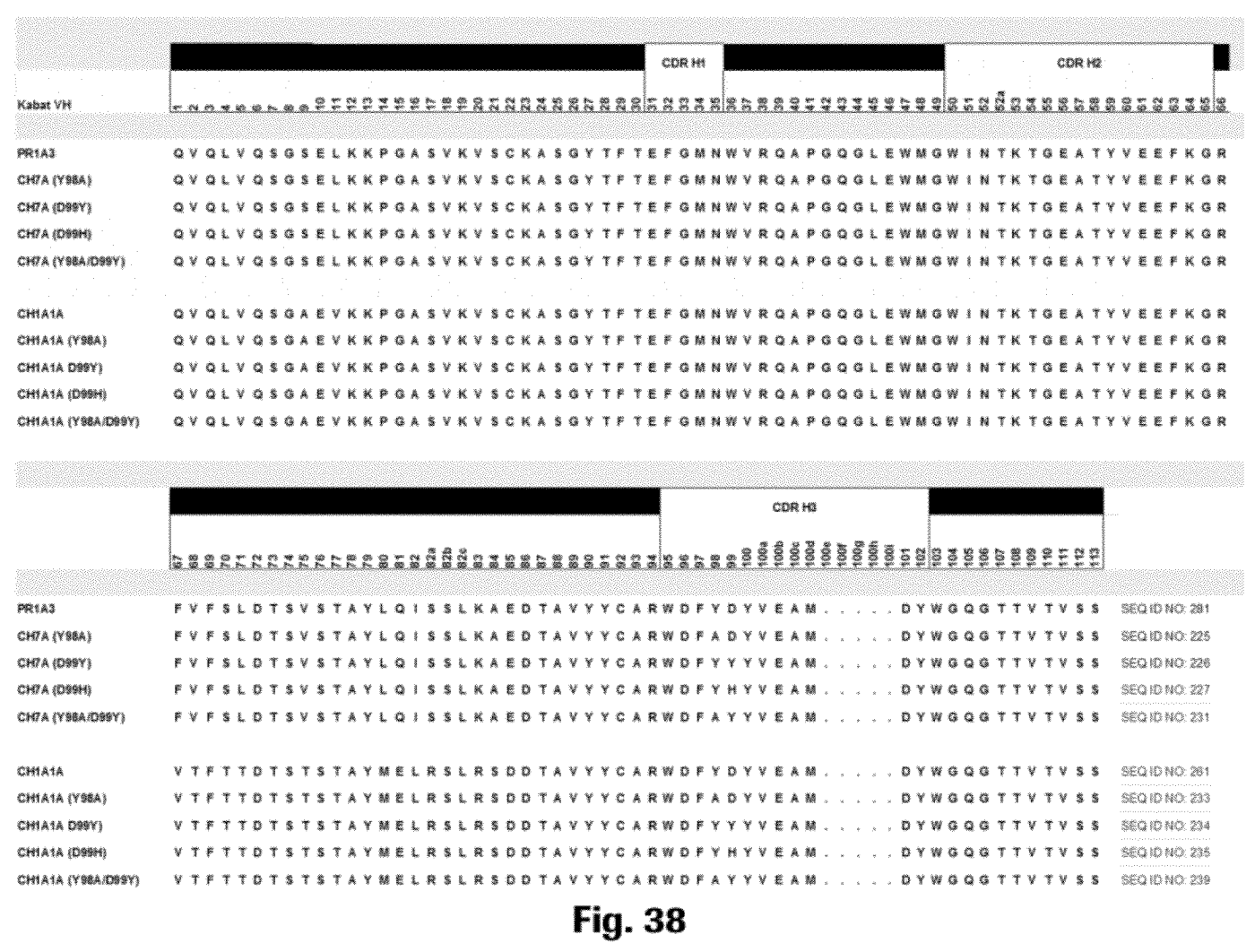

ADCC activity was also observed for CH1A1A and CH1A1B constructs containing the affinity matured CDRH3 with the double mutation Y98A/D99Y. ADCC mediated by the combined framework and CDR-H3 variants and the parental antibody harbouring CH7A was measured after 24 h by lactate dehydrogenase release using MKN45 cells (FIG. 28) or LS174T (FIG. 29) as target cells and human PBMC as effector cells at E:T ratios of 5:1. While MKN45 cells express CEA at high levels, the expression of CEA is medium in LS174T cells. Lactate dehydrogenase release is proportionate to target cell lysis and shown as percent cytotoxicity. All antibodies tested in these ADCC assays had 2F1 as the light chain FIG. 38 shows the amino acid sequence alignments of VH regions of various stability matured anti-CEA antibodies.

Example 7

Figure 30:
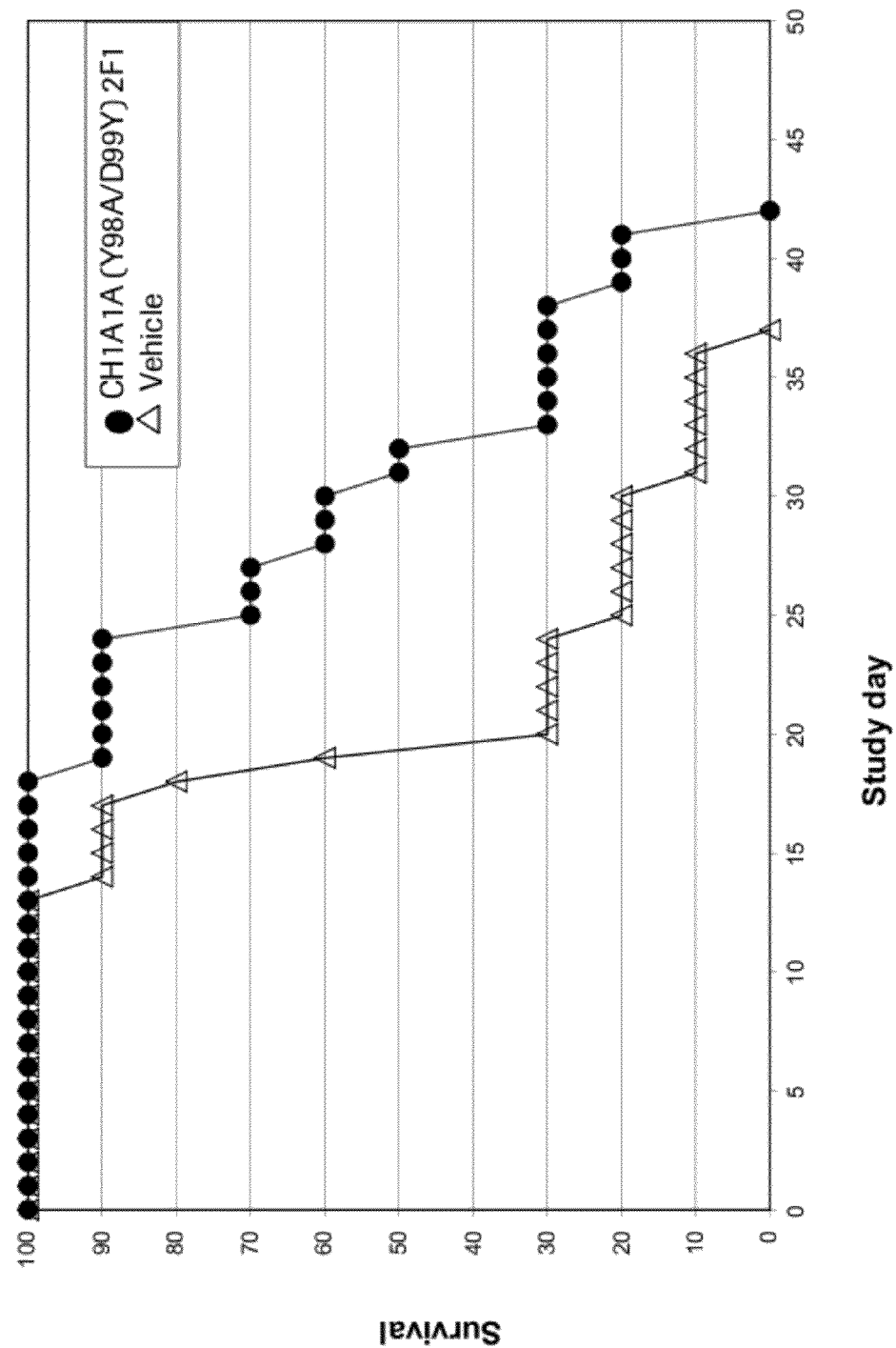
FIG. 30 shows the efficacy of glycoengineered anti-CEA antibody CH1A1A (Y98A/D99Y)×2F1 in a colorectal carcinoma xenograft model in SCID mice transgenic for human CD16.

The glycoengineered version of anti-CEA antibody comprising the CH1A1A (98/99) heavy chain and 2F1 light chain was tested for efficacy in a colorectal carcinoma xenograft model in SCID mice transgenic for human CD16. The model assay conditions are set forth below. The results of the assay indicate that this anti-CEA antibody provides a survival benefit as compared to a vehicle control. FIG. 30.

Animals:

CD16 Scid transgenic female mice; age 7-9 weeks at start of experiment (Charles River France) were maintained under specific-pathogen-free condition with daily cycles of 12 h light/12 h darkness according to committed guidelines (GV-Solas; Felasa; TierschG). Experimental study protocol was reviewed and approved by local government authorities. After arrival, animals were maintained for one week for acclimation and for observation. Continuous health monitoring was carried out on a regular basis.

Cell Culture and Application:

LS174T cells (human colon carcinoma cells; European Collection of Cell Culture) were cultured in DMEM medium containing 10% FCS (PAA Laboratories, Austria). The cells were cultured at 37° C. in a water-saturated atmosphere at 5% $CO_2$. In vitro passage 24 was used for intra-splenic injection, at a viability of 97%.

Tumor Cell Injection:

At day of injection, LS174T tumor cells were harvested using trypsin-EDTA (Gibco, Switzerland) from culture flasks (Greiner Bio-One) and transferred into 50 ml culture medium, washed once and resuspended in AIM V (Gibco, Switzerland). A small incision was made at the left abdomal site of anesthetized SCID/beige mouse. The skin and the muscle were opened and thirty microliters ($3\times10^6$LS174T cells in AimV medium) of cell suspension was injected in the apex of the spleen. The muscle first and then the abdominal skin were sutured with a absorbable sutures (Monosyn® 3-0, Braun).

Treatment:

All anti-CEA antibodies and the corresponding vehicle were administered i.v. once weekly. Three dosings in total. 625 ug of antibody was administered per injection per mouse. The antibody dilutions were prepared freshly from stock before use and formulated in 20 mM Histidine, 140 mM NaCl, pH6.0 at 4.38 mg/ml antibody concentration.

Example 8

Figure 31:
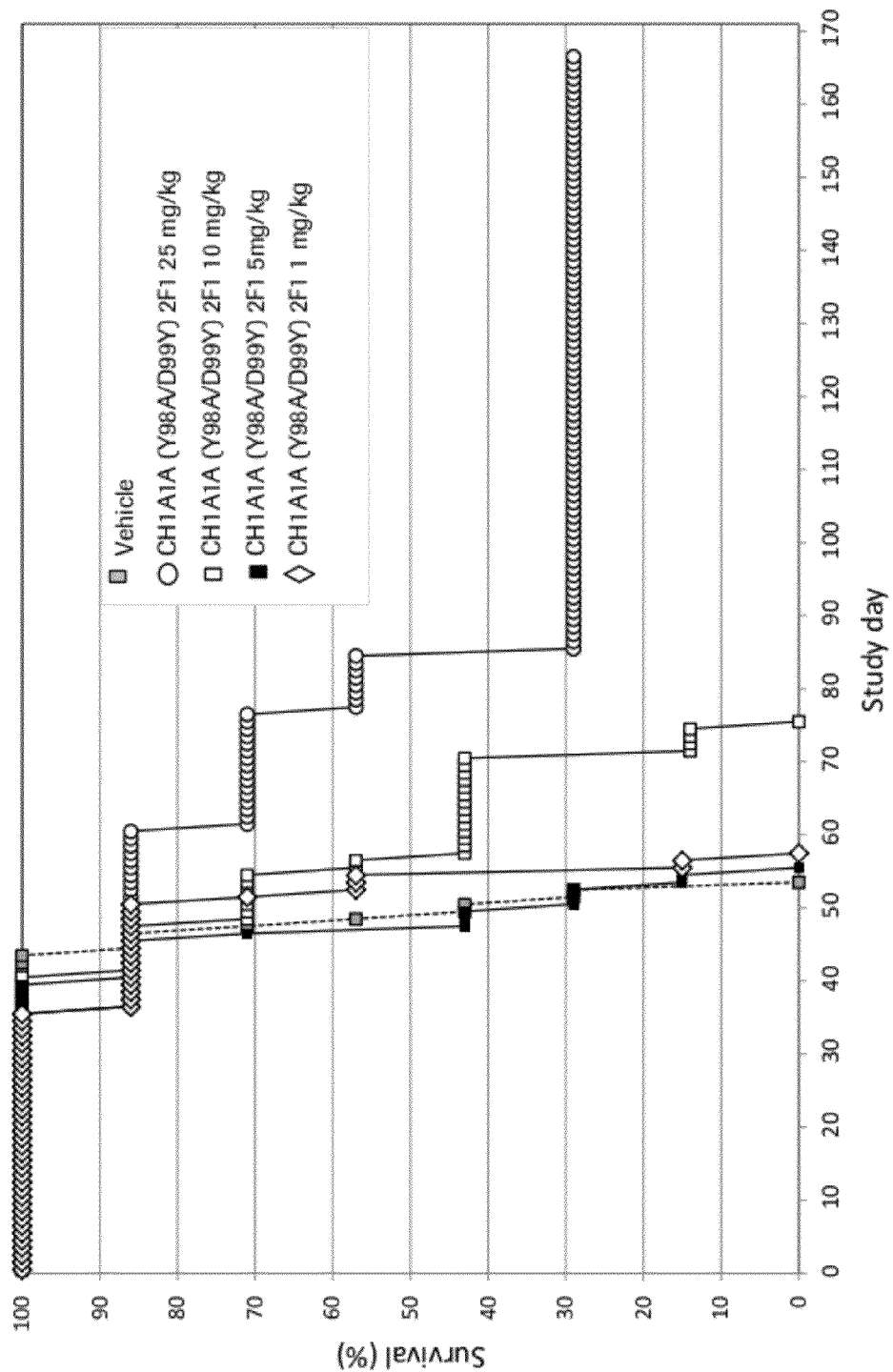
FIG. 31 shows the efficacy of glycoengineered anti-CEA antibody CH1A1A (Y98A/D99Y)×2F1 in an A549 lung carcinoma xenograft model in SCID mice transgenic for human CD16.

The glycoengineered version of anti-CEA antibody comprising CH1A1A (Y98A/D99Y) heavy chain and 2F1 light chain was tested for efficacy in an A549 lung carcinoma xenograft model in scid mice transgenic for human CD16. The model assay conditions are set forth below. The results of the assay indicate that this anti-CEA antibody provides a dose-dependant survival benefit as compared to a vehicle control. FIG. 31.

Animals:

Thirty five CD16 Scid transgenic female mice; age 7-9 weeks at start of experiment (Charles River France) were maintained under specific-pathogen-free condition with daily cycles of 12 h light/12 h darkness according to committed guidelines (GV-Solas; Felasa; TierschG). Experimental study protocol was reviewed and approved by local government authorities. After arrival, animals were maintained for one week for acclimation and for observation. Continuous health monitoring was carried out on a regular basis.

Cell Culture and Application:

A549 cells (human NSCLC cells; American Tissue Culture collection) were cultured in DMEM medium containing 10% FCS (PAA Laboratories, Austria). The cells were cultured at 37° C. in a water-saturated atmosphere at 5% $CO_2$.

Treatment:

Mice were injected i.v. on study day 0 with $1\times10^6$ A549 cells. The antibody started on study day 7 and continued with 2 more weekly injections.

Treatment Groups:

Mice 35 SCID-CD16Tg mice, N=7 per group.
Cells—A549 cells 5 Mio/mouse
Compound and Therapy Schedule
Vehicle 3q7d
CH1A1A(Y98A/D99Y)×2F1 (500 ug) 3q7d (25 mg/kg)
CH 1A1A(Y98A/D99Y)×2F1 (200 ug) 3q7d (10 mg/kg)
CH1A1A(Y98A/D99Y)×2F1 (100 ug) 3q7d (5 mg/kg)
CH1A1A(Y98A/D99Y)×2F1 (50 ug) 3q7d (1 mg/kg)

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody which binds membrane-bound CEA, wherein the antibody comprises a heavy chain variable region comprising:
the heavy chain CDR1 of SEQ ID NO: 1,
the heavy chain CDR2 of SEQ ID NO: 13, and
a heavy chain CDR3 selected from the group consisting of SEQ ID NO:217, SEQ ID NO:218, SEQ ID NO:219, SEQ ID NO:220, SEQ ID NO:221, SEQ ID NO:222, and SEQ ID NO:223; and
a light chain variable region comprising:
the light chain CDR1 of SEQ ID NO:39,
the light chain CDR2 of SEQ ID NO:49, and
the light chain CDR3 of SEQ ID NO:56.

2. The antibody of claim 1, wherein the antibody comprises the framework residues of CH1A1A (SEQ ID NO: 261) or CH1A1B (SEQ ID NO: 262).

3. The antibody of claim 1, wherein the antibody comprises a heavy chain variable region comprising an amino acid sequence selected from the group consisting of SEQ ID NO: 233, SEQ ID NO: 234, SEQ ID NO: 235, SEQ ID NO: 239, SEQ ID NO: 241, SEQ ID NO: 242, SEQ ID NO: 243, and SEQ ID NO: 247 and a light chain variable region comprising the amino acid sequence of SEQ ID NO: 209.

4. The antibody of claim 1, wherein the antibody comprises an Fc region that has been glycoengineered.

5. The antibody of claim 4, wherein at least about 20% to about 100% of the N-linked oligosaccharides in the Fc region are nonfucosylated.

6. The antibody of claim 4, wherein at least about 20% to about 100% of the N-linked oligosaccharides in the Fc region are bisected.

7. The antibody of claim 4, wherein at least about 20% to about 50% of the N-linked oligosaccharides in the Fc region are bisected, nonfucosylated.

8. The antibody of claim 4, wherein the antibody has at least one increased effector function.

9. The antibody of claim 8, wherein the at least one increased effector function is selected from the group consisting of: increased Fc receptor binding affinity, increased antibody-mediated cellular cytotoxicity (ADCC), increased binding to NK cells, increased binding to macrophages, increased binding to monocytes, increased binding to polymorphonuclear cells, direct signaling inducing apoptosis, increased dendritic cell maturation, and increased T cell priming.

10. The antibody of claim 9, wherein the antibody has an increase in ADCC of at least about 40% to about 100% as compared to the non-glycoengineered parent antigen binding molecule.

11. A composition comprising the antibody of claim 9 and a pharmaceutically acceptable carrier.

12. A method of inducing cell lysis of a tumor cell that expresses CEA, the method comprising contacting the tumor cell with the antibody of claim 1.

13. The method of claim 12, wherein the tumor cell is selected from the group consisting of a colorectal cancer cell, NSCLC (non-small cell lung cancer) cell, gastric cancer cell, pancreatic cancer cell and breast cancer cell.

14. The method of claim 12, wherein the cell lysis is induced by antibody dependent cell cytotoxicity of the antibody.

15. A method of treating a subject having a cancer that expresses CEA, the method comprising administering to the subject a therapeutically effective amount of the antibody of claim 1.

16. The method of claim 15, wherein the antibody is administered in combination with chemotherapy or radiation therapy.

17. A composition comprising the antibody of claim 1 and a pharmaceutically acceptable carrier.

18. The method of claim 15, wherein the cancer is selected from the group consisting of colorectal cancer, NSCLC (non-small cell lung cancer), gastric cancer, pancreatic cancer and breast cancer.

* * * * *